US011353454B2

(12) United States Patent
Khurana

(10) Patent No.: US 11,353,454 B2
(45) Date of Patent: Jun. 7, 2022

(54) METHODS FOR DETECTION OF FLAVIVIRUS ANTIBODIES

(71) Applicant: The U.S.A., as represented by the Secretary, Department of Health and Human Services, Silver Spring, MD (US)

(72) Inventor: Surender Khurana, Clarksburg, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 16/831,525

(22) Filed: Mar. 26, 2020

(65) Prior Publication Data

US 2020/0348299 A1 Nov. 5, 2020

Related U.S. Application Data

(60) Provisional application No. 62/823,834, filed on Mar. 26, 2019.

(51) Int. Cl.

| | |
|---|---|
| ***C07K 14/005*** | (2006.01) |
| ***C12N 7/00*** | (2006.01) |
| ***G01N 33/566*** | (2006.01) |
| ***G01N 33/569*** | (2006.01) |

(52) U.S. Cl.

CPC ......... *G01N 33/566* (2013.01); *C07K 14/005* (2013.01); *C12N 7/00* (2013.01); *G01N 33/56983* (2013.01); *C12N 2770/24121* (2013.01)

(58) Field of Classification Search

None

See application file for complete search history.

(56) References Cited

U.S. PATENT DOCUMENTS

| | | | | |
|---|---|---|---|---|
| 10,124,055 | B2 | 11/2018 | Ciaramella et al. | |
| 2012/0178909 | A1* | 7/2012 | Frisch .................. | C07K 14/005 530/387.1 |
| 2018/0127800 | A1* | 5/2018 | Wolkowicz ............ | C12N 9/506 |
| 2018/0136225 | A1 | 5/2018 | Wong et al. | |

OTHER PUBLICATIONS

Wu et al., Activation of dengue protease autocleavage at the NS2B-NS3 junction byrecombinant NS3 and GST-NS2B fusion proteins, 2003, Journal of Virological Methods, vol. 114, pp. 45-54.*

Ravichandran et al., "Differential Human Antibody Repertoires Following Zika Infection and the Implications for Serodiagnostics and Disease Outcome," *Nature Commun.*, vol. 10:1943, 2019.

* cited by examiner

*Primary Examiner* — Benjamin P Blumel

(74) *Attorney, Agent, or Firm* — Klarquist Sparkman, LLP

(57) ABSTRACT

Isolated peptides that include one or more antigenic sites of Zika virus (ZIKV) and methods of their use and production are disclosed. The peptides can be used, for example, to detect exposure of a subject to a flavivirus infection, such as a ZIKV infection.

21 Claims, 73 Drawing Sheets

Specification includes a Sequence Listing.

FIG. 1A
| | IgM Antibodies | | | | IgG Antibodies | | | |
|---|---|---|---|---|---|---|---|---|
| | Naïve Serum | Serum D0 | Serum D7 | Urine D7 | Naïve Serum | Serum D0 | Serum D7 | Urine D7 |
| Phage Titer | 412 | $8.5x10^7$ | $2.02x10^8$ | $2.22x10^8$ | 91 | $9.7x10^4$ | $5.71x10^6$ | 103 |
FIG. 1B
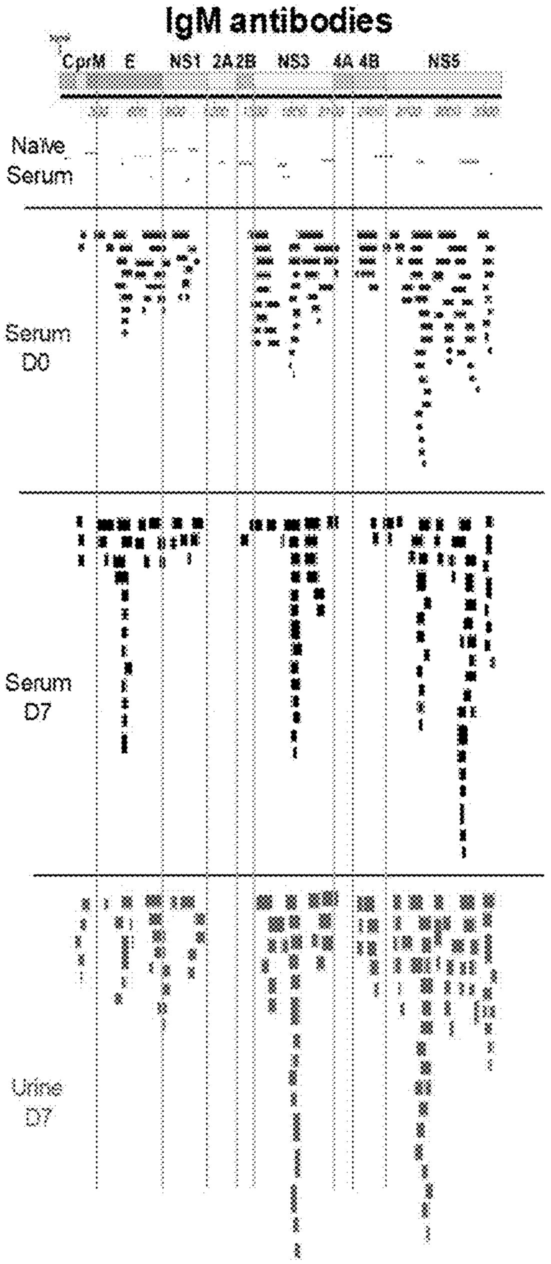
FIG. 1C
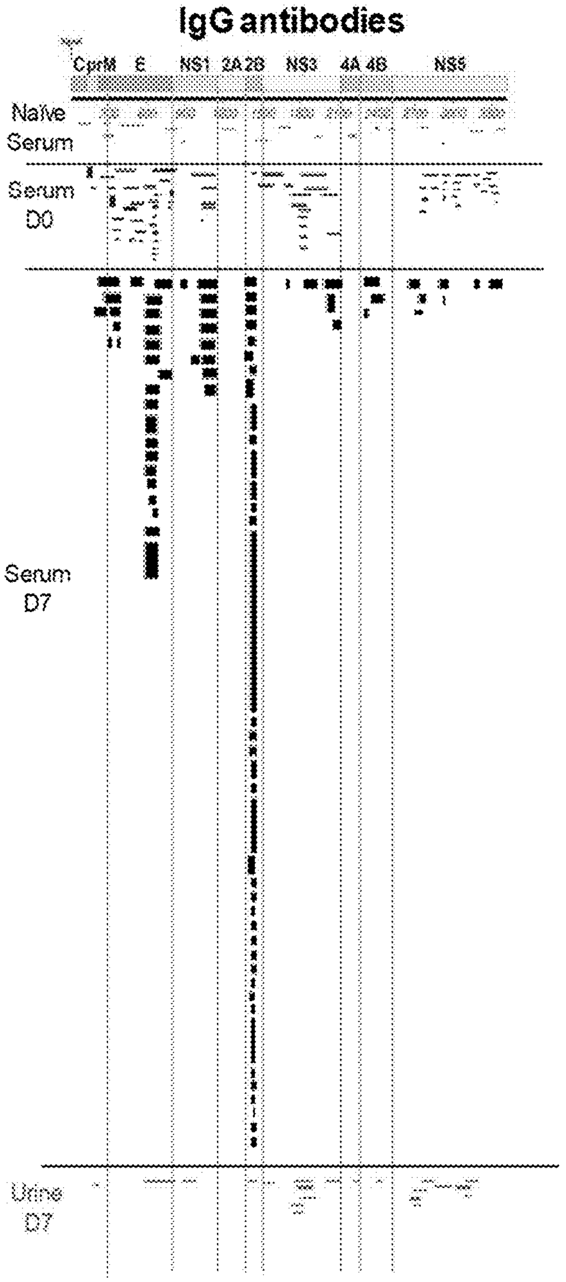

FIG. 4B

| Peptide | Sample | Frequency of values ≥100 | Percent of values ≥100(%) |
|---|---|---|---|
| ZIKV NS1 (1033-1067) | ZIKV-Acute-V0 | 3/19 | 15.79 |
| | ZIKV-Acute-V28 | 9/19 | 47.37 |
| | ZIKV-Conv | 13/13 | 100.00 |
| | DENV | 3/27 | 11.11 |
| ZIKV NS2B (1421-1469) | ZIKV-Acute-V0 | 6/19 | 31.58 |
| | ZIKV-Acute-V28 | 15/19 | 78.95 |
| | ZIKV-Conv | 13/13 | 100.00 |
| | DENV | 1/27 | 3.70 |
| ZIKV NS3 (1805-1873) | ZIKV-Acute-V0 | 3/19 | 15.79 |
| | ZIKV-Acute-V28 | 11/19 | 57.89 |
| | ZIKV-Conv | 10/13 | 76.92 |
| | DENV | 0/27 | 0.00 |
| ZIKV NS4B (2312-2363) | ZIKV-Acute-V0 | 8/19 | 42.11 |
| | ZIKV-Acute-V28 | 13/19 | 68.42 |
| | ZIKV-Conv | 12/13 | 92.31 |
| | DENV | 15/27 | 55.56 |
| ZIKV NS4B (2422-2465) | ZIKV-Acute-V0 | 1/19 | 5.26 |
| | ZIKV-Acute-V28 | 3/19 | 15.79 |
| | ZIKV-Conv | 9/13 | 69.23 |
| | DENV | 1/27 | 3.70 |
| ZIKV NS5 (2860-2901) | ZIKV-Acute-V0 | 4/19 | 21.05 |
| | ZIKV-Acute-V28 | 14/19 | 73.68 |
| | ZIKV-Conv | 6/13 | 46.15 |
| | DENV | 3/27 | 11.11 |
| ZIKV NS5 (2943-2977) | ZIKV-Acute-V0 | 5/19 | 26.32 |
| | ZIKV-Acute-V28 | 12/19 | 63.16 |
| | ZIKV-Conv | 12/13 | 92.31 |
| | DENV | 12/27 | 44.44 |
| ZIKV NS5 (3136-3179) | ZIKV-Acute-V0 | 6/19 | 31.58 |
| | ZIKV-Acute-V28 | 15/19 | 78.95 |
| | ZIKV-Conv | 12/13 | 92.31 |
| | DENV | 20/27 | 74.07 |
| ZIKV NS5 (3263-3330) | ZIKV-Acute-V0 | 1/19 | 5.26 |
| | ZIKV-Acute-V28 | 2/19 | 10.53 |
| | ZIKV-Conv | 5/13 | 38.46 |
| | DENV | 2/27 | 7.41 |

| ZIKV MAb | Neutralizing Strains | Epitope | AA Sequence |
|---|---|---|---|
| ZV54 | ZIKV Asian, African, and American strains (Zika H/PF/2013, MR766, Uganda 1947, Paraiba, Brazil 2015) | Known Site using X-ray crystallography (conformational epitope- lateral ridge of EDIII ) | 589-RLKGVSYSLCTAAFTFTKIPAETLHGTVTVEVQYAGTDGPCKVPAQMAVDMQTLTPVGRLITANPVITESTENSKMMLELDPPFGDSYIVIGVGEKKITHHWHRSGSTI-697 |
| | | GFFDL | 598-CTAAFTFTKIPAETLHGTVTVEVQYAGTDGPCKVPAQMAVDMQTLTPVGRLITANPVITESTENSKMMLELDPPFGDSYIVIGVGEKKITHHWHRSG-694 |

FIG. 11D

| ZIKV Mabs | Neutralizing Strains | Epitope | AA Sequence |
|---|---|---|---|
| ZV67 | ZIKV Asian, African, and American strains (Zika H/PF/2013, MR766, Uganda 1947, Paraiba, Brazil 2015) | Known Site using X-ray crystallography (conformational epitope- lateral ridge of EDIII ) | 589-<br>RLKGVSYSLCTAAFTFTKIPAETLHGTVTVE<br>VQYAGTDGPCKVPAQMAVDMQTLTPVGRLIT<br>ANPVITESTENSKMMLELDPPFGDSYIVIGVGE<br>KKITHHWHRSGSTI-697 |
| | | GFPDL | 595-<br>YSLCTAAFTFTKIPAETLHGTVTVEVQYAGTDGP<br>CKVPAQMAVDMQTLTPVGRLITANPVITESTENS<br>KMMLELDPPFGDSYIVIGVGEKKITHHWHRSGS<br>TIGKAFEATVRGA-708 |

FIG. 12D

| ZIKV Mabs | Neutralizing Strains | Epitope | AA Sequence |
|---|---|---|---|
| Z23 | ZIKV Asian strain SMGC-1 | Known Site using crystallography | ZIKV E DIII tertiary epitope (Z23 mainly binds to DIII of one envelope protein monomer and can cross-react with two envelope protein dimers on the virion surface) |
| | | GFPDL | 594-SYSLCTAAFTFTKIPAETLHGTVTVEVQYAGTDGPCKV PAQMAVDMQTLTPVGRLITANPVITESTENSKMMLELDPPF GDSYIVIGVGEKKITHHWHRSG-694 |

FIG. 13D

| ZIKV Mabs | Neutralizing Strains | Epitope | AA Sequence |
|---|---|---|---|
| ZKA64 | Zika H/PF/2013, MR766 | Known Site | ZIKV E DIII |
| | | GFPDL | 595-YSLCTAAFTFTKIPAETLHGTVTVEVQYAGTDGPCKVPAQ MAVDMQTLTPVGRLITANPVITESTENSKMMLELDPPFGDSYI VIGVGEKKITHHWHRSG-694 |

FIG. 16A
| | IgM antibodies | IgG antibodies |
|---|---|---|
| Phage Titer | $3.29 \times 10^7$ | $3.7 \times 10^5$ |
FIG. 16B
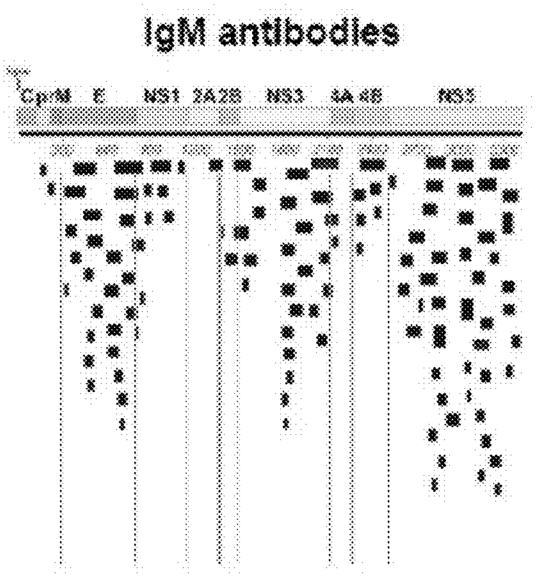
FIG. 16C
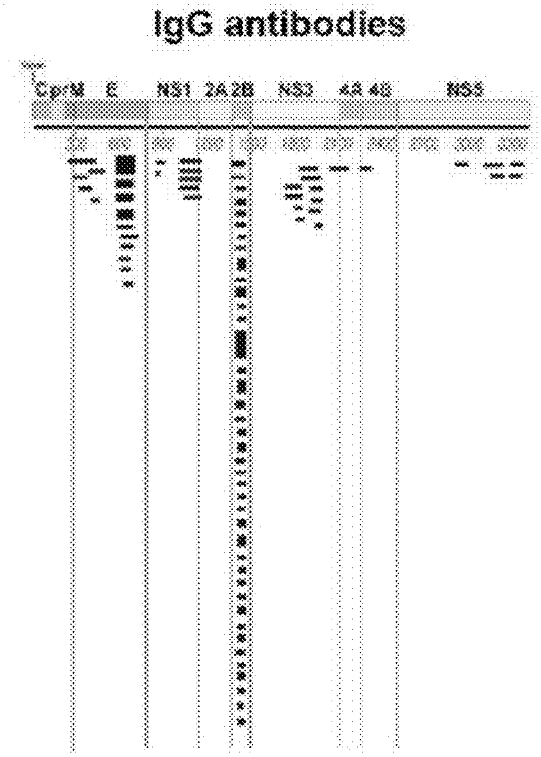

| | IgM | | IgG | | IgA | |
|---|---|---|---|---|---|---|
| | Serum | AF | Serum | AF | Serum | AF |
| Phage Titer | $7.73 \times 10^7$ | $9.9 \times 10^7$ | $6.18 \times 10^5$ | $3.0 \times 10^2$ | $4.4 \times 10^4$ | $6.0 \times 10^4$ |

IgM

| | IgM | | IgG | | IgA | |
|---|---|---|---|---|---|---|
| | Serum | AF | Serum | AF | Serum | AF |
| Phage Titer | $3.29 \times 10^7$ | $1.18 \times 10^7$ | $1.87 \times 10^5$ | $1.1 \times 10^4$ | $1.74 \times 10^3$ | $7.2 \times 10^2$ |

FIG. 31C
IgA Serum
IgA AF
Frequency of clones
0%
10%
20%
30%
40%
50%

METHODS FOR DETECTION OF FLAVIVIRUS ANTIBODIES

CROSS REFERENCE TO RELATED APPLICATIONS

This application claims the benefit of U.S. Provisional Application No. 62/823,834, filed Mar. 26, 2019, which is herein incorporated by reference in its entirety.

ACKNOWLEDGMENT OF GOVERNMENT SUPPORT

This invention was made with government support under project number OCET 2018-698 awarded by the FDA Medical Countermeasures Initiative (MCMi). The government has certain rights in the invention.

FIELD

The present disclosure concerns Zika virus (ZIKV) peptides and their use for detecting a subject's exposure ZIKV or other flaviviruses.

BACKGROUND

Since its discovery in 1947 (Haddow et al., 1952, *Trans. R. Soc. Trop. Med. Hyg.,* 46: 509-520; de Silva et al., 2016, *JAMA.,* 315: 1945-1946), Zika virus (ZIKV) has primarily been associated with sporadic infections in humans and mild symptoms. However, during the recent 2015-2016 outbreak in Latin America, ZIKV infections were associated with developmental and neurological complications including microcephaly in newborns and Guillain-Barré syndrome in adults (Diamond et al., 2016, *J. Virol.,* 90: 4864-4875; Sardi et al., 2015, *Emerg. Infect. Dis.* 21: 1885-1886; Mlakar et al., 2016, *N. Engl. J. Med.,* 374: 951-958; Cao-Lormeau et al., 2016, *Lancet.,* 387: 1531-1539; Faria et al., 2016, *Science,* 352: 345-349). This has prompted an emphasis on vaccine development (Michael et al., 2017, *Immunity,* 46: 176-182; Gaudinski et al., 2017, *Lancet.*; Fauci et al., 2016, *N. Engl. J. Med.,* 375: 1209-1212; Graham et al., 2017, *J. Infect. Dis.,* 216: S957-S963; Shan et al., 2017, *Nat. Commun.,* 8:676; Thomas et al., 2017, *N. Engl. J. Med.,* 376:1883-1886), and isolation/characterization of ZIKV-specific monoclonal antibodies (MAbs) with a low risk of antibody-dependent enhancement (ADE). Additionally, accurate diagnostics for ZIKV infection are hampered by pre-existing cross-reactive antibodies against other flaviviruses circulating in the same geographical areas (Lanciotti et al., 2008, *Emerg. Infect. Dis.,* 14: 1232-1239; Gubler et al., 2016, *Clin. Microbiol. Rev.* 29:487-524). A need exists for identifying new targets in the ZIKV polyprotein that are recognized by antibodies at early stages post-exposure to aid in the development of an improved diagnostic test for ZIKV infection and/or infection by other flaviviruses. Furthermore, a need exists to improve the accuracy and speed of serologic diagnosis for flaviviruses, including ZIKV.

SUMMARY

Disclosed herein are peptide fragments of Zika virus (ZIKV) that can be used, for example, to detect exposure of a subject to a ZIKV infection. Also disclosed are ZIKV peptides for detecting exposure of a subject to any one of a multiple of flaviviruses. For use in diagnostic and/or detection assays, the peptides can be linked or conjugated to a solid support.

Provided herein are isolated peptides that encompass antigenic sites of a ZIKV polyprotein. In some embodiments, the peptides are less than 100 amino acids in length. In some embodiments, the peptides are linked to a solid support, fused to a heterologous protein, or conjugated to a heterologous carrier.

Also provided are solid supports linked to one or more the ZIKV peptides disclosed herein. In some examples, the solid support includes a bead, membrane, multi-well plate, or any solid support suitable for use in an immunoassay.

Further provided is a method for detecting anti-flavivirus antibodies in a biological sample. In some embodiments, the method includes contacting a biological sample with a ZIKV peptide disclosed herein under conditions sufficient to form an immune complex between the one or more peptides and the antibodies present in the biological sample; and detecting the presence or absence of the immune complex. The presence of the immune complex indicates anti-flavivirus antibodies are present in the sample and the absence of the immune complex indicates anti-flavivirus antibodies are not present in the sample. In some examples, the flavivirus is ZIKV. In other examples, the flavivirus is a flavivirus other than ZIKV.

Methods of identifying a subject with a flavivirus infection are also provided. In some embodiments, the method includes contacting a biological sample containing antibodies from the subject with one or more ZIKV peptides disclosed herein under conditions sufficient to form an immune complex between the one or more peptides and the antibodies present in the biological sample; and detecting the presence or absence of the immune complex. The presence of the immune complex identifies the subject as having a flavivirus infection and the absence of the immune complex identifies the subject as not having a flavivirus infection.

Methods for detecting exposure of a subject to a flavivirus infection, such as a ZIKV infection, are disclosed. In such methods, a biological sample from a subject is contacted with an effective amount of an isolated peptide immobilized on a solid support under conditions sufficient to form an immune complex between the isolated peptide and antibodies present in the biological sample. The presence of the immune complex indicates that the biological sample is from a subject with the ZIKV infection or from a subject previously infected with ZIKV or other flavivirus.

Also provided is a process for linking a peptide to a solid support; and test kits containing the peptide linked to a solid support and optionally further comprising buffer, positive or negative control materials, labelling reagents, reagents for detecting a label and other conventional components.

The foregoing and other objects and features of the disclosure will become more apparent from the following detailed description, which proceeds with reference to the accompanying figures.

BRIEF DESCRIPTION OF THE DRAWINGS

FIGS. 1A-1C show IgG and IgM antibody repertoires across the whole ZIKV proteome elicited following ZIKV infection. (FIG. 1A) Number of bound phage clones isolated using ZIKV GFPDL affinity selection against flavivirus naïve negative control serum, pooled serum samples from five acutely ZIKV-infected patients on Day 0 and Day 7 of a hospital visit, and urine samples on Day 7 of the hospital visit (day 0 of the hospital visit corresponds to 0-3 days from the onset of symptoms for these 5 patients).

(FIGS. 1B-1C) Schematic alignment of the peptides recognized by IgM (FIG. 1B) and IgG (FIG. 1C) antibodies in ZIKV-infected human sera (day 0 and day 7) and urine (day 7), and flavivirus naïve negative control serum, identified by panning with ZIKV-GFPDL. The amino acid designation is based on the ZIKV polyprotein sequence encoded by the complete ZIKV-ICD genome (FIG. 8; SEQ ID NO: 9). Bars indicate identified inserts in the different structural (C, prM, E) and non-structural (NS) genes on the ZIKV polyprotein sequence. Graphical distribution of representative clones with a frequency of >2, obtained after affinity selection, are shown. The horizontal position and the length of the bars indicate the peptide sequence displayed on the selected phage clone to its homologous sequence in the ZIKV sequence on alignment. The thickness of each bar represents the frequency of repetitively isolated phages.

(FIG. 2A) Antigenic sites within the ZIKV proteins recognized by serum (Day 0, Day 7) and urine (Day 7) IgM and IgG antibodies following ZIKV infection (based on data presented in FIG. 1). The amino acid designation is based on the ZIKV polyprotein sequence encoded by the complete ZIKV genome (FIG. 8; SEQ ID NO: 9). The amino acid designations on the ZIKV polyprotein are as follows: C, capsid; pr, pre; M, membrane; E, envelope; NS, non-structural. Inset shows expanded version of E protein schematic with domains (D) I, II and III and fusion loop (FL) shown along with their antigenic sites. Previously described epitopes using MAbs are shown above the ZIKV-E schematic. Critical residues for binding of the following MAbs are depicted: 1, ZIKV-117; 2, 2A10G6; 3, ZIKV-12; 4, ZIKV-15; and 5, ZIKV-116. (FIGS. 2B-2C) Distribution and frequency of phage clones expressing each of the ZIKV antigenic sites recognized by IgM (FIG. 2B) and IgG (FIG. 2C) antibodies in post-ZIKV infection serum (Day 0 and Day 7) and urine (Day 7) are shown. The number of phage clones that expressed each antigenic site was divided by the total number of ZIKV-GFPDL selected clones for each pooled sera or urine samples and represented as a percentage.

(FIG. 3A) (left panel) Heat map showing sequence conservation on one monomer chain of mature ZIKV-E protein structure (PDB #5JHM) based on comparison with several ZIKV isolates (Paraiba, Uganda-1947, Nigeria-1968, Senegal-2001, Micronesia-2007 and Brazil-2016 strains) and (right panel) ZIKV vs. other flaviviruses (DENV 1 to 4, West Nile virus (WNV), yellow fever virus (YFV) and ZIKV). (FIG. 3B) Antigenic sites within ZIKV-prM/E identified by the GFPDL analysis are depicted on the structures of both immature (PDB 5U4W) and mature ZIKV E (PDB 5JHM). PDB Structure #5U4W encompasses residues 288-794 and PDB Structure #5JHM encompasses residues 313-699 based on ZIKV_ICD polyprotein sequence (SEQ ID NO: 9; FIG. 8).

FIGS. 4A-4B show seroreactivity of acute ZIKV-infected samples, convalescent ZIKV-infected samples, and DENV seropositive samples with ZIKV antigenic site peptides. (FIG. 4A) End-point titers of acute ZIKV (Acute-V0 and Acute-V28), convalescent ZIKV (ZIKV-Conv) and convalescent DENV human serum samples tested for binding to various ZIKV peptides in ELISA are depicted. ELISA was performed with 5-fold serially diluted (starting at 1:100) samples. One-way ANOVA was performed with a Bonferroni post-hoc analysis. **$p<0.0001$, $p<0.005$ and *$p<0.05$. (FIG. 4B) Table showing frequency and percentage of samples with end-point titers of >100 for each of the sample groups; ZIKV Acute-V0 and Acute-V28, ZIKV-Conv and DENV for each ZIKV peptide determined by peptide ELISA. Frequency and percent seropositivity were calculated for 19 samples each of ZIKV-Acute-V0 and V28, 13 samples for ZIKV-Conv and 27 samples for convalescent DENV infected samples.

FIG. 8 shows the complete ZIKV ICD Paraiba strain whole genome translated sequence (SEQ ID NO: 9) used for construction of ZIKV GFPD library and described in FIGS. 1-3.

FIGS. 10A-10D show GFPDL based epitope mapping of neutralizing MAb ZV54. (FIG. 10A) GFPDL-based epitope mapping of neutralizing ZIKV mouse Mab ZV54 to prME.

(FIG. 10B) The ELISA reactivity of selected GFPDL identified phage clones to MAb ZV54 was confirmed by phage ELISA. (FIG. 10C) Structure of GFPDL-identified epitope on PDB #5JHM for mature E. (FIG. 10D) The highest ELISA reactive sequence for MAb ZV54 identified using GFPDL mapping (residues 598-694 of SEQ ID NO: 9) is shown in the table compared to the sequence previously identified as 'known site' (residues 589-697 of SEQ ID NO: 9).

FIGS. 11A-11D show GFPDL based epitope mapping of neutralizing and protective mouse MAb ZV67. (FIG. 11A) GFPDL-based epitope mapping of neutralizing ZIKV mouse MAb ZV67 to prME. (FIG. 11B) The ELISA reactivity of selected GFPDL identified phage clones to MAb ZV67 was confirmed by phage ELISA. (FIG. 11C) Structure of GFPDL-identified epitope on PDB #5JHM for mature E. (FIG. 11D) The highest ELISA reactive sequence for MAb ZV67 identified using GFPDL mapping (595-708; SEQ ID NO: 9) is shown in the table compared to the sequence previously identified as 'known site' (residues 589-697 of SEQ ID NO: 9).

FIGS. 12A-12D show GFPDL based epitope mapping of a conformational tertiary epitope dependent, DENV-negative, ZIKV-specific neutralizing and protective human MAb Z23. (FIG. 12A) GFPDL-based epitope mapping of neutralizing ZIKV MAb Z23 to prME. (FIG. 12B) The ELISA reactivity of selected GFPDL identified phage clones to MAb Z23 was confirmed by phage ELISA and the ELISA positive clones are shown. (FIG. 12C) Structure of GFPDL-identified epitope on PDB #5JHM for mature E. (FIG. 12D) The minimal reactive sequence for MAb Z23 identified using GFPDL mapping (residues 594-694 of SEQ ID NO: 9) is shown in the table.

FIGS. 13A-13D show GFPDL based epitope mapping of neutralizing and protective human MAb ZKA64. (FIG. 13A) GFPDL-based epitope mapping of neutralizing ZIKV MAb ZKA64 to prME. (FIG. 13B) The ELISA reactivity of selected GFPDL identified phage clones to MAb ZKA64 was confirmed by phage ELISA and the ELISA positive clones are shown. (FIG. 13C) Structure of GFPDL-identified epitope on PDB #5JHM for mature E. (FIG. 13D) The minimal reactive sequence for MAb ZKA64 identified using GFPDL mapping (residues 595-694 of SEQ ID NO: 9) is shown in the table.

FIGS. 16A-16C show individual antibody repertoires elicited following acute ZIKV infection using IgG and IgM specific capture beads by ZIKV GFPDL. (FIG. 16A) Table of phage titers. (FIGS. 16B and 16C) Alignment of bound phage clones to ZIKV genome. Schematic alignment of the peptide sequences recognized by IgM (FIG. 16B) and IgG (FIG. 16C) antibodies in ZIKV infected human sera (42-001-F at day 7 post-onset of illness), identified using ZIKV-GFPDL. The amino acid designation is based on the ZIKV polyprotein sequence encoded by the complete ZIKV-ICD genome (FIG. 8; SEQ ID NO: 9). Bars indicate identified inserts in the different structural (C, prM, E) and non-structural (NS) genes on the ZIKV polyprotein sequence. Graphical distribution of representative clones with a frequency of >2, obtained after affinity selection, are shown. The horizontal position and the length of the bars indicate the peptide sequence displayed on the selected phage clone to its homologous sequence in the ZIKV sequence on alignment. The thickness of each bar represents the frequency of repetitively isolated phages.

(FIG. 17A) Heat map on one monomer chain showing sequence conservation of various ZIKV (left panel; Paraiba, Uganda 1947, Nigeria 1968, Senegal 2001, Micronesia 2007 and Brazil 2016 strains) and flaviviruses (right panel; Dengue 1-4, West Nile, Yellow fever and ZIKV) conservation on ZIKV NS1 protein structure (PDB 5K6K). (FIG. 17B) Antigenic sites have been depicted on surface structures of ZIKV NS1 protein (PDB 5K6K). C- and N-termini have been depicted on the first structure showing antigenic sites. Structure 5K6K encompasses residues 795-1146 of ZIKV_ICD whole genome-encoded polyprotein sequence (SEQ ID NO: 9).

(FIG. 18A) Heat map on one monomer chain showing various ZIKV (left panel; Paraiba/2015, MR766/Uganda/1947, Nigeria/IbH30656_SM21V1-V3/1968, ArD157995/Senegal/2001, Micronesia/2007 and Brazil/2015 strains) and flaviviruses (center panel; Dengue_1-4, West Nile, Yellow fever and ZIKV) conservation on ZIKV NS2B-NS3 protein structure (PDB #SGXJ). C- and N-termini have been depicted on the ribbon structure (right panel). (FIG. 18B) Antigenic sites have been depicted on surface structures of ZIKV NS2B protein (PDB #SGXJ). Structure PDB #SGXJ encompasses residues 1421-1673 on ZIKV ICD whole genome-encoded polyprotein sequence (SEQ ID NO: 9).

(FIG. 19A) Heat map showing various ZIKV (left panel; Paraiba, Uganda 1947, Nigeria 1968, Senegal 2001, Micronesia 2007 and Brazil 2016 strains) and flaviviruses (center panel; Dengue 1-4, West Nile virus, Yellow fever and ZIKV) conservation on ZIKV NS3 protein structure (PDB SJRZ). C- and N-termini have been depicted on the ribbon structure of SJRZ (right panel). (FIG. 19B) Antigenic sites have been depicted on surface structures of ZIKV NS3 protein (PDB SJRZ). Structure SJRZ encompasses residues 1677-2119 on ZIKV ICD whole genome-encoded polyprotein sequence (SEQ ID NO: 9).

(FIG. 20A) Heat map showing various ZIKV (left panel; Paraiba, Uganda 1947, Nigeria 1968, Senegal 2001, Micronesia 2007 and Brazil 2016 strains) and flaviviruses (center panel; Dengue 1-4, West Nile virus, Yellow fever and ZIKV) conservation on ZIKV NS5 protein structure (PDB 5TFR). C- and N-termini have been depicted on the ribbon structure of 5TFR (right panel). (FIG. 20B) Antigenic sites have been depicted on surface structures of ZIKV NS5 protein (PDB 5TFR). Structure 5TFR encompasses residues 2525-3423 on ZIKV ICD whole genome-encoded polyprotein sequence (SEQ ID NO: 9).

(FIG. 21A) Similarity between various ZIKV strains plotted as a percentage of ZIKV Paraiba strain (considered at 100%) whose genome structure with antigenic sites has been depicted. (FIG. 21B) Similarity between various flaviviruses plotted as a percentage of ZIKV Paraiba strain (considered at 100%) whose polyprotein structure with antigenic sites have been depicted. In both cases, ZIKV Paraiba strain was used as a query sequence and was used to generate a plot that shows the percent similarity of the reference sequences (other flaviviruses FIG. 21A, ZIKV strains FIG. 21B) to the query sequence. A sliding window of size 200 bp or 20 bp was used, which passes through the alignment in steps of 1 bp to generate the plot showing different flaviviruses and all ZIKV strains respectively.

(FIG. 24A) ZIKV NS1 1033-1067. (FIG. 24B) ZIKV NS2B 1421-1469. (FIG. 24C) ZIKV NS2B 1424-1457. (FIG. 24D) ZIKV NS3 1805-1873. (FIG. 24E) ZIKV NS4B 2312-2363. (FIG. 24F) ZIKV NS5 2943-2977. (FIG. 24G) ZIKV NS5 3136-3179. (FIG. 24H) ZIKV NS1 1033-1067+NS2B 1421-1469+NS5 2943-2977. (FIG. 24I) ZIKV NS1 1033-1067+NS2B 1421-1469+NS5 3136-3179. (FIG. 24J) ZIKV NS2B 1424-1457+NS5 2943-2977+NS5 3136-3179.

(FIG. 25A) Number of bound phage clones bound by IgM, IgG and IgA antibodies using ZIKV-GFPDL affinity selection of maternal serum and AF samples from first trimester pregnancy (ID #38 in Table 5) at 10 days post onset of symptoms. (FIGS. 25B-25D) The amino acid designation is based on the ZIKV polyprotein sequence encoded by the complete ZIKV-ICD genome (FIG. 8). Antigenic epitope profiles with bars indicating identified inserts in the ZIKV genome are shown for (FIG. 25B) IgM, (FIG. 25C) IgG and (FIG. 25D) IgA antibodies. Graphical distribution of representative clones with a frequency of >2, obtained after affinity selection, are shown. The horizontal position and the length of each of the bars in FIGS. 25B-25D indicate the genomic location of the bound displayed peptides on the ZIKV genome (C, capsid; pr peptide; M, membrane; E, envelope; NS, non-structural 1, 2B, 3, 4A, 4B and 5). The thickness of each bar represents the frequency of repetitively isolated phages.

(FIG. 26A) Number of bound phage clones isolated using ZIKV-GFPDL affinity selection by IgM, IgG and IgA antibodies of maternal serum and AF samples from the third trimester. Antigenic epitope profiles with bars indicating identified inserts in the ZIKV genome are shown for (FIG. 26B) IgM, (FIG. 26C) IgG and (FIG. 26D) IgA antibodies. Graphical distribution of representative clones with a frequency of >2, obtained after affinity selection, are shown. The horizontal position and the length of each of the bars in FIGS. 26B-26D indicate the genomic location of the bound displayed peptides on the ZIKV genome (C, capsid; pr peptide; M, membrane; E, envelope; NS, non-structural 1, 2B, 3, 4A, 4B and 5). The thickness of each bar represents the frequency of repetitively isolated phages. (FIG. 26E) Immunodominant antigenic sites within the ZIKV genome recognized by IgM, IgG and IgA antibodies in maternal serum and AF samples from first and third trimester. Epitopes numbered in black represent sites identified in the acute infection study in non-pregnant adults described in Example 1. Epitopes in blue, red and green numbering represent the epitopes specifically recognized by IgM, IgG and IgA antibodies, respectively. Those highlighted in bold black, blue, red or green represent newly identified antigenic sites in this study.

(FIG. 27A) Total antibody binding is represented in SPR resonance units. Maximum resonance unit (Max RU) values for protein binding by serum vs. AF antibodies obtained from all subjects are linked by connecting lines. (FIG. 27B) Antibody isotype of ZIKV protein binding antibodies in serum and AF following ZIKV infection as measured in SPR. The resonance units for each anti-ZIKV antibody isotype (IgM, IgE, IgG subclasses, and IgA) was divided by the total resonance units for all antibody isotypes combined to calculate the percentage of each antibody isotype for individual serum and AF sample. (FIG. 27C) Antibody affinity of serum vs. AF antibodies to E, E-DIII, NS1, and prM. SPR analysis of sera or AF post-ZIKV infection from each pregnant female was performed with purified recombinant ZIKV E, E-DIII, NS1 and -prM proteins to determine the dissociation kinetics (off-rates) points. Antibody off-rate constants that describe the fraction of antibody-antigen complexes decaying per second were determined directly from the serum or AF sample interaction with recombinant proteins using SPR in the dissociation phase as described in Example 3. Antibody off-rates were calculated for samples with total antibody binding (Max RU shown in FIG. 27A) between 10-100 RU. The statistical significances between each time-point (visit days) were determined using two-tailed paired t-test in GraphPad software. p-values less than 0.05 were considered significant with a 95% confidence interval. Statistically significant with p-values of <0.05 (*), <0.01 (), <0.001 (*) or <0.0001 (****) are shown.

(FIG. 28A) Antigenic sites within the ZIKV prM-E protein schematic with domains (D) I, II and III and fusion loop (FL) shown along with their immunodominant antigenic sites. (FIG. 28B) End-point titers of serum/AF paired samples from ZIKV infected pregnant women were tested for binding to ZIKV peptides in ELISA. ELISA was performed with 5-fold serially diluted (starting at 1:100) samples for combination of IgM +IgG +IgA isotypes. The statistical significances between each time-point (visit days) were determined using two-tailed paired t-test in GraphPad software. p-values less than 0.05 were considered significant with a 95% confidence interval. Statistically significant with p-values of <0.05 (*), <0.01 (), <0.001 (*) or <0.0001 (**) are shown. (FIGS. 28C-28D) Serum and amniotic fluid samples from different patients were tested for impact on ZIKV infection in vitro with Vero cells with both Asian-lineage virus PRVABC59 (FIG. 28C) and African-lineage virus MR766 (FIG. 28**D). The percent virus control from RT-qPCR is plotted against log serum dilution. Mean±standard deviation (SD) data from triplicates for serum (line, filled circle markers) and amniotic fluid (dotted line, empty circle markers) is shown for each matched serum and amniotic fluid pair. The positive control ZKA185 (at starting concentration of 1 μg/ml) is shown in filled black symbols in both panels. The percent of virus control (determined by RT-qPCR) is plotted against log serum dilution.

(FIG. 30A) a combination of IgM, IgG and IgA antibodies recognized by antibodies in maternal serum and AF samples from the first and third trimesters are shown (black numbering). (FIG. 30B) IgM antigenic sites (blue numbering), (FIG. 30C) IgG antigenic sites (red numbering), and (FIG. 30D) IgA antigenic sites (green numbering). Epitopes in bold black, blue, red and green represent newly identified antigenic sites in this study and the others were described in Example 1.

(FIG. 31A) IgM, (FIG. 31B) IgG and (FIG. 31C) IgA antibodies recognizing each antigenic site on the ZIKV genome isolated using GFPDL against the maternal serum (black) and AF (red) samples from the first trimester. The number of clones encoding each antigenic site was divided by the total number of ZIKV GFPDL-selected clones for each sample to calculate clonal frequency. Those epitopes newly identified in the current study have been highlighted in bold black letters on X-axis.

(FIG. 33A) Heat map on one monomer chain showing various ZIKV (Paraiba/2015, MR-766/Uganda/1947, Nigeria/IbH-30656_SM21V1-V3/1968, ArD157995/Senegal/2001, Micronesia/2007 and Brazil/2015 strains) and flaviviruses (DENV1-4, WNV, YFV and ZIKV_Paraiba) conservation on mature ZIKV E protein structure (PDB #5JHM). The heat maps have been color coded from red (0) to green (1), where green signifies complete conservation. Antigenic sites Z-5 and Z-8 respectively have been depicted in blue on surface structures of both mature ZIKV E (PDB #5JHM) and immature (PDB #5U4W), with Domain I of E protein shaded in light grey (PDB #5JHM), pr domain in yellow and M in pink (PDB #5U4W). Structure PDB #5U4W encompasses residues 288-794 and structure PDB #5JHM encompasses residues 313-699 on ZIKV ICD whole genome sequence. (FIG. 33B) NS1 structure. Heat map on one monomer chain showing various ZIKV (Paraiba/2015, MR-766/Uganda/1947, Nigeria/IbH-30656_5 M21V1-V3/1968, ArD157995/Senegal/2001, Micronesia/2007 and Brazil/2015 strains) and flaviviruses (DENV1-4, WNV, YFV (and ZIKV) conservation on ZIKV NS1 protein structure (PDB #5K6K). The heat maps have been color coded from red (0) to green (1), where green signifies complete conservation. Antigenic sites Z-42, Z-12, Z-43, Z-14 respectively have been depicted in blue on surface structures of ZIKV NS1 protein (PDB #5K6K). Structure PDB #5K6K encompasses residues 795-1146 on ZIKV ICD whole genome sequence. (FIG. 33C) NS5 structure. Heat map showing various ZIKV (Paraiba/2015, MR-766/Uganda/1947, Nigeria/IbH-30656_SM21V1-V3/1968, ArD157995/Senegal/2001, Micronesia/2007 and Brazil/2015 strains) and flaviviruses (DENV1-4, WNV, YFV and ZIKV) conservation on ZIKV NS5 protein structure (PDB #5TFR). The heat maps have been color coded from red (0) to green (1), where green signifies complete conservation. Antigenic sites Z-25, Z-28 and Z-29 respectively have been depicted in blue on surface structures of ZIKV NS5 protein (PDB #5TFR). Structure PDB #5TFR encompasses residues 2525-3423 on ZIKV ICD whole genome sequence.

TABLES

Figure 2A:
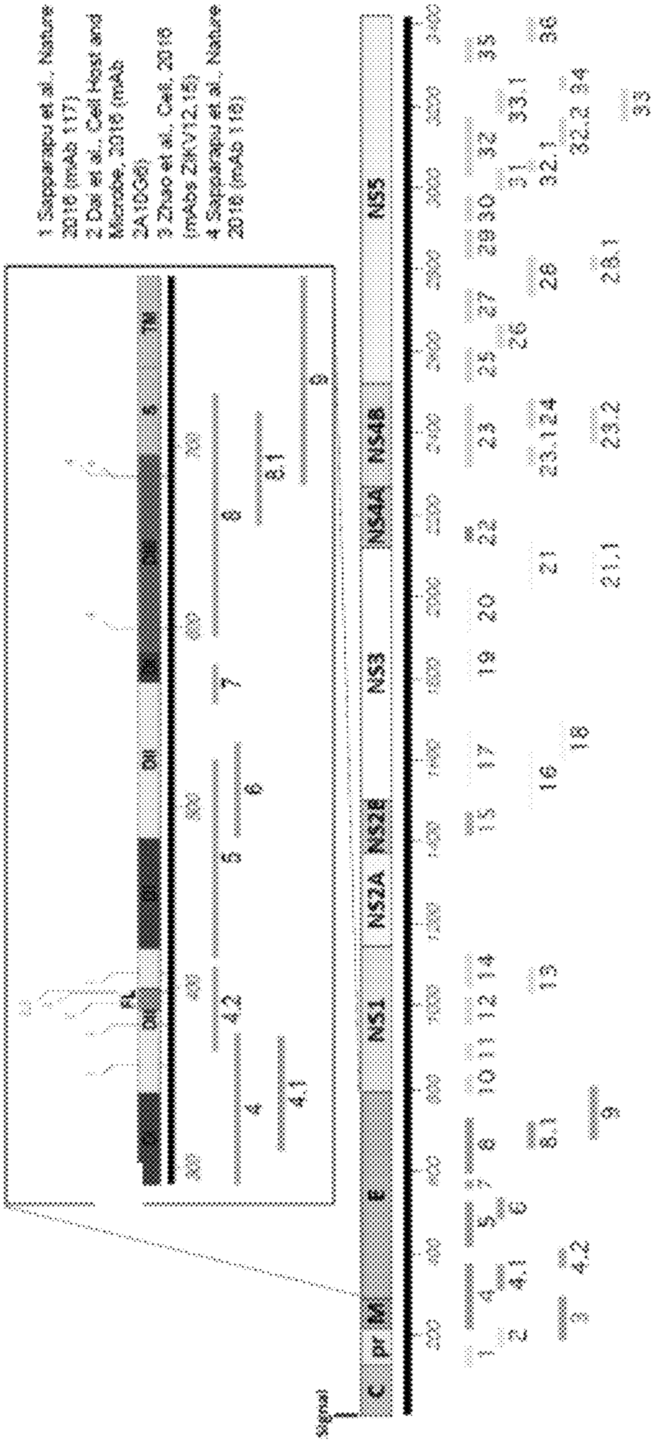
FIGS. 2A-2C show the frequency of ZIKV inserts bound by IgG and IgM antibodies in serum and urine following ZIKV infection in humans.

Table 1: Demographic, epidemiological and diagnostic information of samples used in Example 1.

Table 2: Clinical symptoms for the acute ZIKV infected individuals in Example 1.

Table 3: Frequency of antigenic sites for IgM and IgG antibodies in serum on day 0 and day 7 and in urine on day 7 post-ZIKV exposure (Example 1).

Table 4: Sequence conservation of antigenic regions/sites among different flavivirus strains (Example 1).

Table 5: Demographic, epidemiological and diagnostic information of samples used in Example 3.

Table 6: RT-PCR and serodiagnostic information of samples used in Example 3.

Table 7: Frequency of antigenic sites for IgM, IgG and IgA antibodies in serum and amniotic fluid (AF) during ZIKV infection in the first and third trimester of pregnancy (Example 3).

Table 8: Sequence conservation of antigenic sites among different flavivirus strains (Example 3).

Table 9: Frequency of differentially recognized antigenic sites by serum vs amniotic fluid (AF) following ZIKV infection in first trimester (1st) or 3rd trimester (3rd). Sites Z-5, Z-8, Z-42, Z-12, Z-43, Z-14, Z-25, Z-28, Z-29 have been depicted on structures of the respective proteins in FIG. 32.

SEQUENCE LISTING

The amino acid sequences listed in the accompanying sequence listing are shown using standard three letter code for amino acids, as defined in 37 C.F.R. 1.822. The Sequence Listing is submitted as an ASCII text file, created on Mar. 25, 2020, 33.8 KB, which is incorporated by reference herein. In the accompanying sequence listing:

SEQ ID NO: 1 is the amino acid sequence of the NS1 1033-1067 antigenic site: SDLIIPKSLAGPLSHHNTR-EGYRTQMKGPWHSEEL SEQ ID NO: 2 is the amino acid sequence of the NS2B 1421-1469 antigenic site: VDMYIERAGDITWEK-DAEVTGNSPRLDVALDESGDFSLVEDDGPPMREI SEQ ID NO: 3 is the amino acid sequence of the NS3 1805-1873 antigenic site: TRVEMGEAAAIFMTATPPGTRDAFPDSNSPIMDTE-VEVPERAWSSGFDWVTDHSGKTVWFVPSV RNGNE SEQ ID NO: 4 is the amino acid sequence of the NS4 2422-2465 antigenic site: VVTDIDTM-TIDPQVEKKMGQVLLIAVAVSSAILSRTAWGWGEAG SEQ ID NO: 5 is the amino acid sequence of the NS4B 2312-2363 antigenic site: YAALTTFITPAVQHAVTTSYN-NYSLMAMATQAGVLFGMGKGMPFYAWDFGVP SEQ ID NO: 6 is the amino acid sequence of the NS5 2860-2901 antigenic site: TGIAMTDTTPYGQQRVFKEKVDTRVPDPQEGT SEQ ID NO: 7 is the amino acid sequence of the NS5 2943-2977 antigenic site: AVEAVNDPRFWALVDK-EREHHLRGECQSCVYNMMG SEQ ID NO: 8 is the amino acid sequence of the NS5 3163-3179 antigenic site: NLVVQLIRNME-AEEVLEMQDLWLLRRSEKVTNWLQSNGWDRLKR SEQ ID NO: 9 is the amino acid sequence of ZIKV Paraiba strain polyprotein (see FIG. 8).

SEQ ID NO: 10 is the amino sequence of the NS2B 1424-1457 antigenic site: YIERAGDITWEKDAEVTGN-SPRLDVALDESGDFS

DETAILED DESCRIPTION

Described herein are methods of detecting exposure of a subject to a flavivirus infection, such as a ZIKV infection. The disclosed methods utilize isolated peptides and fragments thereof from ZIKV. Also described are ZIKV peptides and fragments linked to a solid support or conjugated to a heterologous molecule, such as a heterologous protein, linker and/or detectable label.

I. Abbreviations

ADE antibody dependent enhancement
AF amniotic fluid
C capsid
CHICKV Chikungunya virus
DENV dengue virus
E envelope
ELISA enzyme-linked immunosorbent assay
FL fusion loop
WGFPDL Whole-Genome-Fragment-Phage-Display Libraries
HRP horseradish peroxidase
JEV Japanese encephalitis virus
LFA lateral flow assay
Mab monoclonal antibody
M membrane
Max RU maximum resonance unit
NS non-structural
POC point-of-care
prM premembrane
PRNT plaque reduction neutralization test
SPR surface plasmon resonance
TBEV tick-borne encephalitis virus
WNV West Nile virus
YFV yellow fever
ZIKV Zika virus II. Terms Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms “a,” “an,” and “the,” refer to both the singular as well as plural, unless the context clearly indicates otherwise. For example, the term “an antigen” includes single or plural antigens and can be considered equivalent to the phrase “at least one antigen.” As used herein, the term “comprises” means “includes.” It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of an active compound or composition into a subject by a chosen route. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, oral administration, topical administration, subcutaneous administration, intramuscular administration, transdermal administration, or administration by inhalation, when such administration is directed at absorption and distribution throughout the body by the circulatory system.

Antibody or antibodies: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce $F(ab)'_2$, a dimer of Fab which itself is a light chain joined to $V_H$-$C_H$ by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially a Fab with part of the hinge region (see, Fundamental Immunology, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Using Antibodies, A Laboratory Manual*, CSHL, New York, 1998).

The terms "bind specifically" and "specific binding" refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994).

One or more complementarity determining regions (CDRs) may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target, usually a polypeptide, such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Anti-idiotypic antibody: An antibody that binds to the specific antigen binding site of another antibody generated in response to exposure to an antigen, such as an antigen derived from a member of the flavivirus genus or immunological relative thereof.

Biological sample: A sample obtained from a subject. Biological samples include all clinical samples useful for detection of disease or infection (for example, ZIKV infection) in subjects, including, but not limited to, cells, tissues, and bodily fluids, such as blood, derivatives and fractions of blood (such as serum or plasma), cerebrospinal fluid, urine, eye tissue, saliva, semen, breast milk, synovial fluid, amniotic fluid, cord blood; as well as biopsied or surgically removed tissue, for example tissues that are unfixed, frozen, or fixed in formalin or paraffin. In a particular example, a biological sample is obtained from a subject having or suspected of having a ZIKV or other flavivirus infection.

Carrier: An immunogenic molecule to which a peptide can be linked to enhance an immune response to the peptide. Carriers are chosen to increase the immunogenicity of the antigen and/or to elicit antibodies against the carrier which are diagnostically, analytically, and/or therapeutically beneficial. Useful carriers include polymeric carriers, which can be natural (for example, nucleic acid or proteins from bacteria or viruses), aptamers, dyes, semi-synthetic or synthetic materials containing one or more functional groups to which a reactant moiety can be attached.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, Antibodies, A Laboratory Manual, $2^{nd}$ ed. Cold Spring Harbor Publications, New York (2013) for a description of immunoassay formats and conditions. The conditions employed in the methods are “physiological conditions” which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (for example, from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

In several embodiments, the formation of an immune complex can be detected through conventional methods, for instance immunohistochemistry, immunoprecipitation, flow cytometry, immunofluorescence microscopy, ELISA, immunoblotting (for example, Western blot), point-of-care test, rapid assay, biosensors, fluorophores or dyes, flow assay, bead based assay, nitrocellulose/PVDF membrane based assay, magnetic resonance imaging, CT scans, X-ray and affinity chromatography.

Conjugate: A complex of at least two heterologous molecules linked together. In a non-limiting example, an ZIKV peptide as disclosed herein is conjugated to a solid support, such as via a linker.

Consists essentially of and Consists of: A polypeptide comprising an amino sequence that consists essentially of a specified amino acid sequence does not include any additional amino acid residues. However, the residues in the polypeptide can be modified to include non-peptide components, such as labels (for example, fluorescent, radioactive, color, biosensors, or solid particle labels), sugars or lipids, and the N- or C-terminus of the polypeptide can be joined (for example, by peptide bond) to heterologous amino acids, such as a cysteine (or other) residue in the context of a linker for conjugation chemistry. A polypeptide that consists of a specified amino acid sequence does not include any additional amino acid residues, nor does it include additional biological components, such as nucleic acid lipids, sugars, nor does it include labels. However, the N- and C-terminus of the polypeptide can be joined (for example, by peptide bond) to heterologous amino acids, such as a peptide tag, or a cysteine (or other) residue in the context of a linker for conjugation chemistry.

A polypeptide that consists or consists essentially of a specific amino acid sequence can be glycosylated or have an amide modification. A polypeptide that consists or consists essentially of a particular amino acid sequence can be linked via its N- or C-terminus to a heterologous polypeptide, such as in the case of a fusion protein containing a first polypeptide consisting or a first sequence that is linked (via peptide bond) to a heterologous polypeptide consisting of a second sequence. In another example, the N- or C-terminus of a polypeptide that consists of or consists essentially of a particular amino acid sequence can be linked to a peptide linker (via peptide bonds) that is further linked to one or more additional heterologous polypeptides. In a further example, the N- or C-terminus of a polypeptide that consists of or consists essentially of a particular amino acid sequence can be linked to one or more amino acid residues that facilitate further modification or manipulation of the polypeptide.

Control: A reference standard. In some embodiments, the control is a negative control sample obtained from a healthy patient not infected with ZIKV. In other embodiments, the control is a positive control, such as a biological sample obtained from a patient diagnosed with ZIKV infection. In still other embodiments, the control is a historical control or standard reference value or range of values (such as a previously tested control sample, such as a group of ZIKV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Diagnosis: The process of identifying a disease by its signs, symptoms and/or results of various tests. The conclusion reached through that process is also called “a diagnosis.” Forms of testing commonly performed include blood tests, medical imaging, genetic analysis, urinalysis, biopsy and analysis of biological samples obtained from a subject. In one example, diagnosis of a subject as having a flavivirus infection comprises determining whether the subject has antibodies that specifically bind to one or more peptides disclosed herein (see, e.g., Tables 3 and 4).

Effective amount: An amount of agent, such as an antiviral agent, that is sufficient to generate a desired response, such as an inhibition of viral infection in a subject or detection of a particular viral infection in a subject. For instance, this can be the amount necessary to inhibit an infection with one or more flaviviruses or to measurably alter outward symptoms of the infection. In some embodiments, an effective amount is an amount of a peptide that is sufficient for detection of antibodies to the peptide in a biological sample from a subject.

In one example, a desired response is to induce an immune response that elicits an immune response to flavivirus in a subject and/or inhibits or prevents flavivirus infection in a subject. For example, administration of an effective amount of a disclosed flavivirus peptide can induce an immune response in a subject that inhibits subsequent infection of the subject by the flavivirus.

Epitope: An antigenic determinant. These are particular chemical groups or peptide sequences on a molecule that are antigenic, such that they elicit a specific immune response, for example, an epitope is the region of an antigen to which anti-ZIKV antibodies bind. An antibody can bind to a particular antigenic epitope. Epitopes can be formed both from contiguous amino acids or noncontiguous amino acids juxtaposed by tertiary folding of a protein.

Expression: Transcription or translation of a nucleic acid sequence. For example, a gene is expressed when its DNA is transcribed into an RNA or RNA fragment, which in some examples is processed to become mRNA. A gene may also be expressed when its RNA is translated into an amino acid sequence, such as a protein or protein fragment. In a particular example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Flavivirus non-structural protein: There are seven non-structural (NS) proteins of a flavivirus, NS1, NS2A, NS2B, NS3, NS4A, NS4B, and NS5, which are encoded by the portion of the flavivirus genome that is 3' to the structural proteins. NS1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222:159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). NS2 is cleaved into NS2A and NS2B. NS2A is involved in RNA replication and virus particle assembly and secretion and NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and RNA trafficking (Lindenbach and Rice, In: *Fields Virology*, Knipe and Howley, eds., Lippincott, Williams, and Wilkins, 991-1041, 2001). Finally, the NS5 protein is an RNA-dependent RNA polymerase involved in genome replication (Rice et al., *Science* 229:726-733, 1985). NS5 also shows methyltransferase activity commonly found in RNA capping enzymes (Koonin, *J. Gen. Virol.* 74:733-740, 1993).

Flavivirus structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, prM, and E) are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope (Russell et al., The Togaviruses: *Biology, Structure, and Replication*, Schlesinger, ed., Academic Press, 1980). The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Heterologous: Originating from a different genetic source. A nucleic acid molecule that is heterologous to a cell originated from a genetic source other than the cell in which it is expressed. Methods for introducing a heterologous nucleic acid molecule in a cell or organism include, for example, transformation with a nucleic acid, including electroporation, lipofection, particle gun acceleration, and homologous recombination.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immune complex: The binding of antibody to an antigen forms an immune complex. In some embodiments, the formation of an immune complex can be detected through conventional methods, for instance immunodetection, immunohistochemistry, immunoprecipitation, flow cytometry, immunofluorescence microscopy, ELISA, immunoblotting (for example, Western blot), biosensors, magnetic resonance imaging, CT scans, X-ray and affinity chromatography.

Immunogen: A protein or a portion thereof that is capable of inducing an immune response in a mammal, such as a mammal infected or at risk of infection with a pathogen.

Inhibiting a disease or condition: Reducing the full development of a disease or condition in a subject, for example, reducing the full development of ZIKV disease in a subject who has an ZIKV infection, and/or reducing ZIKV infection in a subject or population of subjects at risk thereof. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example, by vaccinating a subject at risk of a flavivirus infection, but not infected by a flavivirus, with an flavivirus peptide as disclosed herein) that reduces subsequent development of the disease or condition, and also to amelioration of one or more signs or symptoms of the disease or condition following development. The term "ameliorating," with reference to inhibiting a disease or condition refers to any observable beneficial effect of the intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters well known in the art that are specific to the particular disease or condition.

In some embodiments, an immune response elicited by administering an effective amount of an flavivirus peptide as disclosed herein inhibits infection of a human subject by the flavivirus, for example, by at least 50% (such as at least 60%, at least 70%, at least 80%, at least 90%, or more) compared to a suitable control.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Label: A detectable compound that is conjugated directly or indirectly to another molecule, such as a peptide or antibody, to facilitate detection of that molecule. For example, the label can be capable of detection by any method including ELISA, spectrophotometry, flow cytometry, or microscopy. Specific, non-limiting examples of labels include fluorophores, chemiluminescent agents, enzymatic linkages, biosensors and radioactive isotopes. Non-limiting methods for labeling and guidance in the choice of labels appropriate for various purposes are discussed for example in Green and Sambrook (*Molecular Cloning: A Laboratory Manual,* $4^{th}$ ed., New York: Cold Spring Harbor Laboratory Press, 2012) and Ausubel et al. (Eds.) (Current Protocols in Molecular Biology, New York: John Wiley and Sons, 2017).

Lateral flow device: A device that absorbs or adsorbs a liquid sample (such as a serum, plasma, urine or amniotic fluid sample), routes that liquid sample to a detection zone, and uses detection methods (such as peptide- or antibody-based detection methods) to generate a visible signal in response to the presence or absence of a specific molecule (such as an antibody specific for a peptide of interest). The device can be a test strip used in lateral flow chromatography, in which a test sample fluid, suspected of containing an analyte (such as an antibody that specifically binds to one or more of the peptides listed in Tables 3 and 4), flows (for example by capillary action) through the strip (which is frequently made of bibulous materials such as paper, nitrocellulose, and cellulose). The test fluid and any suspended analyte can flow along the strip to a detection zone in which the analyte (if present) interacts with a detection agent to indicate a presence, absence and/or quantity of the analyte.

Many lateral flow devices are one-step lateral flow assays in which a biological fluid is placed in a sample area on a bibulous strip (though, non-bibulous materials can be used, and rendered bibulous by applying a surfactant to the material), and allowed to migrate along the strip until the liquid comes into contact with a specific binding partner (such as one or more of the peptides listed in Tables 3 and 4) that interacts with an analyte (such as an antibody that binds to one or more of the peptides listed in Tables 3 and 4) in the liquid. Once the analyte interacts with the binding partner, a signal (such as a fluorescent or otherwise visible dye, or biosensor or enzyme) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker". In several embodiments, linked components are associated in a chemical or physical manner so that the components are not freely dispersible from one another, at least until contacting or entering a cell, such as an immune cell.

Linker: One or more molecules or groups of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker.

Peptide: A polymer in which the monomers are amino acid residues that are linked together through amide bonds. Peptides are typically less than 150 amino acids in length, such as less than 100 amino acids in length. The amino acids included in a peptide may be subject to post-translational modification (e.g., glycosylation or phosphorylation). A "residue" refers to an amino acid or amino acid mimetic incorporated in a peptide by an amide bond or amide bond mimetic. A peptide has an amino terminal (N-terminal) end and a carboxy terminal (C-terminal) end. In some embodiments herein, a ZIKV peptide is no more than 100 amino acids, no more than 90 amino acids, no more than 80 amino acids, no more than 70 amino acids, no more than 60 amino acids, no more than 50 amino acids, or no more than 40 amino acids in length.

Peptide Modifications: Synthetic embodiments of the peptides described herein are also provided. For example, peptides can be modified by a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Any suitable method may be used to introduce cyclic structures into the disclosed peptides to select and provide conformational constraints to the structure that result in enhanced stability.

Each peptide of this disclosure is comprised of a sequence of amino acids, which may be either L- and/or D-amino acids, naturally occurring and otherwise.

Pharmaceutically acceptable carriers: The pharmaceutically acceptable carriers useful in this disclosure are conventional. Remington: *The Science and Practice of Pharmacy*, The University of the Sciences in Philadelphia, Editor, Lippincott, Williams, & Wilkins, Philadelphia, Pa., 21st Edition (2005), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Prime-boost immunization: An immunotherapy including administration of multiple immunogens over a period of time to elicit the desired immune response.

Solid support: Any material which is insoluble or can be made insoluble by a subsequent reaction. Numerous and varied solid supports are known and include, without limitation, nitrocellulose, the walls of wells of a reaction tray, multi-well plates, test tubes, polystyrene (e.g., polystyrene beads), polyvinyl (e.g., polyvinyl beads), magnetic beads, membranes, hydrogel, and microparticles (such as latex particles). Any suitable porous material with sufficient porosity to allow access by detector reagents and a suitable surface affinity to immobilize capture reagents (e.g., peptides or antibodies) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described herein can be in the form of sheets or strips.

The surface of a solid support may be activated by chemical processes that cause covalent linkage of an agent (e.g., a peptide or antibody) to the support. However, any other suitable method may be used for immobilizing an agent (e.g., a peptide or antibody) to a solid support including, without limitation, ionic interactions, hydrophobic interactions, covalent interactions and the like. The particular forces that result in immobilization of an agent on a solid phase are not important for the methods and devices described herein.

A solid phase can be chosen for its intrinsic ability to attract and immobilize an agent, such as a capture reagent (such as an antibody or peptide). Alternatively, the solid phase can possess a factor that has the ability to attract and immobilize an agent, such as a capture reagent. The factor can include a charged substance that is oppositely charged with respect to, for example, the capture reagent itself or to a charged substance conjugated to the capture reagent. In another embodiment, a specific binding member may be immobilized upon the solid phase to immobilize its binding partner (e.g., a capture reagent). In this example, therefore, the specific binding member enables the indirect binding of the capture reagent to a solid phase material.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

A "lateral flow support" is a solid support that is useful in a lateral flow device.

Specifically bind: When referring to the formation of an antibody:antigen protein complex, or a protein:protein complex, refers to a binding reaction which determines the presence of a target protein, peptide, or polysaccharide, in the presence of a heterogeneous population of proteins and other biologics. Thus, under designated conditions, a particular antibody or protein binds preferentially to a particular target protein, peptide or polysaccharide and does not bind in a significant amount to other proteins or polysaccharides present in the sample or subject. Specific binding can be determined by standard methods. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Subject: Living multi-cellular organisms, including vertebrate organisms, a category that includes both human and non-human mammals. In some examples, the subject is human. In specific non-limiting examples, the subject is one who is at risk of or is suspected of having a flavivirus infection, such as a ZIKV infection.

Treating, preventing or ameliorating a disease: "Preventing" a disease refers to inhibiting the full development of a disease. "Treating" refers to a therapeutic intervention that ameliorates a sign or symptom of a disease or pathological condition, such as a viral infection, after it has begun to develop. "Ameliorating" refers to the reduction in the number or severity of signs or symptoms of a disease, such as a viral infection.

Under conditions sufficient for: A phrase that is used to describe any environment that permits the desired activity. In one example, this includes administering an effective amount of a composition that includes, for example, a peptide or antibody sufficient to enable the desired activity.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Whole-Genome-Fragment-Phage-Display Libraries (GFPDL) have been previously used for an unbiased comprehensive analysis of the antibody repertoires in individuals infected with viruses, either early or during recovery (Khurana et al., *PLoS Med* 6:e1000049, 2009; Fuentes et al., *PLoS Pathog* 12:e1005554, 2016). They can also help to determine the diversity of epitopes bound by post-vaccination sera and decipher the impact of novel adjuvants (Khurana et al., *Sci Transl Med* 3:85ra48, 2011; Verma et al., *J Virol* 86:5515-5522, 2012). Such information could help in the development of improved vaccines, therapeutics, and diagnostics. For example, in HIV, panning of virus specific GFPDLs with sera from acute infections identified several antigenic peptides that could be used for serological diagnosis of HIV-1 (Khurana et al., *J Virol* 85:12455-12463, 2011; Khurana et al., *J Acquir Immune Defic Syndr* 43:304-312, 2006), and in avian H5N1, peptides were identified that differentiated infection (across multiple clades) from vaccination (Khurana et al., *J Virol* 85:12455-12463, 2011; Khurana et al., *J Virol* 80:2092-2099, 2006).

In the present disclosure, GFPDL spanning the entire genome of ZIKV was constructed and used for in-depth immune profiling of IgG and IgM antibody repertoires in both serum and urine from individuals acutely infected with ZIKV. Total binding and affinity maturation of antibodies against ZIKV NS1 and E proteins and their evolution during the first month post ZIKV infection was also evaluated using surface plasmon resonance (SPR). The results demonstrated unlinked evolution of antibody responses in terms of antibody epitope repertoire and affinity maturation against structural and non-structural proteins following ZIKV infection in humans, describing differential recognition of various ZIKV proteins by the human immune system.

Zika virus (ZIKV): A member of the virus family Flaviviridae and the genus Flavivirus. Other members of this genus include dengue virus, yellow fever virus, Japanese encephalitis virus, West Nile virus and Spondweni virus. ZIKV is spread by the daytime-active mosquitoes *Aedes aegypti* and *A. albopictus*. This virus was first isolated from a Rhesus macaque from the Zika Forest of Uganda in 1947. Since the 1950s, ZIKV has been known to occur within a narrow equatorial belt from Africa to Asia. The virus spread eastward across the Pacific Ocean in 2013-2014, resulting in ZIKV outbreaks in Oceania to French Polynesia, New Caledonia, the Cook Islands, and Easter Island. In 2015, ZIKV spread to Mexico, Central America, the Caribbean and South America, where ZIKV has reached pandemic levels. Infection by ZIKV generally causes either no symptoms or mild symptoms, including mild headache, maculopapular rash, fever, malaise, conjunctivitis and joint pain. ZIKV causes symptoms in about 20% of infected individuals, and no deaths from the virus have yet been reported. However, ZIKV infection has been linked to the birth of microcephalic infants following maternal infection, as well an increase in cases of GBS. Reports have also indicated that ZIKV has the potential for human blood-borne and sexual transmission. ZIKV has also been found in human saliva and breastmilk.

III. Zika Virus

Zika virus (ZIKV) belongs to the flavivirus genus within the Flaviviridae family Many flaviviruses are significant human pathogens, including ZIKV, yellow fever (YFV), dengue virus (DENV serotypes 1 to 4), Japanese encephalitis virus (JEV), West Nile virus (WNV), and tick-borne encephalitis virus (TBEV). The present disclosure describes methods for detecting flavivirus exposure (such as by detecting anti-flavivirus antibodies), in particular ZIKV, in subjects including humans, non-human animals, and laboratory animals. The disclosure includes any subject that can respond to an infection by a flavivirus, in particular ZIKV, or an equivalent thereof.

The flavivirus genome is a single-strand, positive-sense RNA of approximately 11,000 nucleotides. It contains a 5' untranslated region (UTR), an open-reading frame (ORF), and a 3' UTR. The single ORF encodes a long polyprotein which is processed into ten viral proteins, including three structural proteins—capsid (C), precursor membrane (prM), and envelope (E)—and seven non-structural proteins (NS1, NS2A, NS2B, NS3, NS4A, NS4B, and NS5).

ZIKV is predominantly transmitted to humans by infected *Aedes* spp. mosquitoes, which also transmit DENV and YFV, as well as chikungunya virus (an emerging alphavirus). ZIKV can also be transmitted through the maternofetal route, sex, blood transfusion, and organ transplantation.

ZIKV causes multiple illnesses in humans depending on the infecting virus, the host age and immunological conditions. Approximately 80% of ZIKV infections are asymptomatic. Disease symptoms associated with ZIKV infection include headaches, fever, lethargy, rash, conjunctivitis, myalgia, and arthralgia. Severe diseases resulting from ZIKV infection include neurotropic Guillain-Barre syndrome and congenital microcephaly.

ZIKV infection can be diagnosed by detection of viral components (e.g., viral RNA, viral proteins, or virus isolation) or detection of host immune responses (e.g., antibodies against viral proteins). For viral component-based diagnosis, RT-PCR, immunoassay, and virus isolation can be used to detect ZIKV RNA, viral proteins, and live virus, respectively. Among them, RT-PCR is the most commonly used because of its sensitivity and specificity. The viremic phase of ZIKV infection usually lasts from one to two weeks. The diagnostic window for detection of viral components is narrow because of the short duration of the viremic phase. Host immune response-based assays are also effective techniques, among which enzyme-linked immunosorbent assays (ELISAs), such as IgM-capture ELISA (MAC-ELISA), and plaque reduction neutralization test (PRNT) are the two commonly used serologic assays in ZIKV diagnosis. Serologic diagnosis of ZIKV infection relies upon IgM-capture ELISA which can be flawed due to cross-reactivity with different flaviviruses. The interpretation of conventional IgM-capture ELISA assays for ZIKV and other flaviviruses is challenging due to the cross-reactive nature of anti-flaviviral antibodies conventionally used in such tests, leading to misleading diagnostic results. This challenge confounds ZIKV diagnosis because (i) many flaviviruses (e.g., ZIKV and DENV) produce similar disease symptoms and (ii) antibodies from patients infected with ZIKV cross-react with other flaviviruses. Consequently, ZIKV IgM-capture ELISA results typically require neutralization tests for confirmation. Furthermore, PRNT is time-consuming, labor-intensive, slow, low-throughput, and cost-ineffective, impairing attempts at rapid diagnosis to halt or slow spread of infection. Moreover, PRNT still relies upon both virus-specific and cross-reactive epitopes of viral E protein such that the results may be inconclusive with respect to flavivirus infections. There is therefore a need to improve the accuracy and speed of serologic diagnosis for flaviviruses, ZIKV in particular.

IV. Zika Virus Peptides

Isolated peptides containing fragments of ZIKV proteins are disclosed herein. The ZIKV peptides can be used to detect exposure of a subject to a flavivirus infection, for example a ZIKV infection, such as by detecting anti-flavivirus antibodies. As discussed in the Examples below, the isolated peptides contain antigenic sites of the ZIKV that are targeted by antibodies following ZIKV infection.

In several embodiments, the isolated peptides contain fragments of a ZIKV NS protein, such as from the Paraiba strain of ZIKV. Exemplary ZIKV NS protein sequences are set forth herein as SEQ ID NOs: 1-8.

In some embodiments, the isolated peptide comprises, consists essentially of, or consists of 10-100 consecutive amino acids or longer (such as 10-15, 10-20, 10-30, 10-40, 20-30, 20-40, 20-50, 30-50, 40-50, 10-75, 20-75, 30-75, 40-75, or 75-100 consecutive amino acids) from a native Zika virus sequence.

The isolated peptides include the amino acid sequence of an antigenic site of the ZIKV. For example, the isolated peptide comprises, consists essentially of, or consists of the amino acid sequence of any one of the antigenic sites of Zika Paraiba as set forth in FIG. 8 (SEQ ID NO: 9), such as antigenic site ZIKV-NS1 1033-1067 (SEQ ID NO: 1), ZIKV-NS2B 1421-1469 (SEQ ID NO: 2), ZIKV-NS2B 1424-1457 (SEQ ID NO: 10), ZIKV-NS3 1805-1873 (SEQ ID NO: 3), ZIKV-NS4B 2422-2465 (SEQ ID NO: 4), ZIKV-NS4B 2312-2363 (SEQ ID NO: 5), ZIKV-NS5 2860-2901 (SEQ ID NO: 6), ZIKV-NS5 2943-2977 (SEQ ID NO: 7), or ZIKV-NS5 3136-3179 (SEQ ID NO: 8).

In some embodiments, the isolated peptide comprises, consists essentially of, or consists of the amino acid sequence of ZIKV-NS1 (1033-1067) from ZIKV, such as Zika Paraiba. In some embodiments, the isolated peptide comprises, consists essentially of, or consists of the amino acid sequence set forth as SEQ ID NO: 1 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS2B (1421-1469) from ZIKV, such as Zika Paraiba. In some embodiments, the isolated peptide comprises, consists essentially of, or consists of the amino acid sequence set forth as SEQ ID NO: 2 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS2B (1424-1457) from ZIKV, such as Zika Paraiba. In some embodiments, the isolated peptide comprises, consists essentially of, or consists of the amino acid sequence set forth as SEQ ID NO: 10 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS3 (1805-1873 within Z-19) from ZIKV, such as Zika Paraiba. In some embodiments, the isolated peptide comprises, consists essentially of, or consists of the amino acid sequence set forth as SEQ ID NO: 3 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS4B (2422-2465 within Z-24) from ZIKV, such as Zika Paraiba. In some embodiments, the isolated peptide comprises, consists essentially of, or consists of the amino acid sequence set forth as SEQ ID NO: 4 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS4B (2312-2363 overlapping Z-23.1) from Zika, such as Zika Paraiba. In some embodiments, the isolated peptide comprises, consists essentially of, or consists of the amino acid sequence set forth as SEQ ID NO: 5 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS5 (2860-2901 representing Z-29) from Zika, such as Zika Paraiba. In some embodiments, the isolated peptide comprises, consists essentially of, or consists of the amino acid sequence set forth as SEQ ID NO: 6 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS5 (2943-2977, within Z-30) from Zika, such as Zika Paraiba. In some embodiments, the isolated peptide comprises, consists essentially of, or consists of the amino acid sequence set forth as SEQ ID NO: 7 wherein the peptide is no more than 100 (such as no more than 95, 90, 85, 80, 75, 70, 65, 60, 55, 50, 45, 40, 35, 30, 25, 20, 15 or 10) amino acids in length.

In some embodiments, the isolated peptide comprises, consists essentially of, or consists of the amino acid sequence of ZIKV-NS5 (3136-3179, overlapping Z-32.2) from Zika, such as Zika Paraiba. In some embodiments, the isolated peptide comprises, consists essentially of, or consists of the amino acid sequence set forth as SEQ ID NO: 8 wherein the peptide is no more than 100 (such as no more than 95, 90, 85, 80, 75, 70, 65, 60, 55, 50, 45, 40, 35, 30, 25, 20, 15 or 10) amino acids in length.

Any of the isolated peptides disclosed herein can be linked or conjugated to a solid support, such as via a linker. Suitable linkers include, but are not limited to, straight or branched chain carbon linkers, heterocyclic carbon linkers, nucleic acid linkers, dyes or peptide linkers. For an immunogenic conjugate from two or more constituents, each of the constituents will contain the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. A wide variety of linking groups can be used. In some instances, the linking group can be either hydrophilic or hydrophobic in order to enhance the desired binding characteristics of the peptide. The covalent linkages should be stable relative to the solution conditions under which the conjugate is subjected.

In some embodiments, the linkers may be joined to the constituent amino acids through their side chains (such as through a disulfide linkage to cysteine) or to the alpha carbon, amino, and/or carboxyl groups of the terminal amino acids. In some embodiments, the linker and the peptide can be encoded as a single peptide such that the peptide and the linker are connected by peptide bonds. Peptides typically contain a variety of functional groups; for example, carboxylic acid (COOH), free amine ($—NH_2$) or sulfhydryl (—SH) groups, which are available for reaction with a suitable functional group on a peptide. Alternatively, the peptide is derivatized to expose or attach additional reactive functional groups. The derivitization may involve attachment of any of a number of linker molecules, such as streptavidin.

Although non-limiting examples discussed herein can include using full-length recombinant ZIKV peptides as antigens, full-length peptides would not necessarily be required for use in all embodiments of the method and compositions disclosed herein. For example, specific or portions less than full-length viral proteins may be used rather than full-length protein. A portion less than the full-length protein to which antibodies produced in response to a subject's exposure to a given ZIKV will bind may be used rather than full-length protein. In some embodiments, a portion less than full-length ZIKV to which antibodies produced in response to a subject's exposure to a given ZIKV, but not another flavivirus, will bind may be used. In other examples, portions less than full length protein that bind to antibodies produced in response to either of two or more different flaviviruses may be used.

In one embodiment, an antigen with less than complete homology to a ZIKV protein, such as ZIKV non-structural proteins NS1, NS2B, NS3, NS4B and NS5B, may be used, as may a combination of any two or more of the foregoing. A recombinant ZIKV protein with an amino acid sequence that corresponds to some but not all of the amino acids in the ZIKV protein to which it corresponds may be used. In some embodiments, ZIKV antigen with between 75%-80% homology, 80%-90% homology, or 95%-100% homology may be used. ZIKV protein sequences homologous to known strains may be used, within homology ranges as disclosed herein. A recombinant ZIKV antigen with less than 100% homology to a corresponding ZIKV peptide to which antibodies produced in response to a subject's exposure to a ZIKV will bind may be used rather than a recombinant protein with 100% homology. In some embodiments, a recombinant ZIKV peptide of less than 100% homology to a ZIKV peptide to which antibodies produced in response to a subject's exposure to a given ZIKV, but not another flavivirus, will bind may be used. In other examples, a recombinant flaviviral protein of less than 100% homology to a flaviviral protein to which antibodies produced in response to a subject's exposure to two or more given flaviviruses may be used.

In other embodiments, an antigen with an amino acid sequence that corresponds to only a portion of a full-length ZIKV protein, such as NS1, NS2B, NS3, NS4B, or NS5 may be used, as may a combnation of any two or more of the foregoing. For example, a truncated portion of NS1, NS2B, NS3, NS4B, or NS5, which is recognized by antibodies generated in response to a ZIKV infection, may be used. In some embodiments, an antigen may include amino acids not present in naturally occurring ZIKV proteins. For purposes of antigen synthesis and purification, an antigen may contain an amino acid tag, such as on its C-terminus or N-terminus, without interfering with the binding thereto of an antibody produced by an individual as a result of ZIKV infection. Other possible tags include, a poly-histidine tag, a myc-tag, a FLAG-tag, an HA-tag, or others, all of which can be included as part of an antigen and be within the scope of methods and kits disclosed herein.

Also provided herein are isolated peptides containing an antigenic site of a ZIKV polyprotein, such as the ZIKV Paraiba strain, wherein the peptides are linked to a solid support, fused to a heterologous protein, or conjugated to a heterologous carrier. In some embodiments, the peptide is no more than 100, no more than 90, no more than 80, no more than 70, no more than 60, no more than 50 or no more than 40 amino acids in length. In some examples, the peptide comprises an amino acid sequence set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 10. In specific non-limiting examples, the peptide consists, or consists essentially of, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 10. In particular examples, the amino acid sequence of the peptide comprises, consists, or consists essentially of SEQ ID NO: 2, SEQ ID NO: 5, SEQ ID NO: 7 or SEQ ID NO: 8.

In some embodiments, the peptide is linked to a solid support. In some examples, the peptide is linked to the solid support via a linker, such as, but not limited to, biotin, streptavidin, maleimide, polyethylene glycol (PEG), a peptide, or combinations of thereof. In some examples, the solid support comprises a bead, a membrane, a reaction tray, a multi-well plate, or a test tube.

In other embodiments, the peptide is fused to a heterologous protein. In some examples, the heterologous protein comprises a tag or linker. In specific examples, the tag is a poly-histidine tag, a myc tag, a FLAG tag, an HA tag. In some examples, the linker is a peptide linker.

In other embodiments, the peptide is conjugated to a heterologous carrier. In some examples, the heterologous carrier includes a protein from bacteria, a protein from a virus, keyhole limpet hemocyanin (KLH), ovalbumin (OVA), or bovine serum albumin (BSA).

Further provided herein are solid supports linked to one or more ZIKV peptides disclosed herein. In some embodiments, the one or more peptides include one or more of the peptides listed in Table 3, Table 4, Table 7 or Table 8. In specific embodiments, the one or more peptides comprise amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 10. In some examples, the one or more peptides comprise amino acid sequences selected from SEQ ID NO: 2, SEQ ID NO: 5, SEQ ID NO: 7 and SEQ ID NO: 8. In specific non-limiting examples, the one or more peptides consist or consist essentially of the amino acid sequences set forth as SEQ ID NO: 2, SEQ ID NO: 5, SEQ ID NO: 7 and SEQ ID NO: 8. In some embodiments, the one or more peptides are no more than 100, no more than 90, no more than 80, no more than 70, no more than 60, no more than 50 or no more than 40 amino acids in length. In some embodiments, the solid support comprises a bead, a membrane, a reaction tray, a multi-well plate, or a test tube.

V. Methods for Detection and Diagnosis

Methods are also provided for the detection of the presence of antibodies to flaviviruses, in particular ZIKV, in a biological sample. The method can be used to identify a biological sample from a subject with a ZIKV infection, or from a subject that had a prior infection with a ZIKV. In one example, the presence of ZIKV is detected in a biological sample from a subject, and can be used to identify a subject with ZIKV infection. The sample can be any sample from a subject that contains antibodies induced by ZIKV infection, including, but not limited to biological fluids. In some examples, the biological sample is from a subject, such as a human subject, who is at risk of or is suspected of having a flavivirus infection, for example, a ZIKV infection. The method of detection can include contacting the sample with an isolated ZIKV peptide as disclosed herein and under conditions sufficient to form an immune complex between the peptide and antibodies in the sample, and detecting the immune complex.

In some embodiments, the peptides disclosed herein are used to test vaccines. For example, to test if a vaccine elicits an immune response that targets a particular antigenic site on the ZIKV. Such methods involve immunizing a subject with a vaccine, and then screening a sample from the subject that contains antibodies induced by the immunization for antibody binding to the appropriate peptide.

Thus, the peptides disclosed herein can be used for serodiagnosis as well as the development of assays, including point-of-care (POC) assays.

In some embodiments, the method further includes determining the isotype of the anti-flavivirus antibodies present in a biological sample. Such a method is useful in order to determine the stage of infection; IgM antibodies indicate an early/acute stage of infection, while IgG antibodies indicate a later/convalescent stage of flavivirus infection.

The disclosed methods can also be used for distinguishing between a subject with a natural flavivirus infection and a subject who has been vaccinated against a flavivirus. A subject with a natural infection will have antibodies that will bind the peptides disclosed herein derived from flavivirus non-structural proteins (e.g. NS1, NS2B, NS3, NS4B, NS5), while a vaccinated subject will have antibodies specific for flavivirus structural proteins (e.g. C, prM and/or E).

Heterogeneous immunoassay techniques usually involve the use of a solid phase material that the reaction material becomes bound to, but can be adapted to bind antigens and antibodies. The reaction product is separated from excess sample, assay reagents, and other substances by separating the solid phase from the reaction mixture (e.g. by washing). Sandwich immunoassays are one type of solid phase immunoassay that can be used in the present disclosure. In the sandwich assay, the more analyte present in the sample, the greater the amount of label present on the solid phase. This type of assay is generally preferred for visualization of low analyte concentration, because the appearance of label on the solid phase is more readily detected. In some embodiments, the detection or diagnostic assay is designed for POC. In some examples, the POC assay is a lateral flow assay (LFA).

Provided herein are methods for detecting anti-flavivirus antibodies in a biological sample containing antibodies. In some embodiments, the method includes contacting the biological sample with one or more peptides listed in Table 3, Table 4, Table 7 or Table 8, such as peptides comprising amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 10, under conditions sufficient to form an immune complex between the one or more peptides and the antibodies present in the biological sample; and detecting the presence or absence of the immune complex. The presence of the immune complex indicates anti-flavivirus antibodies are present in the sample and the absence of the immune complex indicates anti-flavivirus antibodies are not present in the sample. In some examples, the one or more peptides comprise amino acid sequences selected from SEQ ID NO: 2, SEQ ID NO: 5, SEQ ID NO: 7 and SEQ ID NO: 8. In specific non-limiting examples, the one or more peptides consist or consist essentially of the amino acid sequences set forth as SEQ ID NO: 2, SEQ ID NO: 5, SEQ ID NO: 7 and SEQ ID NO: 8. In specific non-limiting examples, the one or more peptides consists of SEQ ID NO: 1, SEQ ID NO: 2 and SEQ ID NO: 7; SEQ ID NO: 1, SEQ ID NO: 2 and SEQ ID NO: 7; or SEQ ID NO: 10, SEQ ID NO: 7, SEQ ID NO: 8 and SEQ ID NO: 10.

In some embodiments of the detection method, the flavivirus is ZIKV. In other embodiments, the flavivirus is a non-ZIKV flavivirus, such as, but not limited to JEV, WNV, YFV, DENY-1, DENY-1, DENV-2, DENV-3, DENV-4 or TBEV. In other embodiments, the virus is closely related to flaviviruses, such as Chikungunya virus (CHIKV), an alphavirus that elicits antibodies that can be cross-reactive with flaviviruses.

In some embodiments, the biological sample is from a human subject. In other embodiments, the biological sample is from a non-human animal. In some examples, the biological sample is from a subject who is at risk of or is suspected of having a flavivirus infection, such as a ZIKV infection.

In some embodiments, the biological sample comprises blood, serum, plasma, urine, saliva, tears, feces, semen, mucous, tissue, tissue homogenate, cellular extract, spinal fluid, or any combination of two or more thereof.

In some embodiments, the detection assay is ELISA, SPR, LFA, biosensor, array or any POC assay.

Also provided herein is a method of identifying a subject with a flavivirus infection. In some embodiments, the method includes contacting a biological sample containing antibodies from the subject with one or more peptides listed in Table 3, Table 4, Table 7 or Table 8, such as peptides comprising amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 10, under conditions sufficient to form an immune complex between the one or more peptides and the antibodies present in the biological sample; and detecting the presence or absence of the immune complex. The presence of the immune complex identifies the subject as having a flavivirus infection and the absence of the immune complex identifies the subject as not having a flavivirus infection. In some examples, the one or more peptides comprise amino acid sequences selected from SEQ ID NO: 2, SEQ ID NO: 5, SEQ ID NO: 7 and SEQ ID NO: 8. In specific non-limiting examples, the one or more peptides consist or consist essentially of the amino acid sequences set forth as SEQ ID NO: 2, SEQ ID NO: 5, SEQ ID NO: 7 and SEQ ID NO: 8.

In some embodiments of the diagnostic method, the flavivirus is ZIKV. In other embodiments, the flavivirus is a non-ZIKV flavivirus, such as, but not limited to JEV, WNV, YFV, DENY-1, DENY-1, DENV-2, DENV-3, DENV-4 or TBEV. In other embodiments, the virus is closely related to flaviviruses, such as CHIKV.

In some embodiments, the subject is human. In other embodiments, the subject is a non-human animal. In some examples, the subject is one who is at risk of or is suspected of having a flavivirus infection, such as a ZIKV infection.

In some embodiments, the biological sample comprises blood, serum, plasma, urine, saliva, tears, feces, semen, mucous, tissue, tissue homogenate, cellular extract, spinal fluid, or any combination of two or more thereof.

In some embodiments, the diagnostic assay is ELISA, SPR or LFA.

In some embodiments, the method further includes determining the isotype of anti-flavivirus antibodies present in the biological sample from the subject diagnosed with a flavivirus infection, such as a ZIKV infection. In some examples, the method includes contact the anti-flavivirus antibodies with an isotype-specific secondary antibody, such as an IgM-specific or IgG-specific secondary antibody. In specific non-limiting examples, the secondary antibody is directly labelled for detection.

The majority of flavivirus vaccines include prM/E proteins but do not include any flavivirus non-structural proteins. Accordingly, biological samples from flavivirus (such as ZIKV) vaccinated subjects would not have any antibodies specific for the peptides disclosed herein (i.e. SEQ ID NOs: 1-8 and 10). Thus, the diagnostic method disclosed herein can be used for differential diagnosis of a subject with a natural infection versus a vaccinated subject.

A. Binding Partner

In a one embodiment, the binding partner is any molecule produced in the subject against the ZIKV or related virus components. Preferably, it is an immunointeractive molecule such as an antibody or immunologically active fragment thereof, or a cytotoxic cell. The binding partner includes an immunointeractive molecule that can interact with a ZIKV antigen or equivalent and compete with ZIKV specific immunological agents such as ZIKV specific monoclonal antibodies. The preferred binding partner is an immunointeractive molecule, which preferably refers to any molecule comprising an antigen binding portion or a derivative thereof. Preferably, the immunointeractive molecule is an antibody against any portion of a ZIKV protein produced during a humoral response in the subject of a ZIKV infection or exposure.

In one embodiment, the binding partner is an antibody produced in the subject to a ZIKV or a related virus component. However, a binding partner of the targeted antibody can also be used. An example of such a binding partner is an anti-idiotypic antibody or an antibody specific for a subject antibody specific for the member of the ZIKV or related virus components.

In the early convalescent stages of ZIKV infection, IgG antibody is one of the indications of either secondary or primary ZIKV infection. The antibody can be detected by the formation of an immune complex between the antibody and a component of the ZIKV. The formation of this immune complex with the antibody of the ZIKV specific IgG and antigen at the ZIKV specific IgG or antibody specific epitope is indicated by the absence of the attachment of competing flavivirus or member specific immunological agents.

In some embodiments, the binding partner is an antibody. In some examples, the binding partner is a flavivirus IgG molecule or an immunointeractive portion thereof. In specific non-limiting examples, the flavivirus is a ZIKV virus.

B. Immune Complex Formation

In one embodiment of the present disclosure, a peptide or protein specifically reactive with an anti-flavivirus antibody is immobilized on a solid support and incubated with the biological sample being screened for the presence of an anti-flavivirus antibody. In another embodiment, a peptide or protein specifically reactive with an anti-ZIKV antibody is immobilized on a solid support and incubated with the biological sample being screened for the presence of an anti-ZIKV antibody. A blocking agent may be added to reduce non-specific binding. The peptide may be incubated with the biological sample in an unbound state and then subsequently bound to the solid support (i.e. immobilizable). The supports are washed to remove non-ZIKV antibodies that may be present but failed to bind to the bound peptide. An immune complex forms between the peptide and anti-ZIKV antibody.

A detectably labeled secondary antibody (capable of binding to the initial antibody, e.g., an anti-human IgG antibody) can be added and the support is incubated under conditions sufficient to permit the secondary antibody to bind to any anti-ZIKV antibody present. The support is then extensively treated (e.g. by washing) to remove unbound secondary antibody. If anti-ZIKV antibody is present in the test sample, then the two antibodies form an immune complex with the immobilized peptide (i.e. a secondary antibody/anti-ZIKV antibody/immobilized peptide complex). In such an assay, the secondary antibody bound to the support is indicative of the presence of an anti-ZIKV antibody in the sample being tested. The secondary antibody may be a natural immunoglobulin isolated from a nonhuman species (e.g., a murine anti-human IgG antibody, a goat anti-human IgG antibody, a goat anti-human IgM antibody, etc.), or it can be produced recombinantly or synthetically. It may be an intact immunoglobulin, or an immunoglobulin fragment. Other binding molecules may be used along with or in lieu of secondary antibodies. For example, the anti-ZIKV antibodies can be biotinylated and the secondary antibody can be replaced with labeled avidin or streptavidin. The secondary antibody can comprise HRP-conjugated goat anti-Human IgG-A-M antibody.

To eliminate the bound-free separation step and reduce the time and equipment needed for a chemical binding assay, a homogenous assay format may alternatively be employed. In such assays, one component of the binding pair may still be immobilized; however, the presence of the second component of the binding pair is detected without a bound-free separation.

In all such assay formats, at least one component of the assay reagents will preferably be labeled or otherwise detectable by the evolution or quenching of light. The component may be a secondary antibody, anti-ZIKV antibody, or the peptide that binds to the anti-ZIKV antibody, depending on the immunoassay format employed. Radioisotopic binding assay formats (e.g. a radioimmunoassay, etc.) employ a radioisotope as such label; the signal is detectable by the evolution of light in the presence of a fluorescent or fluorogenic moiety). Enzymatic-binding assay formats (e.g., an ELISA, etc.) employ an enzyme as a label; the signal is detectable by the emission of color or light in the presence of a chromogenic or fluorogenic moiety. Other labels, such a paramagnetic labels, materials used as colored particles, latex particles, colloidal metals such as selenium and gold, and dye particles may also be employed. In some examples, enzymes (e.g., alkaline phosphatase, (3-galactosidase, horseradish peroxidase, or urease) are used as the detectable label (i.e., an enzyme immunoassay or EM). In other examples, the label is a nucleic acid or an aptamer.

A wide variety of solid supports can be employed in the immunoassays of the present disclosure. Suitable materials for the solid support are synthetics such as polystyrene, polyvinyl chloride, polyamide, or other synthetic polymers, natural polymers such as cellulose, as well as derivatized natural polymers such as cellulose acetate or nitrocellulose, glass and glass fibers. The support can take the form of spheres, rods, tubes, and microassay or microtiter plates. Sheet-like structures such as paper strips, small plates, and membranes are also suitable. The surface of the carriers can be permeable and impermeable for aqueous solutions.

The solid support may be a polystyrene 96-well plate, a nitrocellulose membrane, a microtiter plate, a glass slide or a biological microchip wherein the peptides are immobilized. These solid supports in contact with peptide can be used as an immobilized anti-ZIKV antibody capture component subjected to a biological sample to detect ZIKV exposure in a subject.

Although the foregoing description pertains to assays for the presence of anti-ZIKV antibodies in biological sample that are fluids (e.g., sera, blood, urine, saliva, pancreatic juice, cerebrospinal fluid, semen, etc.), it will be appreciated that any fluidic biological sample (e.g., tissue or biopsy extracts, extracts of feces, sputum, etc.) may likewise be employed in the assays of the present invention. In one embodiment, the biological sample being assayed is serum or plasma.

A scrambled peptide can be used as a negative control to detect non-specific reactivity with anti-ZIKV antibodies. A scrambled peptide, wherein the scrambled peptide comprises the amino acid residues of any one of SEQ ID NOs: 1-8 in a scrambled mode for use as a control, or can be another peptide from similar region of DENV, WNV or YF, or any peptide that is non-reactive to ZIKV sera, such as a peptide from the NS2A region.

C. Exposure

The subject may have been exposed to ZIKV but need not show visual symptoms of the infection. The present method detects exposure that may lead to infection (clinical or sub-clinical or non-clinical) or may indicate prior exposure with no symptoms manifested.

The present disclosure is applicable to detecting exposure to ZIKV. Exposure may be current or prior infection with ZIKV or an equivalent thereof. The exposure is sufficient to elicit an immune reaction or response in the body so as to induce a binding partner in response to the ZIKV. Once the subject is exposed, the method of the present invention may be applied at any stage of exposure. The method is used to detect exposure where there are no obvious signs or symptoms of ZIKV infection. In some examples, the method detects exposure of the subject at any phase of ZIKV infection, for example at an early acute phase for secondary infection, or late convalescence stage of exposure to ZIKV or equivalent thereof for the primary infection or vaccination. The exposure may not always manifest in a ZIKV infection or notable signs or symptoms but can cause a response that induces a binding partner. Preferably, the response is an immunological response. The presence of different antibody types following a subject's exposure to ZIKV or other flaviviruses corresponds to different time frames, with IgM antibodies to specific antigens being produced sooner after infection than IgG antibodies to the antigens. In some embodiments, detection of one or both of IgM and IgG, and/or other types of antibodies to ZIKV-derived antigens may indicate exposure to ZIKV relative to when a sample was taken from a subject. For example, presence of IgM anti-ZIKV antibodies may indicate recent exposure while presence of IgG anti-ZIKV antibodies may signify less recent exposure.

D. Immune or Immunological Response

An "immune response" or "immunological response" is understood to be a selective response by the immune system of vertebrates in which specific antibodies or fragments of antibodies and/or cytotoxic cells are produced against invading pathogens and antigens which are recognized as foreign in the body.

E. Biological Sample

The method of the present disclosure detects current or prior infection with ZIKV or equivalent thereof through the use of a biological sample obtained from a subject potentially exposed to ZIKV. The biological sample may be any sample from the body that may contain a binding partner. Such biological samples may be selected from the group including blood, saliva, cerebral spinal fluid, B cells, T cells, plasma, urine, tears, feces, semen, mucous, cellular extract, umbilical cord, and amniotic fluid. In specific examples, the biological sample is serum or urine.

In particular examples, the biological sample is obtained from subjects with possible exposure to ZIKV. A biological sample may also be modified prior to use, such as by dilution, purification of various fractions, and centrifugation. Accordingly, a biological sample may refer to a homogenate, lysate or extract prepared from a whole organism or a subset of tissues, cells or component parts, or a fraction or portion thereof.

A biological sample may also be devoid of a binding partner that can interact with ZIKV or an equivalent thereof. This occurs when the subject has not been exposed to ZIKV or an equivalent thereof. The only complex that may form in this instance would comprise the competing ZIKV specific immunological agent such as a monoclonal antibody designed to compete with the binding partners in the biological sample. Reference to a biological sample being placed in contact with a component of a lysate, preferably an immunogenic component of ZIKV or its immunological relative thereof should be understood as a reference to any method of facilitating the interaction of one or more immunointeractive molecules of the biological sample with a component of ZIKV or its immunological relative thereof. The interaction should be such that coupling or binding or association between the immunointeractive molecule and a specific immunogenic component of the ZIKV or its immunological relative thereof can occur. A subject may be any vertebrate, such as a horse, pig, cow, dog, cat, bat, primate (including human), goat, sheep, deer, rabbit, mouse, rat, chicken or other avian species, or other animal.

F. Kits

The present disclosure provides a kit for detecting ZIKV exposure and/or screening for anti-ZIKV antibodies in a subject comprising any one or more of the following: a solid support in contact with at least one peptide specifically reactive with an anti-ZIKV antibody; a detection reagent according to the present disclosure; at least one positive control, such a reference serum from an infected individual and; at least one negative control, such as a reference serum from a non-infected individual.

In one embodiment, the kit comprises a solid support in contact with at least one peptide specifically reactive with an anti-ZIKV antibody for use in the detection of ZIKV exposure in a subject.

In some embodiments, the kit is designed for use with ELISA. In some embodiments, the kit is designed for use with a POC assay, such as LFA.

The solid support may be a polystyrene 96-well plate, a nitrocellulose membrane, a microtiter plate, a glass slide or a biological microchip, wherein the peptides are immobilized. These solid supports in contact with peptide can be used as an immobilized anti-ZIKV antibody capture component subjected to a biological sample to detect ZIKV exposure in a subject.

In another embodiment, the peptide is selected from the group consisting of ZIKV structural and non-structural proteins, ZIKV particles and fragments thereof, glycoproteins, lipids, carbohydrates derived from ZIKV or any mixture thereof. The ZIKV non-structural proteins can also be selected from a group consisting of NS1, NS2A, NS2B, NS3, NS4A, NS4B, and NS5, or any combination of two or more of the foregoing.

In another embodiment, the kit also comprises detection reagents, reporter molecules capable of providing detectable signals. In a particular embodiment, the detection reagent comprises horseradish peroxidase (HRP) enzyme.

Optionally, the kit will also include additional parts, such as washing buffers, incubation containers, blocking buffers, and instructions for practicing the method.

The kit can also comprise a container with a premeasured amount of a sample suspected of containing a measurable unknown amount of anti-ZIKV antibody, a premeasured amount of support bound ZIKV non-structural peptides present in a first container, and a premeasured amount of the detection reagent in a second container. After an appropriate time for incubation, an immune complex is formed (if the sample contained anti-ZIKV antibody) and is separated from the supernatant fluid, and the immune complex or the supernatant fluid are detected, as by radioactive counting, addition of an enzyme substrate, and color development, or by inclusion of a chemical label (e.g., colloidal gold, latex beads, etc.).

V. Immunogenic Compositions

Immunogenic compositions comprising a disclosed peptide (for example, linked to a carrier) or a nucleic acid molecule or vector encoding the peptide and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. Actual methods for preparing administrable compositions are described in more detail in such publications as *Remingtons Pharmaceutical Sciences,* $19^{th}$ Ed., Mack Publishing Company, Easton, Pa., 1995.

The peptide (for example, linked to a carrier) or a nucleic acid molecule or vector encoding the peptide can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.) may also be used as an adjuvant (Newman et al., 1998*, Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the immunogenic composition can be provided as a sterile composition. The immunogenic composition typically contains an effective amount of a disclosed peptide (for example, linked to a carrier) or a nucleic acid molecule or vector encoding the peptide, and can be prepared by conventional techniques. Typically, the amount of a disclosed peptide (for example, linked to a carrier) or a nucleic acid molecule or vector encoding the peptide in each dose of the immunogenic composition is selected as an amount which elicits an immune response without significant, adverse side effects. In some embodiments, the immunogenic composition can be provided in unit dosage form for use to elicit an immune response in a subject, for example, to prevent ZIKV infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VI. Methods of Inducing an Immune Response

An immunogenic composition comprising a disclosed ZIKV peptide, a nucleic acid molecule (such as an RNA molecule) encoding a disclosed ZIKV peptide, vector including the nucleic acid molecule, or immunogenic composition, can be administered to a subject to induce an immune response to ZIKV and/or other flaviviruses in the subject. In a particular example, the subject is a human. The immune response can be a protective immune response, for example a response that inhibits subsequent infection with a flavivirus (such as ZIKV). Elicitation of the immune response can also be used to treat or inhibit infection and illnesses associated with a flavivirus (such as a ZIKV).

A subject can be selected for immunization that has, or is at risk for developing infection or illness associated with a flavivirus (such as a ZIKV), for example because of exposure or the possibility of exposure to a flavivirus (such as a ZIKV).

Typical subjects intended for administration of the immunogenic compositions include humans, as well as non-human primates and other animals. To identify relevant subjects, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize a flavivirus (such as a ZIKV) infection. These and other routine methods allow the clinician to select patients in need of therapy. In accordance with these methods and principles, the immunogenic composition can be administered according to the teachings herein, or other conventional methods, as an independent prophylaxis or treatment program, or as a follow-up, adjunct or coordinate treatment regimen to other treatments.

The administration of the immunogenic composition can be for prophylactic or therapeutic purpose. When provided prophylactically, the immunogenic composition can be provided in advance of any symptom, for example, in advance of infection. The prophylactic administration serves to prevent or ameliorate any subsequent infection. In some embodiments, the methods can involve selecting a subject at risk for contracting a flavivirus infection (e.g., a ZIKV infection), and administering an effective amount of the immunogenic composition to the subject. The immunogenic composition can be provided prior to the anticipated exposure to the flavivirus infection (e.g., ZIKV infection) so as to attenuate the anticipated severity, duration or extent of an infection and/or associated disease symptoms, after exposure or suspected exposure to the virus, or after the actual initiation of an infection.

The immunogenic composition is provided to the subject in an amount effective to induce or to enhance an immune response against flavivirus (e.g., ZIKV) in the subject, preferably a human. The actual dosage of the immunogenic composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to flavivirus (e.g., ZIKV). Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples, the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example, a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of flavivirus infection (e.g., ZIKV infection) or improvement in disease state (e.g., reduction in viral load). If such monitoring indicates that vaccination is sub-optimal, the subject can be boosted with an additional dose of immunogenic composition, and the vaccination parameters can be modified in a manner expected to potentiate the immune response.

In some embodiments, the prime-boost method can include DNA-prime and protein-boost vaccination protocol to a subject. The method can include two or more administrations of the nucleic acid molecule or the protein.

For peptide therapeutics, typically, each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg.

The amount utilized in an immunogenic composition is selected based on the subject population (e.g., infant or elderly). An optimal amount for a particular composition can be ascertained by standard studies involving observation of antibody titers and other responses in subjects. It is understood that an effective amount of a disclosed immunogenic composition can include an amount that is ineffective at eliciting an immune response by administration of a single dose, but that is effective upon administration of multiple dosages, for example in a prime-boost administration protocol.

Upon administration of the immunogenic composition, the immune system of the subject typically responds to the immunogenic composition by producing antibodies specific for viral protein. Such a response signifies that an immunologically effective dose was delivered to the subject.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, (e.g., ZIKV).

Flavivirus infection (e.g., ZIKV infection) does not need to be completely eliminated or reduced or prevented for the methods to be effective. For example, elicitation of the immune response can reduce or inhibit infection with the flavivirus (e.g., ZIKV) by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to infection with the flavivirus (e.g., ZIKV) in the absence of the immunization.

One approach to administration of nucleic acids is direct immunization with plasmid DNA, such as with a mammalian expression plasmid Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin) or adjuvants. Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed flavivirus peptide (e.g., ZIKV peptide) in a subject. For example, a nucleic acid molecule encoding a disclosed flavivirus peptide (e.g., ZIKV peptide) can be administered to a subject to induce an immune response to flavivirus (e.g., ZIKV).

In another approach, a disclosed flavivirus peptide (e.g., ZIKV peptide) can be expressed by attenuated viral hosts or vectors or bacterial vectors. Recombinant vaccinia virus, adeno-associated virus (AAV), herpes virus, retrovirus, cytomegalovirus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991). These peptides can also be used in combination or with vaccines against other pathogens.

In one embodiment, a nucleic acid encoding a disclosed flavivirus peptide (e.g., ZIKV peptide) is introduced directly into cells to induce the immune response. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed flavivirus peptide (e.g., ZIKV peptide) directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed flavivirus peptide (e.g., ZIKV peptide) include conventional non-amplifying mRNA immunization (see, e.g., Petsch et al., "Protective efficacy of in vitro synthesized, specific mRNA vaccines against influenza A virus infection," *Nature biotechnology,* 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

In some embodiments, administration of an effective amount of one or more of the disclosed immunogens to a subject induces a neutralizing or protective immune response in the subject. To assess neutralization activity, following immunization of a subject, serum can be collected from the subject at appropriate time points, frozen, and stored for neutralization testing. Methods to assay for binding or neutralization activity are known and are further described herein, and include, but are not limited to, ELISA, plaque reduction neutralization (PRNT) assays, microneutralization assays, flow cytometry based assays, single-cycle infection assays. In some embodiments, the serum neutralization activity can be assayed using a panel of flavivirus (e.g., ZIKV) pseudoviruses.

EXAMPLES

The following examples are provided to illustrate certain particular features and/or embodiments. These examples should not be construed to limit the disclosure to the particular features or embodiments described.

Example 1

Blood and urine samples from 19 patients (10 females and 9 males; 18-51 years old) with confirmed acute ZIKV infection in Mexico (Table 1) were analyzed. Only 1/19 individuals reported a known prior exposure to dengue virus. Both serum and urine samples from all individuals at all time-points of collection were PCR-negative for dengue virus (DENV) infection. All these serum samples (and corresponding urine samples) were from acutely ZIKV infected adults collected within 0-5 days of onset of symptoms that were PCR positive for ZIKV RNA in serum/urine (Table 1). Of the 19 individuals, 11 were PCR positive for ZIKV RNA in both serum and urine, 2 were ZIKV positive only in serum, while 6 were only ZIKV-positive in urine within the first 7 days of visit (day 0-day 12 since onset of symptoms). The number of clinical symptoms following ZIKV infection in these adults were highest at day 0 visit, and declined by day 28, in most patients (Table 2). For simplicity, samples are referred by the visit day throughout rather than days post onset of symptoms. For most individuals the first visit ranged between 0-5 days from the day of symptom onset.

Figure 8:
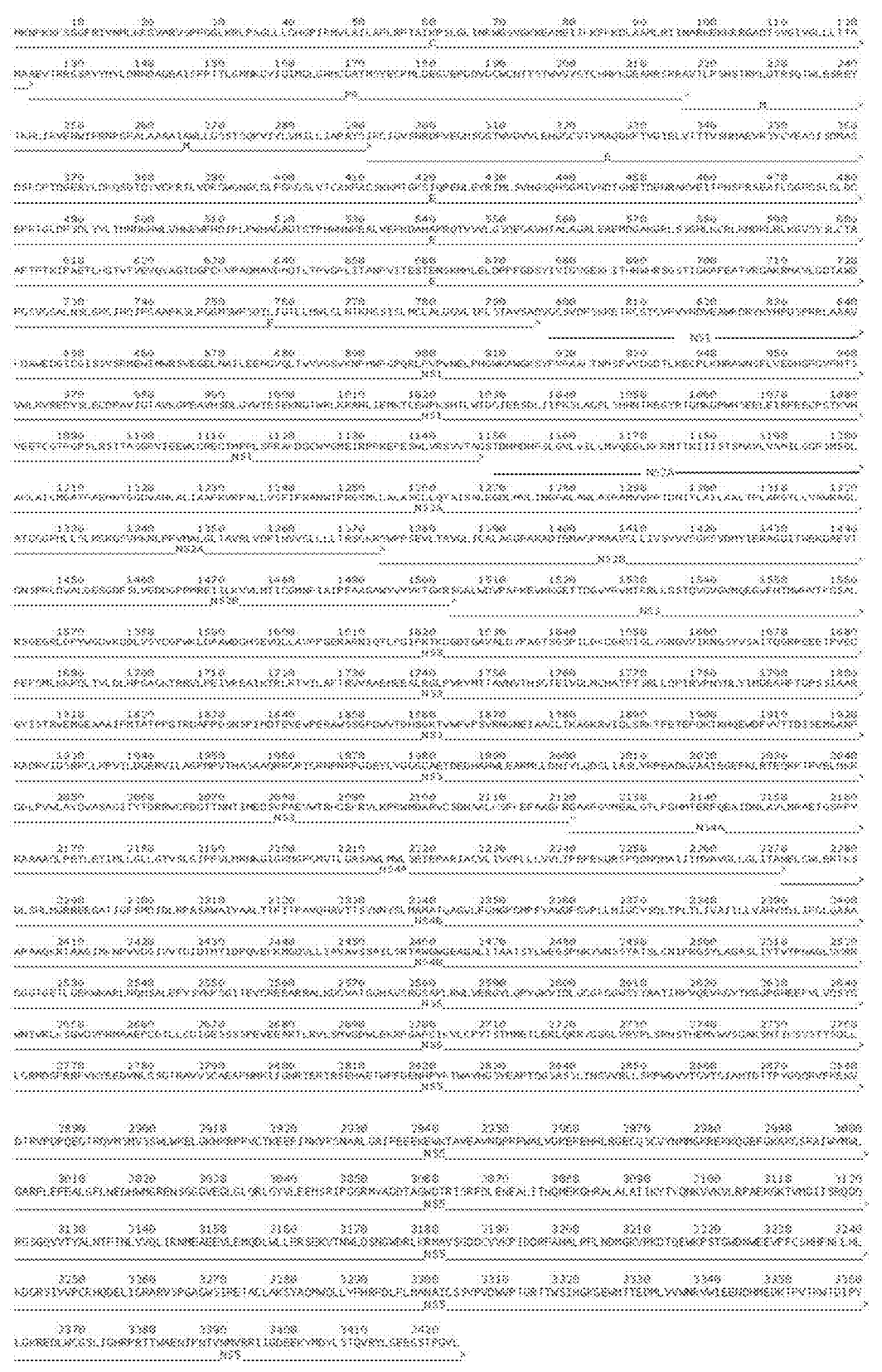
Figure 9:
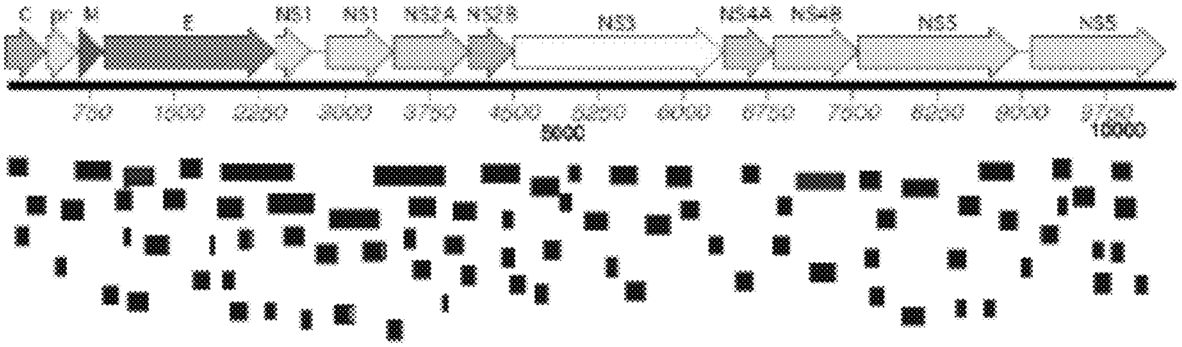
FIG. 9 shows the random distribution of size and sequence of the ZIKV-GFPDL. Sequencing of ZIKV whole genome fragments expressed by the phages of the ZIKV GFPD libraries were aligned to the ZIKV_ICD translated sequence (FIG. 8; SEQ ID NO: 9).

Affinity Selection of ZIKV-GFPDL with Serum and Urine Samples from ZIKV Confirmed Infections Whole genome ZIKV-GFPDL was constructed from the entire genome of Zika virus strain Paraiba_01/2015 (FIG. 8). Sequencing of the ZIKV-GFPDL clones showed unbiased random distribution of peptides with diversity in size including large inserts (>500 bp) that spanned the sequence of the entire ZIKV-genome (FIG. 9).

Figure 10A:
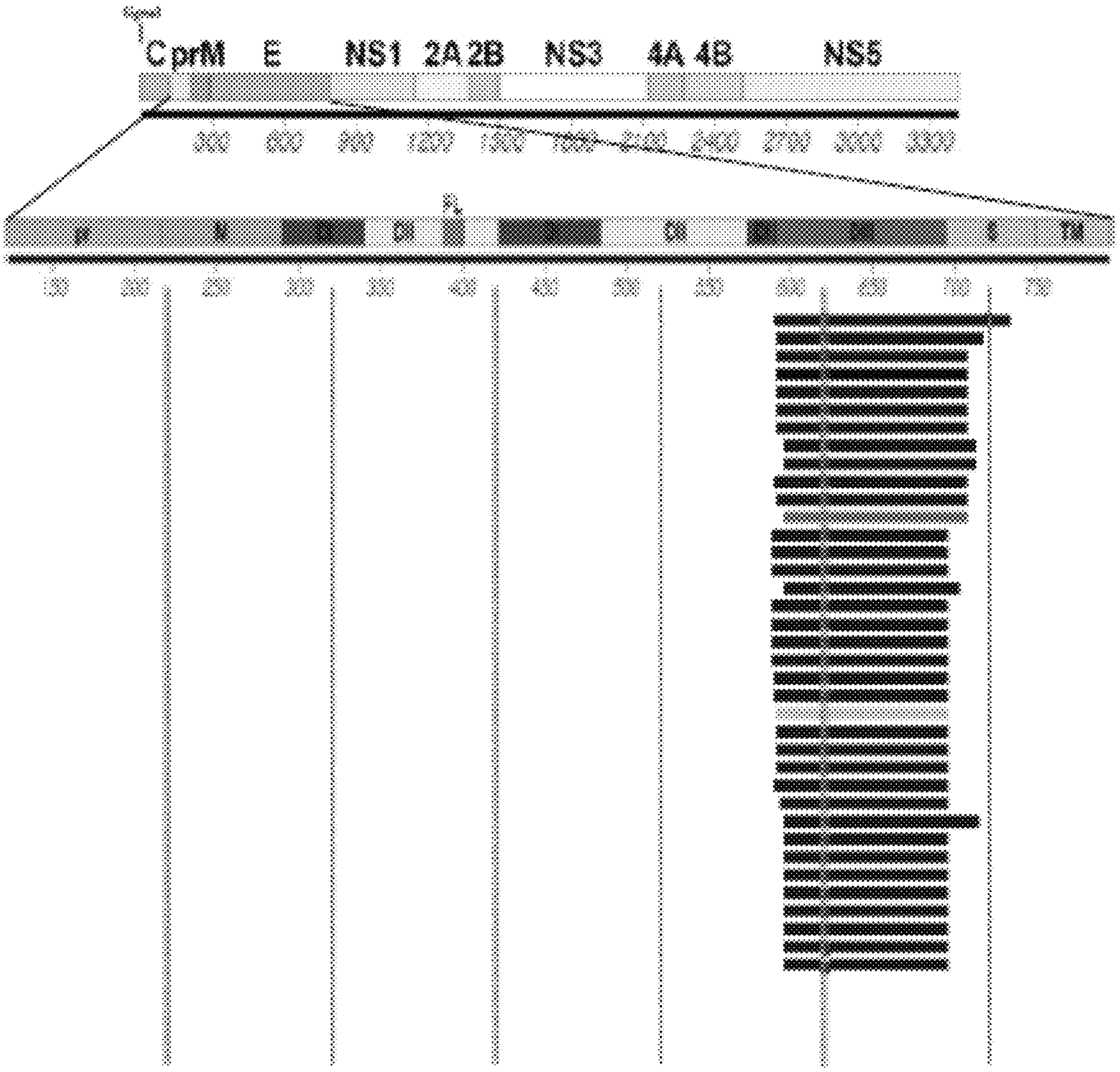
Figure 10B:
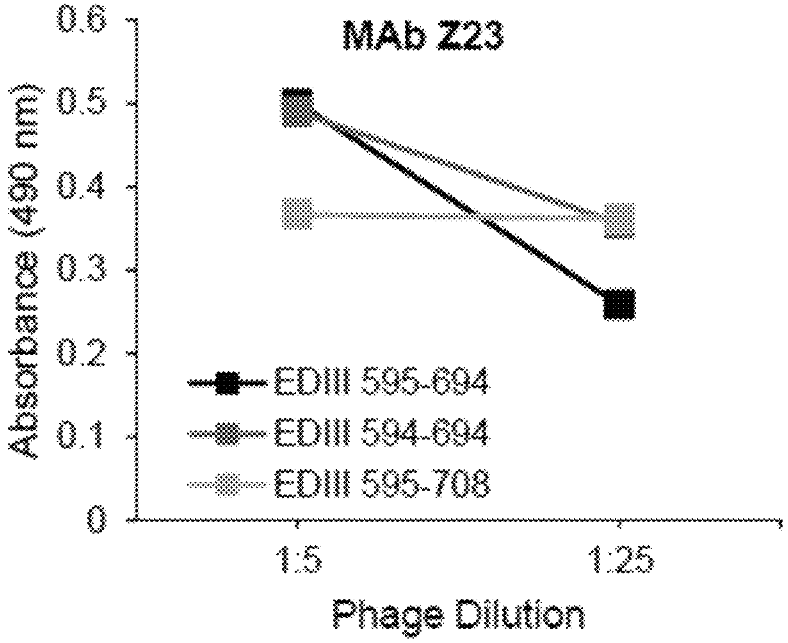
Figure 10C:
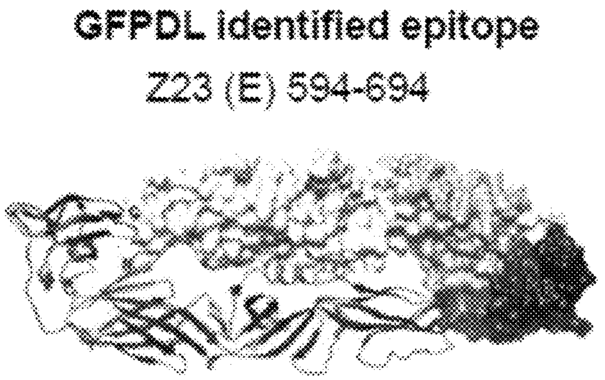
Figure 11A:
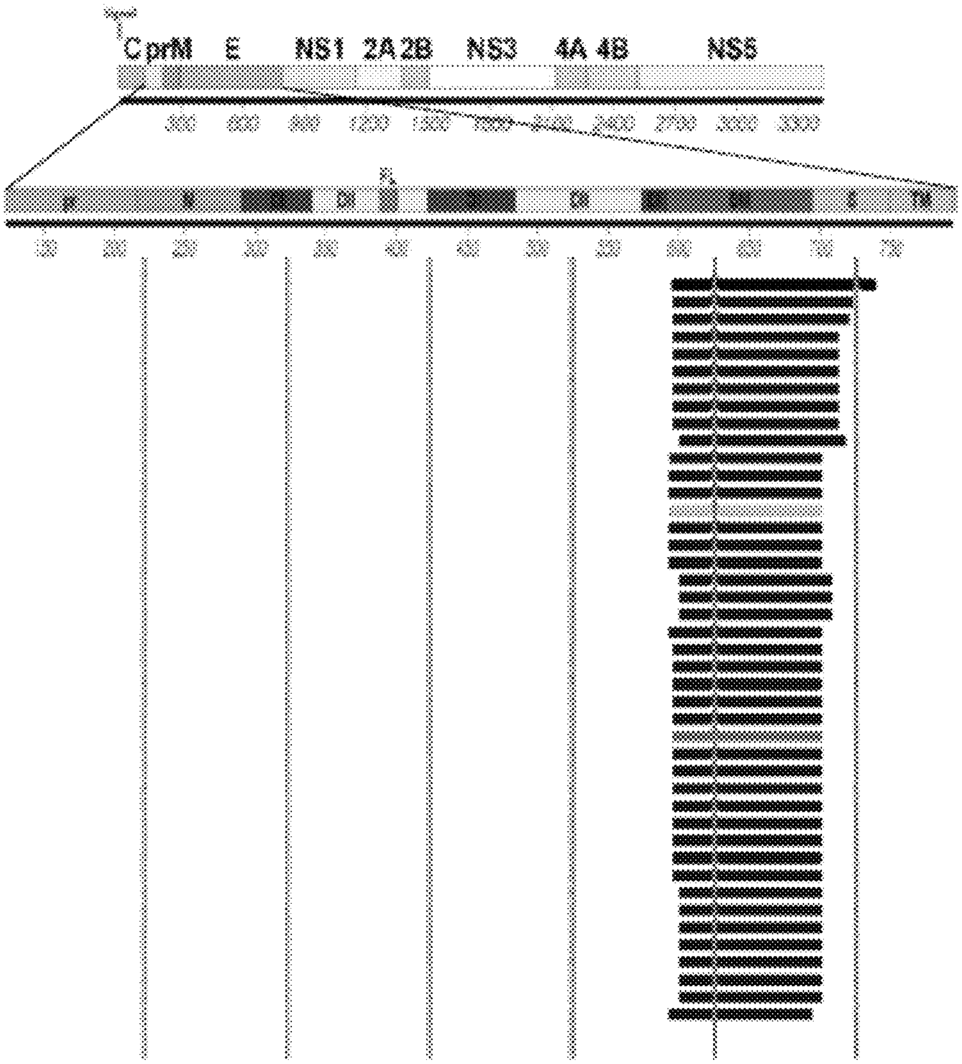
Figure 11B:
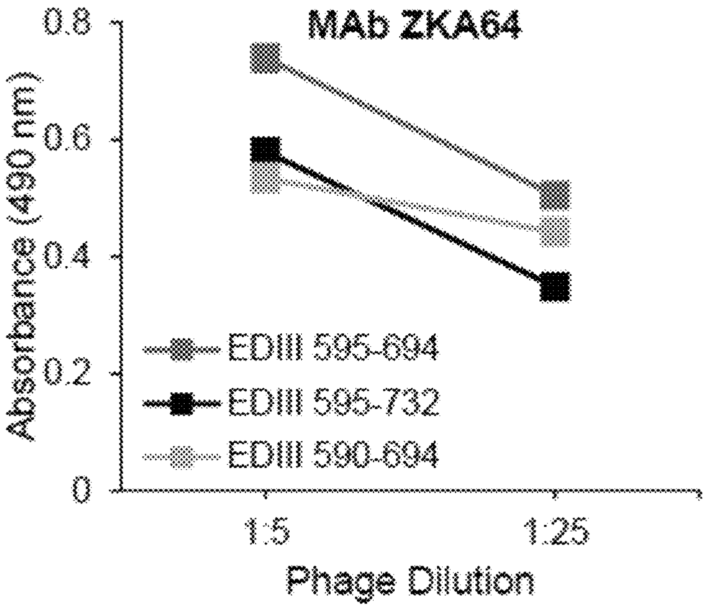
Figure 11C:
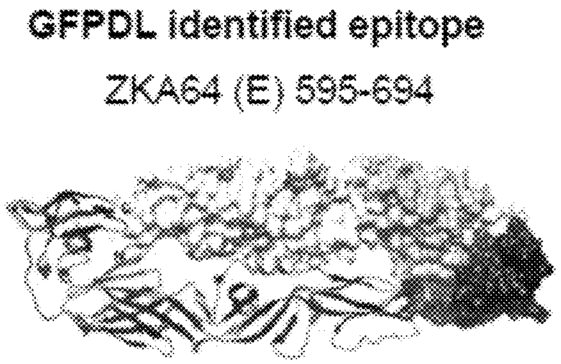
Figure 12A:
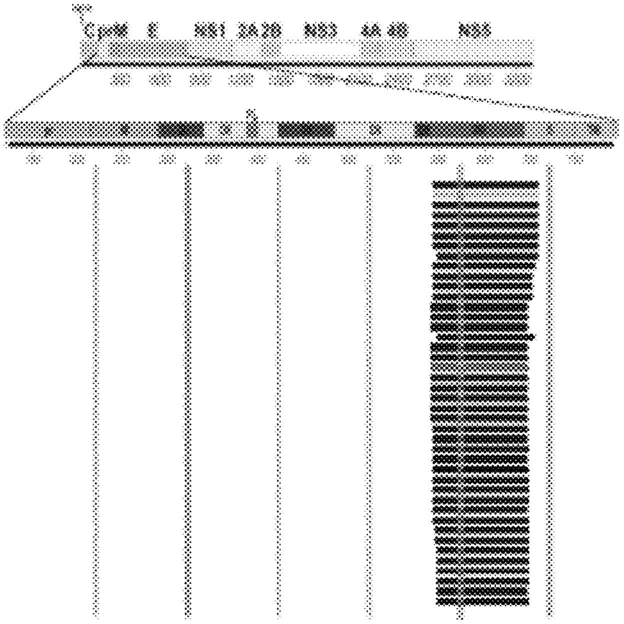
Figure 12B:
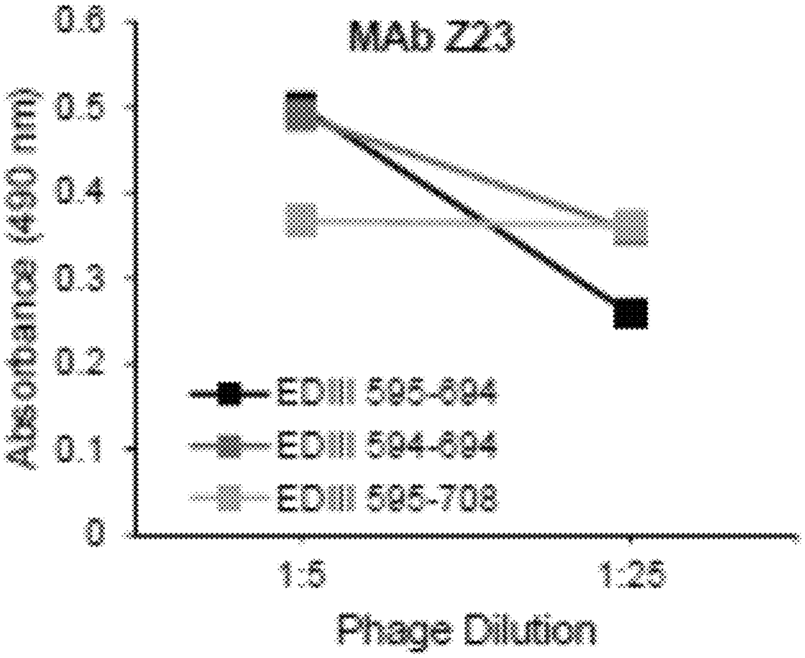
Figure 12C:
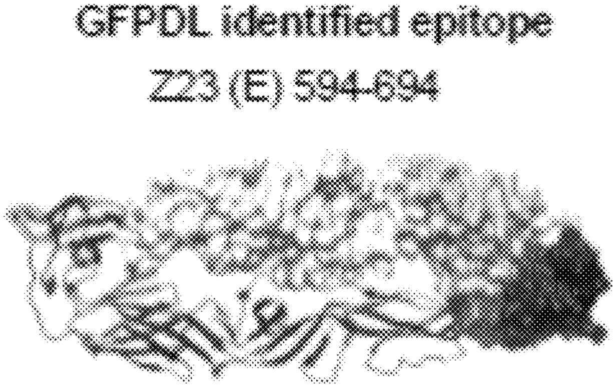
Figure 13A:
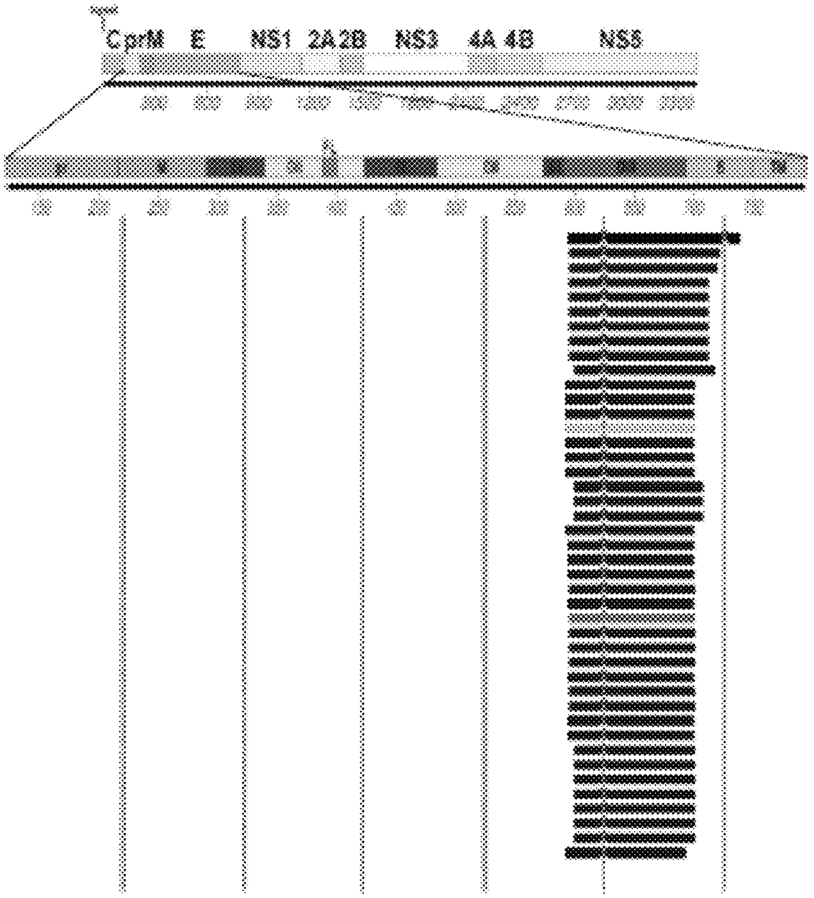
Figure 13B:
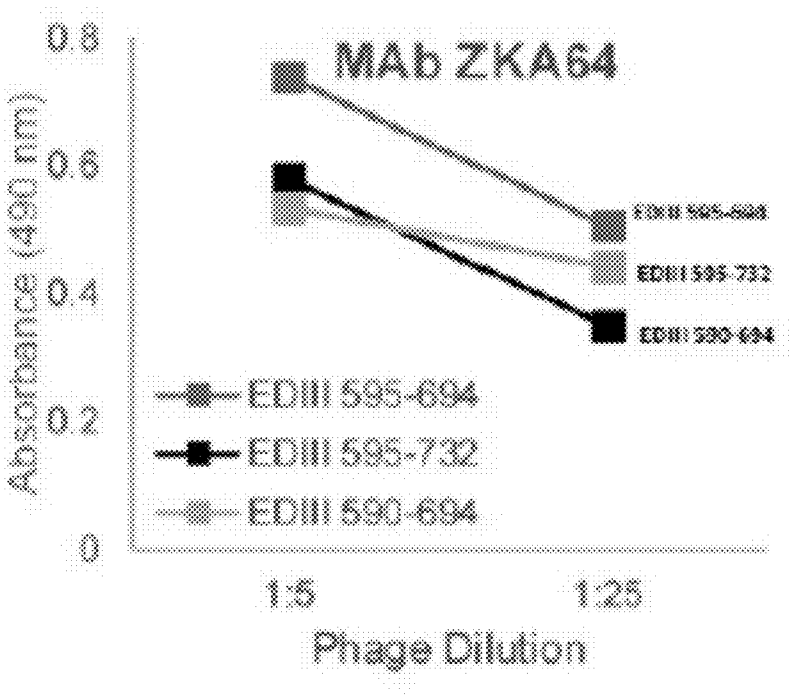
Figure 13C:
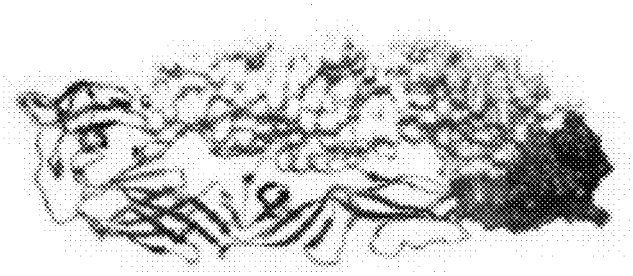

To ascertain that the GFPDL represents both linear and conformational epitopes, two independent experiments were performed. First, the ZIKV-GFPDL was used to map epitopes of a panel of linear and conformation dependent MAbs. GFPDL mapping data is shown for four representative previously described ZIKV-protective MAbs. ZV54 is a ZIKV-specific neutralizing MAb against African, Asian, and American strains to varying degrees. Structurally, it binds the lateral ridge in DIII of the envelope protein similar to MAb ZV67 (Zhao et al., 2016, *Cell,* 166: 1016-1027) (FIG. 10). MAb ZV67 is a cross-reactive neutralizing and protective mouse MAb recognizing a conformational epitope in the lateral ridge of E domain III (Zhao et al., 2016, *Cell,* 166: 1016-1027) (FIG. 11). MAb Z23 is a DENV-negative, ZIKV-specific neutralizing and protective human MAb that recognizes a conformation-dependent tertiary epitope in E domain III; it mainly binds to one envelope protein monomer and can interact with two envelope protein dimers on the virion surface (Wang et al., 2016, *Sci. Transl. Med.,* 18:369ra179) (FIG. 12). MAb ZKA64 is a neutralizing and protective human MAb that recognizes a conformational epitope in E domain III (Stettler et al., 2016, *Science.,* 353: 823-826) (FIG. 13). These MAbs were derived from immune B cells following mouse immunization, or from ZIKV infected survivors (Wang et al., 2016, *Sci. Transl. Med., I*8:369ra179; Stettler et al., 2016, *Science.,* 353: 823-826).

For all four MAbs, strong binding to the ZIKV-GFPDL was observed (FIGS. 10-13). The consensus epitope sequences obtained through GFPDL analysis were very similar to the footprints previously identified for these MAbs (Wang et al., 2016, *Sci. Transl. Med.*, I8:369ra179; Stettler et al., 2016, *Science.,* 353: 823-826; Abbink et al., 2016, *Science.,* 353:1129-1132). The initial binding was confirmed by phage-ELISA using three phages expressing overlapping sequences for each of the MAbs (FIGS. 10B, 11B, 12B and 13B). These results provided proof of concept that the ZIKV-GFPDL approach can identify conformational epitopes recognized by previously described protective ZIKV-E specific MAbs.

Figure 14:
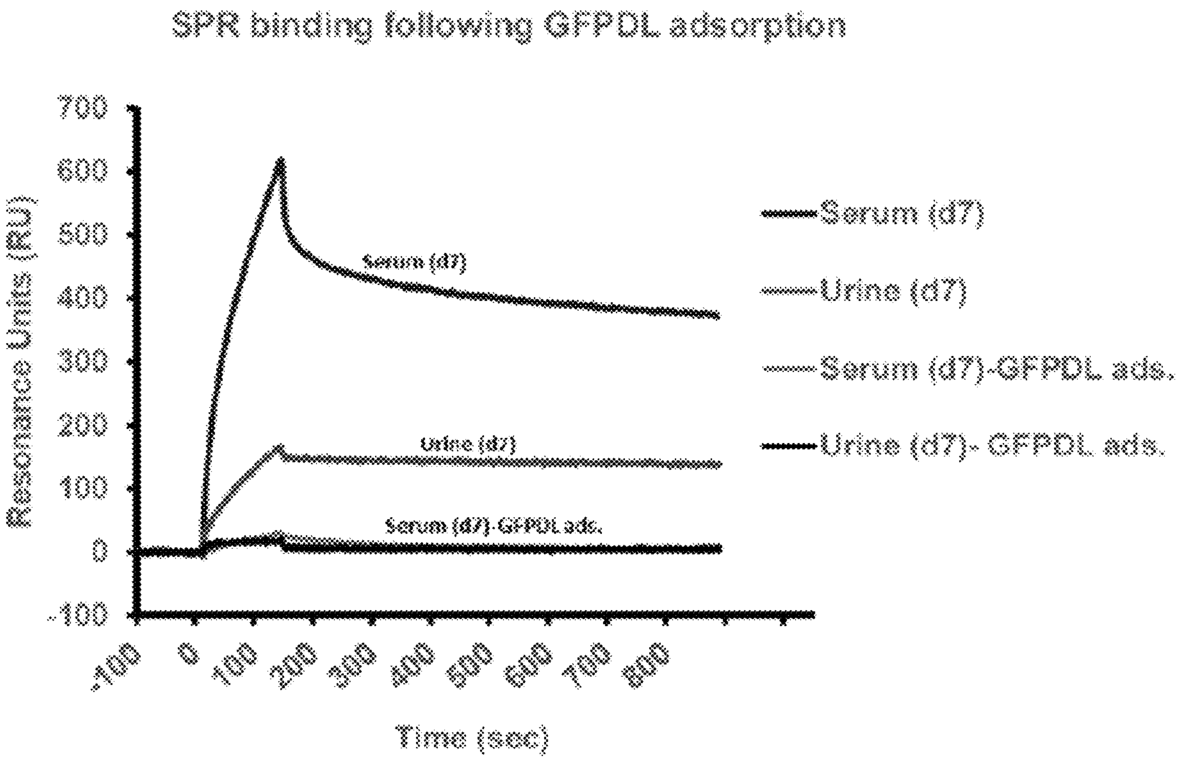
FIG. 14 shows anti-E reactivity of post-infection sera or urine in SPR before and after ZIKV-GFPDL adsorption. Post infection sera or urine at day 7 from individuals was adsorbed on ZIKV-GFPDL coated petri dishes. Binding to recombinant ZIKV-E is shown before and after GFPDL-adsorption in SPR.
Figure 15:
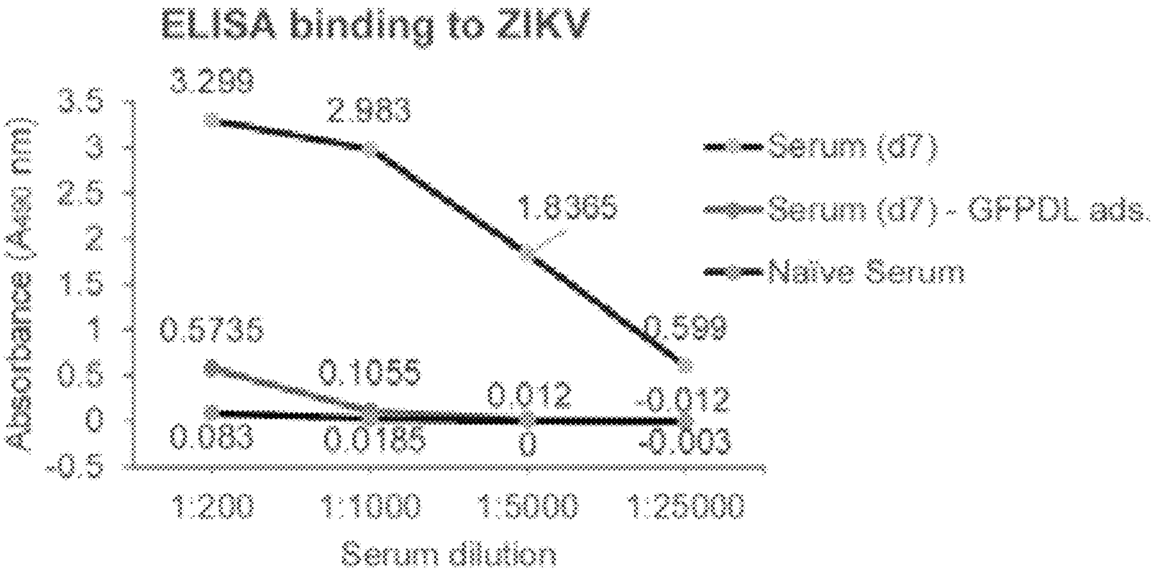
FIG. 15 shows adsorption of anti-ZIKV antibodies in post-infection sera using ZIKV-GFPDL. Post ZIKV infection sera at day 7 (post-onset of symptoms) was adsorbed on ZIKV-GFPDL coated petri dishes. Antibody reactivity to Zika virus coated on polystyrene Immulon 2HB plates is shown before and after GFPDL-adsorption in ELISA was revealed using HRP-conjugated goat anti-human IgA+IgG+IgM specific antibody. All data was normalized to 'virus only' background signal.
Figure 17A:
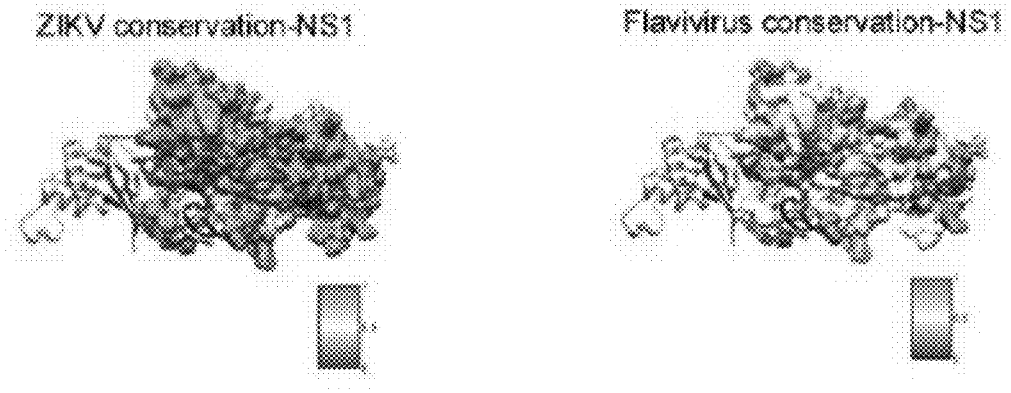
FIGS. 17A-17B show structural representations of antigenic sites identified in ZIKV NS1 protein using GFDPL.
Figure 17B:
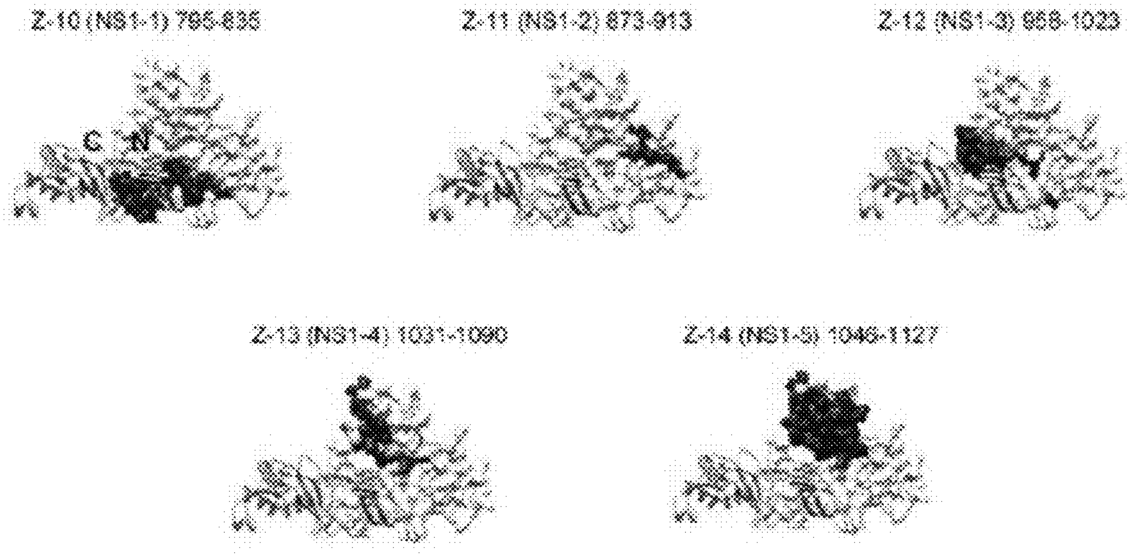
Figure 18A:
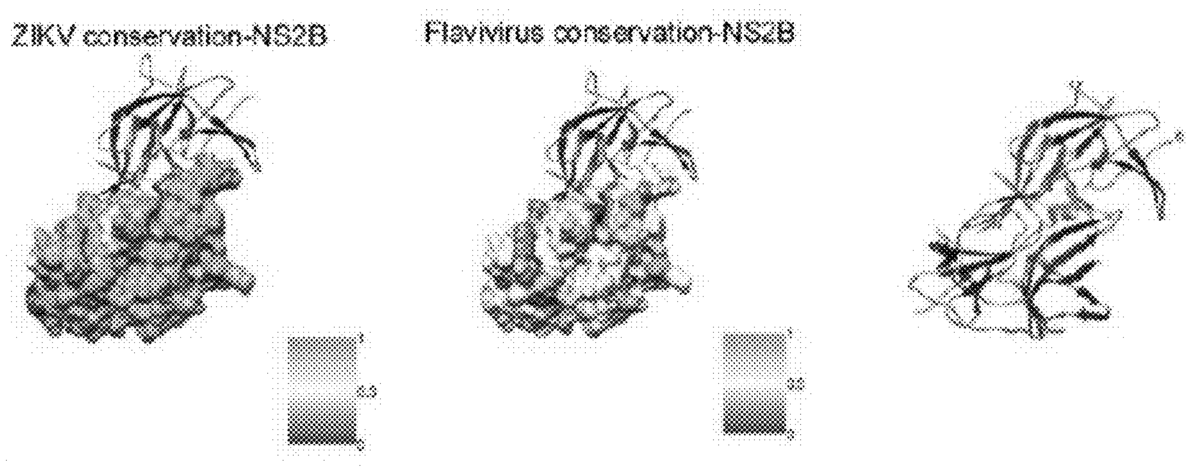
FIGS. 18A-18B show structural representations of antigenic sites identified in ZIKV NS2B protein using GFDPL.
Figure 18B:
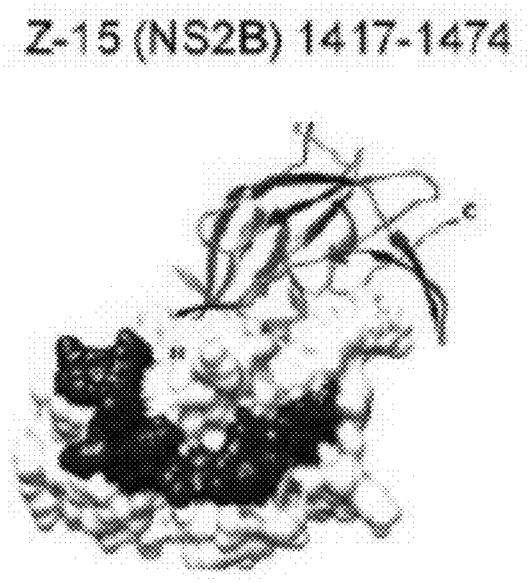
Figure 19A:
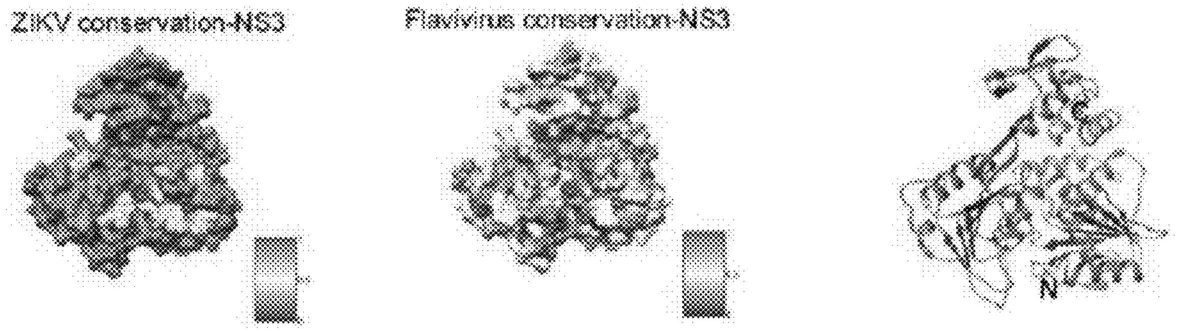
FIGS. 19A-19B show structural representations of antigenic sites identified in ZIKV NS3 protein using GFDPL.
Figure 19B:
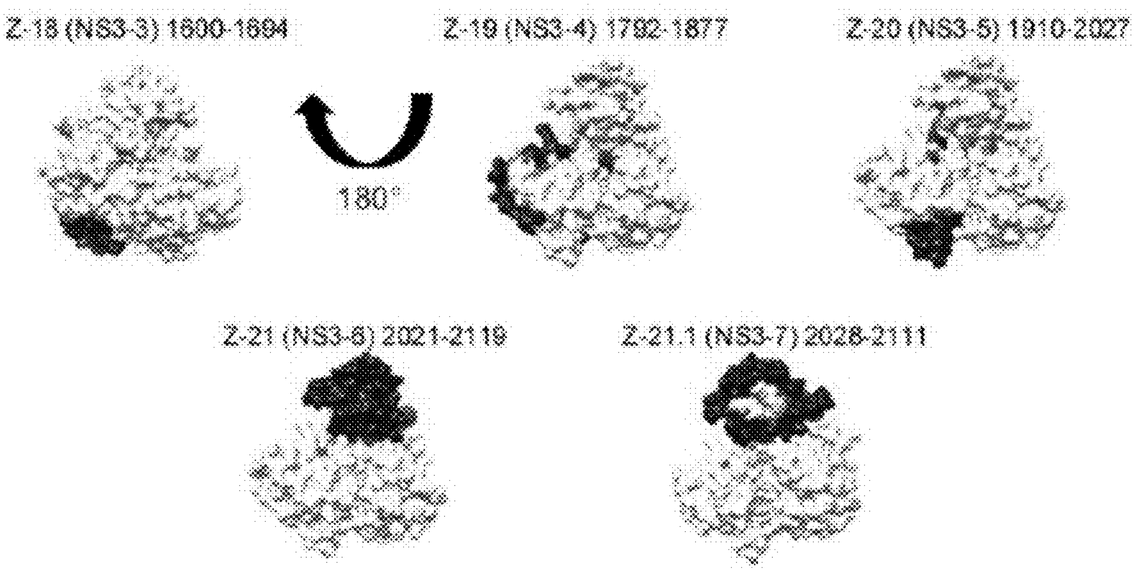

Second, the capacity of a phage display library to adsorb ZIKV-E specific antibodies in the post-ZIKV infected polyclonal human sera and urine was determined. After two rounds of adsorption with the ZIKV-GFPDL, pooled day 7 serum or urine samples demonstrated >90% removal of total anti-ZIKV-E binding antibodies as measured by surface plasmon resonance (FIG. 14). Third, reactivity of the GFPDL-adsorbed sera was evaluated against the ZIKV particles in ELISA, which showed >90% of serum antibodies were adsorbed by the ZIKV-GFPDL (FIG. 15). Together, these studies demonstrated that GFPDL could be used for epitope mapping of post-ZIKV infection polyclonal sera/urine antibody repertoire.

The ZIKV-GFPDL was used for comprehensive analyses of antibody repertoires of blood and urine samples from 5/19 individuals with confirmed acute Zika virus infections in Mexico. For GFPDL analysis, serum (and corresponding urine samples) were pooled from 5 acutely ZIKV infected patients (Table 1). Subjects 41-010-F, 41-017-F, 42-001-F, 42-003-F, and 42-018-F) gave PCR positive results for ZIKV RNA in serum and/or urine on visit 1. They were 1-3 days post onset of symptoms. In ELISA, these patients had low anti-ZIKV reactivity of IgM (O.D. <0.1) and IgG (O.D. <0.4) antibodies that increased in titers on subsequent visits. In all cases, low to moderate reactivity was also observed in dengue virus ELISA, confirming the known cross-reactivity of antibodies between these closely related flaviviruses (Table 1). While none of these 5 subjects reported prior dengue virus infection, the possibility of prior dengue virus exposure cannot be excluded based on the observed ELISA binding results and the high dengue seroprevalence previously reported in the region (Amaya-Larios et al., 2014, *Am. J. Trop. Med. Hyg.,* 91: 1057-1065).

Serum from a flavivirus naïve individual was used as a negative control. This serum bound very few phages of the ZIKV-GFPDL (412 and 103 phages bound by IgM and IgG antibodies, respectively) (FIG. 1A). Sequencing of these bound phage clones showed random distribution across the entire ZIKV genome both for IgM and IgG antibody profile (FIGS. 1B, 1C marked 'Naïve serum').

The pooled sera (day 0 vs. day 7) and urine samples (day 7) from the 5 acutely infected individuals were subjected to panning with the ZIKV-GFPDL (FIG. 1). Both the IgM and IgG antibody epitope repertoires following human ZIKV infection were evaluated. The 2-3 log higher total numbers of bound phages by serum IgM than IgG antibodies observed on days 0 (day of first visit) and 7, and the 1.5-2 log increase in the numbers of bound phages observed on Day 7 compared with Day 0 for both IgM and IgG, confirmed the acute infection status of the study participants (FIG. 1A). Urine samples at day 7 contained IgM that bound large numbers of ZIKV-GFPDL phages. However, very few IgG-bound phages were isolated from the same pooled day 7 urine samples, suggesting predominantly ZIKV-specific IgM antibodies in the urine (FIG. 1A).

Figure 2B:
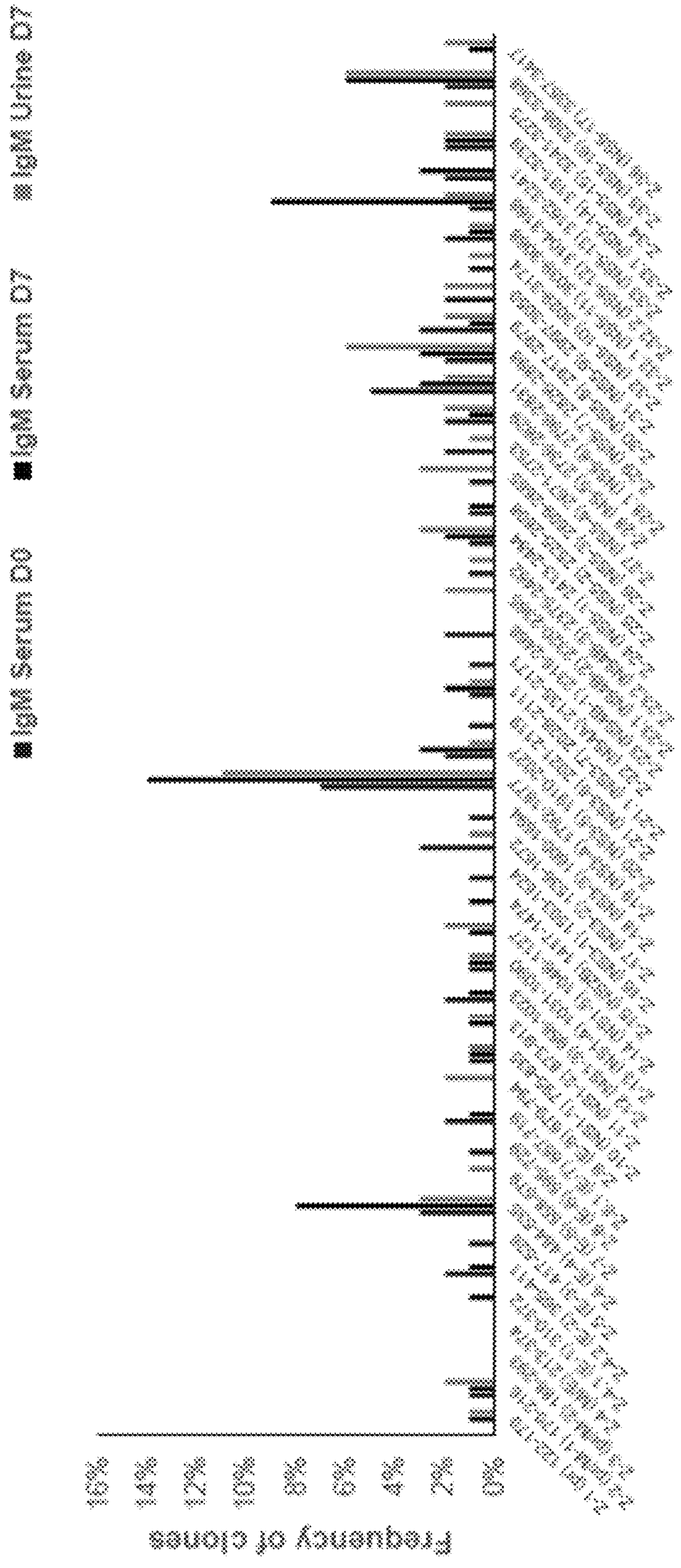

The inserts of the bound phages were sequenced and mapped against the ZIKV genome (FIG. 1B). Overall, 36 antigenic sites were recognized by the IgM antibodies in the serum and urine of the acutely infected individuals (FIG. 2A). At study day 0, serum IgM antibodies recognized a very diverse array of inserts spanning the entire ZIKV genome except for NS2A. The capsid region was only minimally recognized (multiple phages bound but with frequency of 1 for each unique peptide). The relative frequencies of bound phages expressing different inserts are presented in Table 3. By day 7, a significant immune focusing was observed for IgM antibodies with increased binding to antigenic sites in the E (Site Z-6; aa 484-535; 8%), NS3 (Site Z-19; aa 1792-1877; 14%), and NS5 (Site Z-33; aa 3194-3168; 9% & Site Z-35; aa 3308-3368; 6%) (FIG. 1B, FIG. 2B). The distribution of inserts recognized by urine IgM antibodies (from day 7 visit) was similar to the binding pattern of the serum IgM antibodies with predominant binding to the antigenic sites in NS3, but not similar in NS5 (FIG. 1B, FIG. 2B and Table 3).

Figure 2C:
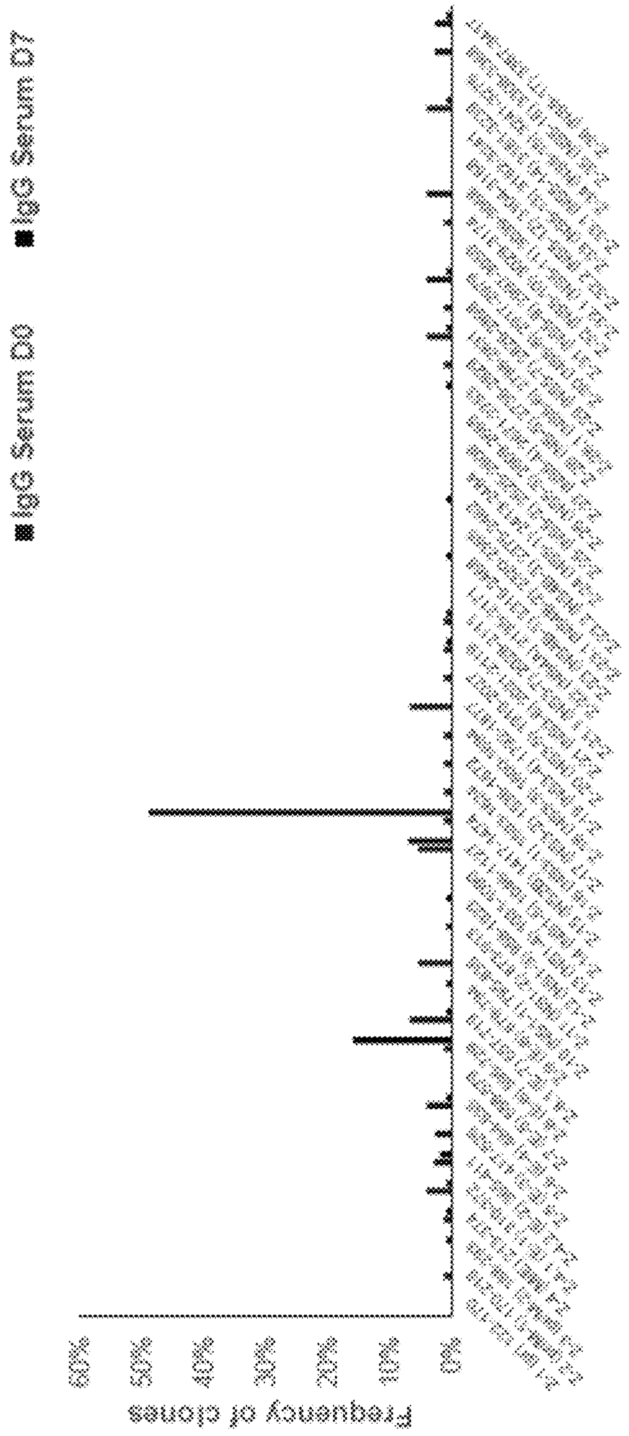

The IgG response in sera on day 0 post-onset was much more limited compared with the IgM response (2 logs fewer bound phages). The IgG antibodies showed binding to diverse antigenic sites mostly in the structural proteins (prM/E) and non-structural proteins NS3 and NS5, but no immunodominant (clonal frequency >10%) IgG antigenic site (FIG. 1C and FIG. 2C). However, by day 7, the IgG antibodies in the serum from the same individuals demonstrated pronounced immune focusing to several antigenic sites in E (Z-8; aa 595-729; 16%), NS1 (Z-14; aa 1046-1127; 7%) and NS2B (Z-15; aa 1417-1474; 49%) (FIG. 1C, FIG. 2C and Table 3). These data suggested early expansion of IgM and isotype-switched IgG B cells recognizing different ZIKV proteins following acute Zika virus infection. Minimal ZIKV-specific IgG antibodies were observed in the urine samples from the same individuals at day 7.

Subsequently, additional IgM and IgG antibody epitope repertoire analysis was performed with a serum sample of an acutely ZIKV-infected individual (Patient #42-001-F) at day 7 visit (day 7 since onset of symptoms) to define the fine epitope specificity in an individual. This individual was part of the 5 pooled samples used for GFPDL analysis in FIGS. 1 and 2. The epitopes recognized by IgM and IgG antibodies identified similar pattern to the pooled samples (FIG. 16). Again, the IgG bound epitopes were more focused than the IgM repertoire, with immunodominance of NS2B and E antibody specificities.

Antigenic Sites Identified by GFPDL Following ZIKV Infection are Largely Exposed on the Surface of Zika Virus Proteins.

Figure 3A:
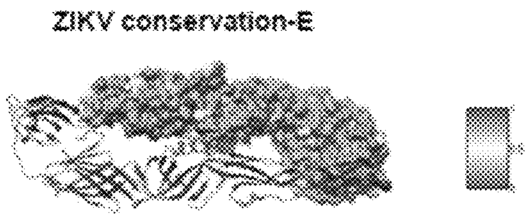
FIGS. 3A-3B show structural representations of antigenic sites identified in ZIKV E protein using GFDPL.
Figure 3B:
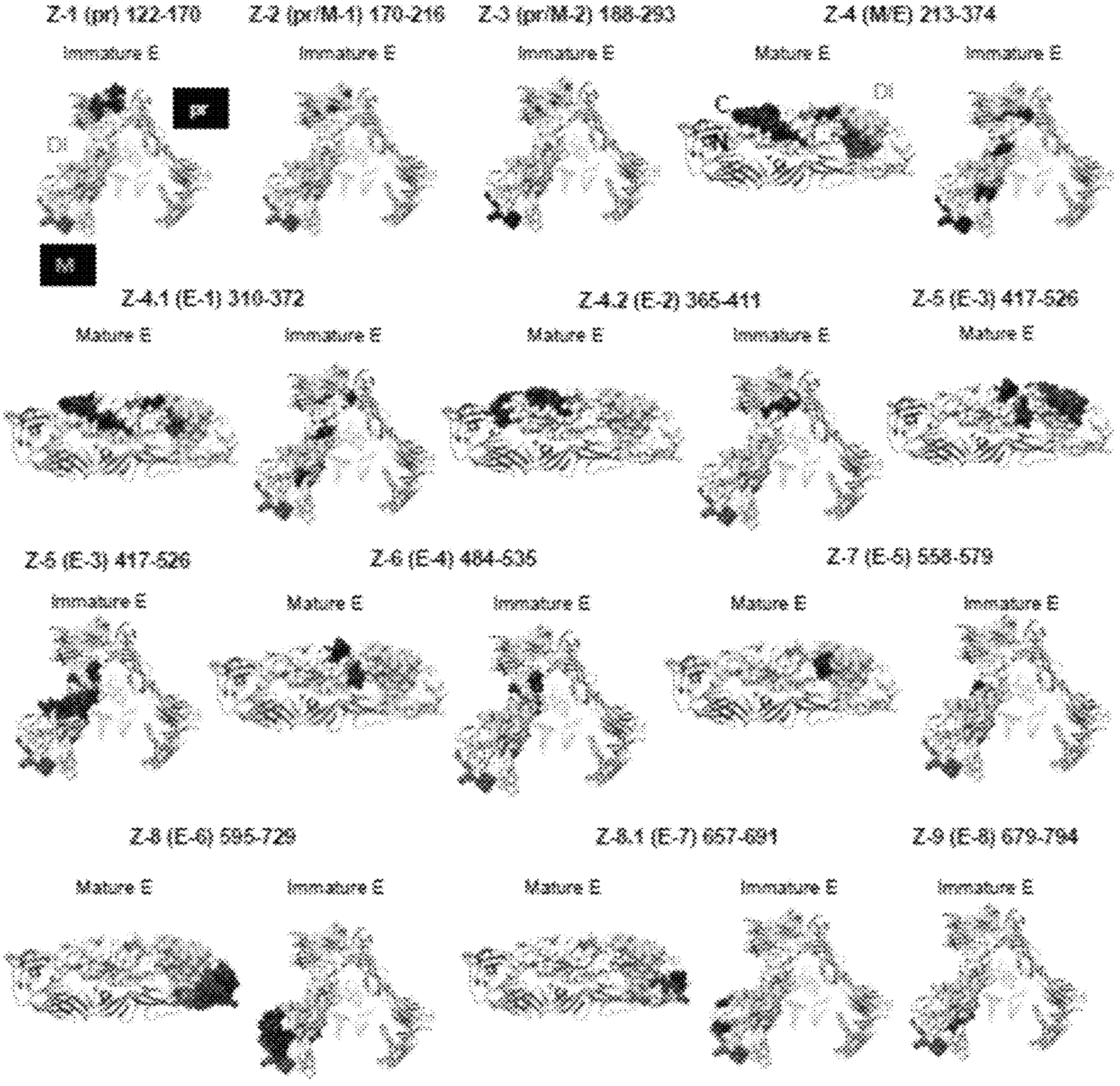
Figure 20A:
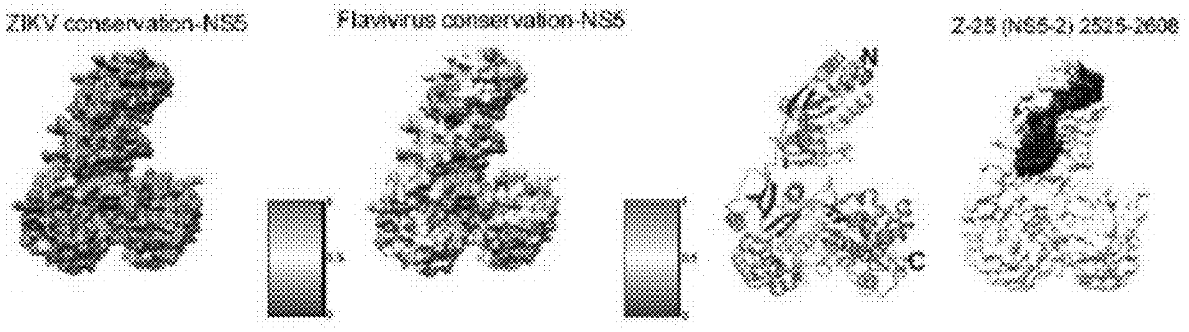
FIGS. 20A-20B show structural representations of antigenic sites identified in ZIKV NS5 protein using GFDPL.
Figure 20B:

It was important to determine whether the epitopes recognized by the ZIKV post-infection serum and urine antibodies, as identified by the GFPDL panning, are likely to be exposed on the surface of the viral proteins expressed on virions or in infected cells. This could be done for proteins for which the structures are available in the ZIKV database: mature and immature E (FIG. 3), NS1 (FIG. 17), NS2B (FIG. 18), NS3 (FIG. 19) and NS5 (FIG. 20). In addition to surface mapping of the antigenic sites on the protein structures, heat maps showing the protein sequence conservation for each antigenic site, either among Zika virus strains or between Zika virus and other flaviviruses are presented (FIGS. 3A, 17A, 18A, 19A and 20A). The majority of antigenic sites identified by GFPDL were found to be expressed on the surface of the individual proteins, while some antigenic sites were only partially exposed (FIGS. 3B, 17B, 18B, 19B and 20B). The GFPDL analyses identified many antigenic sites spanning prM-E (FIGS. 1 and 2 and Table 3). These epitopes were mapped on the crystal structures of ZIKV immature or mature forms of the prM and E protein (FIG. 3B).

Conservation of Antigenic Sites with ZIKV Strains and Other Flaviviruses

Figure 21A:
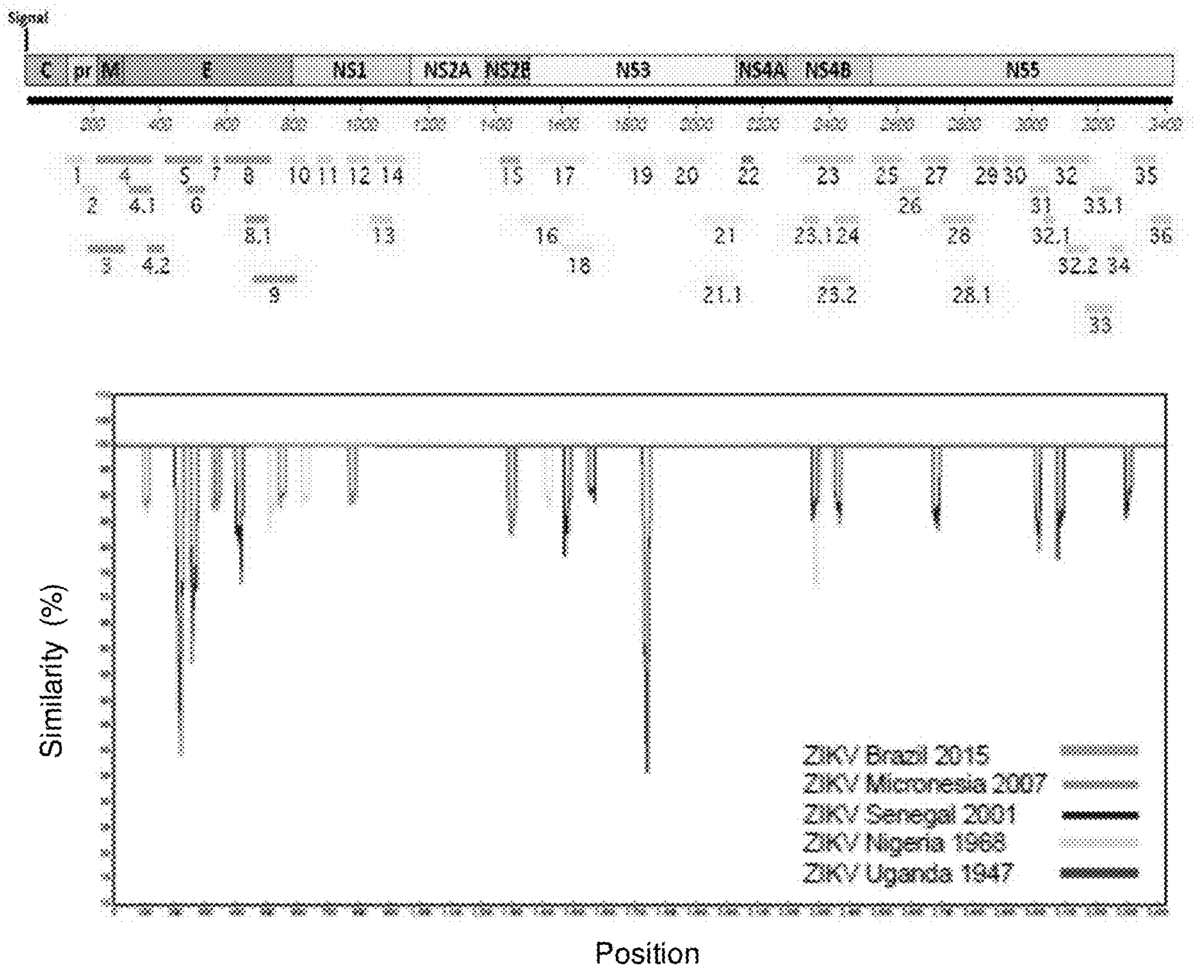
FIGS. 21A-21B show percent similarity between different ZIKV strains and flaviviruses.
Figure 21B:
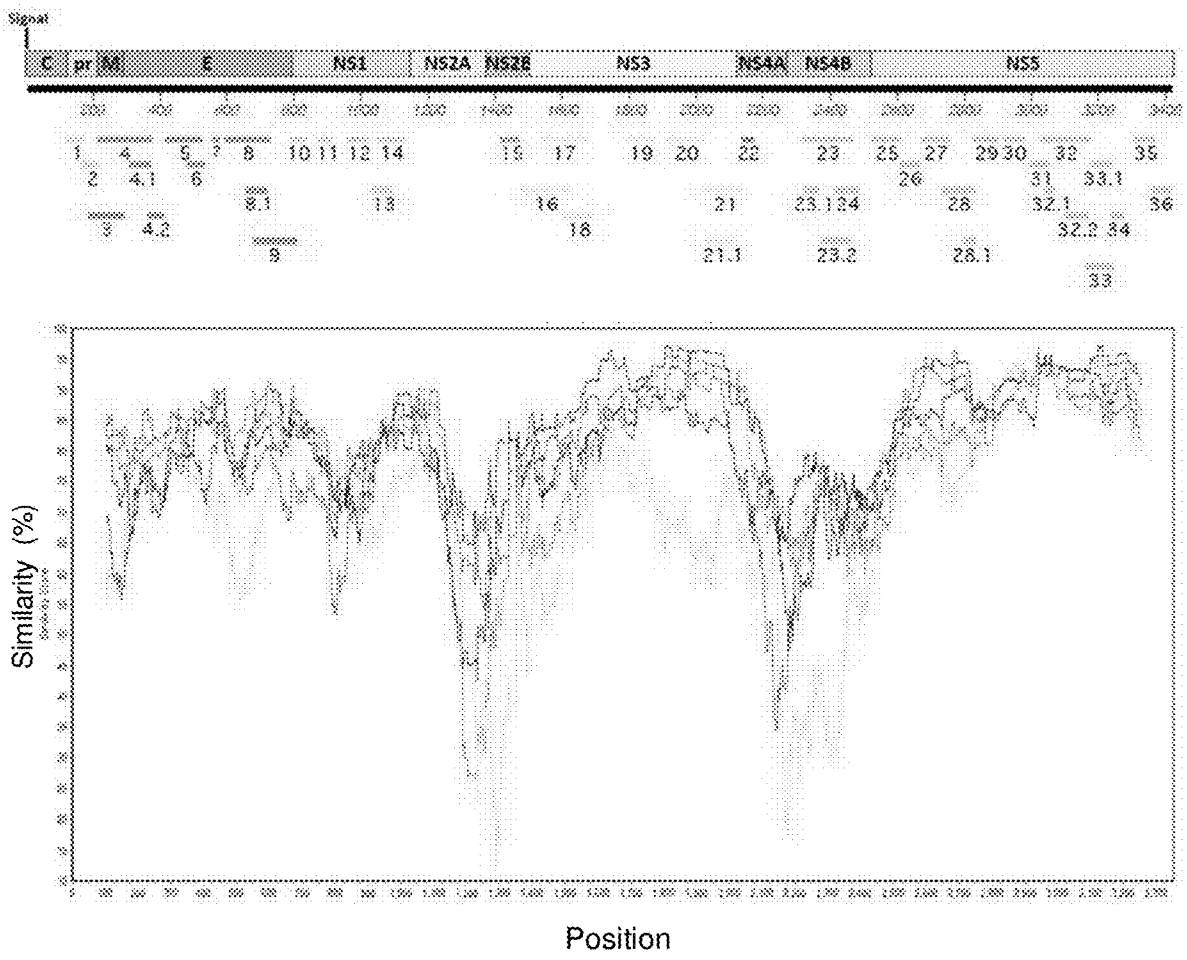
Figure 22:
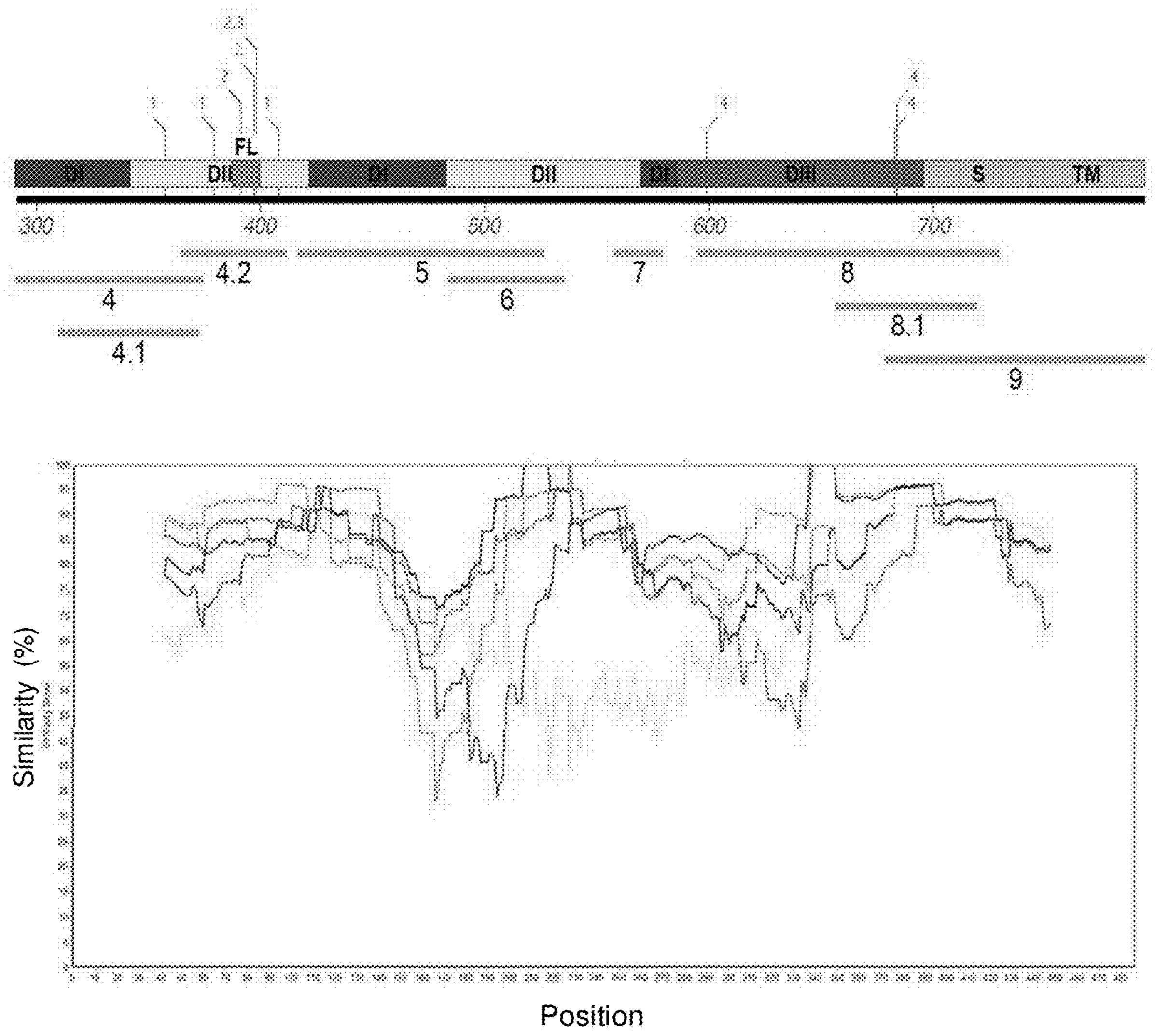
FIG. 22 shows a similarity plot of envelope (E) protein sequences of different flaviviruses. For generating the plot, ZIKV_Paraiba strain was used as the query sequence to obtain the percent similarity of various domains of E protein of different flaviviruses to the ZIKV E. Highest conservation was seen near the fusion loop region while the lowest was seen around domain I (Antigenic sites 5, 6 and 7) showing potential specificity to ZIKV E protein. A sliding window size of 80 bp and a step size of 1 bp was used to generate the plot.

Prior exposure to other flaviviruses may play a role in the observed antibody responses to Zika virus infection. The % similarity among all sequences of old and new Zika virus strains (FIG. 18A), and % similarity between flaviviruses (DENV 1-4, YFV, and WNV) (FIG. 18B) was plotted. In both cases, the sequence of ZIKV_Paraiba strain was used as a reference comparator sequence (considered as 100%). In general, the Zika virus sequences from strains isolated between 1947 and 2015 in diverse geographical areas are highly conserved (FIG. 21A), but conservation between ZIKV and other flaviviruses (DENV 1-4, WNV, and YFV) for these sites is highly variable (FIG. 3A, FIG. 21B and Table 4). Within the ZIKV-E protein, the GFPDL analysis identified IgM and IgG antibody binding to multiple domains including a large antigenic site mapping to Domain III (Z-8/Z-8.1 in FIG. 2A, FIG. 3B). Domain III of ZIKV is divergent compared with other flavivirus E proteins (FIG. 19). Among ZIKV strains, sites of modest variability were identified in the prM, and domains I and II of the E protein covered by antigenic sites Z-3 to Z-6 in the GFPDL analysis, while E-Domain III antigenic sites (Z-8, Z-8.1 and Z-9) and NS1 antigenic sites (Z-10 to Z-14) are highly conserved (FIG. 21A). Most of the antigenic sites recognized by the IgM and IgG antibodies in the serum or urine post-ZIKV infection that mapped to the ZIKV non-structural proteins were highly conserved within the Zika virus strains (FIG. 21A), however, different levels of sequence conservation were observed with other flaviviruses (Z-10 to Z-36) (Table 4). The NS3 contains a single site of variability, which was not covered by any of the antigenic sites identified by either the IgM or IgG antibodies in the GFPDL analysis (FIG. 2A and FIG. 14A). When comparing ZIKV sequence with all the other flaviviruses, much larger sequence diversity scores were found in regions spanning E-domain I (Z-5), E-domain III (Z-8, Z-9), NS1 (Z-10 and Z-11), NS2B (Z-15), NS4A (Z-22), NS4B (Z-23-24) and NS5 (Z-28) (Table 4, FIGS. 21B and 22). The yellow fever viral genome was the most divergent of all the flaviviruses. Several sequences in the non-structural proteins (NS1, NS2B, NS3, NS4B, and NS5) recognized at high frequencies by the IgM and IgG antibodies in the serum or urine post-ZIKV infection and were highly conserved among different ZIKV strains could potentially be used for serodiagnosis of ZIKV infection (FIG. 21 and Table 4). Therefore, the antigenic sites identified by post-infection serum (IgM/IgG) and urine (IgM) spanned both sites of high conservation and several sites of divergence compared with other flaviviruses.

The GFPDL analysis revealed highly diverse antibody repertoires in serum and urine samples from ZIKV-infected individuals that bound to multiple non-structural genes (except NS2A) in addition to prM/E. Differential antibody binding profiles were observed for IgM and IgG antibodies following ZIKV infection and immune focusing of the antibody repertoire was observed on day 7 compared with day 0.

Serodiagnostic Potential of GFPDL Selected Antigenic Site Peptides

Figure 4A:
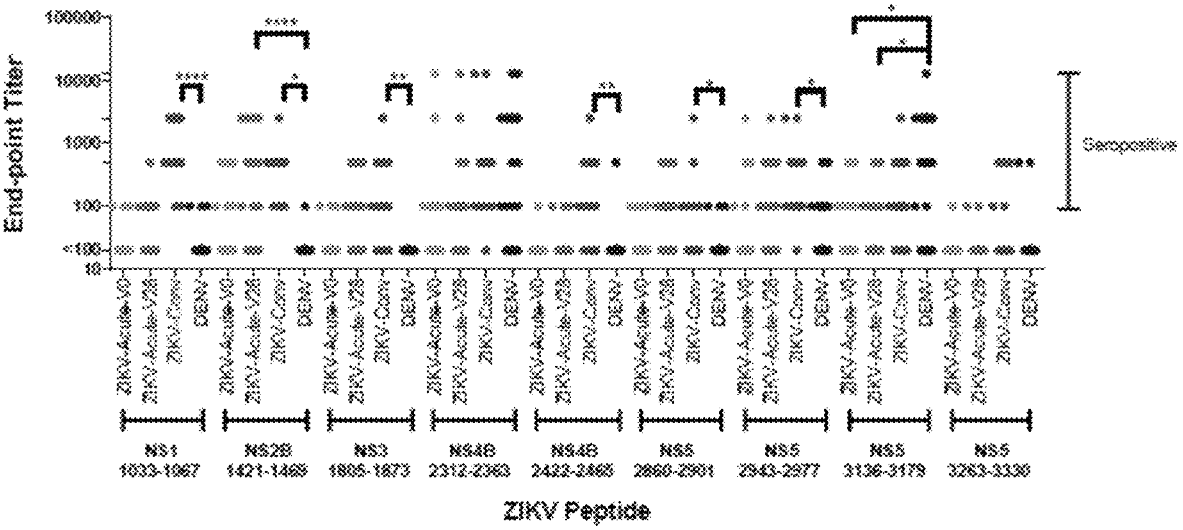

For further evaluation of diagnostic potential of the newly identified ZIKV antigenic sites, sequences in the non-structural proteins (NS1, NS2B, NS3, NS4B, and NS5) recognized at high frequencies by the IgM and IgG antibodies in the serum or urine post-ZIKV infection and were highly conserved among different ZIKV strains were selected (FIG. 18 and Table 4). Representative peptides spanning these selected antigenic sites were synthesized and tested with individual acute-ZIKV infected, convalescent ZIKV, and convalescent DENV infected serum samples in ELISA (FIG. 4). Most acute ZIKV infected serum reacted with NS2B peptide (Z-15) at least once, either at day 0 or day 28 (17/19 were seropositive at least once on either day; 6/19 and 15/19 with end-point titers ≥1:00, respectively). NS2B peptide also showed high reactivity (13/13) with all ZIKV convalescent sera in ELISA (FIGS. 4A-4B). Only 1/27 convalescent sera from DENV infected individuals reacted weakly (end-point tier of 100) with the NS2B peptide, demonstrating ZIKV antibody specificity for this peptide sequence. Peptides from NS1 (1033-1067 within Z-13), NS3 (1805-1873 within Z-19), ZIKV-NS4B (2422-2465 within Z-24), ZIKV-NS5 (2860-2901 representing Z-29), showed variable reactivity (50-76%) with the acutely ZIKV infected samples, moderate reactivity to ZIKV convalescent samples, and minimal or no reactivity to DENV infected samples (FIGS. 4A-4B). The ZIKV-NS5-3263-3330 peptide showed weak reactivity to a few (7-38%) convalescent ZIKV and DENV infected samples. The peptides ZIKV-NS4B-2312-2363 (overlapping Z-23.1), ZIKV-NS5-2943-2977 (within Z-30) and ZIKV-NS5-3136-3179 (overlapping Z-32.2) all showed weak/moderate reactivity with acute ZIKV infected samples (68-76%), but similar reactivity to convalescent sera from ZIKV and DENV infected individuals (60-92%), reflecting the higher degree of antigenic conservation in these peptide sequences among these flaviviruses (FIGS. 4A-4B). Some of these cross-reactive peptides can be used for serodiagnosis of multiple flaviviruses.

Measurements of Real-Time Antibody Kinetics of Polyclonal Antibody Binding to ZIKV-E Ectodomain, Domain III, and NS1 in Individual Post-Infection Serum and Urine Samples Using Surface Plasmon Resonance (SPR)

Figure 5A:
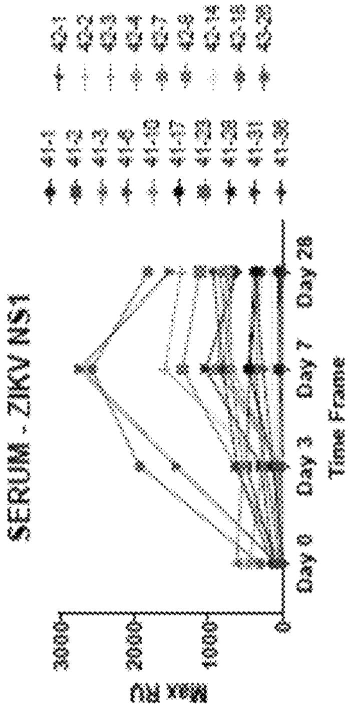
FIGS. 5A-5F are graphs showing the binding of polyclonal antibodies in human sera and urine from post-ZIKV infected individuals to NS1, ZIKV-E, and ZIKV-E domain III purified proteins using surface plasmon resonance (SPR). Serum (FIGS. 5A, 5C, 5D) and urine (FIGS. 5B, 5D, 5F) samples collected at different time points from adults post-ZIKV infection (Days 0, 3, 7 and 28) were analyzed for total binding to purified NS1 (FIGS. 5A-5B), ZIKV-E (FIGS. 5C-5D) and ZIKV-E-domain III (FIGS. 5E-5F) proteins. Total antibody binding is represented in SPR resonance units (RU). Maximum resonance unit (Max RU) values for protein binding by serum or urine antibodies obtained from each individual at different time points post-ZIKV exposure are linked by connecting lines.
Figure 5B:
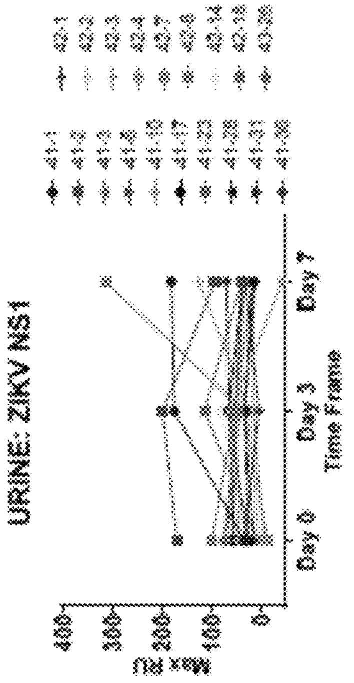
Figure 5D:
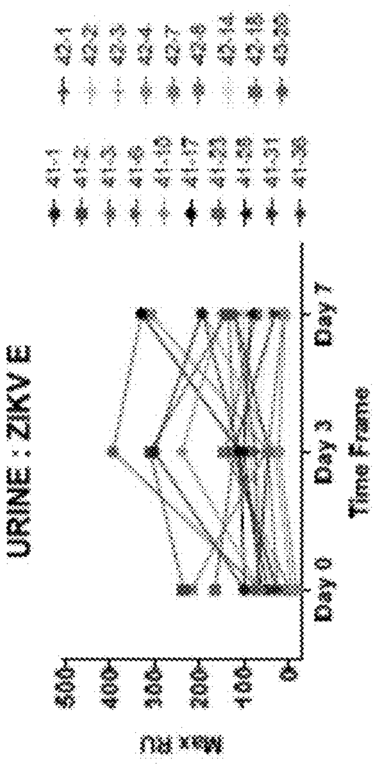

The evolution of antibody binding kinetics in serum and urine samples of each ZIKV-infected individual against the structural and non-structural proteins of ZIKV was performed using SPR-based real-time kinetics assay. The ZIKV Envelope (E) protein is an important target for vaccine development, while NS1 is important for ZIKV diagnosis (Larocca et al., 2016*, Nature.,* 536: 474-476). Therefore, ZIKV E-ectodomain, E-domain III and NS1 proteins were used for the SPR analysis of serum and urine samples from day 0, day 3, day 7 and day 28 visits from ZIKV-infected individuals (FIG. 5). Serum antibody binding to NS1 was variable. For the majority of patients, the total binding (Max RU) started to increase on day 3, peaked on day 7, and either plateaued or started to drop by day 28 visit (FIG. 5A). However, 11% (2/19) of ZIKV-infected individuals did not show significant serum antibody binding (Max RU<20) to NS1 protein following ZIKV exposure. Urine samples from all subjects showed very low NS1 antibody binding on all days, with only 4 post-infection samples binding (Max RU >20) on day 3 or 7 (FIG. 5B).

Figure 5C:
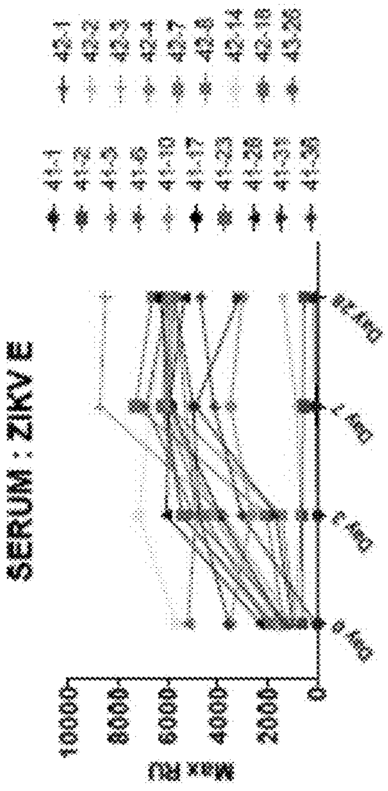
Figure 5F:
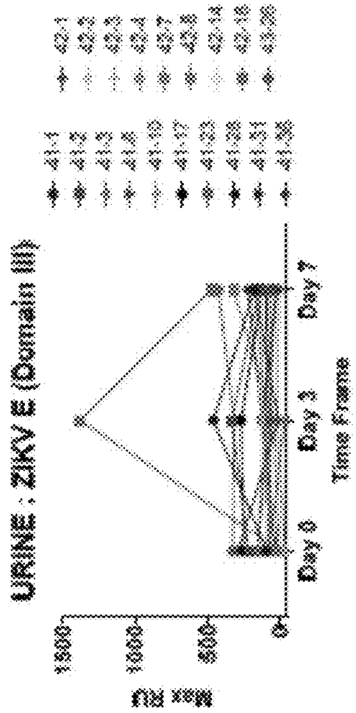
Figure 5E:
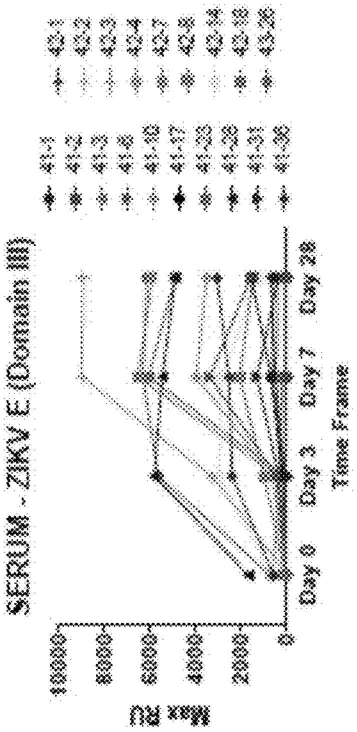

In contrast to NS1, serum antibody binding to the E-ectodomain and to E-domain III was more robust following ZIKV infection, peaking either on day 3 or day 7 visits (day 3 to day 12 post-onset of symptoms) and were largely maintained until day 28 with a moderate decline in few individuals (FIGS. 5C, 5E). The total serum antibody binding to either E-ectodomain or Domain III was about 3-fold higher compared with the antibody binding to NS1 However, 16% (3/19) of ZIKV-infected individuals did not show significant serum antibody binding (Max RU<20) to either the E or domain III proteins following ZIKV exposure. Two of the three ZIKV-E non-responsive individuals were the same individuals that did not show reactivity to NS1 protein (samples 41-2 and 42-2), and the third individual had very low NS1 binding (sample 41-3). These three individuals gave positive reactivity in the commercial ZIKV-ELISA at the first visit but did not show increase in either IgG or IgM binding titers on subsequent visits (Table 1). Only one of these individuals (42-2) acknowledged prior dengue virus infection (Table 1). However, the possibility that these individuals developed some antibodies to quaternary epitopes in ZIKV-E, E-domain III, or NS1 that were not captured by the SPR binding assay cannot be excluded.

Antibody binding of urine samples to E-proteins was generally much lower compared with the serum antibody binding, and there was no direct correlation between reactivity of serum and urine antibodies in SPR. These data demonstrates that not all ZIKV infections lead to seroconversion, which could lead to underestimation of exposure rates in antibody-based serodiagnostic tests.

Figure 6B:
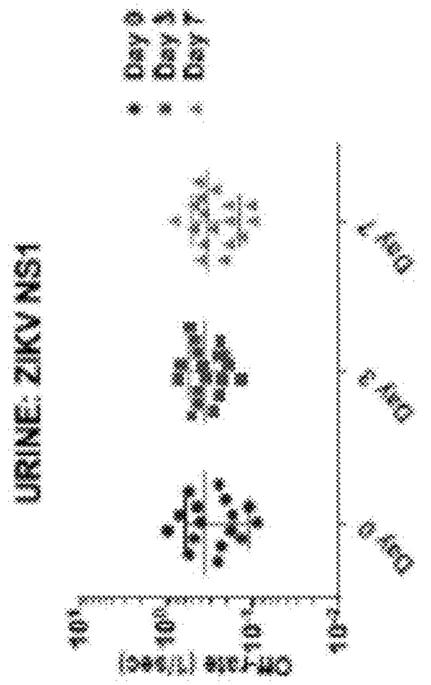
FIGS. 6A-6F show the antibody affinity maturation of polyclonal human sera and urine antibodies to NS1, ZIKV-E, and ZIKV-E domain III proteins following ZIKV infection. SPR analysis of individual sera (FIGS. 6A, 6C, 6E) or urine (FIGS. 6B, 6D, 6F) samples post-ZIKV infection was performed with purified recombinant NS1 (FIGS. 6A-6B), ZIKV-E (FIGS. 6C-6D) and ZIKV-E domain III (FIGS. 6E-6F) proteins to determine the dissociation kinetics (off-rates) at different time points post-infection. Antibody off-rate constants that describe the fraction of antibody-antigen complexes decaying per second were determined directly from the serum/urine sample interaction with recombinant NS1, ZIKV-E, and ZIKV-E domain III proteins using SPR in the dissociation phase. Average values are indicated by the horizontal bar for each group. The statistical significances between each time-point (visit days) were determined using two-tailed paired t-test in GraphPad software. p-values less than 0.05 were considered significant with a 95% confidence interval. Statistically significant with p-values of <0.05 (*), <0.005 (), or <0.001 (*) are shown.
Figure 6A:
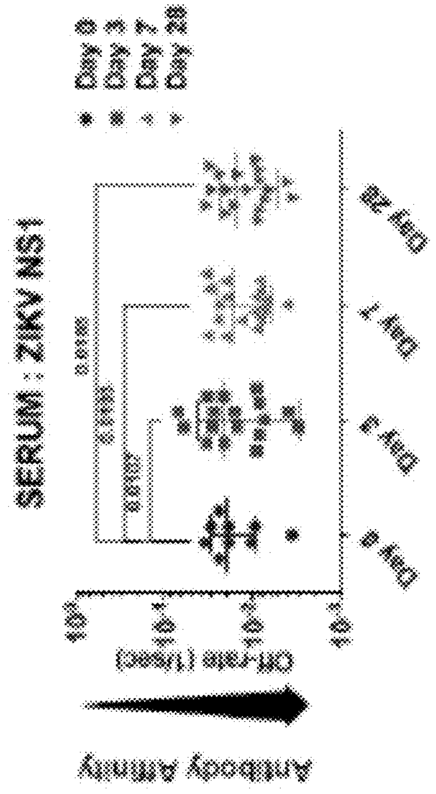
Figure 6C:
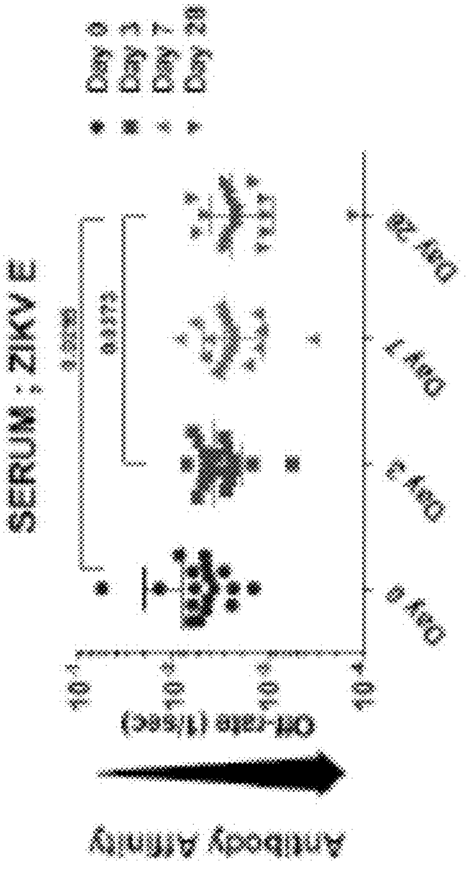
Figure 6D:
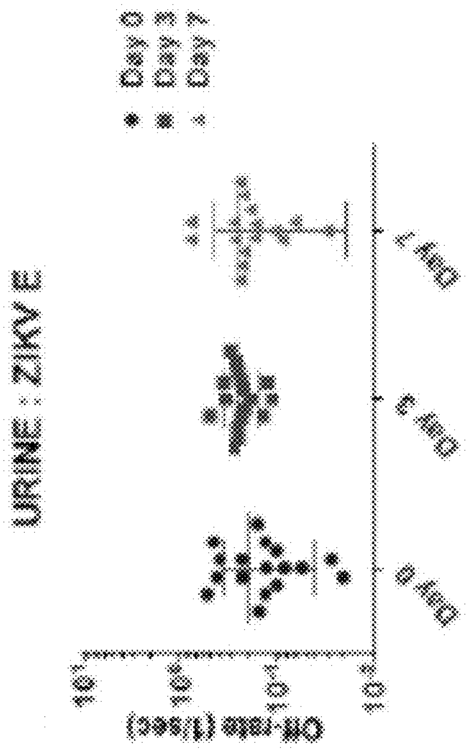
Figure 6F:
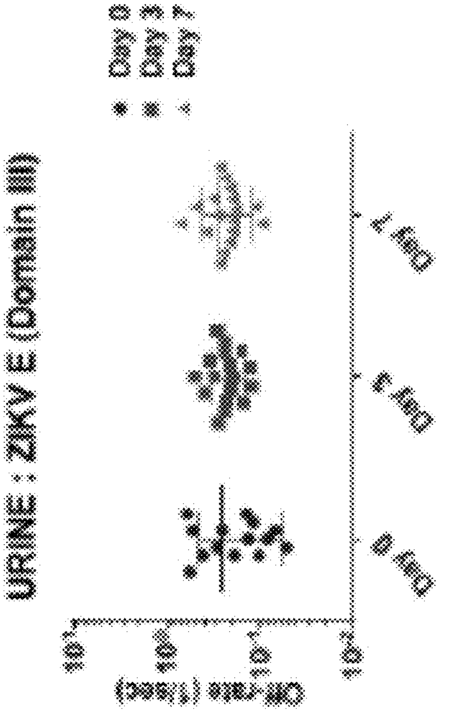
Figure 6E:
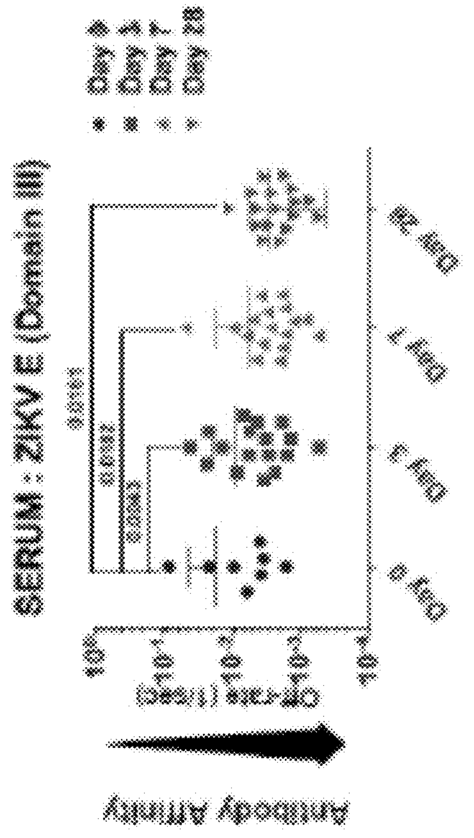
Figure 23A:
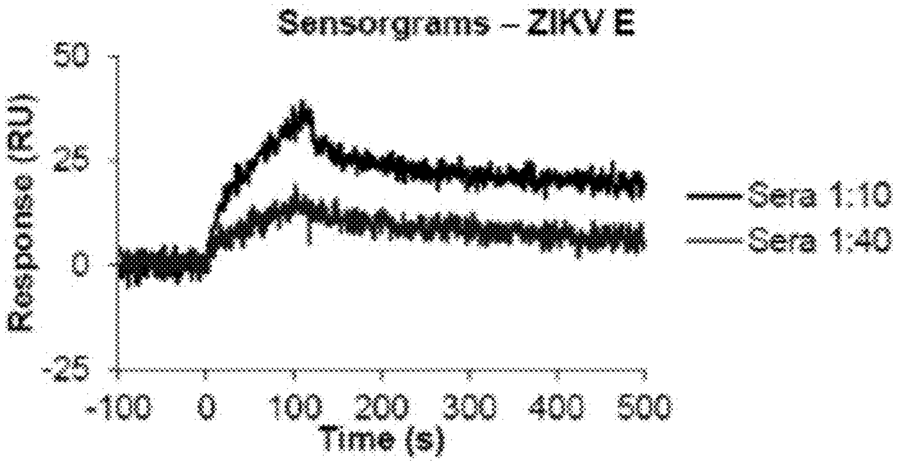
FIGS. 23A-23B show steady-state equilibrium analysis of different dilutions of post-infection sera to ZIKV-E and NS1 protein by SPR. Serial dilutions of post-infection sera were injected simultaneously onto either ZIKV-E (FIG. 23A) or NS1 (FIG. 23B) protein immobilized on a GLC sensor chip and on a surface free of protein (used as a blank). Binding was recorded using BioRad Proteon surface plasmon resonance biosensor instrument. Responses from the protein surface were corrected for the response from the mock surface and for responses from a separate, buffer only injection. Antibody off-rate constants, which describe the fraction of antigen-antibody complexes that decay per second, were determined directly from the serum sample interaction with ZIKV-E using SPR in the dissociation phase only for the sensorgrams with Max RU in the range of 10-100 RU (shown here for 10× and 40× fold dilution of sera) and calculated using the BioRad ProteOn manager software for the heterogeneous sample model.
Figure 23B:
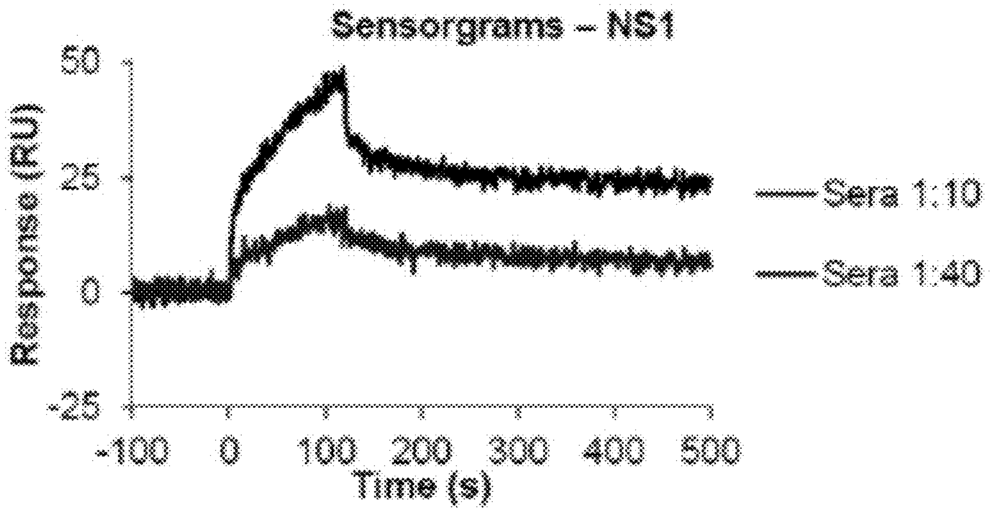
Figure 24A:
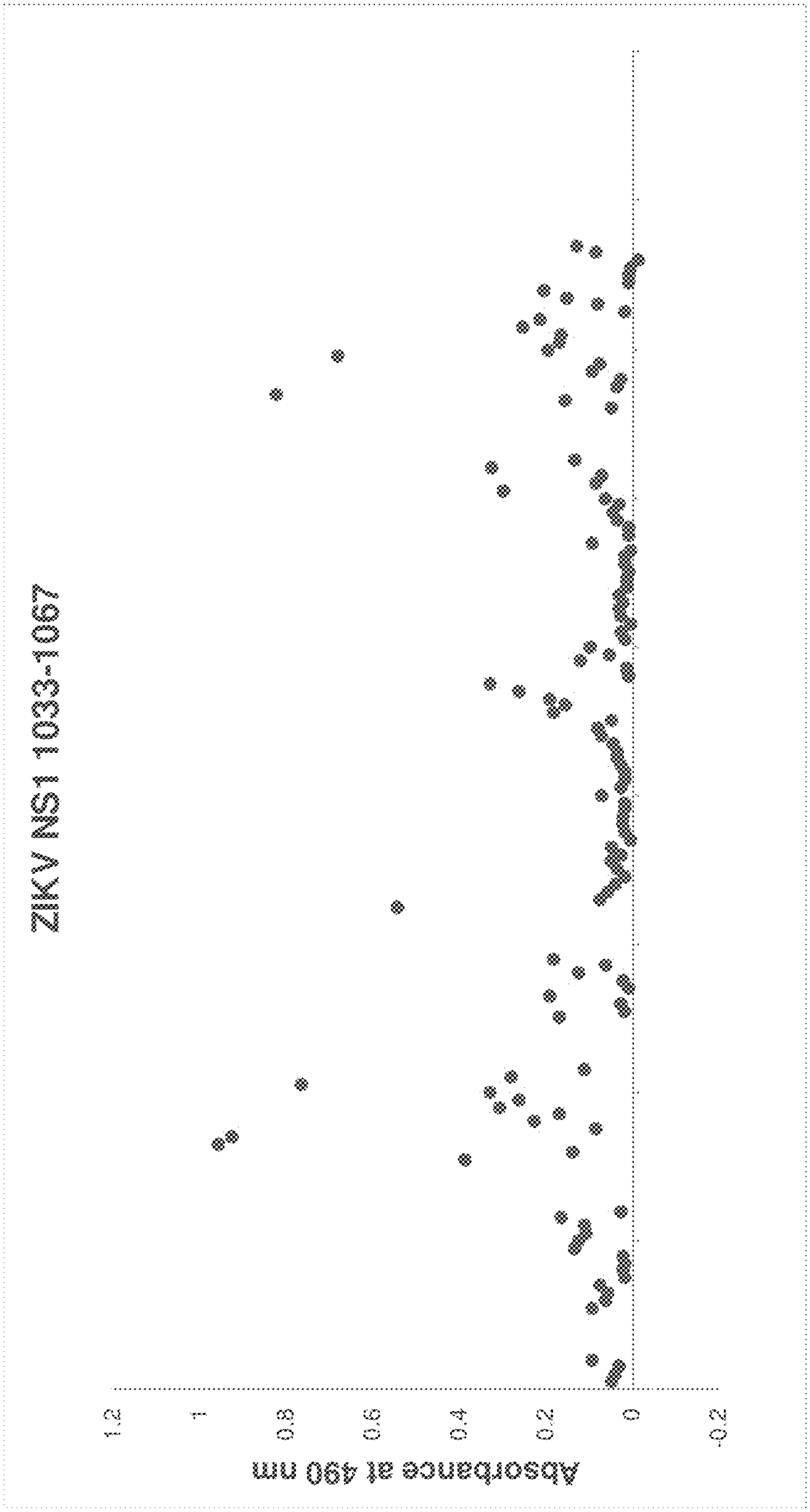
FIGS. 24A-24J are graphs showing seroreactivity of human samples with ZIKV antigenic site peptides. Acute, convalescent (Conv) and late stage ZIKV-infected, DENV seropositive and influenza virus seropositive human sera and plasma samples were tested for binding to individual ZIKV peptides or combinations of three ZIKV peptides by ELISA.
Figure 24B:
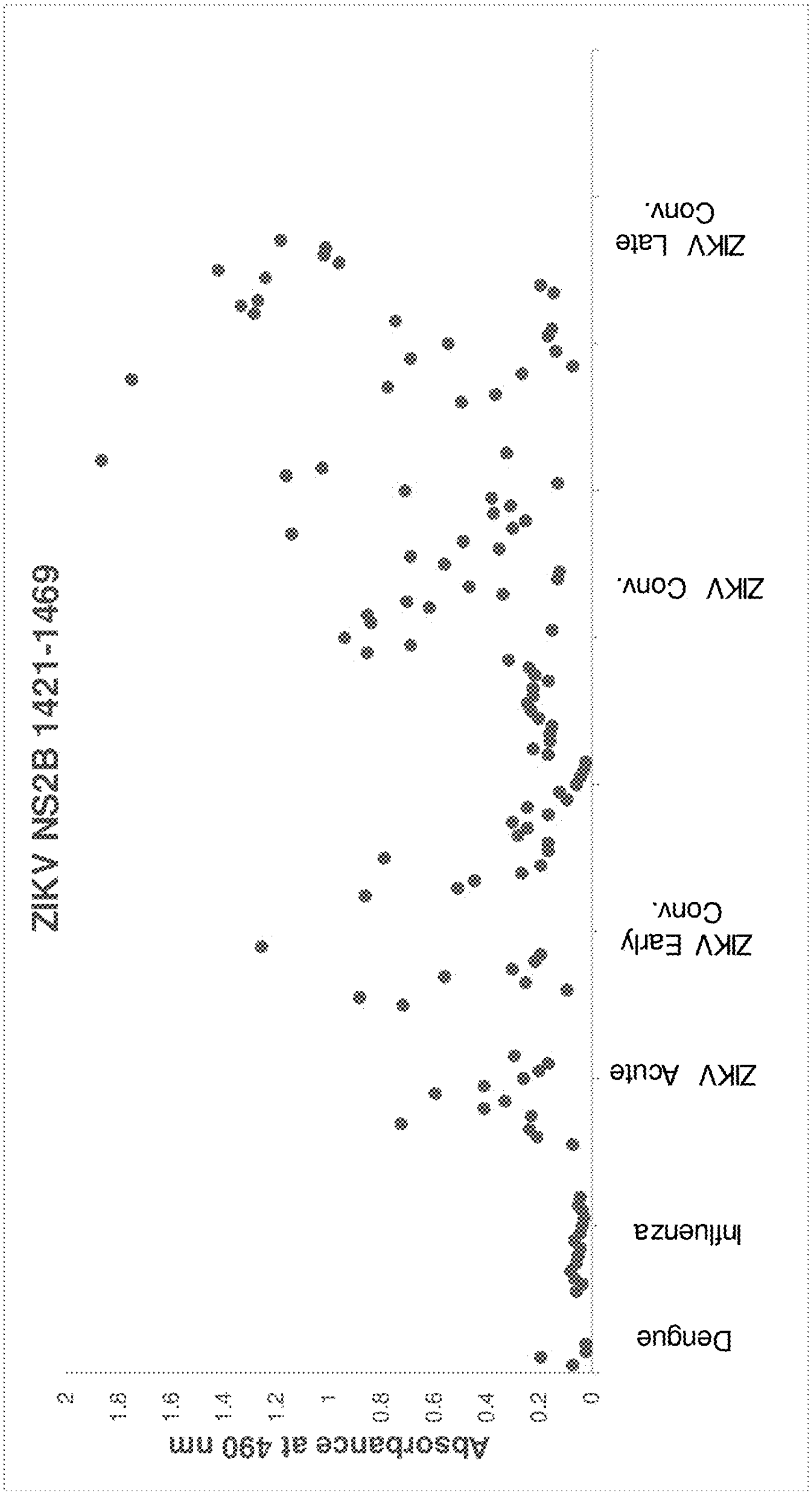
Figure 24C:
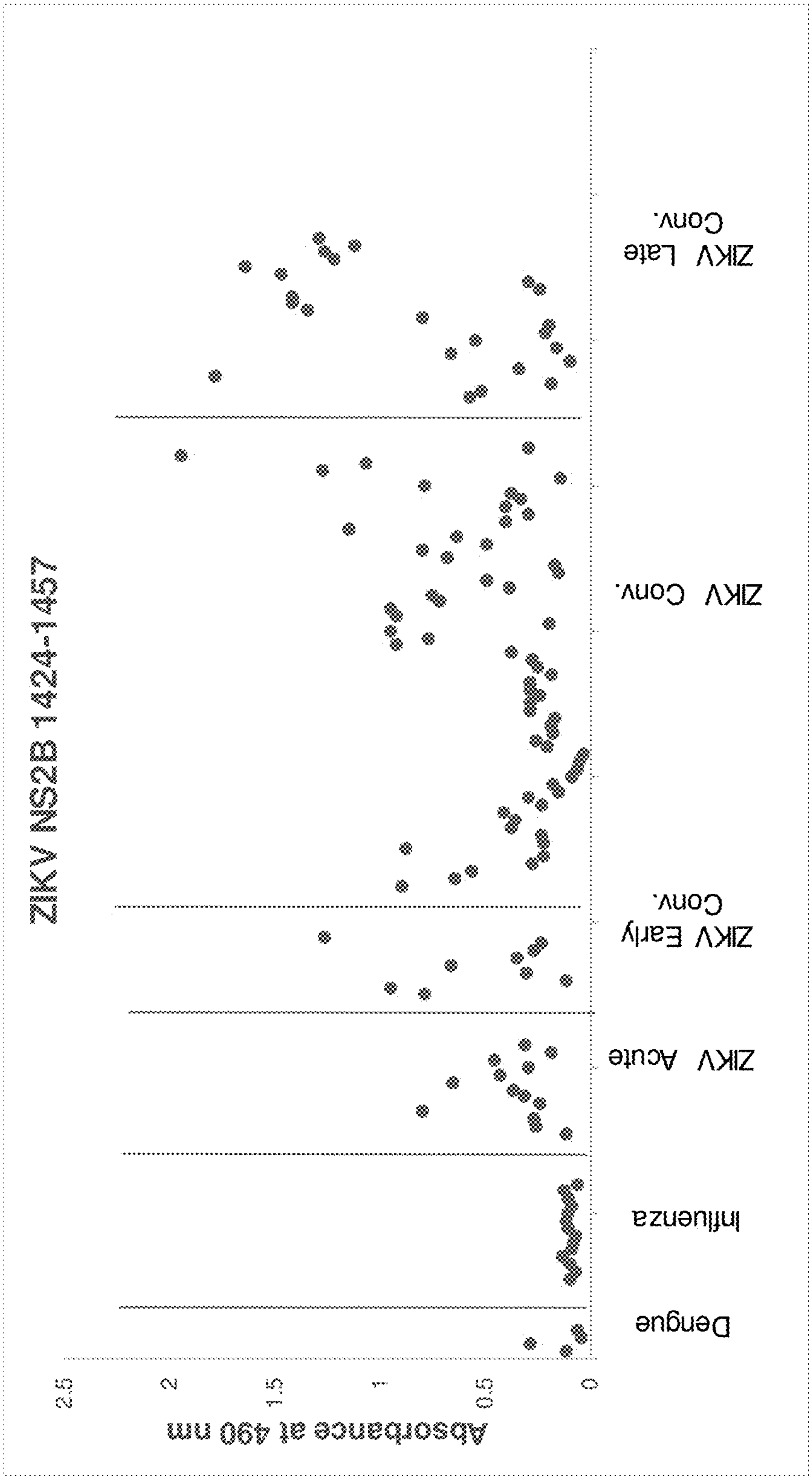
Figure 24D:
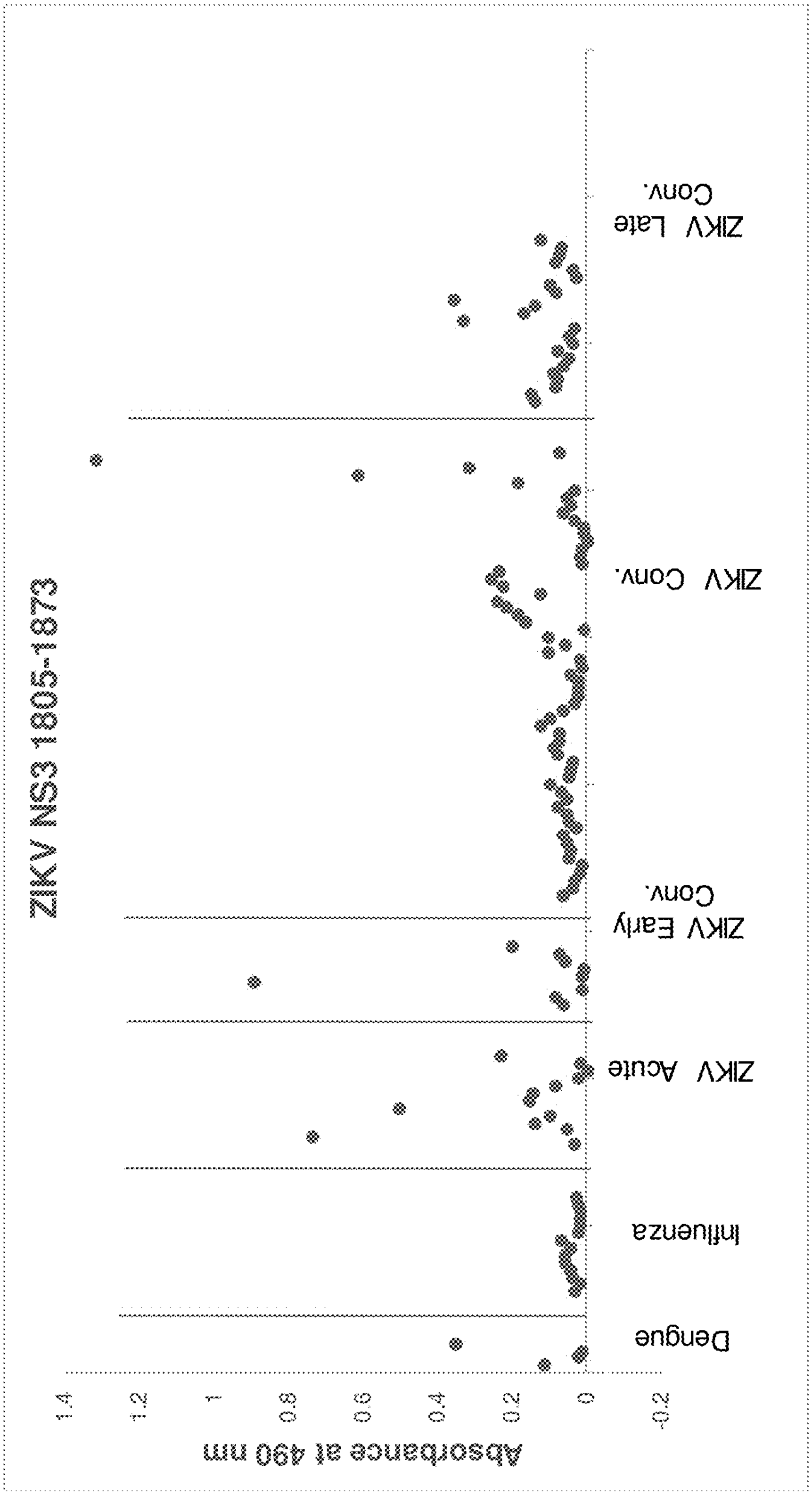
Figure 24E:
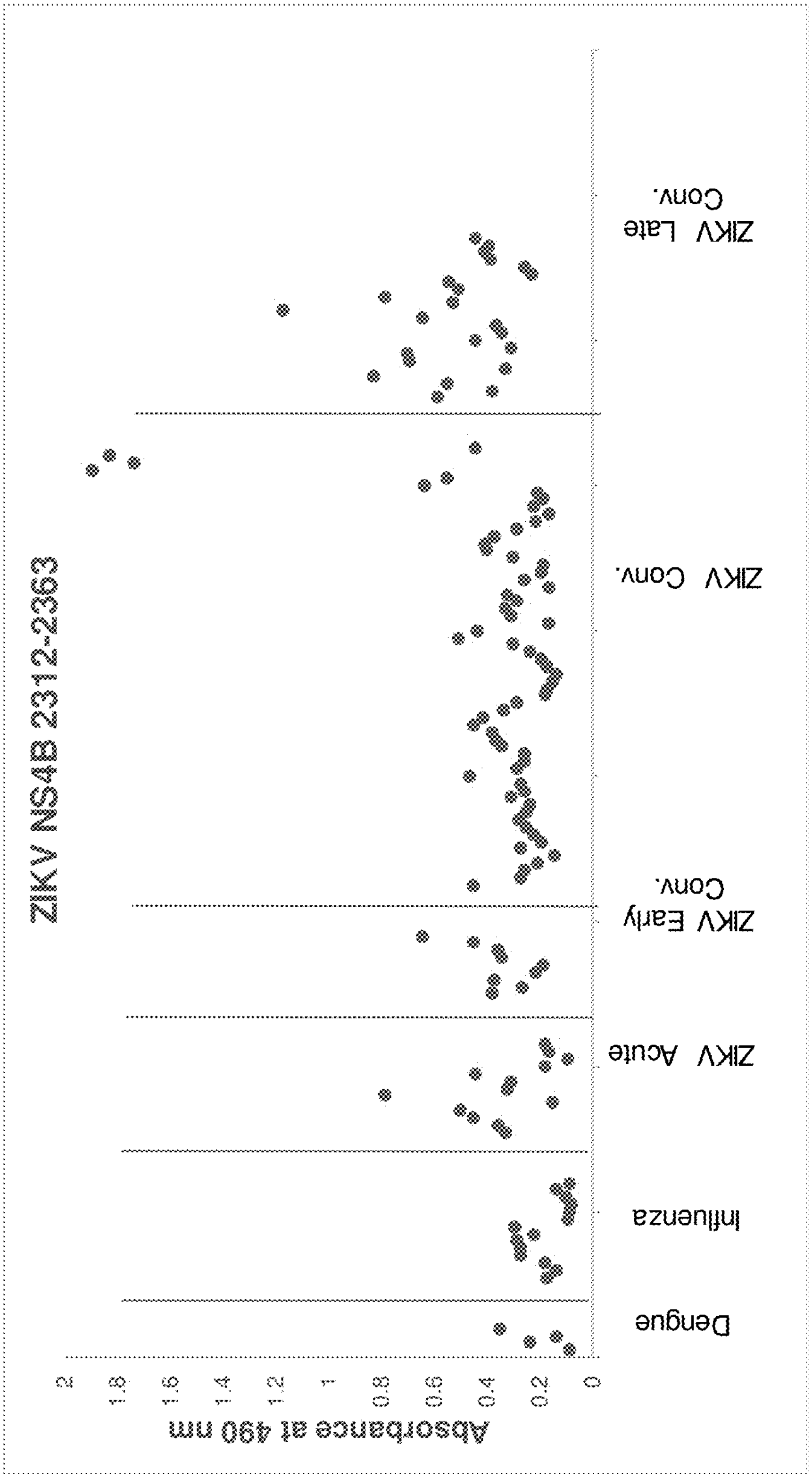
Figure 24F:
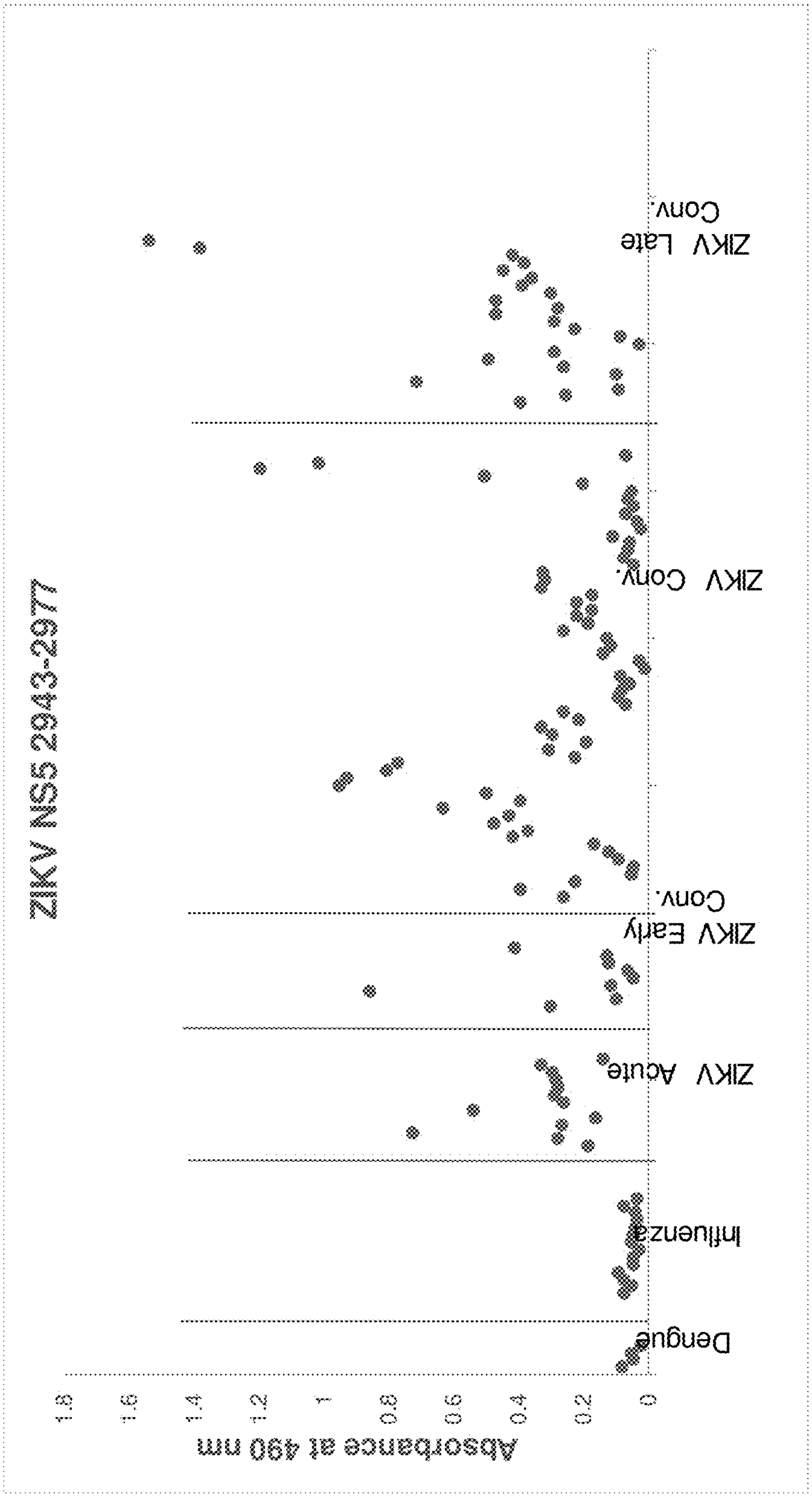
Figure 24G:
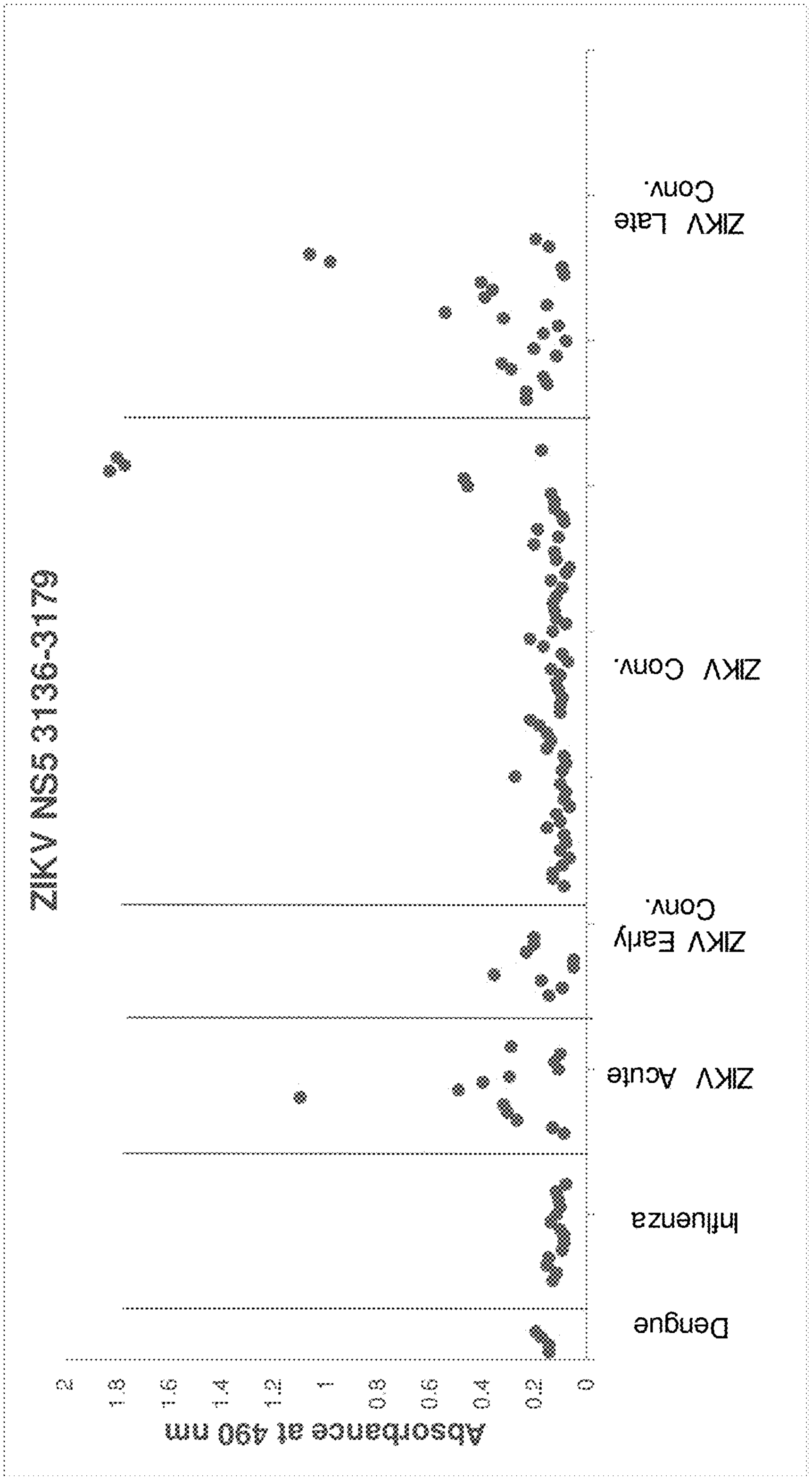
Figure 24H:
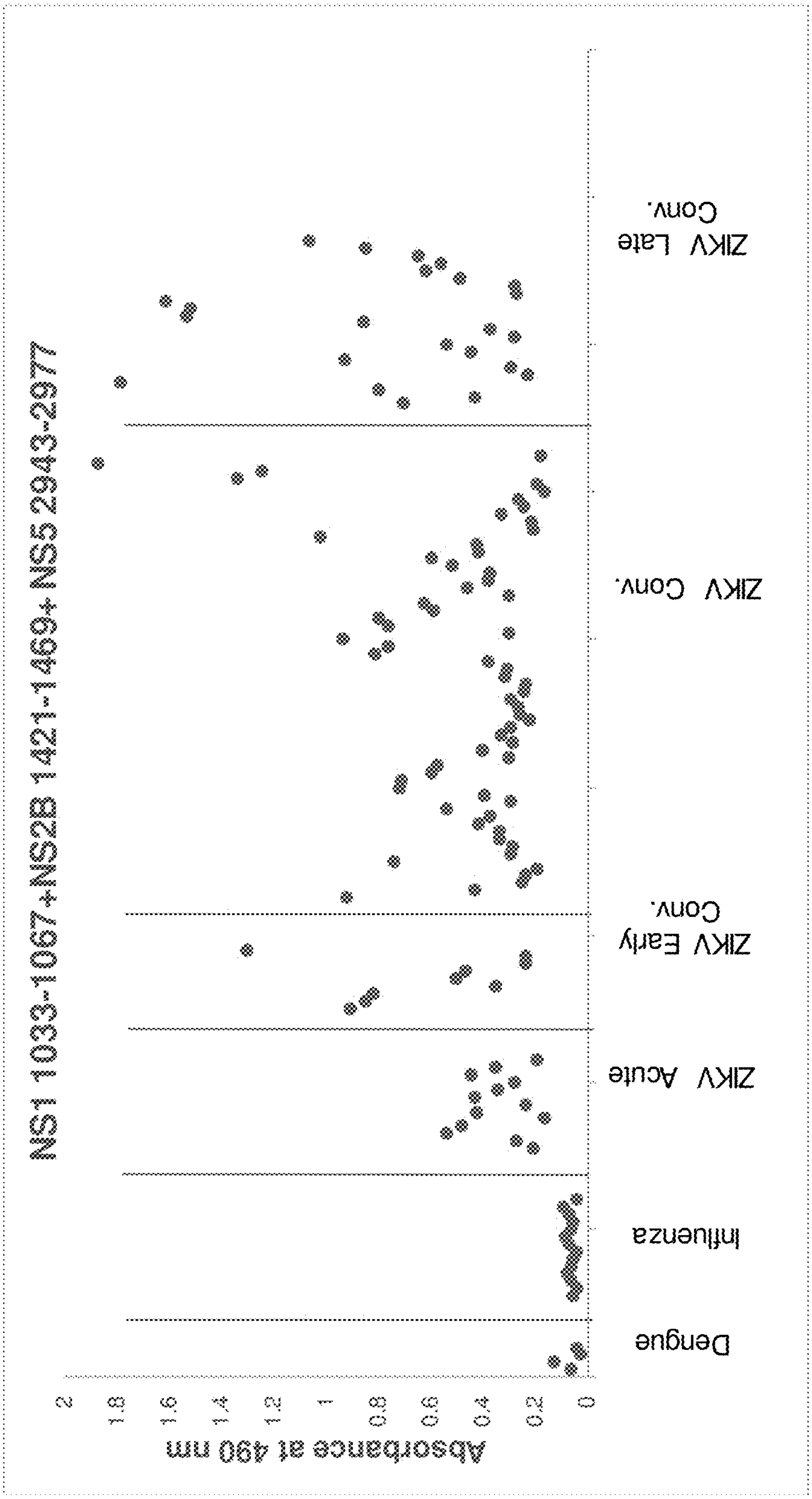
Figure 24I:
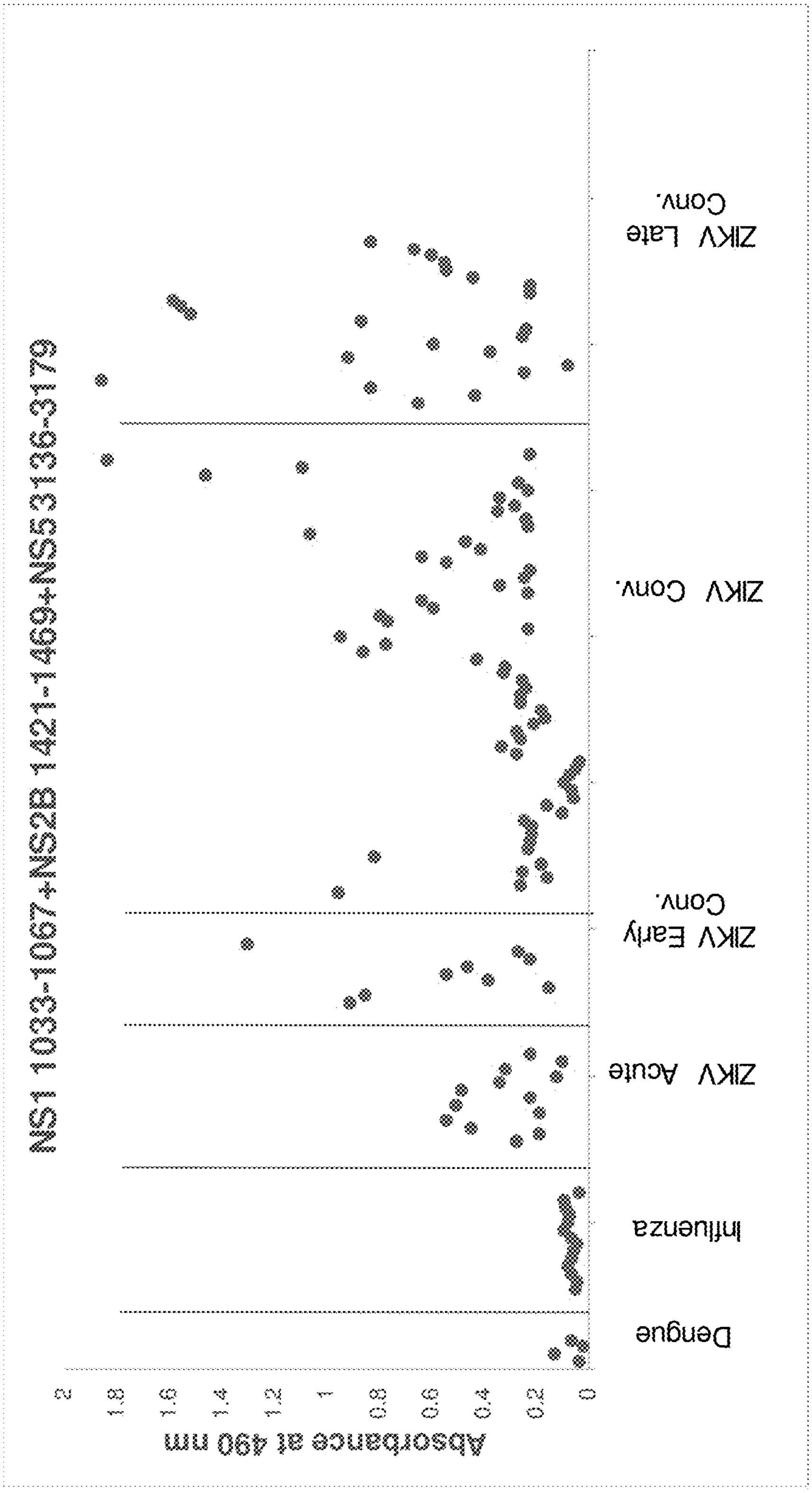
Figure 24J:
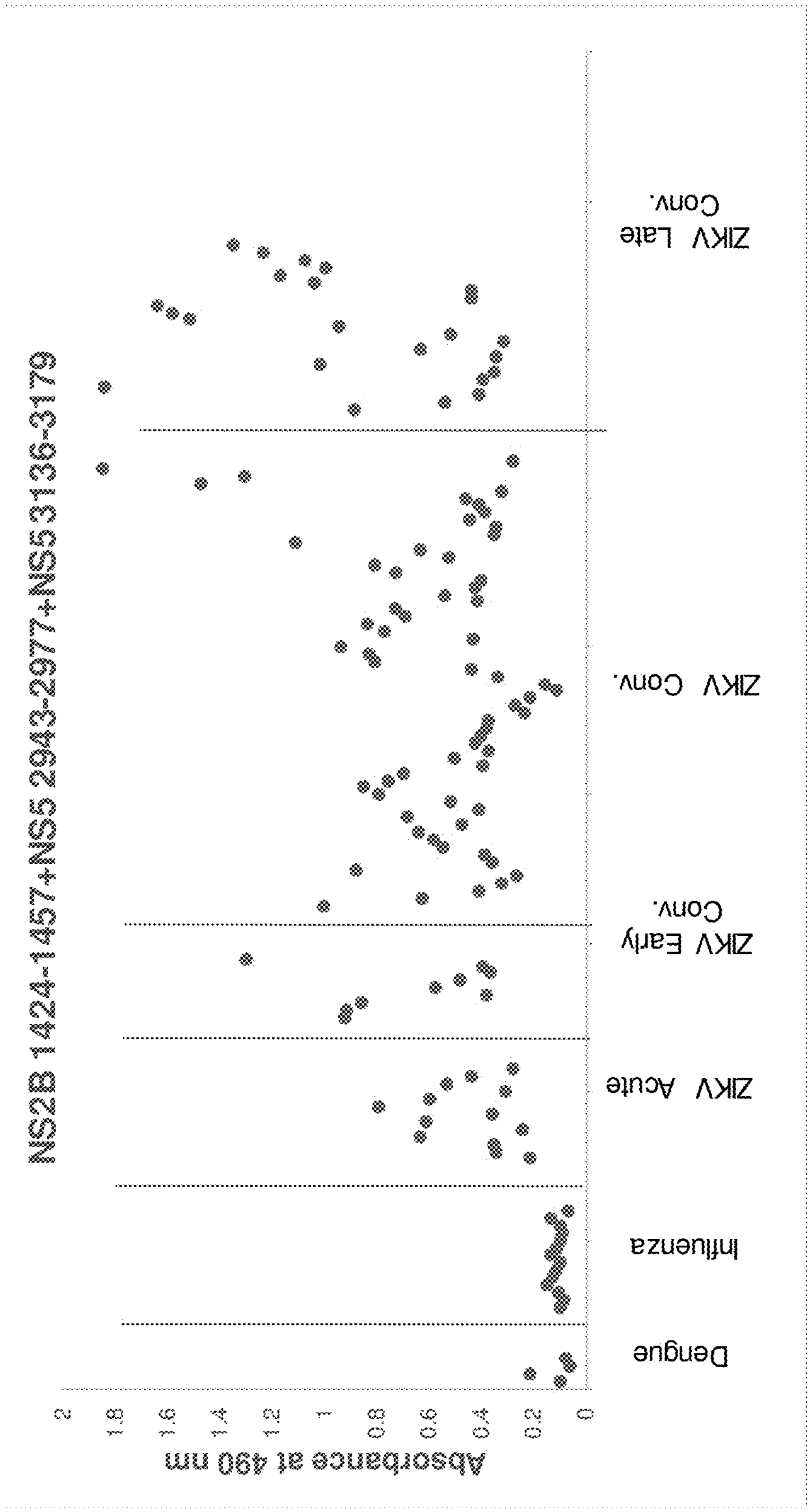

To further evaluate antibody affinity maturation following ZIKV infection against structural ZIKV-E and non-structural NS1 protein, the antibody-antigen complex dissociation rates (off-rate constants) were determined as a surrogate for affinity maturation using SPR. Antibody dissociation kinetics of antigen-antibody complexes are independent of antibody concentration and provide a measure of overall average affinity of polyclonal antibody binding. To that end, serially diluted serum/urine at 10-, 40-, and 160-fold dilutions were injected at a flow rate of 50 μL/min (120-sec contact time) for association, and dissociation was performed over a 600 second interval (at a flow rate of 50 μL/min) on ZIKV proteins (FIGS. 23A and 23B, respectively). Antibody off-rate constants, which describe the fraction of antigen-antibody complexes that decay per second, were determined directly from the plasma antibody interaction with GP in the dissociation phase only for the sensorgrams with maximum RU in range of 10-100 RU using BioRad Proteon SPR machine (FIG. 23) (Khurana et al., 2011, *Sci. Transl. Med.,* 3: 85ra48). Antibody binding to NS1 showed low affinity with fast dissociation rate kinetics (off-rates of $10^{-1}$ to $10^{-2}$/sec). Furthermore, only minimal affinity maturation against NS1 was observed between day 0 and day 28 post infection (FIG. 6A). In contrast, antibody binding to the E-ectodomain and E-Domain III, demonstrated a significant ($p<0.05$) affinity maturation of serum antibodies between days 0 and 28 (FIGS. 6C, 6E), with off rates ranging between $10^{-2}$ to $10^{-3}$/sec. The antibody affinity against the E ectodomain and domain III was ~10-fold higher compared with the NS1 protein. No antibody affinity maturation was observed for urine antibodies (FIGS. 6B, 6D, 6F), which is in line with the fact that only IgM antibodies were found in the urine samples (FIG. 1).

Figure 7A:
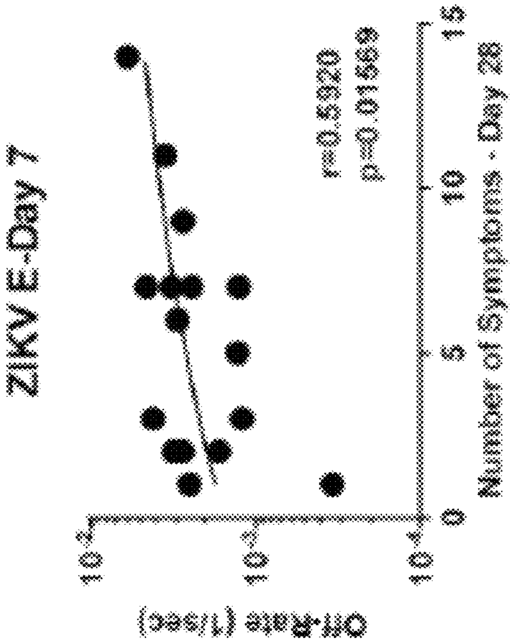
FIGS. 7A-7B show the relationship between antibody affinity of polyclonal human serum antibodies to ZIKV-E and NS1 proteins with clinical symptoms following ZIKV infection in patients. Antibody off-rate constants of the polyclonal serum sample interaction with recombinant ZIKV-E (FIG. 7A) and NS1 (FIG. 7B) proteins on day 7 as measured by SPR was correlated with total number of symptoms on day 28 for the corresponding patient. Inverse Spearman correlations were observed between anti-ZIKV E antibody affinity on day 7 measured by SPR vs. number of symptoms on day 28 ($r=0.592$; $p=0.01569$).
Figure 7B:
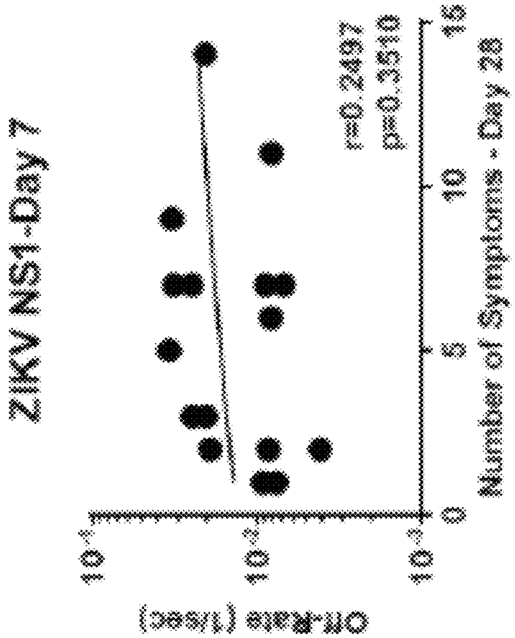

To determine the relevance of antibody affinity maturation with the clinical disease following ZIKV infection, spearman correlations were determined for the polyclonal sera antibody off-rates to ZIKV-E protein and NS1 proteins on the day of peak antibody binding titer (day 7) vs. number of clinical symptoms on day 28 visit. The first visit date ranged from 0-5 days post onset of symptoms, and onset of symptoms can be 3-12 days after infection. While this is still an acute infection response with predominant IgM responses there was evidence of class switching and affinity maturation between visit day 0 and visit day 7. Therefore, it was reasonable to probe the correlation between early antibody affinity maturation and the reduction in clinical symptoms by day 28. Statistically significant inverse correlations were observed between polyclonal serum antibody off-rates to ZIKV-E and the number of clinical symptoms on day 28 ($p=0.01569$; FIG. 7 A). In contrast, no significant correlation was found between binding serum antibody affinities to the NS1 protein and number of symptoms on day 28 (FIG. 7B).

Together, the data demonstrate differential evolution of antibody diversity, class-switching and affinity maturation within structural and non-structural proteins in different body fluids following ZIKV exposure. Some of the new antigenic sites identified in the study can be used as serodiagnostic targets and as countermeasures against ZIKV disease. Antibody affinity maturation against ZIKV-E protein may play an important role in resolution of clinical symptoms following ZIKV infection.

Discussion

While the ZIKV outbreaks of 2015-2016 subsided in 2017, there is still a need to understand the immune responses to the virus in endemic areas where the *Aedes aegypti* mosquito continues to be a source of multiple flavivirus transmissions. Development of an effective vaccine against ZIKV is a high priority, both for pre-epidemic preparedness and for rapid vaccination to control future outbreaks. Protection against ZIKV disease is at least partially attributed to the humoral immune response, since strong correlation was demonstrated between ZIKV-specific antibody responses and protective efficacy after vaccination of mice and non-human primates (NHPs). Furthermore, passive transfer of antibodies to naïve NHPs can protect the recipients against ZIKV challenge (Abbink et al., 2017*, Sci. Transl. Med.,* 9; Dupont-Rouzeyrol et al., 2015*, Emerg. Infect. Dis.,* 21: 84-86; Lamb et al., 2018*, Sci. Rep.,* 8: 3803).

However, there is limited knowledge of the specificities of the antibodies generated following ZIKV infection in humans and their evolution over time. A better understanding of immune profiles in different body fluids following ZIKV infection is important to identify and understand immune markers that can facilitate development of better serodiagnostic tests and vaccines. To address this need, the study disclosed herein used unbiased technologies including ZIKV-GFPDL and SPR to perform a comprehensive analysis of the evolution of antibody repertoires across the whole viral proteome in a group of patients with confirmed exposure to the Zika virus.

The ZIKV-GFPDL panning identified very broad antibody reactivities as early as day 0 (first visit: 0-3 days post symptoms onset) that were predominantly IgM antibodies. The only region not recognized by serum antibodies was the NS2A protein, even though it was well represented in the ZIKV-GFPDL (FIGS. 8 and 9). One of the possible limitations of GFPDL-based assessments is that while the phage display is likely to detect both conformational and linear epitopes on ZIKV, they are unlikely to detect paratopic interactions that require post-translational modifications and rare quaternary epitopes formed by ZIKV proteins. Binding to NS4A was also very low (only one insert bound). The ZIKV genome is organized as a single open reading frame transcribed as one viral transcript that is translated as a single polyprotein, which undergoes proteolytic cleavage by host and viral proteases to generate three structural C, prM/M, and envelope E, and seven nonstructural proteins in cells post-viral infection. It is possible that different viral proteins are processed with different efficiency in vivo following ZIKV infection. It is also unknown whether the individual proteins are being released by infected cells at the same frequency. By day 7, there was an increase in the frequency of IgM-bound phages with inserts mapping to E-domain II (aa 484-535), NS3 (aa 1792-1877) and several sites in NS5. These are regions with significant homology to other flaviviruses (DENV, WNV) (FIG. 21). In Tapachula, Chiapas, Mexico, where the study was conducted, DENV is common (Amaya-Larios et al., 2014*, Am. J. Trop. Med. Hyg.,* 91: 1057-1065), yet only one confirmed prior dengue virus exposure was reported in the current study (Table 1). This individual was not included in the samples for the GFPDL analysis. Therefore, the possibility of unconfirmed prior exposure to other flaviviruses in the study subjects resulting in recall antibody responses shortly after acute Zika virus infection cannot be excluded. The urine day 7 IgM antibodies had similar, but not identical, repertoires to the serum IgM antibodies. The presence of IgM in urine can be explained by a urogenital ZIKV replication, in agreement with previous reports (Dupont-Rouzeyrol et al., 2015*, Emerg. Infect. Dis.,* 21: 84-86; Lamb et al., 2018*, Sci. Rep.* 8: 3803). Recent studies suggest that plasma and urine ZIKV PCR positivity are not linked, supporting local infections in different organs resulting in localized immune responses, in agreement with our findings (Paz-Bailey et al., 2018*, N. Engl. J. Med.,* 379: 1234-1243). These studies supported the use of urine samples, which is used for diagnosis of ZIKV infections.

The numbers of GFPDL phages bound by IgG antibodies were significantly lower (~2 logs) compared with the IgM panning. This was expected in acutely ZIKV-infected patients. The repertoire of the IgG antibodies was not identical to the IgM repertoire on day 7. There were very few IgG antibodies targeting the NS3-NS5 proteins. In contrast, very strong antibody binding was observed to antigenic sites in the E protein, NS1 and NS2B. This is surprising, because all the structural and non-structural proteins are derived from a single ZIKV polyprotein and should be in equivalent amounts following proteolytic cleavage. Unlinked evolution of antibody binding to subdomains in the influenza hemagglutinin (HA1 vs. HA2) and RSV membrane proteins (F vs. G) over time have been reported (Khurana et al., 2009*, PLoS Med.,* 6: e1000049; Khurana et al., 2016*, PLoS Pathog.,* 12: e1005554; Khurana et al., 2011*, Sci. Transl. Med.,* 3: 85ra48; Verma et al., 2012*, J. Virol.,* 86: 5515-5522). The unlinked antibody evolution against these viral proteins in influenza and RSV is most likely due to multiple mechanisms including differential viral protein expression following virus infection, protein secretion/release from infected cells, antigen presentation, immune-dominance, pre-existing immunity and immune selection over time. In contrast, for flaviviruses, a single polyprotein is being cleaved to generate the structural and non-structural proteins at equimolar amounts. In the study disclosed herein, immune responses were measured against more conserved and less conserved proteins shortly after primary acute ZIKV infection. During that time frame, it is unlikely that prior immunity played a key role in the observed differential antibody responses.

These findings of class switching of IgM antibodies to IgG antibodies and affinity maturation for different matured ZIKV proteins suggest that immune dominance following infection is determined by multiple factors including protein concentration, BCR affinity, antigen pick up and processing by B cells, presentation to TFH cells at the T cell-B cell follicle border and germinal center entry, which is required for class switching and affinity maturation (Klein et al., 2015, *Nat. Rev. Immunol.,* 15: 137-148; Victora et al., 2016, *Immunity.,* 45: 471-482; Nussenzweig et al., 2012, *Annu. Rev. Immunol.,* 30: 429-457; Cyster et al., 2017, *Curr. Opin. Immunol.* 45: 21-30). The E protein is expressed on both virions and infected cells and was shown to be highly immunogenic in all flaviviruses. NS1 is expressed in multiple oligomeric forms and is present in different cellular locations including on intracellular membranes, on the cell surface, and extracellularly as soluble secreted lipoparticles. Both secreted and cell-surface associated NS1 proteins are immunogenic, were shown to contribute to virus pathogenesis in the host, and to enhance viral acquisition by mosquitoes (Young et al., 2013, *Antiviral Res.,* 98: 192-208; Akey et al., 2014, *Science.,* 343: 881-885; Liu et al., 2016, *Nat. Microbiol.,* 1: 16087). On the other hand, the strong binding of antibodies to NS2B was not described before. Little is known about the function of NS2B during viral replication and whether it is also secreted from cells. The NS2B antigenic site identified herein (Z-15; FIG. 3) is largely able to discriminate between ZIKV and DENV. Furthermore, this site is 100% conserved among several Zika viruses, but only 30-55% conserved between ZIKV and other flaviviruses (FIG. 21 and Table 4). In a peptide-based ELISA assay, the reactivity of both acute samples in the current study and convalescent sera from DENV and ZIKV infections was evaluated using multiple peptides from the non-structural proteins that were identified in the GFPDL analysis (FIG. 4). These analyses demonstrated that peptides derived from NS1, NS2B, NS3 and one site in NS4B are significantly reactive with both acute and convalescent sera from Zika virus infected individuals (47-79% and 69%-100%) with very low reactivity with dengue virus convalescent sera (0% to 11% cross-reactivity). Therefore, an optimized combination of NS1, NS2B, NS3 and/or NS4B peptide sequence based serodiagnostic assay is contemplated herein.

In order to better understand the interplay between the virus and the immune system and to identify the immune correlates of protection, it is important to follow the kinetics of antibody binding and affinity maturation against different viral gene products in individual patients. These analyses were conducted with currently available recombinant viral proteins, NS1, E-ectodomain, and E-domain III using SPR. While most patients had antibodies against NS1, E, and E-domain III during the 28-day observation period (peak responses on day 7), the antibody binding to NS1 (MAX RU) was at least 3-fold lower than the binding of antibodies targeting the E-proteins (FIG. 5). Furthermore, the affinity of anti-NS1 antibodies (as measured by antigen-antibody dissociation kinetics) was 10-fold lower than anti-E antibodies, and very minimal affinity maturation for anti-NS1 antibodies was observed between day 0 and day 28 (FIG. 6). It is highly likely that antibody affinity maturation continues beyond the 28-day period. The difference in IgM and IgG antibody repertoires and affinity maturation shows that not all the early $IgM^+$ B cells underwent class switching and engaged in germinal center (GC) formation (Cyster et al., 2017, *Curr. Opin Immunol.,* 45: 21-30). Alternatively, the possibility cannot be excluded that the serum antibodies may reflect both long term cross-reactive memory B cells and newly activated naïve B cells. It is not possible to obtain pre-infection serum samples that could help to decipher these possibilities. In urine, no evidence of class switching or affinity maturation was found, showing that the local infections induced primary IgM responses only. The lack of IgG confirmed preservation of kidney function in these patients. It's possible that SPR based assay may not identify all antibodies that recognize quaternary epitopes in ZIKV proteins. The findings in the current study could be extended to other infected populations with additional studies including pregnant mothers that could help to identify the key immune targets that prevent trans-placental viral transfer leading to infections of the developing fetus.

Domain III in the E-ectodomain is the least conserved between ZIKV and other arboviruses including DENV (FIG. 3 and FIG. 18). Several human monoclonal antibodies targeting the ZIKV domain III have been shown to have potent virus neutralizing activity in vitro and in vivo in mouse models, with minimal Antibody dependent enhancement (ADE) (Sapparapu et al., 2016, *Nature.,* 540: 443-447; Abbink et al., 2016, *Science.,* 353: 1129-1132; Dai et al., 2016, *Cell Host Microbe.,* 19: 696-704). Low level cross-reactivity with DENV 1-4 E-domain III was reported for several Zika virus domain III antibodies (Wang et al., 2016, *Sci. Transl. Med.,* 8: 369ra179; Sapparapu et al., 2016, *Nature.,* 540: 443-447; Robbiani et al., 2017, *Cell.,* 169: 597-609 e511; Wu et al., 2017, *Emerg. Microbes. Infect.,* 6: e89). Several potent Domain III specific human monoclonal antibodies with germline (unmutated) Ig were isolated (Wu et al., 2017, *Emerg. Microbes. Infect.,* 6: e89). The data confirm that polyclonal antibodies from acutely infected patients indeed demonstrate strong binding and affinity maturation against E-Domain III supporting the use of Domain III as a targeted vaccine in naïve populations.

Antibody epitope sites, total antibody binding, and antibody affinity maturation may all contribute to epidemiology and disease outcomes. In the current study, there is a statistically significant but modest inverse correlation between the day 7 antibody binding affinity against the E-ectodomain and the number of clinical symptoms on day 28 post-ZIKV infection. The present study provides a rationale for measurements of antibody affinity in future vaccine trials as well as post-exposure studies.

Three of 19 of ZIKV PCR-positive individuals in the current study did not show significant serum antibody binding to the E, E-domain III as well as NS1 proteins in SPR. These data demonstrate that not all ZIKV infections lead to seroconversion, even though they gave positive reactivity in the commercial ZIKV-ELISA on their first visit (with no increase titers in subsequent visits). This could lead to underestimation of exposure rates. A search for additional targets for serodiagnostic and surveillance tests is warranted. The high reactivity with NS2B inserts found in the GFPDL analyses on days 7 and day 28 post-onset, and in 100% of convalescent sera supports further exploration of this peptide along with NS1, NS3 and NS4B peptides in future sero-diagnostic assays.

The study disclosed herein demonstrates independent evolution of antibody binding patterns to structural and non-structural proteins following acute Zika virus infection in terms of antibody epitope repertoire diversity, antibody affinity maturation, and antibody isotype class switch, including importance of predominant anti-ZIKV IgM response in different body fluids. These findings could have significant implications for further development and evaluation of ZIKV serodiagnostics, therapeutics and vaccines.

Materials and Methods

Study Design

Samples were analyzed from patients with confirmed ZIKV infection enrolled in a prospective, longitudinal observational study conducted at 4 hospitals in Tapachula, Chiapas, Mexico: Instituto de Seguridad y Servicios Sociales de los Trabajadores del Estado-Clínica Hospital Dr. Roberto Nettel Flores, Hospital Regional de Alta Especialidad Ciudad Salud, Hospital General de Tapachula, Instituto Mexicano del Seguro Social-Unidad de Medicina Familiar No. 11 to study the natural history of Zika. The study was sponsored by the Mexican Emerging Infectious Disease Clinical Research Network, Mexico (La Red), and conducted in accordance with the applicable regulatory and International Conference on Harmonization—Good Clinical Practice requirements. The study protocol was approved by an institutional review board for each study site as well as by all local and/or country governing bodies as applicable (ClinicalTrials.gov Identifier: NCT02831699).

Individuals of all ages and any gender that met the 12 Feb. 2016 WHO/PAHO case definition (World Health Organization. Zika virus disease: Interim case definitions; of suspected acute Zika (fever and/or rash, and one or more other symptoms including arthralgia, myalgia, non-purulent conjunctivitis or conjunctival hyperemia, headache, and malaise) were eligible for the study if symptoms started in the 6 previous days before first visit. Informed consent was obtained from every participant in this study. After consent, subjects were evaluated on study Days 0, 3, 7, and 28 with a series of clinical assessments, and serum and urine samples were obtained at each visit. For this analysis, only subjects with confirmed Zika (PCR positive) (Lanciotti et al., 2008, *Emerg. Infect. Dis.,* 14: 1232-1239) in serum or urine, on any study day were included, in adherence with the CDC guidance for ZIKV infection. The clinical assessments comprised past medical history, symptoms assessment, complete physical including neurological exam, disability assessment, assessment of complications including hospitalization, and assessment of presence of Guillain-Barre syndrome, with dedicated testing, if present (Zhao et al., 2016, *Cell.,* 166: 1016-1027). Serum and urine were tested on Days 0, 3, and 7 by PCR for ZIKV, Dengue (DENV), and pan-Flavivirus (Lanciotti et al., 2008, *Emerg. Infect. Dis.,* 14: 1232-1239). The age, gender, days since onset of illness, prior Dengue virus exposure, PCR testing for Zika, Dengue and pan-Flavivirus (on both serum and urine samples) and ELISA testing (IgG and IgM antibodies) for Zika virus and Dengue virus of these subjects (all Hispanic ethnicity) are detailed in Table 1. The clinical symptoms experienced by each patient are documented in Table 2. Convalescent Dengue samples were collected in 2012 from a separate cohort study conducted in Cuernavaca, Mexico (prior to emergence of ZIKV in Mexico). Convalescent serum samples from Zika virus infected individuals were obtained from BEI Resources, NIAID, NIH. Researchers performing antibody assays were blinded to the identity of samples.

Clinical Laboratory Assays

Serologic assays were performed for ZIKA IgG and IgM antibodies by ELISA (Euroimmun), DENV IgG and IgM antibodies by ELISA (Panbio) using commercial diagnostic kits. PCR assays for Zika[20] (recommended by WHO), Dengue (Amaya-Larios et al., 2014, Am. J. Trop. Med. Hyg. 91: 1057-1065) and Pan-flavivirus (Bosch et al., 2017, *Sci. Transl. Med.* 9) were performed as described in the respective publications.

ZIKV Whole Genome Fragment Phage Display Library (ZIKV-GFPDL) Construction

Plasmid (ZIKV-ICD) containing cDNAs complementary to the whole genome of Paraiba_01/2015 strain of ZIKV was used. This strain is closely related to circulating ZIKV strains in Mexico in the current study. A gIII display-based phage vector, fSK-9-3, where the desired polypeptide can be displayed on the surface of the phage as a gIII-fusion protein, was used for construction of the ZIKV whole genome fragment phage display library (ZIKV-GFPDL). Purified PCR amplified DNA of whole genome of ZIKV (FIG. 8) amplified using ZIKV-ICD was digested with DNaseI to obtain gene fragments ranging in size from 200-1000 bp, and used for GFPDL construction as described previously (Khurana et al., 2009, *PLoS Med.,* 6: e1000049). PCR-based sequencing of individual clones was performed to ascertain the random distribution of both size and sequence of peptide displayed on the phage surface (FIG. 9).

Adsorption of Polyclonal Human Sera on ZIKV-GFPDL Phages and Residual Reactivity to ZIKV-E To demonstrate the capacity of the ZIKV-GFPDL to remove anti-ZIKV antibodies, 500 μL of 10-fold diluted serum antibodies from five post-infection human sera were adsorbed by incubation with ZIKV-GFPDL phage-coated Petri dishes. To ascertain the residual antibodies binding capacity, an SPR was performed with GLC chips coated with 500 RU of recombinant ZIKV-E. Human serum (with or without ZIKV-GFPDL adsorption) in BSA-PBST buffer (PBS pH 7.4 buffer with Tween-20 and BSA) were injected at a flow rate of 50 μL/min (240 sec contact duration) to determine the total anti-ZIKV-E binding antibodies before and after adsorption on ZIKV-E GFPDL.

Adsorption of Polyclonal Post-Infection Human Sample on EBOV GFPDL Phages and Residual Reactivity to ZIKV Particles Prior to panning of GFPDL, 500 μl of 10-fold diluted serum antibodies from pooled post-infection serum samples collected at day 7 visit was adsorbed by incubation with ZIKV-GFPDL phage-coated Petri dishes. To ascertain the residual antibodies specificity, an ELISA was performed with wells coated with heat inactivated $10^4 TCID_{50}/100$ μl of ZIKV, PRVABC59 virus particles. After blocking with PBST containing 2% milk, serial dilutions of human serum sample (with or without adsorption) in blocking solution were added to each well, incubated for 1 hr at RT, followed by addition of 5000-fold diluted HRP-conjugated goat anti-human IgA+IgG+IgM specific antibody and developed by 100 μl of OPD substrate solution. Absorbance was measured at 490 nm. The absorbance values for test samples were subtracted from "virus only" negative control absorbance values.

Affinity Selection of ZIKV-GFPDL with Serum and Urine Samples

For GFPDL analysis, serum (and corresponding urine samples) were pooled from 5 acutely ZIKV infected patients (Table 1). Prior to panning, serum or urine components that could nonspecifically interact with phage proteins were removed by incubation in UV-killed M13K07 phage-coated petri dishes. Equal volumes of pooled polyclonal human sera (day 0 or day7) or urine (day7) were used for each round of GFPDL panning GFPDL affinity selection was carried out in solution with protein A/G beads (for IgG) or IgM-specific capture beads to define the fine epitope specificity of these polyclonal IgG and IgM isotype antibodies as previously described (Khurana et al., 2009, *PLoS Med.,* 6: e1000049; Khurana et al., 2016, *PLoS Pathog.,* 12: e1005554). The purity of IgG and IgM antibodies in serum was confirmed after bead incubation by SPR using specific anti-human isotyping antibodies. After panning, antibody-bound phage clones were amplified, the inserts were sequenced, and the sequences were aligned to the ZIKV genome. Subsequently, additional IgM and IgG antibody epitope repertoire analysis was performed with serum sample of an acutely ZIKV-infected individual (Patient #42-001-F) at day 7 visit (day 7 since onset of symptoms) to define the fine epitope specificity in an individual. This individual was part of the 5 pooled samples used for GFPDL analysis in FIGS. 1 and 2. GFPDL affinity selection experiments were performed in duplicate (two independent experiments by research fellow, who was blinded to sample identity) and showed similar numbers of phage clones and epitope repertoires.

Protein Alignment of ZIKV and Other Flaviviruses

An alignment of various ZIKV strains [Paraiba/2015 (GenBank #ANT96596.1 MR-766/Uganda/1947 (GenBank #ANK57895.1), Nigeria/IbH-30656_SM21V1-V3/1968 (GenBank #AMR68906.1), ArD157995/Senegal/2001 (GenBank #AHL43503.1), Micronesia/2007 (GenBank #ACD75819.1) and Brazil/2015 (GenBank #AMD16557.1)] and Flaviviruses MENV-1 (NCBI Reference #NP_059433.1), DENV-2 (NCBI Reference #NP_056776.2), DENV-3 (NCBI Reference #YP_001621843.1), DENV-4 (NCBI Reference #NP_073286.1), WNV (UniProt Accession #P06935), and YFV/17D, (UniProt Accession #P03314)] was performed using MUSCLE program prior to generating heat maps showing conservation and similarity plots (SimPlot). Using Simplot, a query sequence (ZIKV_Paraiba strain) was used to generate a plot that will show the percent similarity of the reference sequences to other flaviviruses or to other ZIKV strains. A sliding window of size 200 bp or 20 bp was used, with the alignment in steps of 1 bp to generate the SimPlot showing different flaviviruses and all ZIKV strains, respectively.

Surface Representation of Antigenic Sites of Various ZIKV Proteins

The crystal structures of various proteins that are a part of ZIKV genome E [PDB #5U4W (immature E), 5JHM (mature E)], NS1 (PDB #5K6K), NS2B (PDB #SGXJ), NS3 (PDB #SJRZ) and NS5(PDB #5TFR) were used to depict surface representation of sequence conservation and antigenic sites pertaining to each of these ZIKV proteins.

ELISA

Biotinylated peptides (200 ng/well) were captured onto wells coated with 200 ng of streptavidin. Following three washes with phosphate buffered saline containing Tween-20 (PBST) (20 mM PBS, 0.1% Tween-20) plates were blocked with PBST containing 5% BSA (BSA-PBST). For testing, all specimens were 5-fold serially diluted (starting at 1:100) in BSA-PBST and added to peptide-coated wells for 1 h at room temperature (RT) in duplicate. After three washes with PBST, the wells were reacted with HRP-conjugated goat anti-Human IgG-A-M antibody (diluted 1:2,000) (Jackson ImmunoResearch, West Grove, Pa.) at RT for 1 h, followed by addition of 0-Phenylenediamine (OPD) substrate.

The cut-off values used are twice the average absorbance of negative control sera (at similar dilutions) for each peptide.

Real-Time Antibody Binding Kinetics of Post-ZIKV Infected Human Sera or Urine Samples to Recombinant ZIKV-E, Domain III and NS1 Proteins by Surface Plasmon Resonance (SPR)

Steady-state equilibrium binding of longitudinal samples post-ZIKV infected human polyclonal sera or urine from every individual in the clinical study was monitored at 25° C. using a ProteOn surface plasmon resonance (Bio Rad). The purified recombinant ZIKV proteins (ZIKV-E and ZIKV-E Domain III from Sino Biologicals and ZIKV-NS1 from Meridian Life Sciences) were coupled to a GLC sensor chip via amine coupling with either 100 or 500 resonance units (RU) in the test flow channels. The protein density on the chip was optimized such as to measure only monovalent interactions independent of the antibody isotype. The kinetics of disassociation was identical irrespective of the serum dilution and MAX RU (FIG. 23). Samples of 300 μl freshly prepared sera at 10-fold and 100-fold dilution in BSA-PBST buffer (PBS pH 7.4 buffer with Tween-20 and BSA) were injected at a flow rate of 50 μL/min (240 sec contact duration) for association, and disassociation was performed over a 1200-second interval. Responses from the protein surface were corrected for the response from a mock surface and for responses from a buffer-only injection. SPR was performed with serially diluted serum (10-fold and 100-fold dilution) or 10-fold dilution of urine of each individual participant in this study such that the SPR signal of the samples between 10 to 100 RU was used for further quantitative analysis. The maximum resonance units (Max RU) for each sera and urine sample in the manuscript figures was calculated by multiplying the observed RU signal with the dilution factor to provide the data for undiluted serum/urine sample. Total antibody binding and antibody isotype analysis were calculated with BioRad ProteOn manager software (version 3.1.0). All SPR experiments were performed twice, and the researchers performing the assay were blinded to sample identity. In these optimized SPR conditions, the variation for each sample in duplicate SPR runs was <5%.

Antibody off-rate constants, which describe the stability of the complex, i.e., the fraction of complexes that decays per second, were determined directly from the post-ZIKV infected human polyclonal serum or urine sample interaction with ZIKV proteins using SPR (as described above) and calculated using the BioRad ProteOn manager software for the heterogeneous sample model (Khurana et al., 2011, *Sci. Trans. Med.,* 3: 85ra48).

Example 2

This example describes a study to evaluate seroreactivity of human samples with ZIKV antigenic site peptides. Acute, convalescent and late stage ZIKV-infected, DENV seropositive and influenza virus seropositive human sera and plasma samples were tested for binding to individual ZIKV peptides or combinations of three ZIKV peptides by ELISA.

A large panel of ZIKV positive and negative samples were tested in an ELISA assay for binding to ZIKV-specific IgG antibodies in serum samples. The 7 individual biotinylated peptides and a panel of 3 combinatorial mixtures of peptides were used. The chosen peptides and combinations are as follows: ZIKV NS1 1033-1067; ZIKV NS2B 1421-1469; ZIKV NS2B 1424-1457; ZIKV NS3 1805-1873; ZIKV NS4B 2312-2363; ZIKV NS5 2943-2977; ZIKV NS5 3136-3179; ZIKV NS1 1033-1067+NS2B 1421-1469+NS5 2943-2977; ZIKV NS1 1033-1067+NS2B 1421-1469+NS5 3136-3179; and ZIKV NS2B 1424-1457+NS5 2943-2977+NS5 3136-3179. ELISA plates (96-well; Immulon 2HB) were coated overnight at 4° C. with 200 ng Streptavidin (NEB) in 100 μL PBS in each well. After washing the plates three times with PBST (0.05% Tween-20) each of the biotinylated peptides/peptide mixtures were coated in 100 μL PBS and allowed to bind the streptavidin-coated wells for 1 hour at RT. The plates were then washed three times with PBST and blocked for 2 hours at RT with 5% BSA-PBST. Serially diluted serum samples in 2% BSA-PBST were added to the plates and incubated for 1 hour at RT. After washing the plates, 100 μL of anti-human IgG-Fc antibodies conjugated with HRP were added and incubated for 1 hour at RT. The plates were washed again, and the bound antibodies were developed with 0-phenylenediamine substrate solution. After stopping the reaction with 3.3M $H_2SO_4$, the plates were read at 492 nm. Absorbance values were considered positive if they exceeded twice the mock serum control values for each peptide and were above a cut-off absorbance value of 0.05. The OD values to a mock antigen was subtracted from those of the positive antigen to normalize the values for each sample. The results are shown in FIGS. 24A-24J.

Based on this data, the peptides ZIKV NS1 1033-1067 (SEQ ID NO: 1) and ZIKV NS5 3136-3179 (SEQ ID NO: 8) preferentially recognize early acute ZIKV infection samples. ZIKV NS2B 1421-1469 (SEQ ID NO: 2); ZIKV NS2B 1424-1457 (SEQ ID NO: 10); ZIKV NS4B 2312-2363 (SEQ ID NO: 5); and ZIKV NS5 2943-2977 (SEQ ID NO: 7) peptides recognize ZIKV infected samples across various time points, both during acute and convalescent phase following ZIKV exposure. Therefore, the three peptides combinations: ZIKV NS1 1033-1067+NS2B 1421-1469+NS5 2943-2977 (SEQ ID NOs: 1, 2 and 7); ZIKV NS1 1033-1067+NS2B 1421-1469+NS5 3136-3179 (SEQ ID NOs: 1, 2 and 8); and ZIKV NS2B 1424-1457+NS5 2943-2977+NS5 3136-3179 (SEQ ID NOs: 10, 7 and 8) demonstrate very high sensitivity for all ZIKV infected samples from various time-points post-infection. These peptide mixes also show high specificity with minimal or no reactivity to influenza virus-positive and DENV-positive samples.

Example 3

Zika virus (ZIKV) infection acquired during pregnancy, especially the first and early second trimester, poses a great risk for congenital abnormalities. The contribution of amniotic fluid (AF) antibodies to ZIKV infection of fetuses may depend on the specificity and function of AF antibodies. This Example describes a comprehensive antibody repertoire analyses on IgM, IgG, and IgA antibodies using paired serum and AF samples from pregnant women with confirmed ZIKV infection. In addition, SPR and ELISA-based assays were used to compare total antibody binding, isotype distribution and antibody affinity maturation in serum versus AF from ZIKV-infected pregnant women at different gestational stages. The data indicate that antibodies in the AF contain multiple isotypes and specificities that are not identical to antibodies in the mother's blood. In general, AF contained lower binding to epitopes in E, E-DII, E-DIII, NS1, NS2B and NS5, and lower affinity antibodies against E, E-DIII and NS1. Furthermore, an in vitro ZIKV infection assay provided evidence of both ZIKV infection control (low sample dilutions) and infection enhancement (high sample dilutions) that was more apparent in the AF than sera samples from these ZIKV-infected pregnant women. These findings indicate that antibodies in the amniotic fluid may be derived from B cells in the local ZIKV-infected tissues, and/or the infected fetuses, in addition to transplacental transfer of antibodies from the mother. This is the first study that demonstrates independent antibody response to structural and non-structural proteins in serum and amniotic fluid following Zika virus infection during pregnancy in terms of antibody epitope repertoire diversity, antibody affinity maturation, and antibody isotype class switch in utero.

Introduction

Zika virus (ZIKV) infection acquired during all stages of pregnancy, especially the first and early second trimester, poses a great risk for congenital abnormalities (Melo et al., *JAMA Neurol* 73, 1407-1416, 2016; Xavier-Neto et al., *PLoS Negl Trop Dis* 11, e0005363, 2017). Sampling of amniotic fluids (AFs) provides a powerful tool to detect the presence of ZIKV in utero. Indeed, there have been several reports of detection and sequencing of ZIKV in the AF of pregnant women while their serum and urine samples were negative for the virus (Calvet et al., *Lancet Infect Dis* 16, 653-660, 2016; Benjamin et al., *Fertil Steril* 107, 1319-1322, 2017). Furthermore, transfer of virus to the AF and fetal demise has been reported in a non-human primate (NHP) model of ZIKV-infection (Magnani et al., *Nat Commun* 9, 1624, 2018).

Antibodies play an important role in protecting fetuses from TORCH pathogens (toxoplasma, HIV, syphilis, measles, rubella, cytomegalovirus, and herpes simplex) (Jaspan et al., *J Clin Virol* 31, 190-197, 2004; Fouda et al., *Immunohorizons* 2, 14-25, 2018). Transplacental transfer of IgG in ZIKV-infected pregnant women has been reported (Singh et al., *PLoS Negl Trop Dis* 13, e0007648, 2019). However, in addition to transfer through the cord blood, the AF surrounding the fetus may be another source of anti-pathogen antibodies. Therefore, it is important to explore the repertoire of antibodies present in the AF versus serum in ZIKV-infected pregnant women at different gestational stages to inform the fetal immune responses to congenital ZIKV infection. This is particularly relevant because ZIKV vaccine trials and studies of passive antibody transfer to animals have demonstrated that both antibody specificity and antibody titers may lead to protection and/or enhancement of ZIKV infection (Maciejewski and Pierson, *Cell Host Microbe* 24, 622-624, 2018; Shim et al., *mBio* 10, 2019; Robbiani et al., *J Exp Med* 216, 2302-2315, 2019). However, the role of antibodies during pregnancy is more complex, since there is limited knowledge of quantity and quality of in utero immune responses to virus infection. Fetal immune responses to foreign antigens may develop in utero with memory that lasts into childhood (Odorizzi et al., *Sci Transl Med* 10, 2018; Zhang et al., *Nat Rev Immunol* 17, 495-507, 2017; Zhivaki and Lo-Man, *Semin Immunopathol* 39, 585-592, 2017; Wilcox and Jones, *Front Immunol* 9, 1548, 2018).

Whole-genome-fragment-phage-display-libraries (GFPDL) analysis was conducted on IgM, IgG, and IgA antibodies using paired serum and AF samples from two pregnant DENV-naïve women with confirmed ZIKV infection, one in the first trimester and the second in the third trimester. In addition to GFPDL analysis, SPR and ELISA-based assays were used to compare total antibody binding, isotype distribution and antibody affinity maturation in serum versus AF from five ZIKV-infected pregnant women at different gestational stages. Antibody kinetics measured under optimized SPR conditions represent primarily the monovalent interactions between the antibody-antigen complex. To determine the antibody affinity against different ZIKV proteins following virus infection, the dissociation kinetics (off-rate constants) of antigen-antibody complexes that are independent of antibody concentration were used as a surrogate for overall average affinity of polyclonal antibody against ZIKV proteins using SPR (Khurana et al., *Sci Transl Med* 3, 85ra48, 2011; Khurana et al., *Nat Med* 22, 1439-1447, 2016 Khurana et al., *Nat Commun* 10, 3338, 2019). Furthermore, the impact of antibodies in serum and AF on ZIKV infection was evaluated in vitro.

Materials and Methods

Sample Demographics

Serum and amniotic fluid (AF) pairs following ZIKV infection were obtained from 5 pregnant females at different gestational age in Colombia (Antibody Systems Inc.) after symptom onset (Table 5). All pregnant women presented with clinical symptoms and were confirmed ZIKV PCR positive. All five women were confirmed positive for ZIKV infection but tested negative for DENV and CHIKV by RT-PCR (Table 6). These pregnant females self-reported to be Flavivirus naïve. For GFPDL analysis, two paired serum and amniotic fluid samples were used; first trimester serum/AF samples were collected from an 18-year-old pregnant Colombian female (ID #38 in Table 5) 10 days after diagnosis of ZIKV infection at week 3 gestational stage. For the third trimester samples, paired serum and AF were collected from a 32-year-old pregnant female (ID #19, Table 5) at 42 days post onset of symptoms at 32 weeks of gestation. Both subjects were positive for ZIKV IgM and IgG antibodies and negative for DENV antigen (Table 5). Additionally, all 5 patients' samples showed high antibody binding titers in a ZIKV-specific differential peptide-based serodiagnostic IgG-ELISA against ZIKV-NS2B and ZIKV-NS5 peptides (Table 6), which are divergent between ZIKV and other flaviviruses (Table 8).

Affinity Selection of ZIKV-GFPDL with Serum and AF Samples

ZIKV whole genome (Paraiba_01/2015 strain) phage library with gene fragments ranging in size from 200-1000 bp was used for affinity selection of serum and AF samples (see Example 1). The phage library potentially displays all possible known or unknown viral protein segments as fusion proteins with the gilt protein of a filamentous bacteriophage. Prior to panning with this library, the serum and AF samples were first allowed to incubate with UV-killed M13K07 phage-coated petri dishes to remove any components reacting non-specifically to the phage proteins. The serum and AF samples were then allowed to interact with the phage library and affinity selection was carried out in solution using protein A/G beads (for IgG), anti-human IgM and anti-human IgA beads (Thermofisher) to capture these antibodies respectively, as previously described (Khurana et al., *Nat Med* 22, 1439-1447, 2016). After thorough washing, the phage clones that bind each of these antibodies were eluted in a low pH, their inserts sequenced using PCR and aligned to the ZIKV whole genome. GFPDL affinity selection experiments were performed in duplicate (two independent experiments by a person who was blinded to sample identity) and showed similar numbers of phage clones and epitope repertoires.

Peptide ELISA

Immulon 2 HB 96-well microtiter plates were coated with 100 μl of streptavidin in PBS (100 ng/well) at 4° C. overnight followed by capturing of biotinylated ZIKV-peptide. After blocking with PBST containing 2% BSA, five-fold serial dilutions of post-infection human serum in blocking solution were added to each well, incubated for 1 h at RT, followed by addition of 2,000-fold dilution of HRP-conjugated goat anti-human IgM+IgG+IgA specific antibody, and developed by 100 μl of OPD substrate solution. Absorbance was measured at 490 nm.

For ZIKV-specific peptide serodiagnostic IgG-ELISA, biotinylated ZIKV-NS2B-1424-1457 and ZIKV-NS5-2943-2977 peptide was captured on Sv-coated plates, followed by blocking with PBST containing 2% BSA. Five-fold serial dilutions of post-infection human serum in blocking solution were added to each well, incubated for 1 h at RT, followed by addition of 2,000-fold dilution of HRP-conjugated goat anti-human IgG-Fc specific antibody, and developed by 100 μl of OPD substrate solution. Absorbance was measured at 490 nm.

Surface Representation of Antigenic Sites of Various ZIKV Proteins

The crystal structures of various proteins that are encoded by the ZIKV genome; Envelope (E) [PDB 5U4W (immature E), 5JHM (mature E)]; Non-structural protein (NS), NS1 (5K6K), and NS5(5TFR) were used to depict surface representation of sequence conservation and specific antigenic sites pertaining to each of these ZIKV proteins using Chimera. The selected antigenic sites (Z-5, 8 (ZIKV-E); Z-42, 12,43,14 (ZIKV-NS1); and Z-25, 28, 29 (ZIKV-NS5) were depicted based on their high percent clonal frequency (immunodominant) of IgG or IgA antibodies in the serum or AF samples in the first or third trimester.

Real-Time Antibody Binding Kinetics of Post-ZIKV Infected Human Sera or Amniotic Fluid Samples to Recombinant ZIKV-E, Domain III, NS1 and prM Proteins by Surface Plasmon Resonance (SPR)

Steady-state equilibrium binding of longitudinal samples post-ZIKV infected human polyclonal sera or amniotic fluids from all individuals in the study was monitored at 25° C. using a ProteOn surface plasmon resonance (Bio-Rad). The purified recombinant ZIKV proteins (ZIKV-E and ZIKV-E Domain III (Sino Biologicals), ZIKV-NS1 (Meridian Life Sciences), and ZIKV-prM (Creative Diagnostics) were coupled to a sensor chip via anti-His interaction with either 100 or 500 resonance units (RU) in the test-flow channels to ensure native conformation of the proteins. The protein density on the chip was optimized such as to measure only monovalent interactions independent of the antibody isotype. Importantly, the kinetics of disassociation was identical irrespective of the serum dilution and Max RU as demonstrated in Example 1. Samples of 300 μL freshly prepared dilution were injected at a flow rate of 50 μL/min (120 sec contact duration) for association, and disassociation was performed over a 600-second interval. Responses from the protein surface were corrected for the response from a mock surface and for responses from a buffer-only injection. SPR was performed with serially diluted serum (10-fold, 50-fold) or 2- and 10-fold dilution of amniotic fluid of each individual participant in this study such that the SPR signal of the samples between 10 to 100 RU was used for further quantitative analysis. The maximum resonance units (Max RU) for each serum and AF sample was calculated by multiplying the observed RU signal with the dilution factor to provide the data for undiluted serum/AF sample. Total antibody binding and antibody isotype analysis were calculated with Bio-Rad ProteOn manager software (version 3.1.0). All SPR experiments were performed twice, and were performed blinded to sample identity. In these optimized SPR conditions, the variation for each sample in duplicate SPR runs was <5%.

Antibody off-rate constants, which describe the stability of the complex, i.e., the fraction of complexes that decays per second, were determined directly from the post-ZIKV infected human polyclonal serum or AF sample interaction with ZIKV proteins using SPR (as described above) and calculated using the Bio-Rad ProteOn manager software for the heterogeneous sample model.

ZIKV Infection and Microneutralization Assay

The infection and microneutralization assay were done by an approach described for VSV.EBOV.GP by Lee et al. (*Vaccine* 35, 5481-5486, 2017). Briefly, Vero cells were plated in 96 well-plates at $2\times10^4$ cells/well the day before the experiment. Human sera and amniotic fluid were collected and diluted three-fold starting at 1:10 for the first five dilutions and five-fold for the last two dilutions. Each sample was tested in triplicate runs. Monoclonal antibody ZKA185 was used at 1 μg/mL for the first dilution. The sera were incubated with either the Asian-lineage PRVABC59 or the African-lineage MR766 strain at 2,000 $TCID_{50}$/well for 1 hour at 37° C. The antibody-virus mixture was then added at 100 μL/well to the Vero cells and incubated at 37° C. for 24 hours. The infected cells were then harvested after washing the cells with 1×PBS by adding 100 μL of sample preparing reagent (SPR) buffer (BioRad) to each well and transferred to U-bottom plates which were then stored at −80° C. until PCR analysis. For RT-qPCR analysis, the RNA standard was prepared using 2×iQ SYBR Green Supermix (Biorad) and iScript reverse transcriptase. The mastermix was added to PCR plates and 1 μL of cell lysate sample was added to each well of the PCR plate containing 9 μL mastermix. RT-qPCR analysis was performed and % virus control was calculated.

A standard curve using RNA from ZIKV-infected Vero cells, purified using RNeasy Extraction Kit (Qiagen), was included for quantification; negative controls (lysates from uninfected cells) and no-reverse transcriptase were included. The amount of neutralization was provided by comparing the quantity of ZIKV RNA against a no-antibody control. The positive control was the monoclonal antibody ZKA185 (Absolute Antibody), Statistical Analyses The statistical significances between each time-point (visit days) were determined using two-tailed paired t-test in GraphPad software. One-way ANOVA was performed with a Bonferroni post-hoc analysis for ELISA data. p-values less than 0.05 were considered significant with a 95% confidence interval.

Results

Antibody Repertoire in Maternal Serum and Amniotic Fluid Following ZIKV Infection Whole genome ZIKV-GFPDL was constructed from the complete genome of ZIKV strain Paraiba_01/2015 (FIG. 8). The ZIKV strains that circulated during 2016 in Colombia when these samples were obtained were of Asian lineage and sequence homology analysis showed that circulating strains matched closely with the Paraiba strain used in this study. Sequencing of this library showed that a random distribution of peptides in both size and sequence across the entire ZIKV genome that recognized epitopes of conformational dependent neutralized MAbs, as described in Example 1. This ZIKV-GFPDL was used to analyze paired maternal serum and amniotic fluid (AF) samples collected from an 18-year-old pregnant Colombian female (3 weeks gestation) at 10 days post-symptom onset (ID #38 in Table 5), and from a 32-year old pregnant female in her third trimester (ID #19 in Table 5). Symptoms included fever, rash and conjunctivitis. These pregnant females self-reported to be Flavivirus naïve. All five women were positive for ZIKV but negative for DENV and CHIKV infection (Table 6) by RT-PCR. Additionally, these five patient's samples showed high antibody binding titers in a ZIKV-specific differential peptide-based serodiagnostic IgG-ELISA against ZIKV-NS2B and ZIKV-NS5 peptides (Table 6), which are divergent between ZIKV and other flaviviruses (Ravichandran et al., *Nat Commun* 10, 1943, 2019; Mishra et al., *mBio* 9, 2018) (Table 8). Samples from two patients that were used for antibody repertoire analysis by GFPDL, were negative for DENV antigen and showed positive ZIKV-IgM and IgG response in a commercial diagnostic test (Table 5).

Figures 25A, 25B:
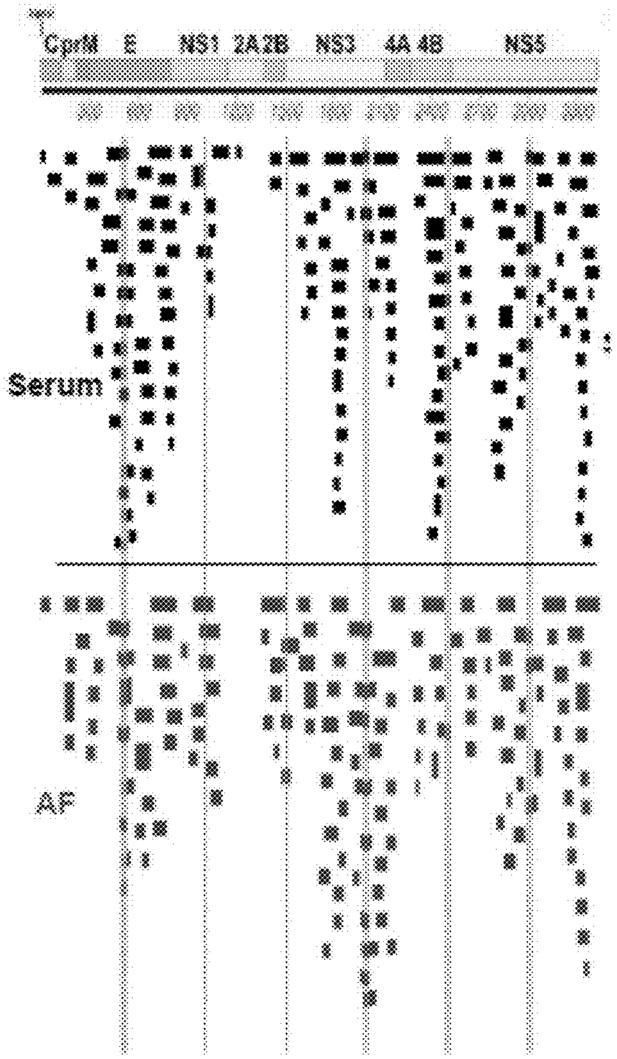
FIGS. 25A-25D show IgM/IgG/IgA antibody repertoires across the whole ZIKV proteome elicited in serum and amniotic fluid samples from A ZIKV-infected woman the first trimester.
Figure 25C:
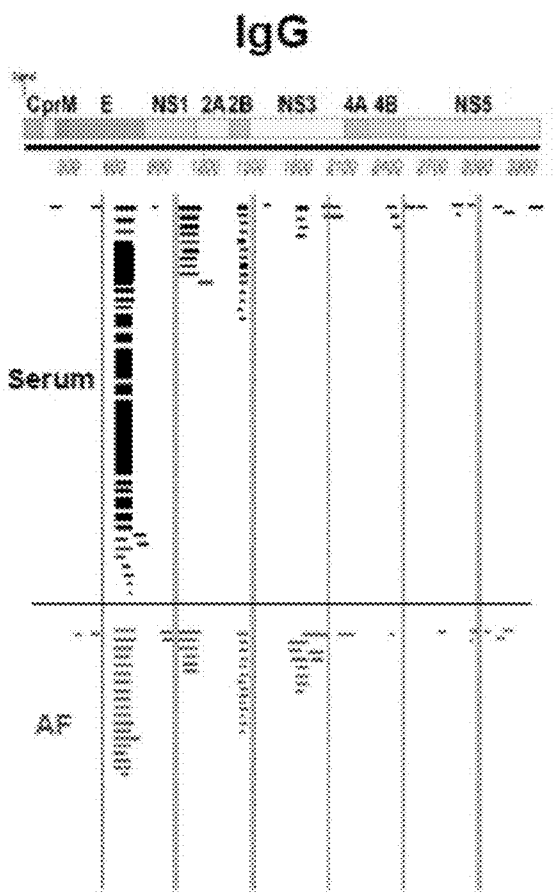
Figure 29:
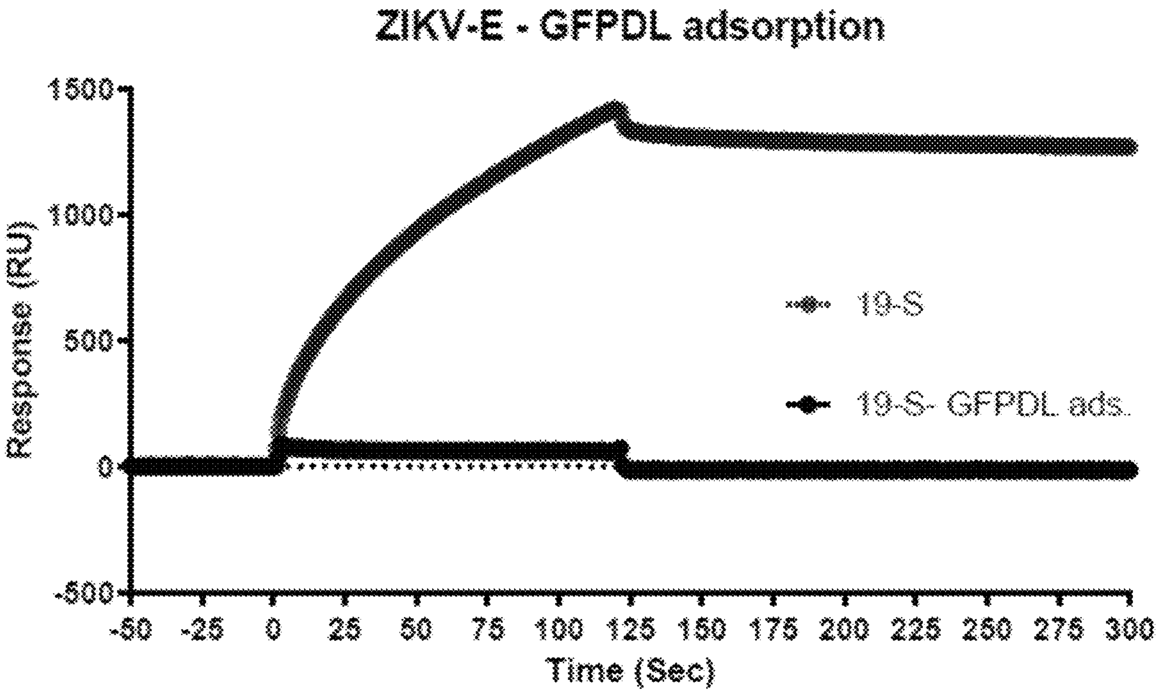
FIG. 29 is a graph showing anti-E reactivity of post-infection sera in SPR before and after ZIKV-GFPDL adsorption. Post infection 19-S sera was adsorbed on ZIKV-GFPDL coated petri dishes. Binding to recombinant ZIKV-E is shown before (blue line) and after (black line) GFPDL-adsorption in SPR.

First, the capacity of the phage display library to adsorb ZIKV-E specific antibodies in the post-ZIKV infected polyclonal human sera was determined. After two rounds of adsorption with the ZIKV-GFPDL, the serum sample demonstrated >90% removal of total anti-ZIKV-E binding antibodies as measured by SPR (FIG. 29). Together with the study described in Example 1, this adsorption analysis provided a rationale for using this GFPDL for epitope mapping of post-ZIKV infection polyclonal sera/AF antibody repertoire. The serum and AF samples were evaluated individually for ZIKV-specific IgM, IgG and IgA antibody repertoires by GFPDL analysis (FIGS. 25 and 26). For the first trimester pregnant woman, the number of bound phages by serum IgM antibodies ($7.7\times10^7$/mL) was ~100-fold higher than those bound by IgG ($6.2\times10^5$/mL) and 1000-fold higher than IgA antibodies ($4.4\times10^4$/mL), respectively (FIG. 25A). The amniotic fluid also contained predominantly IgM at similar levels as serum, while, the number of IgG-bound phages by AF antibodies was 1000-fold lower than for the serum antibodies; IgA-bound phages were similar in serum and AF samples.

Figure 25D:
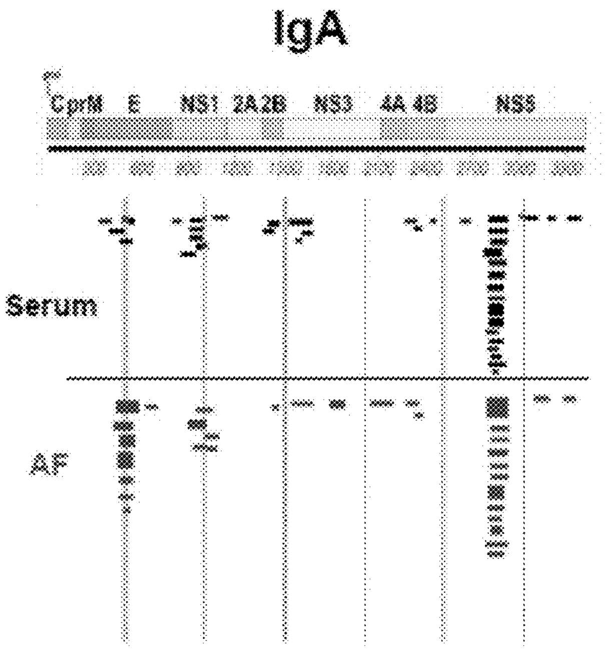
Figure 30A:
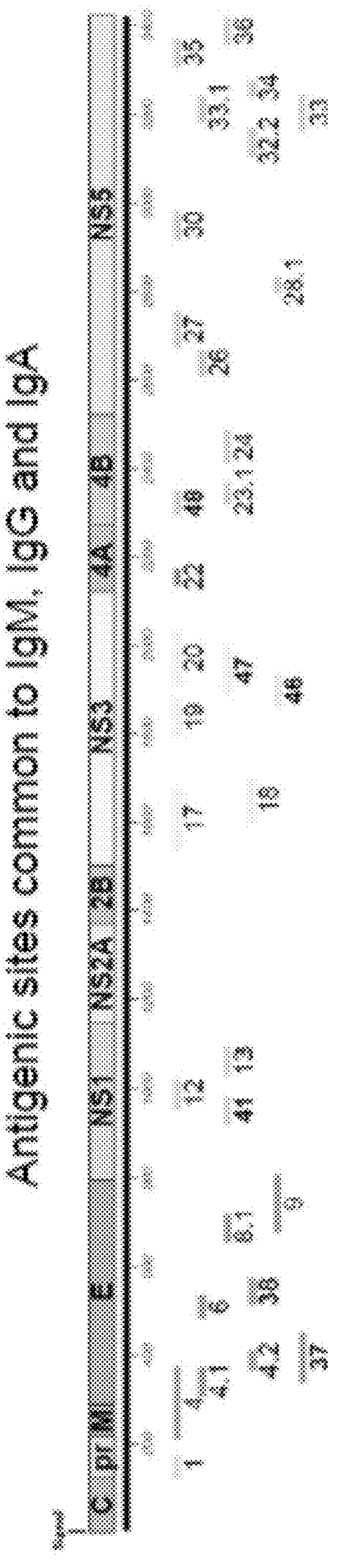
FIGS. 30A-30D show immunodominant antigenic sites within ZIKV genome by IgM, IgG and IgA antibodies.
Figure 30B:
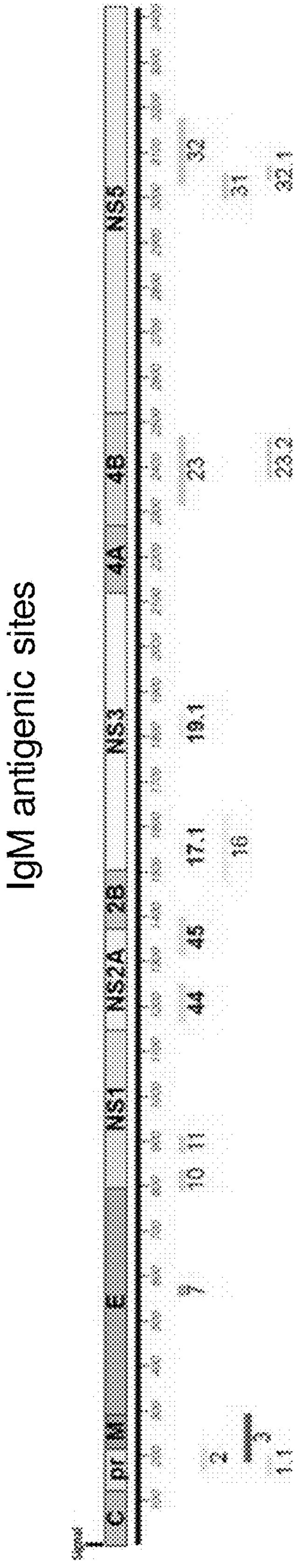
Figure 30C:
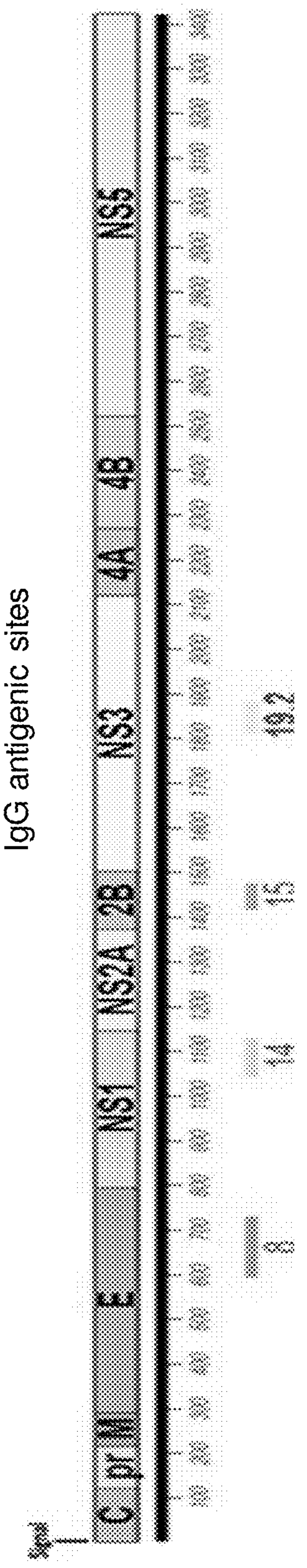
Figure 30D:
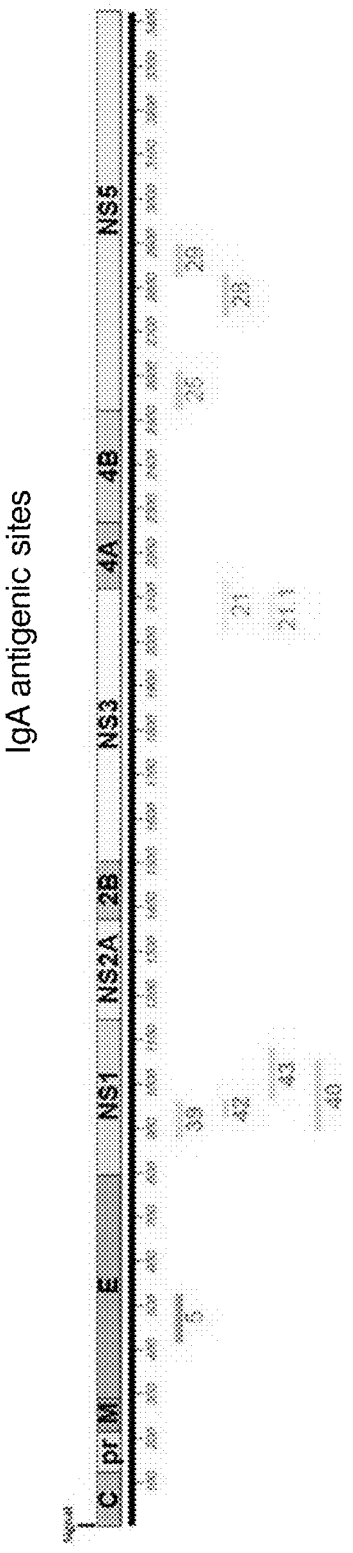

The inserts of bound phages were sequenced and mapped against the entire ZIKV genome to gain insight into the epitope repertoire of the antibodies in serum and amniotic fluid (FIG. 25B). The epitope distribution of the serum IgM antibodies was much broader than that for the serum IgG and IgA and spanned the entire ZIKV genome. The serum IgG bound predominantly to an epitope in the E protein (spanning aa 595-729 in domain III, FIG. 30C) followed by much lower frequencies of bound-epitopes in NS1, NS2B, NS3, and NS5 (Table 7, FIG. 30C). The IgA antibodies were more focused on epitopes in NS5 (aa 2826-2898; FIG. 25D, Table 7, and FIG. 30D). These isotype-specific epitope profiles suggested that not all the IgM B cells underwent class switching at this early stage of infection. For this individual, the epitope repertoires bound by IgM and IgG antibodies in AF were similar to those of the serum antibodies (FIGS. 25B-25D and FIGS. 31A-31C, red vs. black bars), while for IgA, there was higher frequency of antibody clones binding to Domain II of ZIKV E protein in the AF compared with serum.

Figures 26A, 26B:
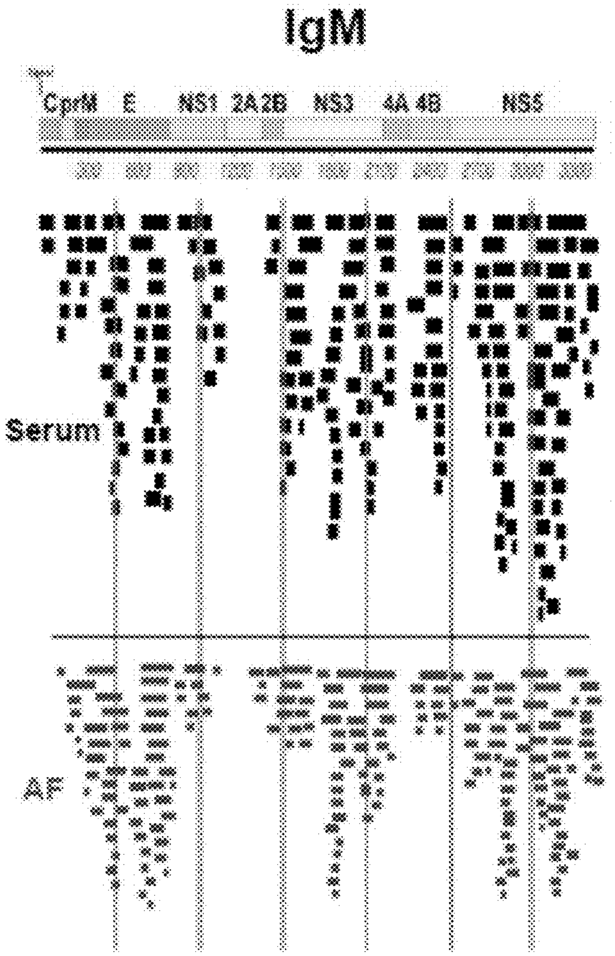
FIGS. 26A-26E show whole ZIKV proteome IgM/IgG/IgA antibody repertoires in serum and amniotic fluid samples in pregnancy following Zika virus infection in the third trimester. GFPDL analysis conducted with serum and AF from a ZIKV infected pregnant woman in the third trimester (ID #19 in Table 5) at 42 days post onset of symptoms.
Figure 26C:
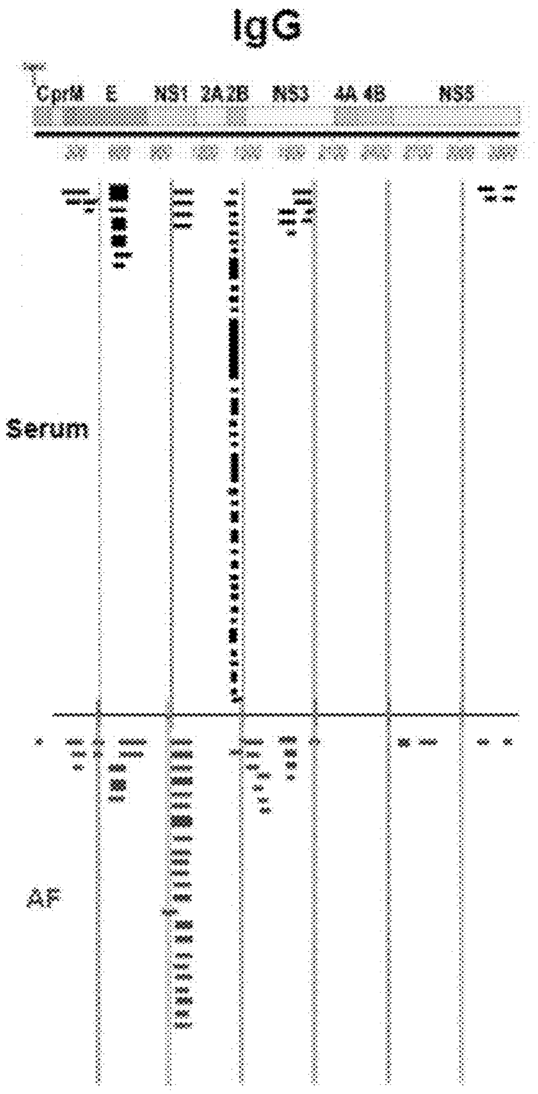
Figure 26D:
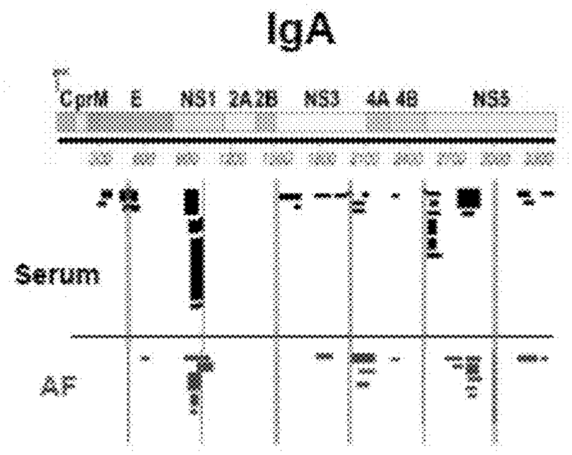
Figure 32A:
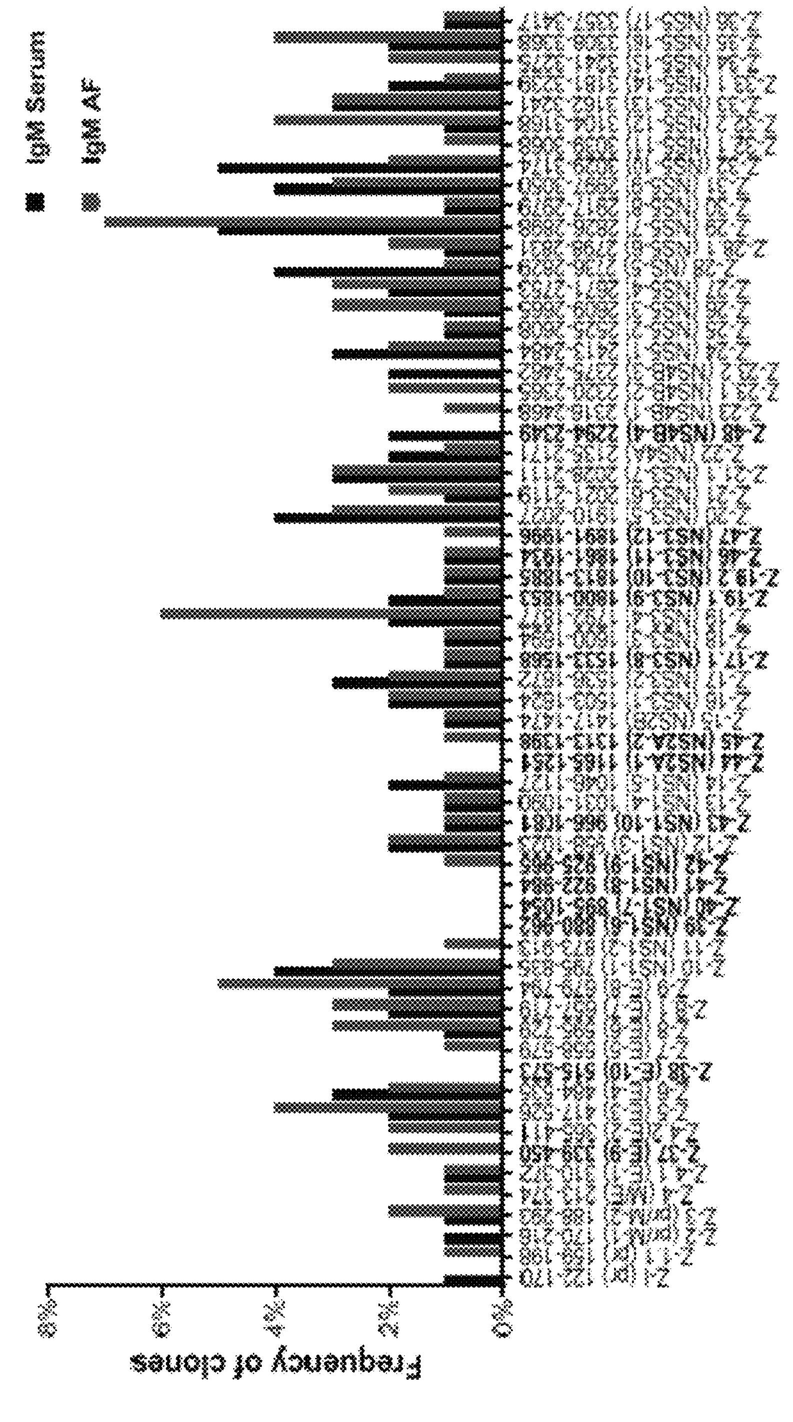
FIGS. 32A-32C show distribution of phage clones and frequency of phage clones binding in serum and AF antibodies following ZIKV infection in third trimester (Subject ID #19) at 42 days post onset of symptoms. Distribution of phage clones and frequency of phage clones binding (FIG. 32A) IgM, (FIG. 32B) IgG and (FIG. 32C) IgA antibodies expressing each antigenic site on the ZIKV genome isolated using GFPDL against the maternal serum (black) and AF (red) samples from the first trimester. The number of clones encoding each antigenic site was divided by the total number of ZIKV GFPDL-selected clones for each sample to calculate frequency. Those epitopes newly identified in the current study have been highlighted in bold black labeling on X-axis.
Figure 32B:
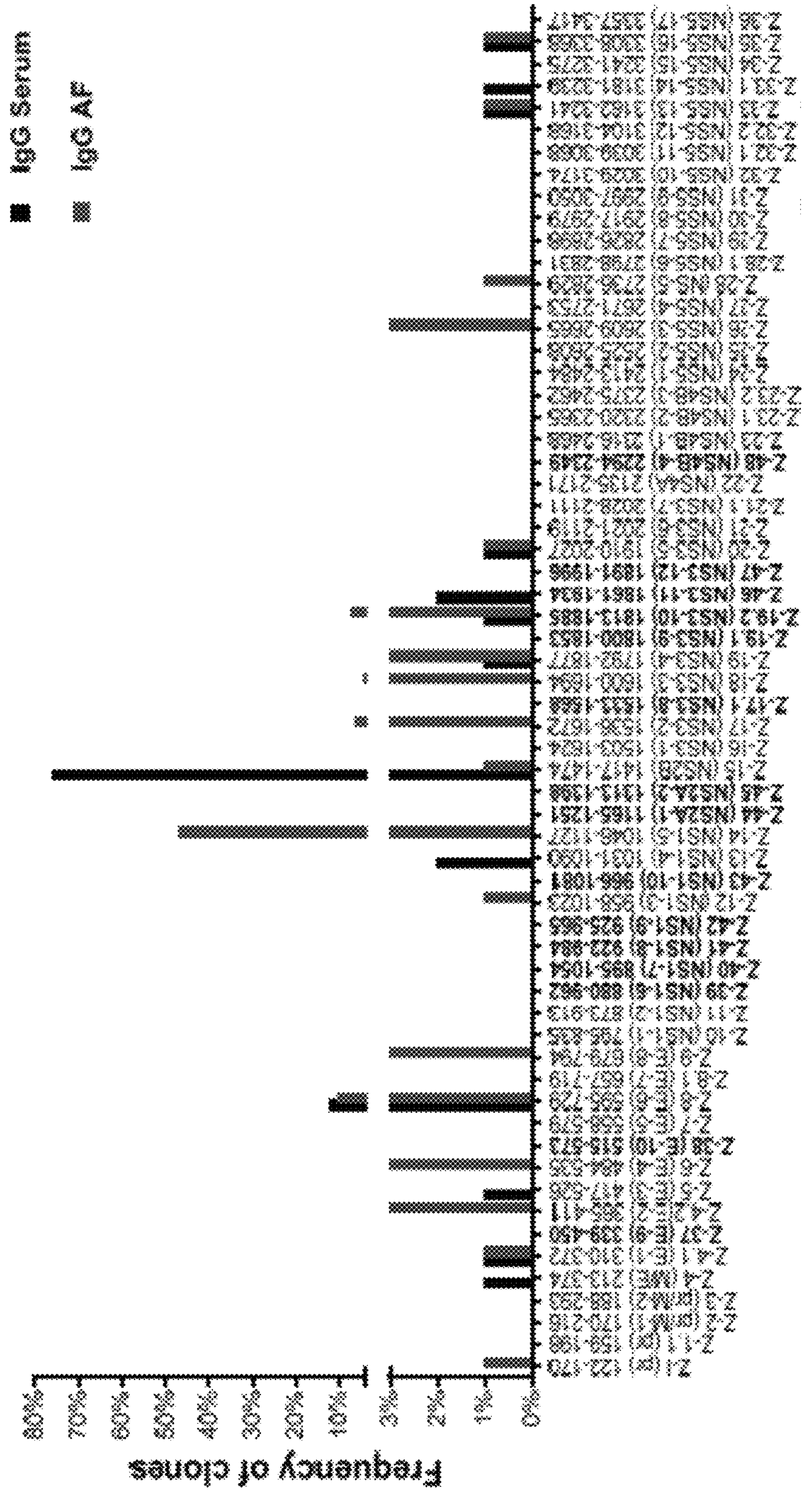
Figure 32C:
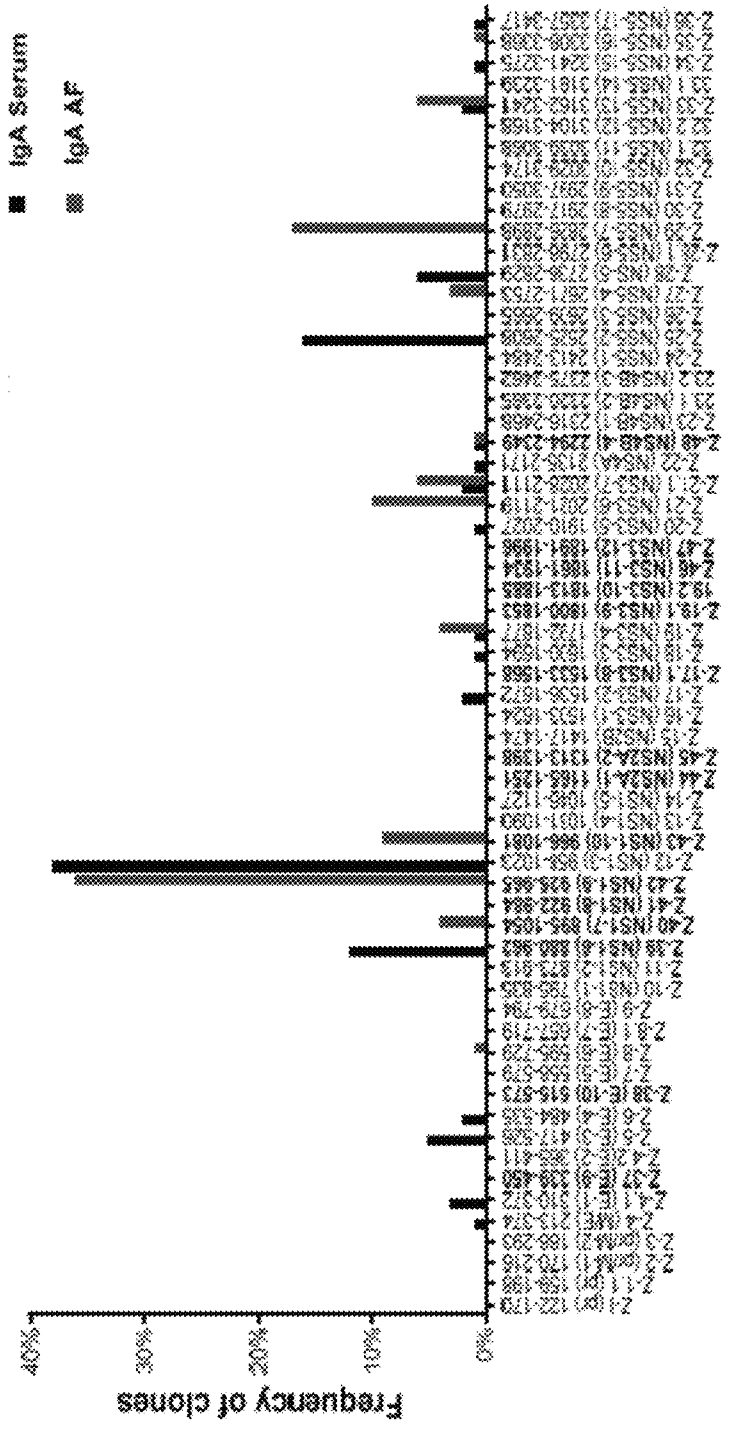

In the case of the third-trimester pregnancy, serum and AF samples were collected later in post-ZIKV infection (42 days). The number of serum IgM-bound phages ($3.3\times10^7$/mL) was still ~100-fold higher than the number of IgG-bound phages ($1.8\times10^5$/mL) followed by IgA-bound phages ($1.7\times10^3$/mL) (FIG. 26A). The AF IgM bound similar number of phages to the serum ($1.1\times10^7$/mL), while the AF IgG and IgA bound 10-fold fewer phages compared with the serum antibodies (FIG. 26A). In terms of epitope diversity, again broad repertoires were observed for both serum and AF IgM with no clear difference in distribution along the ZIKV genome (FIG. 26B, Table 7 and FIG. 32A). However, for the IgG antibodies, a very high frequency of an NS2B-bound epitope was observed in the serum (aa 1417-1474, FIG. 32B), while for the AF IgG there was a predominance of binding to an NS1 epitope (aa 1046-1127; FIG. 26C, Table 7, FIG. 32B). The serum and AF IgA antibodies gave similar epitope profiles with a high frequency of phages expressing an NS1 epitope (aa 925-965) and few epitopes in E, NS3, and NS5, with serum displaying a predominant selection of clones displaying NS5-7 (aa 2826-2898) (FIG. 26D, Table 7, FIG. 32C).

Figure 26E:
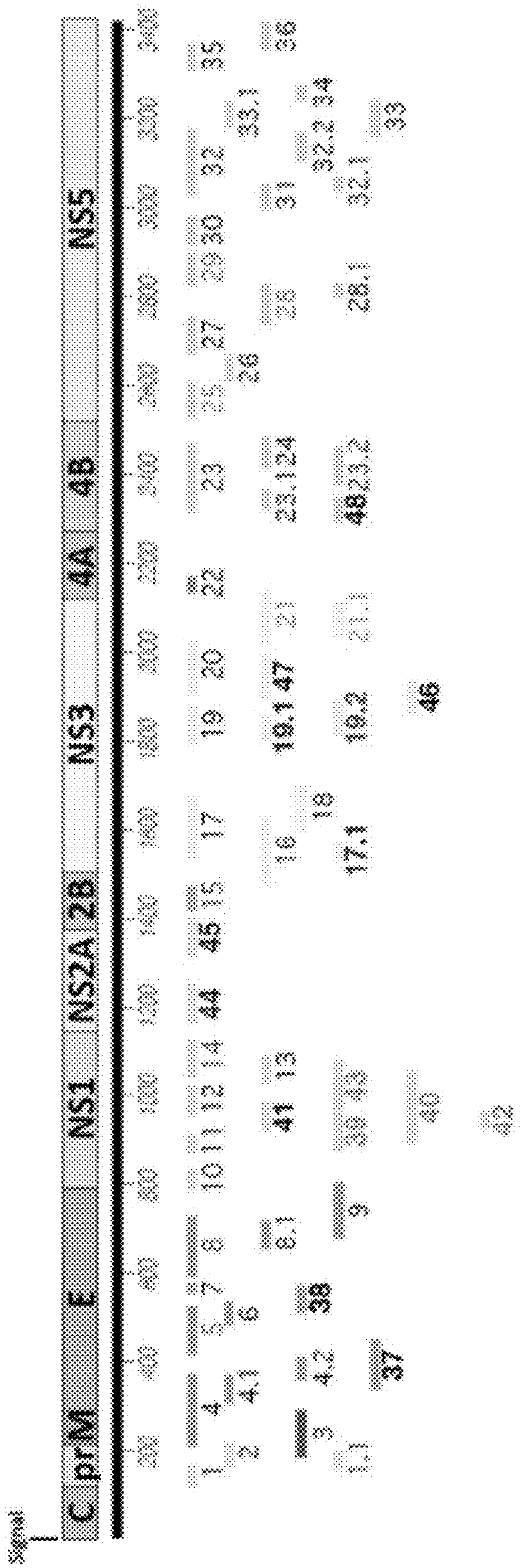

The combined GFPDL analysis, including serum and AF from the two ZIKV-infected pregnant women, identified ~40 antigenic sites (FIG. 26E). Many of these sites were previously identified using serum and urine samples from acute ZIKV infected individuals (see Example 1) (black-numbered antigenic sites, FIG. 26E). Relative frequencies of the inserts in each region is shown in Table 7 and in FIGS. 31 and 32 for ID #38 and #19, respectively. Those epitopes newly identified in the current study have been highlighted in bold black letters on the X-axis in FIG. 26E. For serum IgM, sites in E, NS1, NS3, NS4B and NS5 regions appeared relatively dominant, particularly, Site Z-10 (NS1, aa 795-835), and Site Z-23.2 (NS4B, aa 2375-2462). For the AF samples, a similar epitope-recognition pattern was observed spanning the entire ZIKV genome, with NS3 (Sites Z-18, 19 and 21) and NS5 (Sites Z-26, 35) regions appearing relatively dominant. Sites uniquely recognized by IgM but not IgG or IgA in the maternal serum and AF samples have been highlighted with blue numbering in FIG. 26E.

Figure 31A:
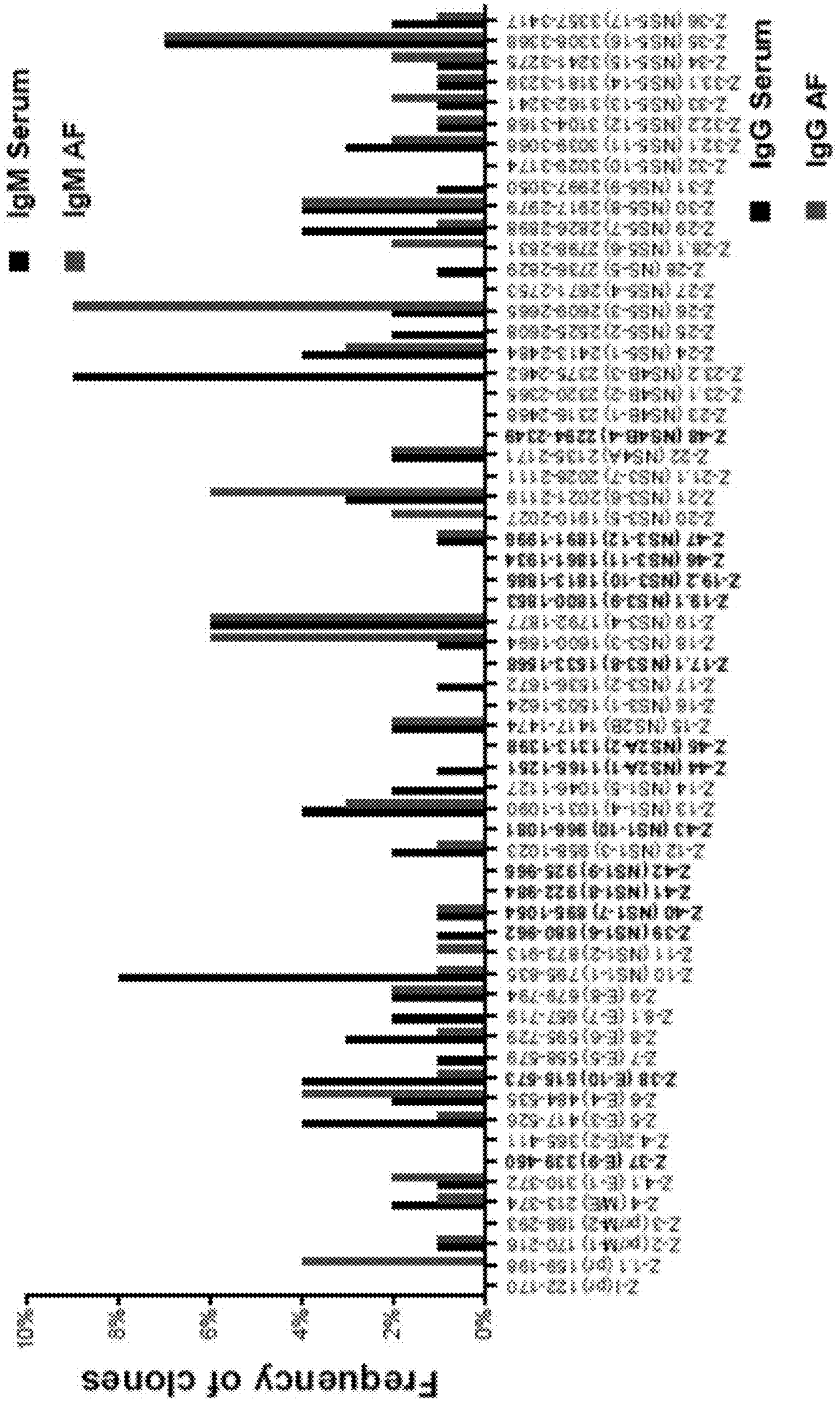
FIGS. 31A-31C show distribution of phage clones and frequency of phage clones binding in serum and AF antibodies following ZIKV infection in first trimester (Subject ID #38) at 10 days post onset of symptoms.
Figure 31B:
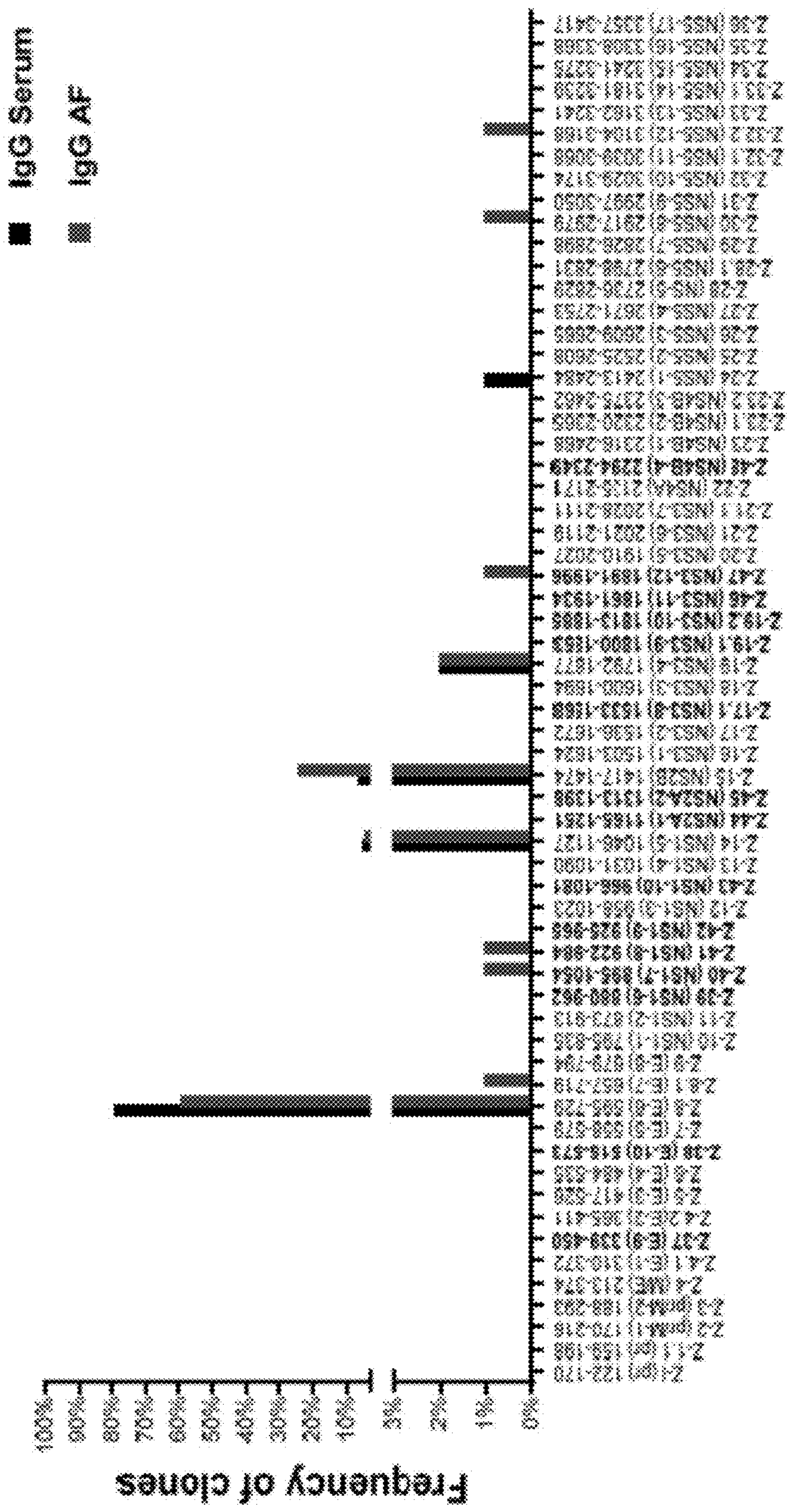
Figure 31C:

IgG in maternal serum showed an epitope-recognition pattern different from IgM, where it was mostly confined to E (FIG. 25C), followed by NS2B and NS1 proteins. Binding to the E protein was mainly in the Domain III region of the protein, which is the most divergent between ZIKV and other flaviviruses, thereby indicating a potentially primary immune response to ZIKV infection in both serum and AF compartments. The strong binding of serum IgG to NS2B, especially for subject ID #19 was also seen with serum samples from acute ZIKV infections (see Example 1). Site Z-15 in the NS2B protein (aa 1417-1474) is only 30-55% conserved between ZIKV and other flaviviruses while being 100% conserved among different ZIKV strains indicating a potential serodiagnostic marker of the ZIKV-specific IgG response. We also observed IgG binding to an NS1 epitope (Site Z-14, aa 1046-1127) in the serum and AF from subject ID #38, but only in AF from subject ID #19. (FIGS. 31B and 32B). Epitopes unique or predominantly bound by IgG are highlighted in red numbering in FIG. 26E.

In the case of IgA, similar epitope diversity was observed for serum and AF in both subjects. The predominant epitope for subject ID #38 was mapped to NS5 (FIGS. 25D and 26D; site Z-28; aa 2736 and Z-29; 2826-2898 in FIG. 30C). But IgA from subject ID #19 was more focused on NS1 (FIG. 26D and sites Z-12; AA 958-1023, in FIG. 32C). However, serum recognized antigenic site NS5-7 (aa 2826-2898) preferentially compared with AF in this patient. Sites uniquely or predominantly identified by IgA are highlighted with green numbering in FIG. 26E.

Figure 33A:
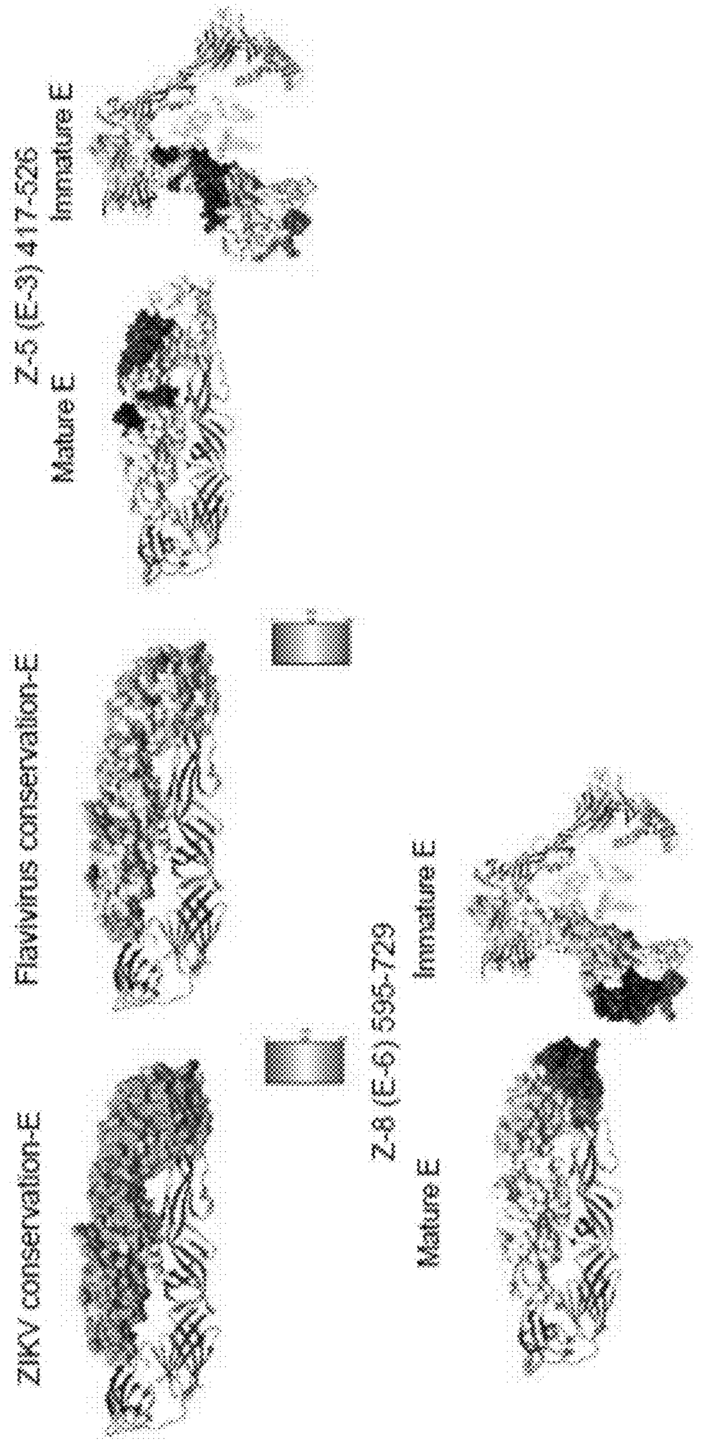
FIGS. 33A-33C are structural representations of antigenic sites differentially identified in serum vs AF in ZIKV E, NS1 and NS5 proteins using GFPDL. Frequency of differentially recognized antigenic sites by serum vs AF following ZIKV infection are shown in Table 7.
Figure 33B:
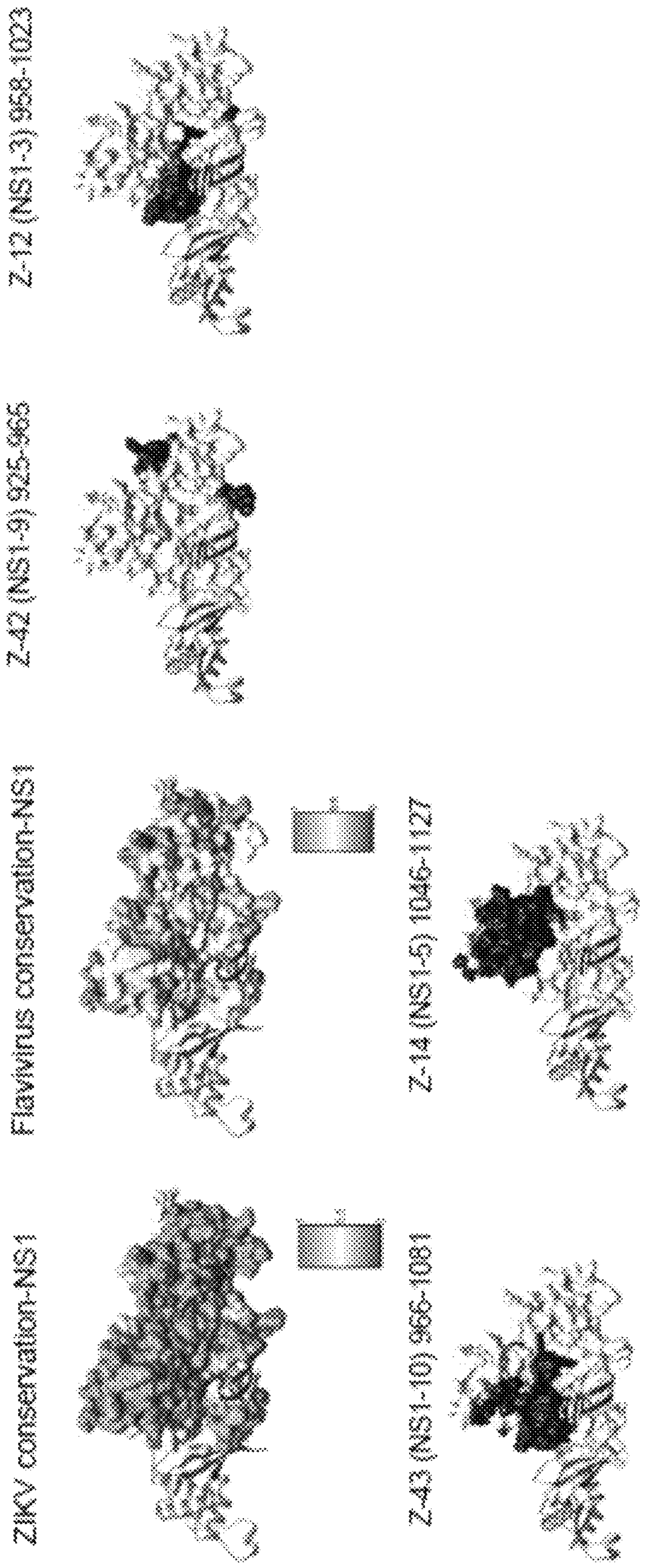
Figure 33C:
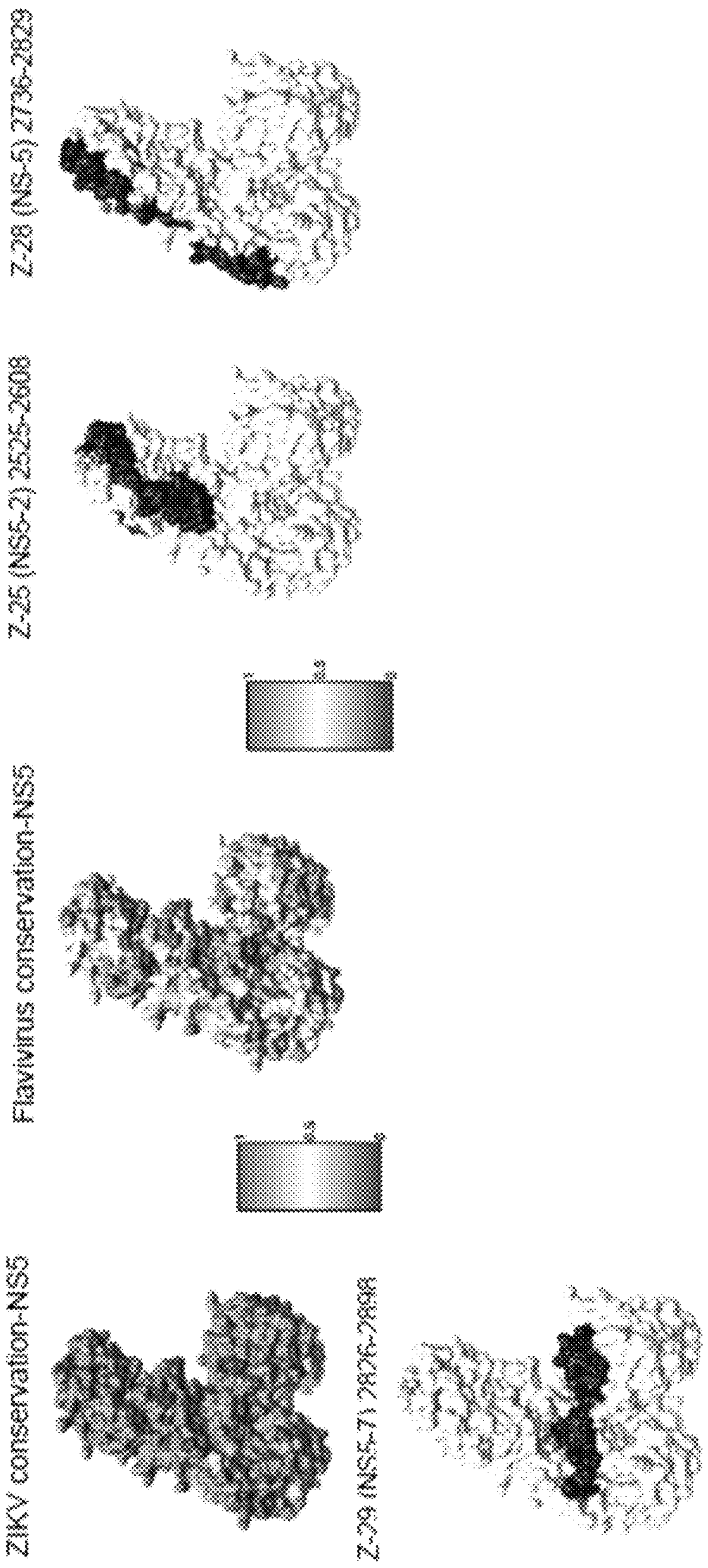
Figure 34:
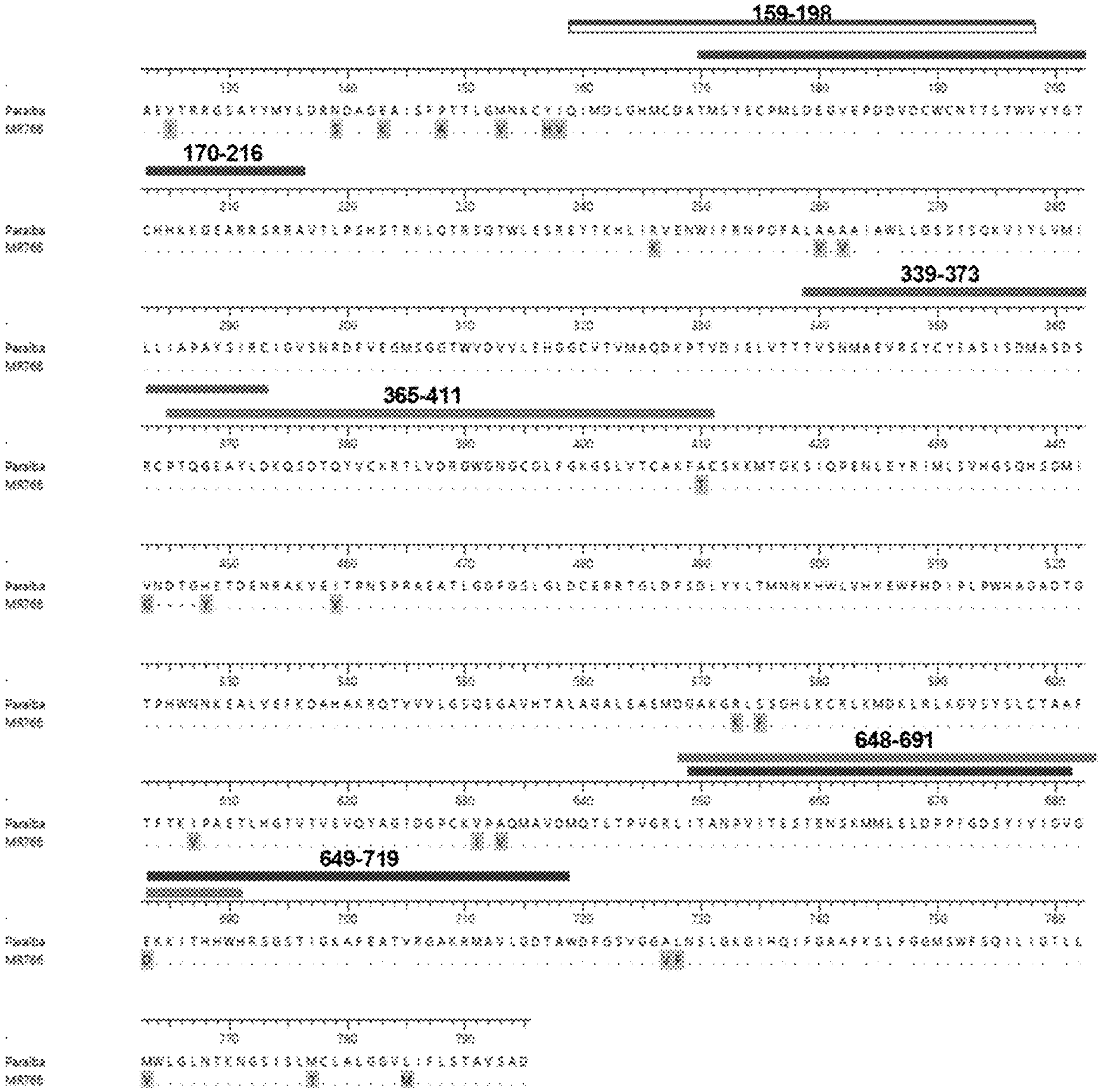
FIG. 34 shows sequence identity (%) of immunodominant prM-E antigenic site within African and Asian lineage ZIKV strains. The sequence shown in the figure corresponds to residues 123-795 of SEQ ID NO: 9.

In the current study, several new epitopes were identified in E, NS1 and NS5 proteins that were preferentially recognized by IgG or IgA (Table 7). Structural representation of the new antigenic sites is shown in FIG. 33. The E sites are shown on both immature and mature forms of the E-protein. The heat maps delineate the conservation of these sites among ZIKV strains and among flaviviruses. All the sites are predicted to be expressed on the surface of both immature and mature E proteins. Similarly, the NS1 and NS5 sites are predicted to be surface exposed. These sites are highly conserved among ZIKV strains, but poorly conserved between ZIKV and other flaviviruses (Table 8). Therefore, they likely represent ZIKV-specific early immune responses to infection.

Figure 27A:
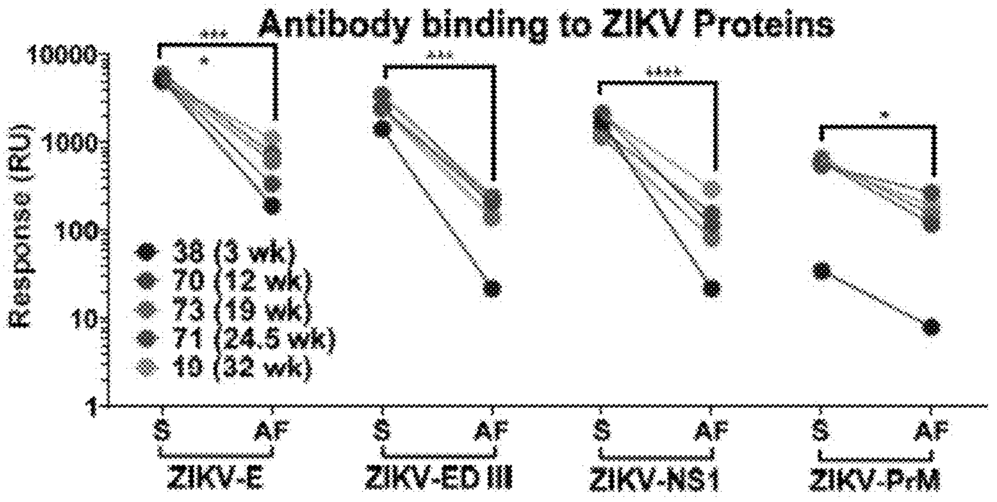
FIGS. 27A-27C show antibody binding, isotype distribution, and affinity of serum and AF paired samples to E, E-DIII, NS1, and prM using SPR. Serum and AF samples, collected from pregnant females post-ZIKV infection, were analyzed for antibody binding to purified ZIKV E, E-domain III, NS1 and prM proteins in SPR.

Measurements of Binding, Isotype Profiles, and Affinity of Serum and AF Antibodies from ZIKV Infected Women to E, E-DIII, NS1, and prM Using SPR The GFPDL analyses identified multiple epitopes recognized by antibodies in serum and AF from recent ZIKV-infected pregnant women. Some were common and some showed differences between subjects and between the compartments (FIGS. 25 and 26). Several of these antigenic sites that were differentially recognized by IgG and IgA in serum versus AF following ZIKV infection in first trimester or 3rd trimester are shown in Table 9. To further compare the quantity and quality of antibodies found in the serum vs amniotic fluids from pregnant women, serum/AF paired samples from five women who were infected at different gestational stages with ZIKV were evaluated (Table 5, Table 6). SPR was used to measure total antibody binding to surface ZIKV proteins [prM, E, and E-domain III (E-DIII)] and to NS1 non-structural protein (FIG. 27A). The maximum resonance units (Max RU) for each serum and AF sample was calculated by multiplying the observed RU signal with the dilution factor to provide the data for undiluted serum/AF sample. Irrespective of the gestational stage and days post onset of symptoms (ranging between 10 and 42 days, Table 5), similar total binding was observed for the serum samples of the five women against the E and NS1 proteins. Total binding (Max RU) of serum antibodies was higher for ZIKV E, E-DIII, and NS1 compared with prM. Sample #38 (infected at −3 weeks of gestational age; 10-days post onset of symptoms) displayed lower antibody binding to the E-domain III and prM proteins compared with samples from the other 4 women who were infected later in pregnancy and were sampled at later time-points post-onset of symptoms. In all cases, the total binding of AF antibodies to the 4 proteins was significantly lower (1-2 logs) compared with the serum antibodies (FIG. 27A).

Figure 27B:
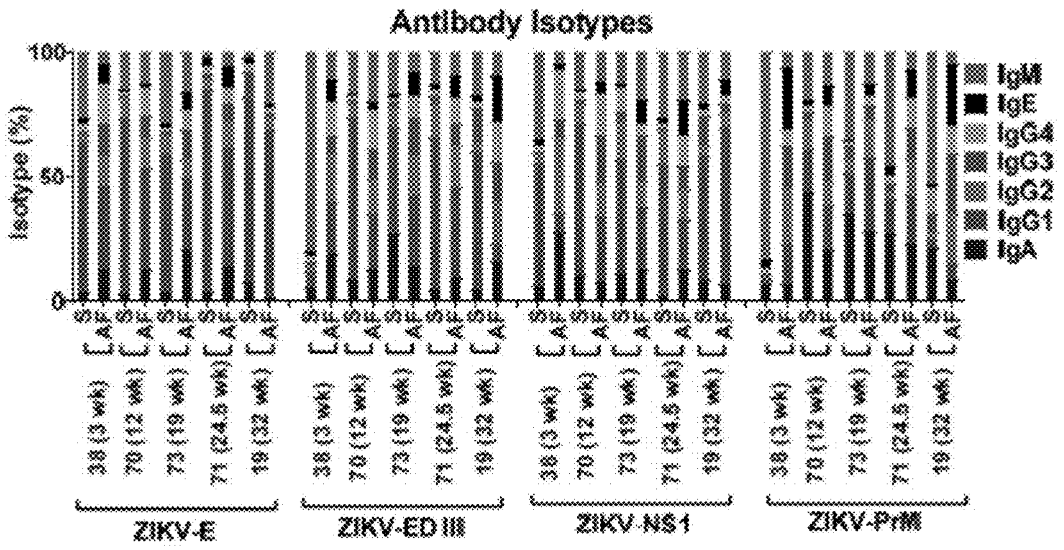

Next, the relative contributions of different isotypes (IgM, IgG, IgA, IgE) and IgG subclasses (IgG1-4) to the binding of serum and AF antibodies to the four ZIKV proteins was determined. High IgM contribution was found primarily in the binding to E-DIII and prM with the serum from the first trimester woman (ID #38) (10 days post-onset of symptoms). All isotypes and IgG subclasses contributed to the serum binding to all four proteins with highest relative contribution of IgG1 to the binding to E and NS1 proteins. The relative isotype contributions for ZIKV-specific antibodies for paired serum and AF were not identical. There was a discordance between the bound antibody isotype distribution of paired serum and AF samples, wherein AF samples showed more equal distribution of each antibody isotype (especially IgG3, IgG4 and IgE) for antibodies binding to E-DIII, NS1 and prM, but bound serum antibodies were predominantly either IgG1 (E-DIII and NS1) or IgM (for prM) (FIG. 27B).

Figure 27C:
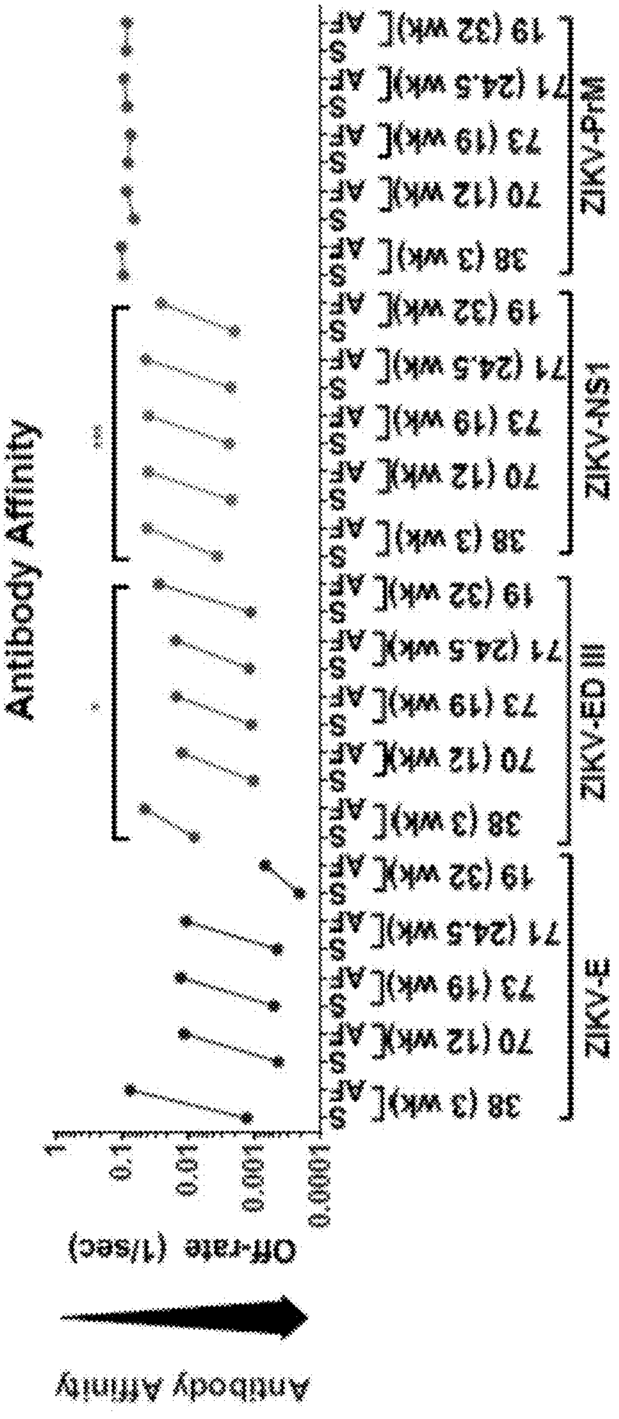

Finally, the antibody off-rate constants that describe the fraction of antibody-antigen complexes decaying per second were determined directly from the serum or AF sample interaction with recombinant ZIKV-E, E-DIII, NS1, and prM proteins using SPR in the dissociation phase, as described above in the Materials and Methods section. Since the SPR chip surface is coated with low antigen density to assure monovalent interactions, the calculated off-rates can be used as a surrogate of antibody affinity as previously described (Ravichandran et al., *Nat Commun* 10, 1943, 2019; Khurana et al., *Sci Transl Med* 3, 85ra48, 2011;

Khurana et al., *Nat Commun* 10, 3338, 2019). As can be seen in FIG. 27C, the highest antibody affinities (i.e., slowest off rates) were measured against the ZIKV E protein (<$10^{-3}$/sec) followed by E-DIII (~$10^{-3}$/sec) and NS1 (<$10^{2}$/sec). Subject ID #38 (10 days post onset of symptoms in first trimester) exhibited lower binding affinities against the three proteins compared with the other four subjects (24-42 days post onset of symptoms). The affinity of binding to the prM was very low (~$10^{-1}$/sec) across the board. The disassociation off rates of the amniotic fluid antibody binding to E, E-DIII, and NS1 proteins were faster (>1 log) than the serum antibodies, reflecting lower binding affinity (FIG. 27C). These findings of discordance in antibody isotyping and antibody affinity between AF and serum suggest that the antibodies in the amniotic fluid not only consist of maternal antibodies following direct transfer from the mother's blood but also contributed by local immune response in utero.

Figure 28A:
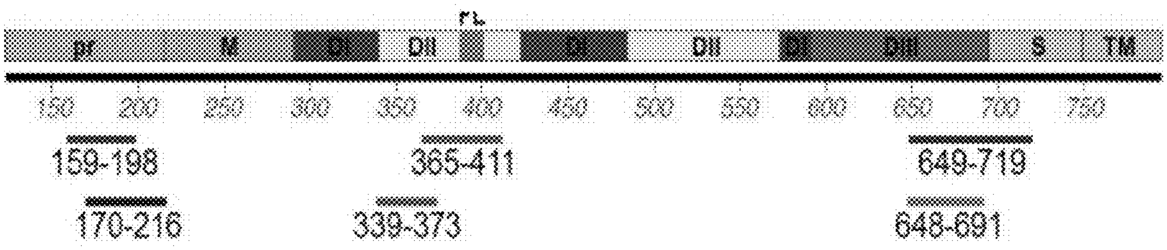
FIGS. 28A-28D show seroreactivity of serum and AF samples with selected ZIKV prM and E antigenic site peptides and impact of serum and AF antibodies on ZIKV infection in vitro.
Figure 28B:
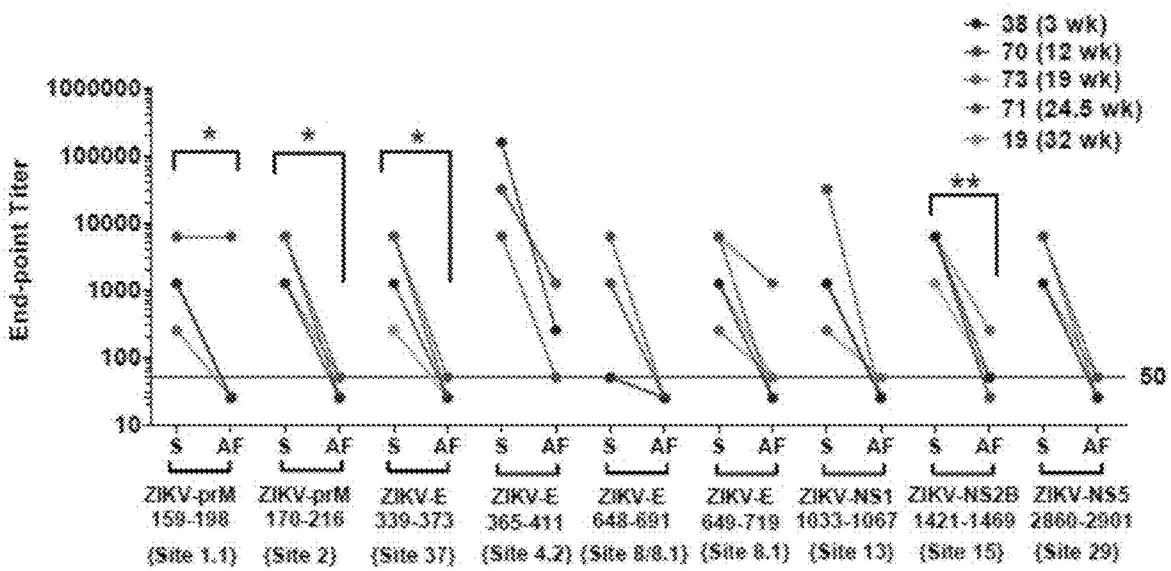
Figure 35:
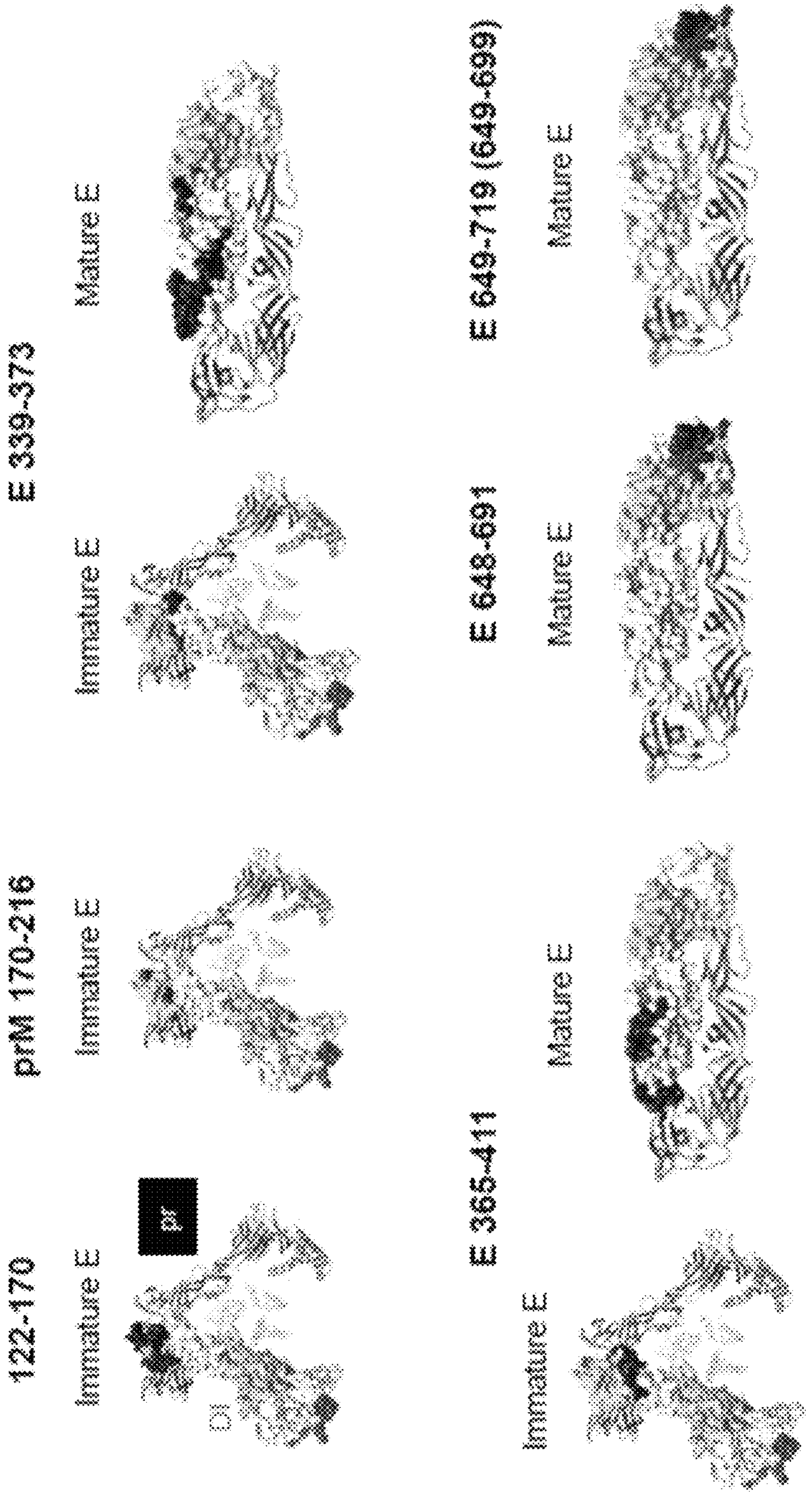
FIG. 35 depicts antigenic sites within ZIKV-prM/E identified by the GFPDL analysis in blue on the structures of both immature (PDB 5U4W) and mature ZIKV E (PDB 5JHM). Domain I is shaded in light grey (PDB 5JHM), pr domain is shaded in yellow and M in pink (PDB 5U4W). PDB Structure #5U4W encompasses residues 288-794 and PDB Structure #5JHM encompasses residues 313-699 based on ZIKV_ICD polyprotein sequence (FIG. 8).

Antibody Binding of Serum and Amniotic Fluid to Immunodominant IgG/IgA Selected Antigenic Site Peptides To further evaluate the specificity of post-ZIKV infection antibodies in serum and AF to several antigenic sites in prM, E, NS1, NS2B, and NS5 that were identified at high frequency in IgG/IgA GFPDL analysis, peptides were chemically synthesized and analyzed in ELISA (FIG. 28A). These immunodominant antigenic sites are surface exposed on the prM and E protein structures (FIG. 35). Peptide ELISA using the patient sera and AF showed that the strongest serum antibody binding (combined binding of IgM+IgG+IgA antibody isotypes) was to the ZIKV peptide E 365-411 that spans domain II containing the fusion peptide (site 4.2), followed by peptide E 649-719 at the C-terminus of domain III (site 8.1), and to peptide 170-216 (site 2) in the C-terminus of prM (FIG. 28B). Among the NS peptides, the strongest serum-antibody binding was to NS2B, which was also identified as a dominant target of early post ZIKV infection antibodies in the study described in Example 1. The binding of AF antibodies to all the peptides was significantly lower compared with serum, in agreement with the binding to the whole proteins in SPR (FIG. 27A), but still showed positive reactivity with the E-domain II peptide 365-411(FIG. 28B).

Impact of Serum/AF Antibodies on ZIKV Infection in Vero Cells

In addition to binding profiles, the relative capacity of the paired serum and AF samples on infection of two ZIKV strains was evaluated in vitro.

Figure 28C:
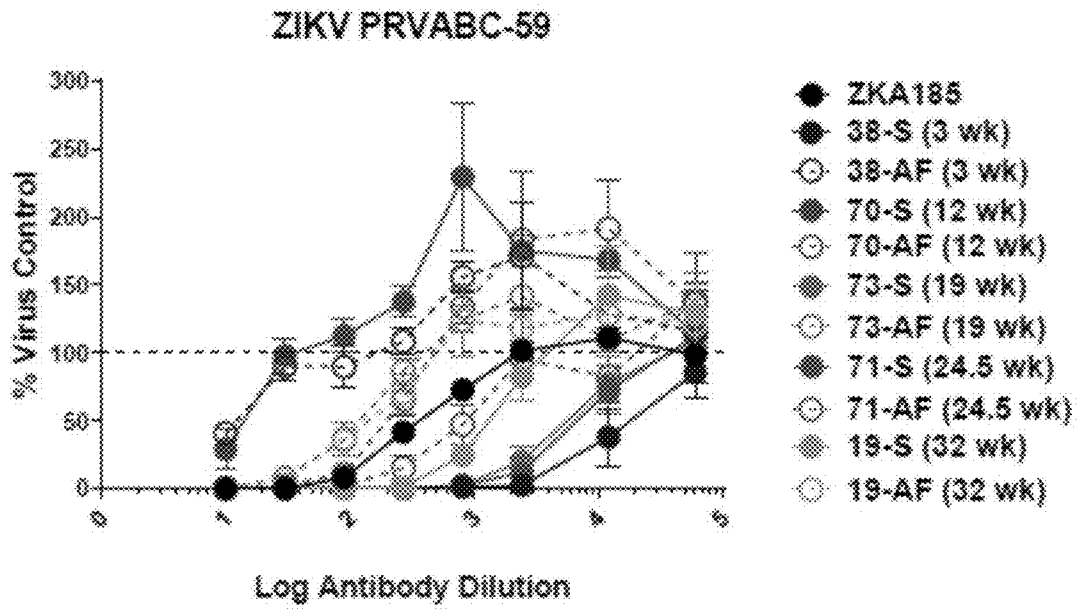
Figure 28D:
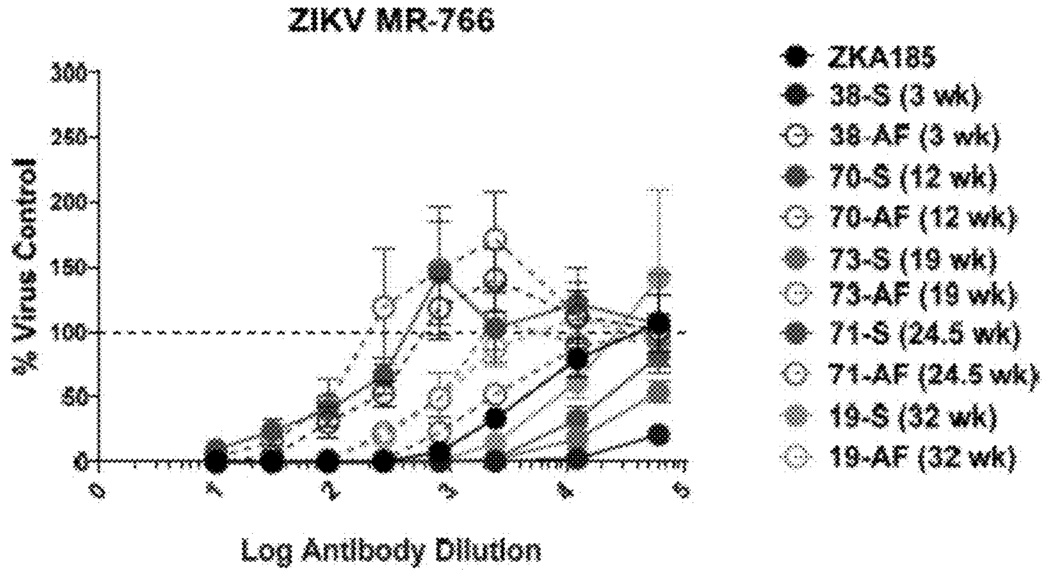

Sera and AF were serially diluted and mixed with ZIKV strains PRVABC59 (Asian lineage) or MR766 (African lineage) and added to Vero cells. The percent of virus control (determined by RT-qPCR) was plotted against log serum dilution (FIGS. 28C and 28D). The ZIKV-neutralizing monoclonal antibody ZKA-185 (Mishra et al., mBio 9, 2018) was used as a positive control (at starting concentration of 1 μg/ml). The $ID_{50}$ of this MAb was ~1:10,000 and ~1:5,000 against PRVABC59 and MR766, respectively (FIGS. 28C and 28D; black symbols). The viral infectivity curves for sera demonstrated potent inhibition of both ZIKV strains at low serum dilutions (high antibody concentration) that was lost rapidly upon further dilution of sera. One serum sample from subject ID #70 (12 weeks gestation) demonstrated low $ID_{50}$ (<1:100), moreover upon serial dilutions it showed an increase in ZIKV PRVABC59 infection of Vero cells and to lesser degree of ZIKV MR766 infection (FIGS. 28C and 28D, red closed symbols). Compared with the serum samples from the same subjects, the AF samples (open symbols in FIGS. 28C and 28D) demonstrated lower neutralization titers (presented as different open-symbol colors in FIGS. 28C and 28D). Modest enhancement of ZIKV PRVABC59 virus infection was observed with 4/5 AF samples at higher dilutions.

Discussion

In the current study, GFPDL analyses was conducted on IgM, IgG, and IgA antibodies using paired serum and AF samples from pregnant women at the first trimester and third trimester with confirmed ZIKV infections (both women were seronegative for DENV antibodies). These pregnant females self-reported to be flavivirus naïve. The ZIKV infection in vivo was confirmed for all pregnant women samples by the RT-PCR test (Table 6). Samples from all women at time-points of collection were PCR-negative for DENV and CHIKV infection (Table 6). Furthermore, the two pregnant female samples used for GFPDL based antibody repertoire analysis were negative for the DENV antigen but showed seropositivity for both IgM and IgG antibodies to ZIKV (Table 5). Moreover, all these samples used in the study reacted strongly in a research grade ZIKV-specific peptide serodiagnostic IgG-ELISA based on ZIKV-NS2B and ZIKV-NS5 peptides (Table 6), which are divergent between ZIKV and other flaviviruses (Table 8). The NS2B peptide was also demonstrated by Mishra et al. to be suitable for ZIKV serodiagnosis based on its sensitivity (96%) and specificity (95.9%) (Mishra et al., *mBio* 9, 2018).

In the two GFPDL analyses conducted in this study, the largest number of phages were bound by IgM antibodies followed by IgG and IgA. Furthermore, the epitope repertoires of IgM antibodies in both serum and AF were very broad, spanning the entire ZIKV genome. In contrast, the IgG and IgA antibodies were more focused on sites in E, NS1, NS2B and NS5. Between the two cases, several new epitopes were identified that were not described in Example 1. Structural modeling demonstrated that these epitopes are located on the exposed surfaces of the E (mature and immature), NS1, and NS5 proteins (FIGS. 33 and 35). The GFPDL was performed on each individual antibody IgM, IgG and IgA isotype and showed a diverse antibody response across ZIKV-E protein (FIGS. 25, 26, 31 and 32). The ELISA data shown in FIG. 28B is a sum combination of all IgM/IgG/IgA antibody binding to these peptides and therefore a strong response to domain II (including the FL) is possibly due to contribution of all antibody isotypes in the patient plasma/AF samples.

Analysis of paired serum and AF samples from ZIKV-infected pregnant women (including the two sentinel subjects), at different gestational stages (Table 5) by SPR with E, E-DIII, NS1 and prM proteins revealed several discordances between sera and AF antibodies: a) ZIKV-specific different antibody isotype distribution; b) difference in total binding (serum Max RU >>AF) and c) difference in antibody affinity to E, E-DIII, and NS1 (AF antibodies showed 1-2 log lower affinity than serum antibodies), but not prM (low affinity binding among both serum and AF). These findings strongly suggest that the AF antibodies may not be only comprised of maternally derived antibodies, but instead were produced locally by ZIKV infection of cells in utero. The transfer of maternal IgG to fetuses via the placenta has been well documented, especially in the second and third trimesters (Jennewein et al., *Semin Immunopathol* 39, 605-613, 2017). However, in agreement with the present findings, Calvet et al. reported the presence of anti-ZIKV IgM in amniotic fluid of two pregnant women who were seronegative (no IgM in serum or urine) (Calvet et al., *Lancet Infect Dis* 16, 653-660, 2016). These findings suggest that mothers were infected with Zika virus early in pregnancy and cleared the infection, but the virus entered the fetus where it persisted for a longer time.

Recent studies on the immune cell make up of human decidua from in term and preterm parturition described the presence of a variety of lymphocytes including NK cells, T cells, B cells, and iNKT cells (Rinaldi et al., *Mol Hum Reprod* 23, 708-724, 2017). In another study, the frequency of B cells was reported to be higher in basalis compared with parietalis, but parietalis contained a higher proportion of mature/naïve B cells at the expense of transitional B cells (Solders et al., *Stem Cells Int* 2017, 8010961, 2017). Thus, it is highly likely that the presence of ZIKV in the placenta and fetus results in activation of local tissue resident B cells that tend to be more immature and less likely to undergo affinity maturation.

Flavivirus infections and vaccination may result in the generation of antibodies that can provide protection or antibody-dependent enhancement of infection or disease leading to fetal developmental abnormalities (including microcephaly and other CNS pathology) (Maciejewski and Pierson, *Cell Host Microbe* 24, 622-624, 2018; Shim et al., *mBio* 10, 2019; Robbiani et al., *J Exp Med* 216, 2302-2315, 2019). In the current study, 4 of 5 AF samples and 1 of 5 serum samples showed dilution dependent ZIKV neutralization or enhancement. The Vero cells used in the assay are $FcR^-$, which are different from the commonly used $FcR^+$ K-562 cells in which enhancement is entirely dependent on FcR binding of antibody. The mechanism of enhancement in Vero cells requires further investigation and may not correlate directly with the in vivo scenario. Nevertheless, the impact of antibodies in serum and AF (or other body compartments) on virus infection of target cells may be correlated with antibody specificity and affinity (apart from FcR binding), since many target cells in vivo are $FcR^-$.

Together, the data demonstrate the importance of applying unbiased comprehensive analyses to evaluate the specificity, quantity, and quality of antibodies in different body compartments (blood vs. amniotic fluid) following infection with the Zika virus. The findings indicate that the antibodies found in the amniotic fluid may derive from resident immune cells in utero (in the placenta as well as in the developing fetuses), especially at early gestational stages before active transfer of IgG antibodies via the FcRn in placenta. The AF antibodies tend to be of lower affinity compared with the serum antibodies. Moreover, in addition to protective antibodies, some antibodies with enhanced ZIKV infection potential were observed in AF (and one serum) from infected pregnant women posing additional risks for the developing fetuses and indicating careful evaluation of antibody response in ZIKV infected pregnant women.

TABLE 1

Demographic, epidemiological, serology and diagnostic information of samples in Example 1

| Sample Characteristic | | | | | | | | | | | | | | | |
|---|---|---|---|---|---|---|---|---|---|---|---|---|---|---|---|
| | | | | Prior DENV | Days since Onset of | ELISA (Absorbance)^ | | | | PCR* | | | | | |
| ID | Visit (Day) | Gender | Age (Yr) | exposure | Symptoms | ZIKV-IgG | ZIKV IgM | DENV-IgG | DENV-IgM | ZIKV-Serum | ZIKV-Urine | DENV-Serum | DENV-Urine | Pan-Flavi-Serum | Pan-Flavi-Urine |
| 41- | 0 | F | 41 | NO | 2 | 1.696 | 0.19 | 1.904 | 0.157 | 1 | 0 | 0 | 0 | 0 | 1 |
| 001-F | 3 | | | | 5 | 0.019 | 0.536 | 0.019 | 0.127 | 0 | 1 | 0 | 0 | 0 | 1 |
| | 7 | | | | 9 | 0.185 | 1.572 | 0.014 | 0.127 | 0 | 1 | 0 | 0 | 0 | 1 |
| | 28 | | | | 30 | 0.755 | 0.995 | 0.044 | 0.139 | | | | | | |
| 41- | 0 | M | 37 | NO | 2 | 1.222 | 0.022 | 0.797 | 0.116 | 0 | 0 | 0 | 0 | 0 | 0 |
| 002-F | 3 | | | | 5 | 1.168 | 0.024 | 0.832 | 0.12 | 0 | 0 | 0 | 0 | 0 | 0 |
| | 7 | | | | 9 | 1.137 | 0.029 | 0.774 | 0.117 | 1 | 0 | 0 | 0 | 1 | 0 |
| | 28 | | | | 30 | 1.036 | 0.03 | 0.681 | 0.112 | | | | | | |
| 41- | 0 | M | 51 | NO | 3 | 1.603 | 0.183 | 1.93 | 0.106 | 0 | 0 | 0 | 0 | 0 | 0 |
| 003-F | 3 | | | | 6 | 1.519 | 0.14 | 1.788 | 0.09 | 1 | 0 | 0 | 0 | 1 | 0 |
| | 28 | | | | 31 | 1.787 | 0.18 | 1.321 | 0.082 | | | | | | |
| 41- | 0 | M | 49 | NO | 3 | 0.979 | 0.048 | 0.863 | 0.311 | 1 | 1 | 0 | 0 | 1 | 1 |
| 006-F | 3 | | | | 6 | 2.569 | 0.292 | 2.185 | 0.373 | 1 | 1 | 0 | 0 | 1 | 1 |
| | 7 | | | | 10 | 2.544 | 0.332 | 9.999 | 0.531 | 0 | 1 | 0 | 0 | 0 | 1 |
| | 28 | | | | 31 | 2.494 | 0.245 | 9.999 | 0.457 | | | | | | |
| 41- | 0 | F | 32 | NO | 3 | 0.171 | 0.079 | 0.602 | 0.082 | 0 | 1 | 0 | 0 | 0 | 1 |
| 010-F | 3 | | | | 6 | 1.032 | 0.176 | 1.38 | 0.101 | 0 | 0 | 0 | 0 | 0 | 0 |
| | 7 | | | | 10 | 1.943 | 0.635 | 9.999 | 0.246 | 0 | 0 | 0 | 0 | 0 | 0 |
| | 28 | | | | 31 | 1.692 | 0.972 | 2.935 | 0.24 | | | | | | |
| 41- | 0 | F | 34 | NO | 3 | 0.229 | 0.085 | 0.815 | 0.317 | 1 | 1 | 0 | 0 | 1 | 1 |
| 017-F | 3 | | | | 6 | 1.162 | 0.271 | 1.861 | 0.363 | 0 | 1 | 0 | 0 | 0 | 1 |
| | 7 | | | | 10 | 1.591 | 0.626 | 9.999 | 0.806 | 0 | 1 | 0 | 0 | 0 | 1 |
| | 28 | | | | 31 | 2.282 | 0.231 | 9.999 | 0.635 | | | | | | |
| 41- | 0 | F | 33 | NO | 0 | 0.83 | 0.152 | 1.358 | 0.211 | 1 | 1 | 0 | 0 | 0 | 0 |
| 023-F | 3 | | | | 3 | 2.629 | 0.251 | 9.999 | 0.478 | 0 | 1 | 0 | 0 | 0 | 1 |
| | 7 | | | | 7 | 2.684 | 0.348 | 9.999 | 0.685 | 0 | 1 | 0 | 0 | 0 | 0 |
| | 28 | | | | 28 | 2.613 | 0.266 | 9.999 | 0.524 | | | | | | |
| 41- | 0 | M | 38 | NO | 5 | 1.257 | 0.04 | 0.484 | 9.999 | 1 | 0 | 0 | 0 | 0 | 0 |
| 028-F | 3 | | | | 8 | 2.445 | 0.168 | 9.999 | 9.999 | 0 | 1 | 0 | 0 | 0 | 0 |
| | 7 | | | | 12 | 2.445 | 0.382 | 9.999 | 9.999 | 0 | 0 | 0 | 0 | 0 | 0 |
| | 28 | | | | 33 | 2.024 | 0.122 | 2.851 | 9.999 | | | | | | |

TABLE 1-continued

Demographic, epidemiological, serology and diagnostic information of samples in Example 1

| Sample Characteristic | | | | | | ELISA (Absorbance)^ | | | | PCR* | | | | | |
|---|---|---|---|---|---|---|---|---|---|---|---|---|---|---|---|
| ID | Visit (Day) | Gender | Age (Yr) | Prior DENV expo-sure | Days since Onset of Symp-toms | ZIKV-IgG | ZIKV IgM | DENV-IgG | DENV-IgM | ZIKV-Serum | ZIKV-Urine | DENV-Serum | DENV-Urine | Pan-Flavi-Serum | Pan-Flavi-Urine |
| 41-031-F | 0 | M | 19 | NO | 2 | 1.858 | 0.037 | 0.374 | 0.04 | 0 | 1 | | | | |
| | 3 | | | | 5 | 2.576 | 0.062 | 0.593 | 0.059 | 0 | 1 | 0 | 0 | 0 | 0 |
| | 7 | | | | 9 | 2.867 | 0.217 | 1.159 | 0.085 | 0 | 1 | 0 | 0 | 0 | 0 |
| | 28 | | | | 30 | 2.678 | 0.045 | 1.022 | 0.075 | | | | | | |
| 41-036-F | 0 | M | 50 | NO | 3 | 1.32 | 0.566 | 1.583 | 0.135 | 0 | 1 | 0 | 0 | 0 | 1 |
| | 3 | | | | 6 | 2.599 | 1.146 | 9.999 | 0.307 | 0 | 1 | 0 | 0 | 0 | 0 |
| | 7 | | | | 10 | 2.486 | 0.734 | 9.999 | 0.295 | 0 | 1 | 0 | 0 | 0 | 0 |
| | 28 | | | | 31 | 2.455 | 0.163 | 9.999 | 0.276 | | | | | | |
| 42-001-F | 0 | F | 35 | NO | 0 | 0.063 | 0.023 | 0.075 | 0.185 | 1 | 1 | 0 | 0 | 1 | 1 |
| | 3 | | | | 3 | 1.417 | 0.142 | 1.396 | 0.578 | 0 | 1 | 0 | 0 | 0 | 1 |
| | 7 | | | | 7 | 2.233 | 0.218 | 9.999 | 0.99 | 0 | 1 | 0 | 0 | 0 | 1 |
| | 28 | | | | 28 | 1.218 | 0.137 | 2.187 | 0.401 | | | | | | |
| 42-002-F | 0 | M | 18 | YES | 0 | 0.893 | 0.028 | 1.591 | 0.178 | 0 | 0 | 0 | 0 | 0 | 0 |
| | 3 | | | | 3 | 0.938 | 0.031 | 1.502 | 0.171 | 0 | 1 | 0 | 0 | 0 | 1 |
| | 7 | | | | 7 | 0.915 | 0.025 | 1.437 | 0.179 | 0 | 0 | 0 | 0 | 0 | 0 |
| | 28 | | | | 28 | 0.968 | 0.038 | 1.344 | 0.238 | | | | | | |
| 42-003-F | 0 | M | 37 | NO | 1 | 0.397 | 0.017 | 0.205 | 0.114 | 1 | 1 | 0 | 0 | 1 | 1 |
| | 3 | | | | 4 | 1.8 | 0.025 | 0.45 | 0.194 | 0 | 1 | 0 | 0 | 0 | 1 |
| | 7 | | | | 8 | 2.386 | 0.2 | 9.999 | 0.802 | 0 | 1 | 0 | 0 | 0 | 1 |
| | 28 | | | | 29 | 2.172 | 0.135 | 9.999 | 1.049 | | | | | | |
| 42-004-F | 0 | F | 27 | NO | 5 | 1.663 | 0.057 | 1.556 | 0.079 | 0 | 1 | 0 | 0 | 0 | 0 |
| | 3 | | | | 8 | 1.516 | 0.065 | 1.673 | 0.083 | 0 | 0 | 0 | 0 | 0 | 0 |
| | 7 | | | | 12 | 1.452 | 0.039 | 1.486 | 0.072 | 0 | 0 | 0 | 0 | 0 | 0 |
| | 28 | | | | 33 | 1.414 | 0.089 | 1.504 | 0.075 | | | | | | |
| 42-007-F | 0 | F | 24 | NO | 5 | 0.291 | 0.088 | 1.112 | 0.18 | 1 | 1 | 0 | 0 | 1 | 1 |
| | 3 | | | | 8 | 0.956 | 0.111 | 1.505 | 0.222 | 0 | 1 | 0 | 0 | 0 | 1 |
| | 7 | | | | 12 | 2.426 | 0.235 | 9.999 | 0.61 | 0 | | 0 | | 0 | |
| | 28 | | | | 33 | 2.908 | 0.151 | 9.999 | 0.46 | | | | | | |
| 42-008-F | 0 | M | 35 | NO | 4 | 0.837 | 0.025 | 1.464 | 0.134 | 0 | 1 | | | 0 | 1 |
| | 3 | | | | 7 | 2.32 | 0.041 | 9.999 | 0.395 | 0 | 1 | 0 | 0 | 0 | 0 |
| | 7 | | | | 11 | 2.516 | 0.314 | 9.999 | 0.511 | 0 | 0 | 0 | 0 | 0 | 0 |
| | 28 | | | | 32 | 9.999 | 0.154 | 9.999 | 0.39 | | | | | | |
| 42-014-F | 0 | F | 32 | NO | 5 | 0.091 | 0.337 | 1.762 | 0.661 | 1 | 1 | 0 | 0 | 0 | 0 |
| | 3 | | | | 8 | 0.397 | 0.88 | 9.999 | 0.787 | 0 | 1 | 0 | 0 | 0 | 1 |
| | 7 | | | | 12 | 0.954 | 0.553 | 9.999 | 0.795 | 0 | 1 | 0 | 0 | 0 | 0 |
| | 28 | | | | 33 | 0.938 | 0.372 | 9.999 | 0.742 | | | | | | |
| 42-018-F | 0 | F | 33 | NO | 0 | 0.269 | 0.043 | 0.496 | 0.111 | 1 | 1 | 0 | 0 | 1 | 0 |
| | 3 | | | | 3 | 1.425 | 0.086 | 0.812 | 0.128 | 1 | 1 | 0 | 0 | 0 | 1 |
| | 7 | | | | 7 | 2.711 | 0.405 | 9.999 | 0.577 | 0 | 1 | 0 | 0 | 1 | 0 |
| | 28 | | | | 28 | 2.289 | 0.125 | 9.999 | 0.346 | | | | | | |
| 43-026-F | 0 | F | 46 | NO | 3 | 1.768 | 0.109 | 0.669 | 0.235 | 1 | 1 | 0 | 0 | 0 | 1 |
| | 3 | | | | 6 | 2.716 | 0.169 | 9.999 | 0.517 | 0 | 1 | 0 | 0 | 0 | 1 |
| | 7 | | | | 10 | 2.79 | 0.156 | 9.999 | 0.696 | 0 | 1 | 0 | 0 | 0 | 1 |
| | 28 | | | | 31 | 2.682 | 0.182 | 9.999 | 0.365 | | | | | | |

^Serologic assays were performed for ZIKA IgG and IgM antibodies by ELISA (Euroimmun), DENV IgG and IgM antibodies by ELISA (Panbio) using commercial diagnostic kits.

*PCR assays for Zika (recommended by WHO), Dengue and Pan-flavivirus were performed as described in Example 1. PCR results are shown as: 1; positive, and 0; negative.

TABLE 2

Clinical Symptoms, collection dates and days since onset of symptoms for the acutely ZIKV infected patients

| Sample Characteristic | | | | | | Symptoms |
|---|---|---|---|---|---|---|
| ID | Visit (Day) | Gender | Age (Yr) | Date of Sample | Days since Onset of Symptoms | Number of symptoms[a] |
| 41-001-F | 0 | F | 41 | Jun. 21, 2016 | 2 | 13 |
| | 3 | | | Jun. 23, 2016 | 5 | 10 |
| | 7 | | | Jun. 28, 2016 | 9 | 6 |
| | 28 | | | Jul. 22, 2016 | 30 | |

TABLE 2-continued

Clinical Symptoms, collection dates and days since onset of symptoms for the acutely ZIKV infected patients

| Sample Characteristic | | | | | | Symptoms |
|---|---|---|---|---|---|---|
| ID | Visit (Day) | Gender | Age (Yr) | Date of Sample | Days since Onset of Symptoms | Number of symptoms[a] |
| 41-002-F | 0 | M | 37 | Jun. 22, 2016 | 2 | 8 |
| | 3 | | | Jun. 24, 2016 | 5 | 8 |
| | 7 | | | Jun. 29, 2016 | 9 | 4 |
| | 28 | | | Jul. 20, 2016 | 30 | 7 |
| 41-003-F | 0 | M | 51 | Jun. 27, 2016 | 3 | 11 |
| | 3 | | | Jun. 29, 2016 | 6 | 14 |
| | 28 | | | Jul. 25, 2016 | 31 | 8 |
| 41-006-F | 0 | M | 49 | Jul. 5, 2016 | 3 | 5 |
| | 3 | | | Jul. 8, 2016 | 6 | 9 |
| | 7 | | | Jul. 13, 2016 | 10 | 2 |
| | 28 | | | Aug. 1, 2016 | 31 | 2 |
| 41-010-F | 0 | F | 32 | Jul. 13, 2016 | 3 | 13 |
| | 3 | | | Jul. 15, 2016 | 6 | 5 |
| | 7 | | | Jul. 20, 2016 | 10 | 4 |
| | 28 | | | Aug. 12, 2016 | 31 | 2 |
| 41-017-F | 0 | F | 34 | Aug. 8, 2016 | 3 | 13 |
| | 3 | | | Aug. 10, 2016 | 6 | 6 |
| | 7 | | | Aug. 15, 2016 | 10 | 6 |
| | 28 | | | Sep. 5, 2016 | 31 | 3 |
| 41-023-F | 0 | F | 33 | Aug. 22, 2016 | 0 | 16 |
| | 3 | | | Aug. 25, 2016 | 3 | 10 |
| | 7 | | | Aug. 29, 2016 | 7 | 2 |
| | 28 | | | Sep. 20, 2016 | 28 | 6 |
| 41-028-F | 0 | M | 38 | Sep. 6, 2016 | 5 | 11 |
| | 3 | | | Sep. 9, 2016 | 8 | 3 |
| | 7 | | | Sep. 14, 2016 | 12 | 1 |
| | 28 | | | Oct. 5, 2016 | 33 | 1 |
| 41-031-F | 0 | M | 19 | Sep. 12, 2016 | 2 | 12 |
| | 3 | | | Sep. 14, 2016 | 5 | 13 |
| | 7 | | | Sep. 19, 2016 | 9 | 5 |
| | 28 | | | Oct. 10, 2016 | 30 | 11 |
| 41-036-F | 0 | M | 50 | Oct. 10, 2016 | 3 | 19 |
| | 3 | | | Oct. 13, 2016 | 6 | 7 |
| | 7 | | | Oct. 17, 2016 | 10 | 11 |
| | 28 | | | Nov. 9, 2016 | 31 | 14 |
| 42-001-F | 0 | F | 35 | Jun. 24, 2016 | 0 | 17 |
| | 3 | | | Jun. 217 2016 | 3 | 15 |
| | 7 | | | Jul. 1, 2016 | 7 | 12 |
| | 28 | | | Jul. 22, 2016 | 28 | 7 |
| 42-002-F | 0 | M | 18 | Jun. 29, 2016 | 0 | 7 |
| | 3 | | | Jul. 1, 2016 | 3 | 9 |
| | 7 | | | Jul. 6, 2016 | 7 | 4 |
| | 28 | | | Jul. 29, 2016 | 28 | 3 |
| 42-003-F | 0 | M | 37 | Jul. 8, 2016 | 1 | 5 |
| | 3 | | | Jul. 11, 2016 | 4 | 8 |
| | 7 | | | Jul. 15, 2016 | 8 | 8 |
| | 28 | | | Aug. 5, 2016 | 29 | 1 |
| 42-004-F | 0 | F | 27 | Jul. 11, 2016 | 5 | 6 |
| | 3 | | | Jul. 15, 2016 | 8 | 9 |
| | 7 | | | Jul. 18, 2016 | 12 | 5 |
| | 28 | | | Aug. 8, 2016 | 33 | 7 |
| 42-007-F | 0 | F | 24 | Jul. 26, 2016 | 5 | 11 |
| | 3 | | | Jul. 29, 2016 | 8 | 12 |
| | 7 | | | Aug. 2, 2016 | 12 | 11 |
| | 28 | | | Aug. 23, 2016 | 33 | 5 |
| 42-008-F | 0 | M | 35 | Jul. 26, 2016 | 4 | 6 |
| | 3 | | | Jul. 29, 2016 | 7 | 6 |
| | 7 | | | Aug. 2, 2016 | 11 | 6 |
| | 28 | | | Aug. 23, 2016 | 32 | |
| 42-014-F | 0 | F | 32 | Aug. 17, 2016 | 5 | 13 |
| | 3 | | | Aug. 19, 2016 | 8 | 10 |
| | 7 | | | Aug. 24, 2016 | 12 | 10 |
| | 28 | | | Sep. 14, 2016 | 33 | 7 |
| 42-018-F | 0 | F | 33 | Sep. 21, 2016 | 0 | 11 |
| | 3 | | | Sep. 23, 2016 | 3 | 10 |
| | 7 | | | Sep. 28, 2016 | 7 | 10 |
| | 28 | | | Oct. 20, 2016 | 28 | 9 |

TABLE 2-continued

Clinical Symptoms, collection dates and days since onset of symptoms for the acutely ZIKV infected patients

| Sample Characteristic | | | | | | Symptoms |
|---|---|---|---|---|---|---|
| ID | Visit (Day) | Gender | Age (Yr) | Date of Sample | Days since Onset of Symptoms | Number of symptoms[a] |
| 43-026-F | 0 | F | 46 | Oct. 28, 2016 | 3 | 9 |
| | 3 | | | Oct. 31, 2016 | 6 | 8 |
| | 7 | | | Nov. 4, 2016 | 10 | 3 |
| | 28 | | | Nov. 25, 2016 | 31 | 2 |

[a]Symptom checklist included the following-Back pain, Bleeding, Confusion/disorientation, Conjunctivitis, Difficult standing upright/hunched, Difficulty walking, Fatigue, Headache, Itchiness, Joint ache (severe arthralgia), Malaise, Mouth ulcers, Muscle ache, Muscular weakness, Paresthesias, Periorbital pain, Photophobia, Rash, Sore throat

TABLE 3

Frequency of antigenic sites for IgM and IgG antibodies in serum on day 0 and 7 and urine on day 7 post-ZIKV exposure

| | AA of | | IgM | | | IgG | | |
|---|---|---|---|---|---|---|---|---|
| Antigenic Site | SEQ ID NO: 9 | Sequence | Serum D0 | Serum D7 | Urine D7 | Serum D0 | Serum D7 | Urine D7 |
| Z-1 (pr) 122-170 | 122-170 | AAEVTRRGSAYYMYLDRNDAGEAISFPTTLGM NKCYIQIMDLGHMCDAT | 0% | 1% | 1% | 0% | 0% | 0% |
| Z-2 (pr/M-1) 170-216 | 170-216 | TMSYECPMLDEGVEPDDVDCWCNTTSTWVVYG TCHHKKGEARRSRRA | 1% | 1% | 2% | 1% | 0% | 16% |
| Z-3 (pr/M-2) 188-293 | 188-293 | DCWCNTTSTWVVYGTCHHKKGEARRSRRAVTL PSHSTRKLQTRSQTWLESREYTKHLIRVENWI FRNPGFALAAAAIAWLLGSSTSQKVIYLVMIL LIAPAYSIRC | 0% | 0% | 0% | 0% | 1% | 0% |
| Z-4 (M/E) 213-374 | 213-374 | SRRAVTLPSHSTRKLQTRSQTWLESREYTKHL IRVENWIFRNPGFALAAAAIAWLLGSSTSQKV IYLVMILLIAPAYSIRCIGVSNRDFVEGMSGG TWVDVVLEHGGCVTVMAQDKPTVDIELVTTTV SNMAEVRSYCYEASISDMASDSRCPTQGEAYL DK | 0% | 0% | 0% | 1% | 1% | 0% |
| Z-4.1 (E-1) 310-372 | 310-372 | WVDVVLEHGGCVTVMAQDKPTVDIELVTTTVS NMAEVRSYCYEASISDMASDSRCPTQGEAYL | 0% | 1% | 0% | 4% | 1% | 0% |
| Z-4.2 (E-2) 365-411 | 365-411 | PTQGEAYLDKQSDTQYVCKRTLVDRGWGNGCG LFGKGSLVTCAKFAC | 2% | 1% | 0% | 3% | 2% | 0% |
| Z-5 (E-3) 417-526 | 417-526 | GKSIQPENLEYRIMLSVHGSQHSGMIVNDTGH ETDENRAKVEITPNSPRAEATLGGFGSLGLDC EPRTGLDFSDLYYLTMNNKHWLVHKEWFHDIP LPWHAGADTGTPHW | 1% | 0% | 0% | 3% | 0% | 0% |
| Z-6 (E-4) 484-535 | 484-535 | TGLDFSDLYYLTMNNKHWLVHKEWFHDIPLPW HAGADTGTPHWNNKEALVEF | 3% | 8% | 3% | 4% | 1% | 0% |
| Z-7 (E-5) 558-579 | 558-579 | ALAGALEAEMDGAKGRLSSGHL | 0% | 0% | 1% | 0% | 0% | 0% |
| Z-8 (E-6) 595-729 | 595-729 | YSLCTAAFTFTKIPAETLHGTVTVEVQYAGTD GPCKVPAQMAVDMQTLTPVGRLITANPVITES TENSKMMLELDPPFGDSYIVIGVGEKKITHHW HRSGSTIGKAFEATVRGAKRMAVLGDTAWDFG SVGGALN | 1% | 0% | 0% | 1% | 16% | 17% |
| Z-8.1 (E-7) 657-719 | 657-719 | ESTENSKMMLELDPPFGDSYIVIGVGEKKITH HWHRSGSTIGKAFEATVRGAKRMAVLGDTAW | 2% | 1% | 0% | 7% | 1% | 0% |
| Z-9 (E-8) 679-794 | 679-806 | IGVGEKKITHHWHRSGSTIGKAFEATVRGAKR MAVLGDTAWDFGSVGGALNSLGKGIHQIFGAA FKSLFGGMSWFSQILIGTLLMWLGLNTKNGSI SLMCLALGGVLIFLSTAVSADVGCSVDFSKKE | 0% | 0% | 2% | 0% | 1% | 0% |
| Z-10 (NS1-1) 795-835 | 789-835 | STAVSADVGCSVDFSKKETRCGTGVFVYNDVE AWRDRYKYHPDSPRR | 1% | 1% | 1% | 5% | 0% | 0% |

TABLE 3-continued

Frequency of antigenic sites for IgM and IgG antibodies in serum on day 0 and 7 and urine on day 7 post-ZIKV exposure

| Antigenic Site | AA of SEQ ID NO: 9 | Sequence | IgM Serum D0 | IgM Serum D7 | IgM Urine D7 | IgG Serum D0 | IgG Serum D7 | IgG Urine D7 |
|---|---|---|---|---|---|---|---|---|
| Z-11 (NS1-2) 873-913 | 873-913 | LEENGVQLTVVVGSVKNPMWRGPQRLPVPVNE LPHGWKAWG | 0% | 1% | 1% | 0% | 1% | 0% |
| Z-12 (NS1-3) 958-1023 | 958-1023 | HTSVWLKVREDYSLECDPAVIGTAVKGKEAVH SDLGYWIESEKNDTWRLKRAHLIEMKTCEWPK SH | 2% | 1% | 0% | 0% | 1% | 0% |
| Z-13 (NS1-4) 1031-1090 | 1031-1090 | EESDLIIPKSLAGPLSHHNTREGYRTQMKGPW HSEELEIRFEECPGTKVHVEETCGTRGP | 1% | 1% | 1% | 0% | 0% | 0% |
| Z-14 (NS1-5) 1046-1127 | 1046-1127 | SHHNTREGYRTQMKGPWHSEELEIRFEECPGT KVHVEETCGTRGPSLRSTTASGRVIEEWCCRE CTMPPLSFRAKDGCWYGM | 0% | 1% | 2% | 5% | 7% | 0% |
| Z-15 (NS2B) 1417-1474 | 1417-1474 | SGKSVDMYIERAGDITWEKDAEVTGNSPRLDV ALDESGDFSLVEDDGPPMREIILKVV | 0% | 1% | 0% | 1% | 49% | 17% |
| Z-16 (NS3-1) 1503-1624 | 1477-1624 | TICGMNPIAIPFAAGAWYVYVKTGKRSGALWD VPAPKEVKKGETTDGVYRVMTRRLLGSTQVGV GVMQEGVFHTMWHVTKGSALRSGEGRLDPYWG DVKQDLVSYCGPWKLDAAWDGHSEVQLLAVPP GERARNIQTLPGIFKTKDGD | 1% | 0% | 0% | 1% | 0% | 0% |
| Z-17 (NS3-2) 1536-1672 | 1536-1672 | TQVGVGVMQEGVFHTMWHVTKGSALRSGEGRL DPYWGDVKQDLVSYCGPWKLDAAWDGHSEVQL LAVPPGERARNIQTLPGIFKTKDGDIGAVALD YPAGTSGSPILDKCGRVIGLYGNGVVIKNGSY VSAITQGRR | 3% | 0% | 1% | 1% | 0% | 0% |
| Z-18 (NS3-3) 1600-1694 | 1600-1694 | LAVPPGERARNIQTLPGIFKTKDGDIGAVALD YPAGTSGSPILDKCGRVIGLYGNGVVIKNGSY VSAITQGRREEETPVECFEPSMLKKKQLTVL | 1% | 0% | 0% | 1% | 0% | 0% |
| Z-19 (NS3-4) 1792-1877 | 1792-1877 | TDPSSIAARGYISTRVEMGEAAAIFMTATPPG TRDAFPDSNSPIMDTEVEVPERAWSSGFDWVT DHSGKTVWFVPSVRNGNEIAAC | 7% | 14% | 11% | 7% | 0% | 17% |
| Z-20 (NS3-5) 1910-2027 | 1910-2027 | TTDISEMGANFKADRVIDSRRCLKPVILDGER VILAGPMPVTHASAAQRRGRIGRNPNKPGDEY LYGGGCAETDEDHAHWLEARMLLDNIYLQDGL IASLYRPEADKVAAIEGEFKLR | 2% | 3% | 1% | 1% | 0% | 0% |
| Z-21 (NS3-6) 2021-2119 | 2021-2136 | EGEFKLRTEQRKTFVELMKRGDLPVWLAYQVA SAGITYTDRRWCFDGTTNNTIMEDSVPAEVWT RHGEKRVLKPRWMDARVCSDHAALKSFKEFAA GKRGAAFGVMEALGTLPGHM | 1% | 0% | 0% | 1% | 1% | 0% |
| Z-21.1 (NS3-7) 2028-2111 | 2028-2111 | TEQRKTFVELMKRGDLPVWLAYQVASAGITYT DRRWCFDGTTNNTIMEDSVPAEVWTRHGEKRV LKPRWMDARVCSDHAALKSF | 1% | 2% | 1% | 1% | 1% | 0% |
| Z-22 (NS4A) 2135-2171 | 2135-2171 | HMTERFQEAIDNLAVLMRAETGSRPYKAAAAQ LPETL | 1% | 0% | 0% | 0% | 0% | 0% |
| Z-23 (NS4B-1) 2316-2468 | 2316-2468 | TTFITPAVQHAVTTSYNNYSLMAMATQAGVLF GMGKGMPFYAWDFGVPLLMIGCYSQLTPLTLI VAIILLVAHYMYLIPGLQAAAARAAQKRTAAG IMKNPVVDGIVVTDIDTMTIDPQVEKKMGQVL LIAVAVSSAILSRTAWGWGEAGALI | 2% | 0% | 0% | 0% | 1% | 0% |
| Z-23.1 (NS4B-2) 2320-2365 | 2320-2365 | TPAVQHAVTTSYNNYSLMAMATQAGVLFGMGK GMPFYAWDFGVPLL | 0% | 0% | 2% | 0% | 0% | 0% |
| Z-23.2 (NS4B-3) 2375-2462 | 2375-2462 | PLTLIVAIILLVAHYMYLIPGLQAAAARAAQK RTAAGIMKNPVVDGIVVTDIDTMTIDPQVEKK MGQVLLIAVAVSSAILSRTAWGWG | 1% | 0% | 1% | 0% | 1% | 0% |
| Z-24 (NS5-1) 2413-2484 | 2413-2484 | MKNPVVDGIVVTDIDTMTIDPQVEKKMGQVLL IAVAVSSAILSRTAWGWGEAGALITAATSTLW EGSPNKYW | 1% | 2% | 3% | 0% | 0% | 17% |

TABLE 3-continued

Frequency of antigenic sites for IgM and IgG antibodies in serum on day 0 and 7 and urine on day 7 post-ZIKV exposure

| Antigenic Site | AA of SEQ ID NO: 9 | Sequence | IgM Serum D0 | IgM Serum D7 | IgM Urine D7 | IgG Serum D0 | IgG Serum D7 | IgG Urine D7 |
|---|---|---|---|---|---|---|---|---|
| Z-25 (NS5-2) 2525-2608 | 2525-2608 | GETLGEKWKARLNQMSALEFYSYKKSGITEVCREEARRALKDGVATGGHAVSRGSAKLRWLVERGYLQPYGKVIDLGCGRGGWS | 1% | 1% | 0% | 0% | 0% | 0% |
| Z-26 (NS5-3) 2609-2665 | 2609-2665 | YYAATIRKVQEVKGYTKGGPGHEEPVLVQSYGWNIVRLKSGVDVFHMAAEPCDTLLC | 1% | 0% | 3% | 0% | 0% | 0% |
| Z-27 (NS5-4) 2671-2753 | 2671-2753 | SSSPEVEEARTLRVLSMVGDWLEKRPGAFCIKVLCPYTSTMMETLERLQRRYGGGLVRVPLSRNSTHEMYWVSGAKSNTIKSV | 2% | 0% | 1% | 0% | 1% | 0% |
| Z-28 (NS-5) 2736-2829 | 2736-2829 | THEMYWVSGAKSNTIKSVSTTSQLLLGRMDGPRRPVKYEEDVNLGSGTRAVVSCAEAPNMKIIGNRIERIRSEHAETWFFDENHPYRTWAYHGS | 2% | 1% | 2% | 1% | 0% | 0% |
| Z-28.1 (NS5-6) 2798-2831 | 2798-2831 | IGNRIERIRSEHAETWFFDENHPYRTWAYHGSYE | 5% | 3% | 2% | 4% | 1% | 0% |
| Z-29 (NS5-7) 2826-2898 | 2826-2898 | YHGSYEAPTQGSASSLINGVVRLLSKPWDVVTGVTGIAMTDTTPYGQQRVFKEKVDTRVPDPQEGTRQVMSMV | 2% | 3% | 6% | 1% | 0% | 0% |
| Z-30 (NS5-8) 2917-2979 | 2917-2979 | KEEFINKVRSNAALGAIFEEEKEWKTAVEAVNDPRFWALVDKEREHHLRGECQSCVYNMMGKR | 3% | 1% | 2% | 4% | 1% | 0% |
| Z-31 (NS5-9) 2997-3050 | 2997-3050 | YMWLGARFLEFEALGFLNEDHWMGRENSGGGVEGLGLQRLGYVLEEMSRIPGGR | 2% | 0% | 2% | 0% | 0% | 0% |
| Z-32 (NS5-10) 3029-3174 | 3029-3174 | EGLGLQRLGYVLEEMSRIPGGRMYADDTAGWDTRISRFDLENEALITNQMEKGHRALALAIIKYTYQNKVVKVLRPAEKGKTVMDIISRQDQRGSGQVVTYALNTFTNLVVQLIRNMEAEEVLEMQDLWLLRRSEKVTNWLQSNGW | 1% | 0% | 1% | 1% | 0% | 0% |
| Z-32.1 (NS5-11) 3039-3068 | 3039-3068 | VLEEMSRIPGGRMYADDTAGWDTRISRFDL | 2% | 1% | 1% | 4% | 0% | 0% |
| Z-32.2 (NS5-12) 3104-3168 | 3104-3168 | PAEKGKTVMDIISRQDQRGSGQVVTYALNTFTNLVVQLIRNMEAEEVLEMQDLWLLRRSEKVTNW | 1% | 9% | 2% | 0% | 0% | 16% |
| Z-33 (NS5-13) 3162-3241 | 3162-3241 | SEKVTNWLQSNGWDRLKRMAVSGDDCVVKPIDDRFAHALRFLNDMGKVRKDTQEWKPSTGWDNWEEVPFCSHHFNKLHLK | 2% | 3% | 0% | 0% | 0% | 0% |
| Z-33.1 (NS5-14) 3181-3239 | 3181-3239 | AVSGDDCVVKPIDDRFAHALRFLNDMGKVRKDTQEWKPSTGWDNWEEVPFCSHHFNKLH | 2% | 2% | 2% | 4% | 1% | 0% |
| Z-34 (NS5-15) 3241-3275 | 3241-3275 | KDGRSIVVPCRHQDELIGRARVSPGAGWSIRETAC | 0% | 0% | 2% | 0% | 0% | 0% |
| Z-35 (NS5-16) 3308-3368 | 3308-3368 | DWVPTGRTTWSIHGKGEWMTTEDMLVVWNRVWIEENDHMEDKTPVTKWTDIPYLGKREDLW | 2% | 6% | 6% | 3% | 0% | 0% |
| Z-36 (NS5-17) 3357-3417 | 3357-3417 | DIPYLGKREDLWCGSLIGHRPRTTWAENIKNTVNMVRRIIGDEEKYMDYLSTQVRYLGEEG | 0% | 1% | 2% | 3% | 1% | 0% |
| | | Total* | 63% | 71% | 68% | 78% | 91% | 100% |

*Total percentage of clones are comprised of clones represented in these antigenic sites for the analyzed sample. The remaining clones are not represented by any unique antigenic site as clonal frequency is less than 2 for all analyzed samples.

TABLE 4

Sequence conservation of Antigenic regions/ sites among different Flavivirus strains

| Antigenic Site | AA of SEQ ID NO: 9 | Sequence | Similarity of ZIKV antigenic Sites to other flaviviruses (%) DENV-1 | DENV-2 | DENV-3 | DENV-4 | YFV | WNV |
|---|---|---|---|---|---|---|---|---|
| Z-1 (pr) 122-170 | 122-170 | AAEVTRRGSAYYMYLDRNDAGEAISF PTTLGMNKCYIQIMDLGHMCDAT | 35% | 35% | 39% | 37% | 14% | 29% |
| Z-2 (pr/M-1) 170-216 | 170-216 | TMSYECPMLDEGVEPDDVDCWCNTTS TWVVYGTCHHKKGEARRSRRA | 62% | 57% | 60% | 57% | 50% | 51% |
| Z-3 (pr/M-2) 188-293 | 188-293 | DCWCNTTSTWVVYGTCHHKKGEARRS RRAVTLPSHSTRKLQTRSQTWLESRE YTKHLIRVENWIFRNPGFALAAAAIA WLLGSSTSQKVIYLVMILLIAPAYSI RC | 43% | 43% | 43% | 51% | 42% | 47% |
| Z-4 (M/E) 213-374 | 213-374 | SRRAVTLPSHSTRKLQTRSQTWLESR EYTKHLIRVENWIFRNPGFALAAAAI AWLLGSSTSQKVIYLVMILLIAPAYS IRCIGVSNRDFVEGMSGGTWVDVVLE HGGCVTVMAQDKPTVDIELVTTTVSN MAEVRSYCYEASISDMASDSRCPTQG EAYLDK | 51% | 47% | 49% | 55% | 46% | 51% |
| Z-4.1 (E-1) 310-372 | 310-372 | WVDVVLEHGGCVTVMAQDKPTVDIEL VTTTVSNMAEVRSYCYEASISDMASD SRCPTQGEAYL | 68% | 55% | 62% | 65% | 48% | 52% |
| Z-4.2 (E-2) 365-411 | 365-411 | PTQGEAYLDKQSDTQYVCKRTLVDRG WGNGCGLFGKGSLVTCAKFAC | 77% | 66% | 79% | 72% | 64% | 70% |
| Z-5 (E-3) 417-526 | 417-526 | GKSIQPENLEYRIMLSVHGSQHSGMI VNDTGHETDENRAKVEITPNSPRAEA TLGGFGSLGLDCEPRTGLDFSDLYYL TMNNKHWLVHKEWFHDIPLPWHAGAD TGTPHW | 47% | 47% | 48% | 46% | 22% | 35% |
| Z-6 (E-4) 484-535 | 484-535 | TGLDFSDLYYLTMNNKHWLVHKEWFH DIPLPWHAGADTGTPHWNNKEALVEF | 56% | 58% | 62% | 56% | 35% | 42% |
| Z-7 (E-5) 558-579 | 558-579 | ALAGALEAEMDGAKGRLSSGHL | 41% | 45% | 41% | 41% | 32% | 50% |
| Z-8 (E-6) 595-729 | 595-729 | YSLCTAAFTFTKIPAETLHGTVTVEV QYAGTDGPCKVPAQMAVDMQTLTPVG RLITANPVITESTENSKMMLELDPPF GDSYIVIGVGEKKITHHWHRSGSTIG KAFEATVRGAKRMAVLGDTAWDFGSV GGALN | 55% | 52% | 53% | 54% | 42% | 62% |
| Z-8.1 (E-7) 657-719 | 657-719 | ESTENSKMMLELDPPFGDSYIVIGVG EKKITHHWHRSGSTIGKAFEATVRGA KRMAVLGDTAW | 56% | 56% | 52% | 65% | 48% | 68% |
| Z-9 (E-8) 679-794 | 679-806 | IGVGEKKITHHWHRSGSTIGKAFEAT VRGAKRMAVEGDTAWDFGSVGGALNS EGKGIHQIFGAAFKSLFGGMSWFSQI LIGTLLMWLGLNTKNGSISLMCLALG GVLIFLSTAVSADVGCSVDFSKKE | 55% | 48% | 57% | 56% | 48% | 62% |
| Z-10 (NS1-1) 795-835 | 789-835 | STAVSADVGCSVDFSKKETRCGTGVF VYNDVEAWRDRYKYHPDSPRR | 43% | 40% | 45% | 45% | 40% | 55% |
| Z-11 (NS1-2) 873-913 | 873-913 | LEENGVQLTVVVGSVKNPMWRGPQRL PVPVNELPHGWKAWG | 37% | 41% | 41% | 46% | 41% | 46% |
| Z-12 (NS1-3) 958-1023 | 958-1023 | HTSVWLKVREDYSLECDPAVIGTAVK GKEAVHSDLGYWIESEKNDTWRLKRA HLIEMKTCEWPKSH | 58% | 50% | 58% | 53% | 34% | 58% |
| Z-13 (NS1-4) 1031-1090 | 1031-1090 | EESDLIIPKSLAGPLSHHNTREGYRT QMKGPWHSEELEIRFEECPGTKVHVE ETCGTRGP | 57% | 60% | 63% | 60% | 45% | 57% |

TABLE 4-continued

Sequence conservation of Antigenic regions/ sites among different Flavivirus strains

| Antigenic Site | AA of SEQ ID NO: 9 | Sequence | Similarity of ZIKV antigenic Sites to other flaviviruses (%) DENV-1 | DENV-2 | DENV-3 | DENV-4 | YFV | WNV |
|---|---|---|---|---|---|---|---|---|
| Z-14 (NS1-5) 1046-1127 | 1046-1127 | SHHNTREGYRTQMKGPWHSEELEIRF EECPGTKVHVEETCGTRGPSLRSTTA SGRVIEEWCCRECTMPPLSFRAKDGC WYGM | 62% | 65% | 62% | 65% | 57% | 55% |
| Z-15 (NS2B) 1417-1474 | 1417-1474 | SGKSVDMYIERAGDITWEKDAEVTGN SPRLDVALDESGDFSLVEDDGPPMRE IILKVV | 29% | 33% | 34% | 34% | 31% | 55% |
| Z-16 (NS3-1) 1503-1624 | 1477-1624 | TICGMNPIAIPFAAGAWYVYVKTGKR SGALWDVPAPKEVKKGETTDGVYRVM TRRLLGSTQVGVGVMQEGVFHTMWHV TKGSALRSGEGRLDPYWGDVKQDLVS YCGPWKLDAAWDGHSEVQLLAVPPGE RARNIQTLPGIFKTKDGD | 51% | 49% | 49% | 51% | 44% | 60% |
| Z-17 (NS3-2) 1536-1672 | 1536-1672 | TQVGVGVMQEGVFHTMWHVTKGSALR SGEGRLDPYWGDVKQDLVSYCGPWKL DAAWDGHSEVQLLAVPPGERARNIQT LPGIFKTKDGDIGAVALDYPAGTSGS PILDKCGRVIGLYGNGVVIKNGSYVS AITQGRR | 56% | 58% | 59% | 60% | 57% | 58% |
| Z-18 (NS3-3) 1600-1694 | 1600-1694 | LAVPPGERARNIQTLPGIFKTKDGDI GAVALDYPAGTSGSPILDKCGRVIGL YGNGVVIKNGSYVSAITQGRREEETP VECFEPSMLKKKQLTVL | 49% | 53% | 54% | 55% | 55% | 65% |
| Z-19 (NS3-4) 1792-1877 | 1792-1877 | TDPSSIAARGYISTRVEMGEAAAIFM TATPPGTRDAFPDSNSPIMDTEVEVP ERAWSSGFDWVTDHSGKTVWFVPSVR NGNEIAAC | 72% | 77% | 74% | 77% | 48% | 71% |
| Z-20 (NS3-5) 1910-2027 | 1910-2027 | TTDISEMGANFKADRVIDSRRCLKPV ILDGERVILAGPMPVTHASAAQRRGR IGRNPNKPGDEYLYGGGCAETDEDHA HWLEARMLLDNIYLQDGLIASLYRPE ADKVAAIEGEFKLR | 73% | 71% | 71% | 70% | 49% | 63% |
| Z-21 (NS3-6) 2021-2119 | 2021-2136 | EGEFKLRTEQRKTFVELMKRGDLPVW LAYQVASAGITYTDRRWCFDGTTNNT IMEDSVPAEVWTRHGEKRVLKPRWMD ARVCSDHAALKSFKEFAAGKRGAAFG VMEALGTLPGHM | 57% | 60% | 58% | 59% | 47% | 59% |
| Z-21.1 (NS3-7) 2028-2111 | 2028-2111 | TEQRKTFVELMKRGDLPVWLAYQVAS AGITYTDRRWCFDGTTNNTIMEDSVP AEVWTRHGEKRVLKPRWMDARVCSDH AALKSF | 43% | 54% | 43% | 38% | 32% | 35% |
| Z-22 (NS4A) 2135-2171 | 2135-2171 | HMTERFQEAIDNLAVLMRAETGSRPY KAAAAQLPETL | 52% | 55% | 52% | 50% | 31% | 42% |
| Z-23 (NS4B-1) 2316-2468 | 2316-2468 | TTFITPAVQHAVTTSYNNYSLMAMAT QAGVLFGMGKGMPFYAWDFGVPLLMI GCYSQLTPLTLIVAIILLVAHYMYLI PGLQAAAARAAQKRTAAGIMKNPVVD GIVVTDIDTMTIDPQVEKKMGQVLLI AVAVSSAILSRTAWGWGEAGALI | 47% | 49% | 47% | 44% | 34% | 42% |
| Z-23.1 (NS4B-2) 2320-2365 | 2320-2365 | TPAVQHAVTTSYNNYSLMAMATQAGV LFGMGKGMPFYAWDFGVPLL | 46% | 52% | 50% | 50% | 37% | 37% |
| Z-23.2 (NS4B-3) 2375-2462 | 2375-2462 | PLTLIVAIILLVAHYMYLIPGLQAAA ARAAQKRTAAGIMKNPVVDGIVVTDI DTMTIDPQVEKKMGQVLLIAVAVSSA ILSRTAWGWG | 55% | 55% | 52% | 50% | 30% | 44% |

TABLE 4-continued

Sequence conservation of Antigenic regions/ sites among different Flavivirus strains

| Antigenic Site | AA of SEQ ID NO: 9 | Sequence | Similarity of ZIKV antigenic Sites to other flaviviruses (%) DENV-1 | DENV-2 | DENV-3 | DENV-4 | YFV | WNV |
|---|---|---|---|---|---|---|---|---|
| Z-24 (NS5-1) 2413-2484 | 2413-2484 | MKNPVVDGIVVTDIDTMTIDPQVEKK MGQVLLIAVAVSSAILSRTAWGWGEA GALITAATSTLWEGSPNKYW | 47% | 49% | 47% | 44% | 34% | 42% |
| Z-25 (NS5-2) 2525-2608 | 2525-2608 | GETLGEKWKARLNQMSALEFYSYKKS GITEVCREEARRALKDGVATGGHAVS RGSAKLRWLVERGYLQPYGKVIDLGC GRGGWS | 69% | 67% | 70% | 67% | 57% | 64% |
| Z-26 (NS5-3) 2609-2665 | 2609-2665 | YYAATIRKVQEVKGYTKGGPGHEEPV LVQSYGWNIVRLKSGVDVFHMAAEPC DTLLC | 67% | 65% | 69% | 67% | 51% | 77% |
| Z-27 (NS5-4) 2671-2753 | 2671-2753 | SSSPEVEEARTLRVLSMVGDWLEKRP GAFCIKVLCPYTSTMMETLERLQRRY GGGLVRVPLSRNSTHEMYWVSGAKSN TIKSV | 58% | 60% | 63% | 66% | 57% | 69% |
| Z-28 (NS-5) 2736-2829 | 2736-2829 | THEMYWVSGAKSNTIKSVSTTSQLLL GRMDGPRRPVKYEEDVNLGSGTRAVV SCAEAPNMKIIGNRIERIRSEHAETW FFDENHPYRTWAYHGS | 53% | 52% | 52% | 57% | 49% | 57% |
| Z-28.1 (NS5-6) 2798-2831 | 2798-2831 | IGNRIERIRSEHAETWFFDENHPYRT WAYHGSYE | 68% | 65% | 65% | 65% | 56% | 68% |
| Z-29 (NS5-7) 2826-2898 | 2826-2898 | YHGSYEAPTQGSASSLINGVVRLLSK PWDVVTGVTGIAMTDTTPYGQQRVFK EKVDTRVPDPQEGTRQVMSMV | 70% | 70% | 71% | 73% | 62% | 70% |
| Z-30 (NS5-8) 2917-2979 | 2917-2979 | KEEFINKVRSNAALGAIFEEEKEWKT AVEAVNDPRFWALVDKEREHHLRGEC QSCVYNMMGKR | 63% | 71% | 63% | 71% | 68% | 71% |
| Z-31 (NS5-9) 2997-3050 | 2997-3050 | YMWLGARFLEFEALGFLNEDHWMGRE NSGGGVEGLGLQRLGYVLEEMSRIPG GR | 74% | 72% | 74% | 76% | 74% | 80% |
| Z-32 (NS5-10) 3029-3174 | 3029-3174 | EGLGLQRLGYVLEEMSRIPGGRMYAD DTAGWDTRISRFDLENEALITNQMEK GHRALALAIIKYTYQNKVVKVLRPAE KGKTVMDIISRQDQRGSGQVVTYALN TFTNLVVQLIRNMEAEEVLEMQDLWL LRRSEKVTNWLQSNGW | 60% | 60% | 62% | 62% | 57% | 62% |
| Z-32.1 (NS5-11) 3039-3068 | 3039-3068 | VLEEMSRIPGGRMYADDTAGWDTRIS RFDL | 70% | 63% | 70% | 63% | 57% | 63% |
| Z-32.2 (NS5-12) 3104-3168 | 3104-3168 | PAEKGKTVMDIISRQDQRGSGQVVTY ALNTFTNLVVQLIRNMEAEEVLEMQD LWLERRSEKVTNW | 52% | 58% | 54% | 55% | 58% | 64% |
| Z-33 (NS5-13) 3162-3241 | 3162-3241 | SEKVTNWLQSNGWDREKRMAVSGDDC VVKPIDDRFAHALRFLNDMGKVRKDT QEWKPSTGWDNWEEVPFCSHHFNKLH LK | 68% | 65% | 68% | 65% | 66% | 67% |
| Z-33.1 (NS5-14) 3181-3239 | 3181-3239 | AVSGDDCVVKPIDDRFAHALRFLNDM GKVRKDTQEWKPSTGWDNWEEVPFCS HHFNKLH | 73% | 71% | 73% | 71% | 71% | 75% |
| Z-34 (NS5-15) 3241-3275 | 3241-3275 | KDGRSIVVPCRHQDELIGRARVSPGA GWSIRETAC | 86% | 83% | 83% | 86% | 83% | 80% |

TABLE 4-continued

Sequence conservation of Antigenic regions/ sites among different Flavivirus strains

| Antigenic Site | AA of SEQ ID NO: 9 | Sequence | Similarity of ZIKV antigenic Sites to other flaviviruses (%) | | | | | |
|---|---|---|---|---|---|---|---|---|
| | | | DENV-1 | DENV-2 | DENV-3 | DENV-4 | YFV | WNV |
| Z-35 (NS5-16) 3308-3368 | 3308-3368 | DWVPTGRTTWSIHGKGEWMTTEDMLV VWNRVWIEENDHMEDKTPVTKWTDIP YLGKREDLW | 77% | 79% | 77% | 75% | 75% | 81% |
| Z-36 (NS5-17) 3357-3417 | 3357-3417 | DIPYLGKREDLWCGSLIGHRPRTTWA ENIKNTVNMVRRIIGDEEKYMDYLST QVRYLGEEG | 54% | 57% | 52% | 57% | 46% | 57% |

TABLE 5

Demographic, epidemiological and diagnostic information of samples used in Example 3

| | | | Sample Characteristic | | | | | | | | | | | |
|---|---|---|---|---|---|---|---|---|---|---|---|---|---|---|
| | | | Immunoassay for ZIKV and DENV using CTKbiotech EIA kit* | | | Days since Onset | ZIKA SYMPTOMS | | | | | | | |
| ID | Age (Yr) | Gestational Week | Zika IgM S/CO | Zika IgG S/CO | Dengue Ag S/CO | of Symptoms | Fever | Skin Rash | Joint Pain | Myalgia | Ocular Pain | Cephalgia | Conjuntivitis | Diarrhea |
| 38 | 18 | 3 | 7.6 | 4.0 | 0.1 | 10 | YES | YES | NO | NO | YES | YES | YES | NO |
| 70 | 30 | 12 | ND | ND | ND | 34 | YES | YES | YES | YES | YES | YES | NO | NO |
| 73 | 23 | 19 | ND | ND | ND | 33 | YES | YES | YES | YES | NO | NO | YES | NO |
| 71 | 31 | 24.5 | ND | ND | ND | 24 | YES | YES | YES | YES | NO | YES | NO | NO |
| 19 | 32 | 32 | 1.7 | 10.0 | 0.3 | 42 | NO | YES | YES | YES | YES | YES | YES | NO |

*Interpretation Criteria: Pos > 1.00.
ND - Not done

TABLE 6

RT-PCR and serodiagnostic information of samples used in Example 3

| | | | ZINK/DENV/CHIKV Real-Time PCR using CTKbiotech kit | | | ZIKV-specific peptide serodiagnostic IgG ELISA (End-Point titer) | |
|---|---|---|---|---|---|---|---|
| ID | Age (Yr) | Gestational Week | ZIKV RT-PCR | DENV RT-PCR | CHIKV RT-PCR | ZIKV-NS2B-1424-1457 | ZIKV-NS5-2943-2977 |
| 38 | 18 | 3 | Pos | Neg | Neg | 2500 | 2500 |
| 70 | 30 | 12 | Pos | Neg | Neg | 12500 | 2500 |
| 73 | 23 | 19 | Pos | Neg | Neg | 2500 | 500 |
| 71 | 31 | 24.5 | Pos | Neg | Neg | 12500 | 500 |
| 19 | 32 | 32 | Pos | Neg | Neg | 500 | 100 |

TABLE 7

Frequency of antigenic sites for IgM, IgG and IgA antibodies in serum and amniotic fluid (AF) during ZIKV infection in the first and third trimester of pregnancy

| Antigenic Site | AA of SEQ ID NO: 9 | Sequence | First Trimester IgM Serum | First Trimester IgM AF | First Trimester IgG Serum | First Trimester IgG AF | First Trimester IgA Serum | First Trimester IgA AF | Third Trimester IgM Serum | Third Trimester IgM AF | Third Trimester IgG Serum | Third Trimester IgG AF | Third Trimester IgA Serum | Third Trimester IgA AF |
|---|---|---|---|---|---|---|---|---|---|---|---|---|---|---|
| Z-I (pr) 122-170 | 122-170 | AAEVTRRGSAYYMYLDRNDAGEAISFPTTLGMNKCYIQIMDLGHMCDAT | 0% | 0% | 0% | 0% | 0% | 0% | 1% | 0% | 0% | 1% | 0% | 0% |
| Z-1.1 (pr) 159-198 | 159-198 | QIMDLGHMCDATMSYECPMLDEGVEPDDVDCWCNTTSTWV | 0% | 4% | 0% | 0% | 0% | 0% | 0% | 1% | 0% | 0% | 0% | 0% |
| Z-2 (pr/M-1) 170-216 | 170-216 | TMSYECPMLDEGVEPDDVDCWCNTTSTWVVYGTCHHKKGEARRSRRA | 1% | 1% | 0% | 0% | 0% | 0% | 1% | 0% | 0% | 0% | 0% | 0% |
| Z-3 (pr/M-2) 188-293 | 188-293 | DCWCNTTSTWVVYGTCHHKKGEARRSRRAVTLPSHSTRKLQTRSQTWLESREYTKHLIRVENWIFRNPGFALAAAAIAWLLGSSTSQKVIYLVMILLIAPAYSIRC | 0% | 0% | 0% | 0% | 0% | 0% | 1% | 2% | 0% | 0% | 0% | 0% |
| Z-4 (M/E) 213-374 | 213-374 | SRRAVTLPSHSTRKLQTRSQTWLESREYTKHLIRVENWIFRNPGFALAAAAIAWLLGSSTSQKVIYLVMILLIAPAYSIRCIGVSNRDFVEGMSGGTWVDVVLEHGGCVTVMAQDKPTVDIELVTTTVSNMAEVRSYCYEASISDMASDSRCPTQGEAYLDK | 2% | 1% | 0% | 0% | 0% | 0% | 0% | 1% | 1% | 0% | 1% | 0% |
| Z-4.1 (E-1) 310-372 | 310-372 | WVDVVLEHGGCVTVMAQDKPTVDIELVTTTVSNMAEVRSYCYEASISDMASDSRCPTQGEAYL | 1% | 2% | 0% | 0% | 0% | 0% | 1% | 1% | 1% | 1% | 3% | 0% |
| **Z-37 (E-9) 339-450** | 339-450 | TVSNMAEVRSYCYEASISDMASDSRCPTQGEAYLDKQSDTQYVCKRTLVDRGWGNGCGLFGKGSLVTCAKFACSKKMTGKSIQPENLEYRIMLSVHGSQHSGMIVNDTGHET | 0% | 0% | 0% | 0% | 0% | 6% | 0% | 2% | 0% | 0% | 0% | 0% |
| Z-4.2(E-2) 365-411 | 365-411 | PTQGEAYLDKQSDTQYVCKRTLVDRGWGNGCGLFGKGSLVTCAKFAC | 0% | 0% | 0% | 0% | 2% | 0% | 0% | 2% | 0% | 3% | 0% | 0% |
| Z-5 (E-3) 417-526 | 417-526 | GKSIQPENLEYRIMLSVHGSQHSGMIVNDTGHETDENRAKVEITPNSPRAEATLGGFGSLGLDCEPRTGLDFSDLYYLTMNNKHWLVHKEWFHDIPLPWHAGADTGTPHW | 4% | 1% | 0% | 0% | 2% | 22% | 2% | 4% | 1% | 0% | 5% | 0% |
| Z-6 (E-4) 484-535 | 484-535 | TGLDFSDLYYLTMNNKHWLVHKEWFHDIPLPWHAGADTGTPHWNNKEALVEF | 2% | 4% | 0% | 0% | 4% | 1% | 3% | 2% | 0% | 3% | 2% | 0% |

TABLE 7-continued

Frequency of antigenic sites for IgM, IgG and IgA antibodies in serum and amniotic fluid (AF) during ZIKV infection in the first and third trimester of pregnancy

| Antigenic Site | AA of SEQ ID NO: 9 | Sequence | First Trimester IgM Serum | First Trimester IgM AF | First Trimester IgG Serum | First Trimester IgG AF | First Trimester IgA Serum | First Trimester IgA AF | Third Trimester IgM Serum | Third Trimester IgM AF | Third Trimester IgG Serum | Third Trimester IgG AF | Third Trimester IgA Serum | Third Trimester IgA AF |
|---|---|---|---|---|---|---|---|---|---|---|---|---|---|---|
| **Z-38 (E-10) 515-573** | 515-573 | WHAGADTGTPHWNN KEALVEFKDAHAKR QTVVVLGSQEGAVH TALAGALEAEMDGA KGR | 4% | 1% | 0% | 0% | 0% | 6% | 0% | 0% | 0% | 0% | 0% | 0% |
| Z-7 (E-5) 558-579 | 558-579 | ALAGALEAEMDGAK GRLSSGHL | 1% | 0% | 0% | 0% | 0% | 0% | 0% | 1% | 0% | 0% | 0% | 0% |
| Z-8 (E-6) 595-729 | 595-729 | YSLCTAAFTFTKIP AETLHGTVTVEVQY AGTDGPCKVPAQMA VDMQTLTPVGRLIT ANPVITESTENSKM MLELDPPFGDSYIV IGVGEKKITHHWHR SGSTIGKAFEATVR GAKRMAVLGDTAWD FGSVGGALN | 3% | 1% | 79% | 59% | 0% | 0% | 1% | 3% | 12% | 10% | 0% | 1% |
| Z-8.1 (E-7) 657-719 | 657-719 | ESTENSKMMLELDP PFGDSYIVIGVGEK KITHHWHRSGSTIG KAFEATVRGAKRMA VLGDTAW | 2% | 0% | 0% | 1% | 0% | 0% | 2% | 3% | 0% | 0% | 0% | 0% |
| Z-9 (E-8) 679-794 | 679-806 | IGVGEKKITHHWHR SGSTIGKAFEATVR GAKRMAVLGDTAWD FGSVGGALNSLGKG IHQIFGAAFKSLFG GMSWFSQILIGTLL MWLGLNTKNGSISL MCLALGGVLIFLST AVSADVGCSVDFSK KE | 2% | 2% | 0% | 0% | 0% | 0% | 2% | 5% | 0% | 3% | 0% | 0% |
| Z-10 (NS1-1) 795-835 | 789-835 | STAVSADVGCSVDF SKKETRCGTGVFVY NDVEAWRDRYKYHP DSPRR | 8% | 1% | 0% | 0% | 0% | 0% | 4% | 3% | 0% | 0% | 0% | 0% |
| Z-11 (NS1-2) 873-913 | 873-913 | LEENGVQLTVVVGS VKNPMWRGPQRLPV PVNELPHGWKAWG | 0% | 1% | 0% | 0% | 0% | 0% | 0% | 1% | 0% | 0% | 0% | 0% |
| **Z-39 (NS1-6) 880-962** | 880-962 | LTVVVGSVKNPMWR GPQRLPVPVNELPH GWKAWGKSYFVRAA KTNNSFVVDGDTLK ECPLKHRAWNSFLV EDHGFGVFHTSVW | 1% | 0% | 0% | 0% | 0% | 0% | 0% | 0% | 0% | 0% | 12% | 0% |
| **Z-40 (NS1-7) 895-1054** | 895-1054 | PQRLPVPVNELPHG WKAWGKSYFVRAAK TNNSFVVDGDTLKE CPLKHRAWNSFLVE DHGFGVFHTSVWLK VREDYSLECDPAVI GTAVKGKEAVHSDL GYWIESEKNDTWRL KRAHLIEMKTCEWP KSHTLWTDGIEESD LIIPKSLAGPLSHH NTREGY | 1% | 1% | 0% | 1% | 0% | 0% | 0% | 0% | 0% | 0% | 0% | 4% |

TABLE 7-continued

Frequency of antigenic sites for IgM, IgG and IgA antibodies in serum and amniotic fluid (AF) during ZIKV infection in the first and third trimester of pregnancy

| Antigenic Site | AA of SEQ ID NO: 9 | Sequence | IgM First Trimester Serum | IgM First Trimester AF | IgG First Trimester Serum | IgG First Trimester AF | IgA First Trimester Serum | IgA First Trimester AF | IgM Third Trimester Serum | IgM Third Trimester AF | IgG Third Trimester Serum | IgG Third Trimester AF | IgA Third Trimester Serum | IgA Third Trimester AF |
|---|---|---|---|---|---|---|---|---|---|---|---|---|---|---|
| **Z-41 (NS1-8) 922-984** | 922-984 | KTNNSFVVDGDTLK<br>ECPLKHRAWNSFLV<br>EDHGFGVFHTSVWL<br>KVREDYSLECDPAV<br>IGTAVKG | 0% | 0% | 0% | 1% | 5% | 6% | 0% | 0% | 0% | 0% | 0% | 0% |
| **Z-42 (NS1-9) 925-965** | 925-965 | NSFVVDGDTLKECP<br>LKHRAWNSFLVEDH<br>GFGVFHTSVWLKV | 0% | 0% | 0% | 0% | 0% | 0% | 0% | 1% | 0% | 0% | 0% | 36% |
| Z-12 (NS1-3) 958-1023 | 958-1023 | HTSVWLKVREDYSL<br>ECDPAVIGTAVKGK<br>EAVHSDLGYWIESE<br>KNDTWRLKRAHLIE<br>MKTCEWPKSH | 2% | 1% | 0% | 0% | 5% | 1% | 2% | 2% | 0% | 1% | 38% | 0% |
| **Z-43 (NS1-10) 966-1081** | 966-1081 | REDYSLECDPAVIG<br>TAVKGKEAVHSDLG<br>YWIESEKNDTWRLK<br>RAHLIEMKTCEWPK<br>SHTLWTDGIEESDL<br>IIPKSLAGPLSHHN<br>TREGYRTQMKGPWH<br>SEELEIRFEECPGT<br>KVHV | 0% | 0% | 0% | 0% | 0% | 0% | 1% | 1% | 0% | 0% | 0% | 9% |
| Z-13 (NS1-4) 1031-1090 | 1031-1090 | EESDLIIPKSLAGP<br>LSHHNTREGYRTQM<br>KGPWHSEELEIRFE<br>ECPGTKVHVEETCG<br>TRGP | 4% | 3% | 0% | 0% | 0% | 3% | 1% | 1% | 2% | 0% | 0% | 0% |
| Z-14 (NS1-5) 1046-1127 | 1046-1127 | SHHNTREGYRTQMK<br>GPWHSEELEIRFEE<br>CPGTKVHVEETCGT<br>RGPSLRSTTASGRV<br>IEEWCCRECTMPPL<br>SFRAKDGCWYGM | 2% | 0% | 5% | 4% | 0% | 0% | 2% | 1% | 0% | 47% | 0% | 0% |
| **Z-44 (NS2A-1) 1165-1251** | 1165-1251 | MVQEGLKKRMTTKI<br>IISTSMAVLVAMIL<br>GGFSMSDLAKLAIL<br>MGATFAEMNTGGDV<br>AHLALIAAFKVRPA<br>LLVSFIFRANWTPR<br>ESM | 1% | 0% | 0% | 0% | 0% | 0% | 0% | 0% | 0% | 0% | 0% | 0% |
| **Z-45 (NS2A-2) 1313-1398** | 1313-1398 | LVAWRAGLATCGGF<br>MLLSLKGKGSVKKN<br>LPFVMALGLTAVRL<br>VDPINVVGLLLLTR<br>SGKRSWPPSEVLTA<br>VGLICALAGGFAKA<br>DI | 0% | 0% | 0% | 0% | 0% | 0% | 0% | 1% | 0% | 0% | 0% | 0% |
| Z-15 (NS2B) 1417-1474 | 1417-1474 | SGKSVDMYIERAGD<br>ITWEKDAEVTGNSP<br>RLDVALDESGDFSL<br>VEDDGPPMREIILK<br>VV | 2% | 2% | 6% | 24% | 4% | 1% | 1% | 1% | 76% | 1% | 0% | 0% |

TABLE 7-continued

Frequency of antigenic sites for IgM, IgG and IgA antibodies in serum and amniotic fluid (AF) during ZIKV infection in the first and third trimester of pregnancy

| Antigenic Site | AA of SEQ ID NO: 9 | Sequence | First Trimester IgM Serum | First Trimester IgM AF | First Trimester IgG Serum | First Trimester IgG AF | First Trimester IgA Serum | First Trimester IgA AF | Third Trimester IgM Serum | Third Trimester IgM AF | Third Trimester IgG Serum | Third Trimester IgG AF | Third Trimester IgA Serum | Third Trimester IgA AF |
|---|---|---|---|---|---|---|---|---|---|---|---|---|---|---|
| Z-16 (NS3-1) 1503-1624 | 1477-1624 | TICGMNPIAIPFAAGAWYVYVKTGKRSGALWDVPAPKEVKKGETTDGVYRVMTRRLLGSTQVGVGVMQEGVFHTMWHVTKGSALRSGEGRLDPYWGDVKQDLVSYCGPWKLDAAWDGHSEVQLLAVPPGERARNIQTLPGIFKTKDGD | 0% | 0% | 0% | 0% | 0% | 0% | 2% | 2% | 0% | 0% | 0% | 0% |
| Z-17 (NS3-2) 1536-1672 | 1536-1672 | TQVGVGVMQEGVFHTMWHVTKGSALRSGEGRLDPYWGDVKQDLVSYCGPWKLDAAWDGHSEVQLLAVPPGERARNIQTLPGIFKTKDGDIGAVALDYPAGTSGSPILDKCGRVIGLYGNGVVIKNGSYVSAITQGRR | 1% | 0% | 0% | 0% | 4% | 1% | 3% | 2% | 0% | 6% | 2% | 0% |
| **Z-17.1 (NS3-8) 1533-1568** | 1533-1568 | LGSTQVGVGVMQEGVFHTMWHVTKGSALRSGEGRLD | 0% | 0% | 0% | 0% | 0% | 0% | 1% | 1% | 0% | 0% | 0% | 0% |
| Z-18 (NS3-3) 1600-1694 | 1600-1694 | LAVPPGERARNIQTLPGIFKTKDGDIGAVALDYPAGTSGSPILDKCGRVIGLYGNGVVIKNGSYVSAITQGRREEETPVECFEPSMLKKKQLTVL | 1% | 6% | 0% | 0% | 0% | 0% | 1% | 1% | 0% | 4% | 1% | 0% |
| Z-19 (NS3-4) 1792-1877 | 1792-1877 | TDPSSIAARGYISTRVEMGEAAAIFMTATPPGTRDAFPDSNSPIMDTEVEVPERAWSSGFDWVTDHSGKTVWFVPSVRNGNEIAAC | 6% | 6% | 2% | 2% | 0% | 4% | 2% | 6% | 1% | 3% | 1% | 4% |
| **Z-19.1 (NS3-9) 1800-1853** | 1800-1853 | RGYISTRVEMGEAAAIFMTATPPGTRDAFPDSNSPIMDTEVEVPERAWSSGFDW | 0% | 0% | 0% | 0% | 0% | 0% | 2% | 1% | 0% | 0% | 0% | 0% |
| **Z-19.2 (NS3-10) 1813-1885** | 1813-1885 | AAIFMTATPPGTRDAFPDSNSPIMDTEVEVPERAWSSGFDWVTDHSGKTVWFVPSVRNGNEIAACLTKAGKRV | 0% | 0% | 0% | 0% | 0% | 0% | 1% | 1% | 1% | 7% | 0% | 0% |
| **Z-46 (NS3-11) 1861-1934** | 1861-1934 | TVWFVPSVRNGNEIAACLTKAGKRVIQLSRKTFETEFQKTKHQEWDFVVTTDISEMGANFKADRVIDSRRCLKP | 0% | 0% | 0% | 0% | 0% | 0% | 1% | 1% | 2% | 0% | 0% | 0% |

TABLE 7-continued

Frequency of antigenic sites for IgM, IgG and IgA antibodies in serum and amniotic fluid (AF) during ZIKV infection in the first and third trimester of pregnancy

| Antigenic Site | AA of SEQ ID NO: 9 | Sequence | First Trimester IgM Serum | First Trimester IgM AF | First Trimester IgG Serum | First Trimester IgG AF | First Trimester IgA Serum | First Trimester IgA AF | Third Trimester IgM Serum | Third Trimester IgM AF | Third Trimester IgG Serum | Third Trimester IgG AF | Third Trimester IgA Serum | Third Trimester IgA AF |
|---|---|---|---|---|---|---|---|---|---|---|---|---|---|---|
| **Z-47 (NS3-12) 1891-1996** | 1891-1996 | KTFETEFQKTKHQE WDFVVTTDISEMGA NFKADRVIDSRRCL KPVILDGERVILAG PMPVTHASAAQRRG RIGRNPNKPGDEYL YGGGCAETDEDHAH WLEARMLL | 1% | 1% | 0% | 1% | 0% | 0% | 0% | 1% | 0% | 0% | 0% | 0% |
| Z-20 (NS3-5) 1910-2027 | 1910-2027 | TTDISEMGANFKAD RVIDSRRCLKPVIL DGERVILAGPMPVT HASAAQRRGRIGRN PNKPGDEYLYGGGC AETDEDHAHWLEAR MLLDNIYLQDGLIA SLYRPEADKVAAIE GEFKLR | 0% | 2% | 0% | 0% | 0% | 0% | 4% | 3% | 1% | 1% | 1% | 0% |
| Z-21 (NS3-6) 2021-2119 | 2021-2136 | EGEFKLRTEQRKTF VELMKRGDLPVWLA YQVASAGITYTDRR WCFDGTTNNTIMED SVPAEVWTRHGEKR VLKPRWMDARVCSD HAALKSFKEFAAGK RGAAFGVMEALGTL PGHM | 3% | 6% | 0% | 0% | 0% | 1% | 1% | 2% | 0% | 0% | 0% | 10% |
| Z-21.1 (NS3-7) 2028-2111 | 2028-2111 | TEQRKTFVELMKRG DLPVWLAYQVASAG ITYTDRRWCFDGTT NNTIMEDSVPAEVW TRHGEKRVLKPRWM DARVCSDHAALKSF | 0% | 0% | 0% | 0% | 0% | 0% | 3% | 3% | 0% | 0% | 2% | 6% |
| Z-22 (NS4A) 2135-2171 | 2135-2171 | HMTERFQEAIDNLA VLMRAETGSRPYKA AAAQLPETL | 2% | 2% | 0% | 0% | 0% | 0% | 2% | 1% | 0% | 0% | 1% | 0% |
| **Z-48 (NS4B-4) 2294-2349** | 2294-2349 | TIGFSMDIDLRPAS AWAIYAALTTFITP AVQHAVTTSYNNYS LMAMATQAGVLFGM | 0% | 0% | 0% | 0% | 0% | 0% | 2% | 0% | 0% | 0% | 1% | 1% |
| Z-23 (NS4B-1) 2316-2468 | 2316-2468 | TTFITPAVQHAVTT SYNNYSLMAMATQA GVLFGMGKGMPFYA WDFGVPLLMIGCYS QLTPLTLIVAIILL VAHYMYLIPGLQAA AARAAQKRTAAGIM KNPVVDGIVVTDID TMTIDPQVEKKMGQ VLLIAVAVSSAILS RTAWGWGEAGALI | 0% | 0% | 0% | 0% | 0% | 0% | 0% | 1% | 0% | 0% | 0% | 0% |
| Z-23.1 (NS4B-2) 2320-2365 | 2320-2365 | TPAVQHAVTTSYNN YSLMAMATQAGVLF GMGKGMPFYAWDFG VPLL | 0% | 0% | 0% | 0% | 4% | 3% | 0% | 2% | 0% | 0% | 0% | 0% |
| Z-23.2 (NS4B-3) 2375-2462 | 2375-2462 | PLTLIVAIILLVAH YMYLIPGLQAAAAR AAQKRTAAGIMKNP VVDGIVVTDIDTMT IDPQVEKKMGQVLL IAVAVSSALLSRTA WGWG | 9% | 0% | 0% | 0% | 0% | 0% | 2% | 0% | 0% | 0% | 0% | 0% |

TABLE 7-continued

Frequency of antigenic sites for IgM, IgG and IgA antibodies in serum and amniotic fluid (AF) during ZIKV infection in the first and third trimester of pregnancy

| | AA of | | IgM | | IgG | | IgA | | IgM | | IgG | | IgA | |
|---|---|---|---|---|---|---|---|---|---|---|---|---|---|---|
| Antigenic | SEQ ID | | First Trimester | | | | | | Third Trimester | | | | | |
| Site | NO: 9 | Sequence | Serum | AF | Serum | AF | Serum | AF | Serum | AF | Serum | AF | Serum | AF |
| Z-24 (NS5-1) 2413-2484 | 2413-2484 | MKNPVVDGIVVTDIDTMTIDPQVEKKMGQVLLIAVAVSSAILSRTAWGWGEAGALITAATSTLWEGSPNKYW | 4% | 3% | 1% | 0% | 0% | 0% | 3% | 2% | 0% | 0% | 0% | 0% |
| Z-25 (NS5-2) 2525-2608 | 2525-2608 | GETLGEKWKARLNQMSALEFYSYKKSGITEVCREEARRALKDGVATGGHAVSRGSAKLRWLVERGYLQPYGKVIDLGCGRGGWS | 2% | 0% | 0% | 0% | 0% | 0% | 1% | 1% | 0% | 0% | 16% | 0% |
| Z-26 (NS5-3) 2609-2665 | 2609-2665 | YYAATIRKVQEVKGYTKGGPGHEEPVLVQSYGWNIVRLKSGVDVFHMAAEPCDTLLC | 2% | 9% | 0% | 0% | 2% | 0% | 1% | 3% | 0% | 3% | 0% | 0% |
| Z-27 (NS5-4) 2671-2753 | 2671-2753 | SSSPEVEEARTLRVLSMVGDWLEKRPGAFCIKVLCPYTSTMMETLERLQRRYGGGLVRVPLSRNSTHEMYWVSGAKSNTIKSV | 0% | 0% | 0% | 0% | 0% | 0% | 2% | 3% | 0% | 0% | 0% | 3% |
| Z-28 (NS5-5) 2736-2829 | 2736-2829 | THEMYWVSGAKSNTIKSVSTTSQLLLGRMDGPRRPVKYEEDVNLGSGTRAVVSCAEAPNMKIIGNRIERIRSEHAETWFFDENHPYRTWAYHGS | 1% | 0% | 0% | 0% | 7% | 21% | 4% | 1% | 0% | 1% | 6% | 0% |
| Z-28.1 (NS5-6) 2798-2831 | 2798-2831 | IGNRIERIRSEHAETWFFDENHPYRTWAYHGSYE | 0% | 2% | 0% | 0% | 4% | 0% | 1% | 2% | 0% | 0% | 0% | 0% |
| Z-29 (NS5-7) 2826-2898 | 2826-2898 | YHGSYEAPTQGSASSLINGVVRLLSKPWDVVTGVTGIAMTDTTPYGQQRVFKEKVDTRVPDPQEGTRQVMSMV | 4% | 1% | 0% | 0% | 47% | 16% | 5% | 7% | 0% | 0% | 0% | 17% |
| Z-30 (NS5-8) 2917-2979 | 2917-2979 | KEEFINKVRSNAALGAIFEEEKEWKTAVEAVNDPRFWALVDKEREHHLRGECQSCVYNMMGKR | 4% | 4% | 0% | 1% | 0% | 0% | 1% | 1% | 0% | 0% | 0% | 0% |
| Z-31 (NS5-9) 2997-3050 | 2997-3050 | YMWLGARFLEFEALGFLNEDHWMGRENSGGGVEGLGLQRLGYVLEEMSRIPGGR | 1% | 0% | 0% | 0% | 0% | 0% | 4% | 3% | 0% | 0% | 0% | 0% |
| Z-32 (NS5-10) 3029-3174 | 3029-3174 | EGLGLQRLGYVLEEMSRIPGGRMYADDTAGWDTRISRFDLENEALITNQMEKGHRALALAIIKYTYQNKVVKVLRPAEKGKTVMDIISRQDQRGSGQVVTYALNTFTNLVVQLIRNMEAEEVLEMQDLWLLRRSEKVTNWLQSNGW | 0% | 0% | 0% | 0% | 0% | 0% | 5% | 2% | 0% | 0% | 0% | 0% |

TABLE 7-continued

Frequency of antigenic sites for IgM, IgG and IgA antibodies in serum and amniotic fluid (AF) during ZIKV infection in the first and third trimester of pregnancy

| Antigenic Site | AA of SEQ ID NO: 9 | Sequence | First Trimester IgM Serum | First Trimester IgM AF | First Trimester IgG Serum | First Trimester IgG AF | First Trimester IgA Serum | First Trimester IgA AF | Third Trimester IgM Serum | Third Trimester IgM AF | Third Trimester IgG Serum | Third Trimester IgG AF | Third Trimester IgA Serum | Third Trimester IgA AF |
|---|---|---|---|---|---|---|---|---|---|---|---|---|---|---|
| Z-32.1 (NS5-11) 3039-3068 | 3039-3068 | VLEEMSRIPGGRMYADDTAGWDTRISRFDL | 3% | 2% | 0% | 0% | 0% | 0% | 0% | 1% | 0% | 0% | 0% | 0% |
| Z-32.2 (NS5-12) 3104-3168 | 3104-3168 | PAEKGKTVMDIISRQDQRGSGQVVTYALNTFTNLVVQLIRNMEAEEVLEMQDLWLLRRSEKVTNW | 1% | 1% | 0% | 1% | 0% | 0% | 1% | 4% | 0% | 0% | 0% | 0% |
| Z-33 (NS5-13) 3162-3241 | 3162-3241 | SEKVTNWLQSNGWDRLKRMAVSGDDCVVKPIDDRFAHALRFLNDMGKVRKDTQEWKPSTGWDNWEEVPFCSHHFNKLHLK | 1% | 2% | 0% | 0% | 2% | 1% | 3% | 3% | 1% | 1% | 2% | 6% |
| Z-33.1 (NS5-14) 3181-3239 | 3181-3239 | AVSGDDCVVKPIDDRFAHALRFLNDMGKVRKDTQEWKPSTGWDNWEEVPFCSHHFNKLH | 1% | 1% | 0% | 0% | 0% | 1% | 2% | 1% | 1% | 0% | 0% | 0% |
| Z-34 (NS5-15) 3241-3275 | 3241-3275 | KDGRSIVVPCRHQDELIGRARVSPGAGWSIRETAC | 1% | 2% | 0% | 0% | 0% | 0% | 0% | 2% | 0% | 0% | 1% | 0% |
| Z-35 (NS5-16) 3308-3368 | 3308-3368 | DWVPTGRTTWSIHGKGEWMTTEDMLVVWNRVWIEENDHMEDKTPVTKWTDIPYLGKREDLW | 7% | 7% | 0% | 0% | 2% | 0% | 2% | 4% | 1% | 1% | 0% | 1% |
| Z-36 (NS5-17) 3357-3417 | 3357-3417 | DIPYLGKREDLWCGSLIGHRPRTTWAENIKNTVNMVRRIIGDEEKYMDYLSTQVRYLGEEG | 2% | 1% | 0% | 0% | 0% | 0% | 1% | 1% | 0% | 0% | 1% | 0% |
| | | Total* | 96% | 89% | 95% | 98% | 91% | 99% | 96% | 98% | 99% | 100% | 95% | 100% |

Sites in bold represent the new sited identified in the present study compared to those identified in Example 1.
*Total percentage of clones are comprised of clones represented in these antigenic sites for the analyzed sample.

TABLE 8

Sequence conservation of antigenic sites among different flavivirus strains

| Antigenic Site | AA of SEQ ID NO: 9 | Sequence | Dengue 1 | Dengue 2 | Dengue 3 | Dengue 4 | Yellow Fever | West Nile | MR766 |
|---|---|---|---|---|---|---|---|---|---|
| Z-I (pr) 122-170 | 122-170 | AAEVTRRGSAYYMYLDRNDAGEAISFPTTLGMNKCYIQIMDLGHMCDAT | 35% | 35% | 39% | 37% | 14% | 29% | 85% |
| Z-1.1 (pr) 159-198 | 159-198 | QIMDLGHMCDATMSYECPMLDEGVEPDDVDCWCNTTSTWV | 63% | 58% | 65% | 60% | 39% | 48% | 100% |
| Z-2 (pr/M-1) 170-216 | 170-216 | TMSYECPMLDEGVEPDDVDCWCNTTSTWVVYGTCHHKKGEARRSRRA | 62% | 57% | 60% | 57% | 50% | 51% | 100% |

TABLE 8-continued

Sequence conservation of antigenic sites among different flavivirus strains

| Antigenic Site | AA of SEQ ID NO: 9 | Sequence | Dengue 1 | Dengue 2 | Dengue 3 | Dengue 4 | Yellow Fever | West Nile | MR766 |
|---|---|---|---|---|---|---|---|---|---|
| Z-3 (pr/M-2) 188-293 | 188-293 | DCWCNTTSTWVVYGTCHHKKGEARRSRRAVTLPSHSTRKLQTRSQTWLESREYTKHLIRVENWIFRNPGFALAAAAIAWLLGSSTSQKVIYLVMILLIAPAYSIRC | 43% | 43% | 43% | 51% | 42% | 47% | 97% |
| Z-4 (M/E) 213-374 | 213-374 | SRRAVTLPSHSTRKLQTRSQTWLESREYTKHLIRVENWIFRNPGFALAAAAIAWLLGSSTSQKVIYLVMILLIAPAYSIRCIGVSNRDFVEGMSGGTWVDVVLEHGGCVTVMAQDKPTVDIELVTTTVSNMAEVRSYCYEASISDMASDSRCPTQGEAYLDK | 51% | 47% | 49% | 55% | 46% | 51% | 98% |
| Z-4.1 (E-1) 310-372 | 310-372 | WVDVVLEHGGCVTVMAQDKPTVDIELVTTTVSNMAEVRSYCYEASISDMASDSRCPTQGEAYL | 68% | 55% | 62% | 65% | 48% | 52% | 100% |
| **Z-37 (E-9) 339-450** | 339-450 | TVSNMAEVRSYCYEASISDMASDSRCPTQGEAYLDKQSDTQYVCKRTLVDRGWGNGCGLFGKGSLVTCAKFACSKKMTGKSIQPENLEYRIMLSVHGSQHSGMIVNDTGHET | 55% | 49% | 50% | 54% | 38% | 53% | 97% |
| Z-4.2 (E-2) 365-411 | 365-411 | PTQGEAYLDKQSDTQYVCKRTLVDRGWGNGCGLFGKGSLVTCAKFAC | 77% | 66% | 79% | 72% | 64% | 70% | 98% |
| Z-5 (E-3) 417-526 | 417-526 | GKSIQPENLEYRIMLSVHGSQHSGMIVNDTGHETDENRAKVEITPNSPRAEATEGGFGSLGLDCEPRTGLDFSDLYYLTMNNKHWLVHKEWFHDIPLPWHAGADTGTPHW | 47% | 47% | 48% | 46% | 22% | 35% | 97% |
| Z-6 (E-4) 484-535 | 484-535 | TGLDFSDLYYLTMNNKHWLVHKEWFHDIPLPWHAGADTGTPHWNNKEALVEF | 56% | 58% | 62% | 56% | 35% | 42% | 100% |
| **Z-38 (E-10) 515-573** | 515-573 | WHAGADTGTPHWNNKEALVEFKDAHAKRQTVVVLGSQEGAVHTALAGALEAEMDGAKGR | 56% | 58% | 63% | 59% | 34% | 46% | 98% |
| Z-7 (E-5) 558-579 | 558-579 | ALAGALEAEMDGAKGRLSSGHL | 41% | 45% | 41% | 41% | 32% | 50% | 90% |
| Z-8 (E-6) 595-729 | 595-729 | YSLCTAAFTFTKIPAETLHGTVTVEVQYAGTDGPCKVPAQMAVDMQTLTPVGRLITANPVITESTENSKMMLELDPPFGDSYIVIGVGEKKITHHWHRSGSTIGKAFEATVRGAKRMAVLGDTAWDFGSVGGALN | 55% | 52% | 53% | 54% | 42% | 62% | 96% |
| Z-8.1 (E-7) 657-719 | 657-719 | ESTENSKMMLELDPPFGDSYIVIGVGEKKITHHWHRSGSTIGKAFEATVRGAKRMAVLGDTAW | 56% | 56% | 52% | 65% | 48% | 68% | 98% |
| Z-9 (E-8) 679-794 | 679-806 | IGVGEKKITHHWHRSGSTIGKAFEATVRGAKRMAVLGDTAWDFGSVGGALNSLGKGIHQIFGAAFKSLFGGMSWFSQILIGTLLMWLGLNTKNGSISLMCLALGGVLIFLSTAVSADVGCSVDFSKKE | 55% | 48% | 57% | 56% | 48% | 62% | 95% |

TABLE 8-continued

Sequence conservation of antigenic sites among different flavivirus strains

| Antigenic Site | AA of SEQ ID NO: 9 | Sequence | Dengue 1 | Dengue 2 | Dengue 3 | Dengue 4 | Yellow Fever | West Nile | MR766 |
|---|---|---|---|---|---|---|---|---|---|
| Z-10 (NS1-1) 795-835 | 789-835 | STAVSADVGCSVDFSKKETRCGTGVFVYNDVEAWRDRYKYHPDSPRR | 43% | 40% | 45% | 45% | 40% | 55% | 98% |
| Z-11 (NS1-2) 873-913 | 873-913 | LEENGVQLTVVVGSVKNPMWRGPQRLPVPVNELPHGWKAWG | 37% | 41% | 41% | 46% | 41% | 46% | 100% |
| **Z-39 (NS1-6) 880-962** | 880-962 | LTVVVGSVKNPMWRGPQRLPVPVNELPHGWKAWGKSYFVRAAKTNNSFVVDGDTLKECPLKHRAWNSFLVEDHGFGVFHTSVW | 41% | 43% | 47% | 46% | 42% | 45% | 99% |
| **Z-40 (NS1-7) 895-1054** | 895-1054 | PQRLPVPVNELPHGWKAWGKSYFVRAAKTNNSFVVDGDTLKECPLKHRAWNSFLVEDHGFGVFHTSVWLKVREDYSLECDPAVIGTAVKGKEAVHSDLGYWIESEKNDTWRLKRAHLIEMKTCEWPKSHTLWTDGIEESDLIIPKSLAGPLSHHNTREGY | 51% | 51% | 57% | 51% | 39% | 58% | 97% |
| **Z-41 (NS1-8) 922-984** | 922-984 | KTNNSFVVDGDTLKECPLKHRAWNSFLVEDHGFGVFHTSVWLKVREDYSLECDPAVIGTAVKG | 44% | 46% | 51% | 46% | 44% | 52% | 98% |
| **Z-42 (NS1-9) 925-965** | 925-965 | NSFVVDGDTLKECPLKHRAWNSFLVEDHGFGVFHTSVWLKV | 57% | 67% | 62% | 57% | 48% | 48% | 98% |
| Z-12 (NS1-3) 958-1023 | 958-1023 | HTSVWLKVREDYSLECDPAVIGTAVKGKEAVHSDLGYWIESEKNDTWRLKRAHLIEMKTCEWPKSH | 58% | 50% | 58% | 53% | 34% | 58% | 97% |
| **Z-43 (NS1-10) 966-1081** | 966-1081 | REDYSLECDPAVIGTAVKGKEAVHSDLGYWIESEKNDTWRLKRAHLIEMKTCEWPKSHTLWTDGIEESDLIIPKSLAGPLSHHNTREGYRTQMKGPWHSEELEIRFEECPGTKVHV | 57% | 54% | 60% | 58% | 40% | 61% | 96% |
| Z-13 (NS1-4) 1031-1090 | 1031-1090 | EESDLIIPKSLAGPLSHHNTREGYRTQMKGPWHSEELEIRFEECPGTKVHVEETCGTRGP | 57% | 60% | 63% | 60% | 45% | 57% | 97% |
| Z-14 (NS1-5) 1046-1127 | 1046-1127 | SHHNTREGYRTQMKGPWHSEELEIRFEECPGTKVHVEETCGTRGPSLRSTTASGRVIEEWCCRECTMPPLSFRAKDGCWYGM | 62% | 65% | 62% | 65% | 57% | 55% | 98% |
| **Z-44 (NS2A-1) 1165-1251** | 1165-1251 | MVQEGLKKRMTTKIIISTSMAVLVAMILGGFSMSDLAKLAILMGATFAEMNTGGDVAHLALIAAFKVRPALLVSFIFRANWTPRESM | 31% | 36% | 30% | 34% | 41% | 47% | 95% |
| **Z-45 (NS2A-2) 1313-1398** | 1313-1398 | LVAWRAGLATCGGFMLLSLKGKGSVKKNLPFVMALGLTAVRLVDPINVVGLLLLTRSGKRSWPPSEVLTAVGLICALAGGFAKADI | 21% | 25% | 29% | 28% | 26% | 33% | 98% |
| Z-15 (NS2B) 1417-1474 | 1417-1474 | SGKSVDMYIERAGDITWEKDAEVTGNSPRLDVALDESGDFSLVEDDGPPMREIILKVV | 29% | 33% | 34% | 34% | 31% | 55% | 98% |

TABLE 8-continued

Sequence conservation of antigenic sites among different flavivirus strains

| Antigenic Site | AA of SEQ ID NO: 9 | Sequence | Dengue 1 | Dengue 2 | Dengue 3 | Dengue 4 | Yellow Fever | West Nile | MR766 |
|---|---|---|---|---|---|---|---|---|---|
| Z-16 (NS3-1) 1503-1624 | 1477-1624 | TICGMNPIAIPFAAGAWYVY VKTGKRSGALWDVPAPKEVK KGETTDGVYRVMTRRLLGST QVGVGVMQEGVFHTMWHVTK GSALRSGEGRLDPYWGDVKQ DLVSYCGPWKLDAAWDGHSE VQLLAVPPGERARNIQTLPG IFKTKDGD | 51% | 49% | 49% | 51% | 44% | 60% | 98% |
| Z-17 (NS3-2) 1536-1672 | 1536-1672 | TQVGVGVMQEGVFHTMWHVT KGSALRSGEGRLDPYWGDVK QDLVSYCGPWKLDAAWDGHS EVQLLAVPPGERARNIQTLP GIFKTKDGDIGAVALDYPAG TSGSPILDKCGRVIGLYGNG VVIKNGSYVSAITQGRR | 56% | 58% | 59% | 60% | 57% | 58% | 98% |
| **Z-17.1 (NS3-8) 1533-1568** | 1533-1568 | LGSTQVGVGVMQEGVFHTMW HVTKGSALRSGEGRLD | 67% | 53% | 64% | 64% | 58% | 78% | 97% |
| Z-18 (NS3-3) 1600-1694 | 1600-1694 | LAVPPGERARNIQTLPGIFK TKDGDIGAVALDYPAGTSGS PILDKCGRVIGLYGNGVVIK NGSYVSAITQGRREEETPVE CFEPSMLKKKQLTVL | 49% | 53% | 54% | 55% | 55% | 65% | 99% |
| Z-19 (NS3-4) 1792-1877 | 1792-1877 | TDPSSIAARGYISTRVEMGE AAAIFMTATPPGTRDAFPDS NSPIMDTEVEVPERAWSSGF DWVTDHSGKTVWFVPSVRNG NEIAAC | 72% | 77% | 74% | 77% | 48% | 71% | 100% |
| **Z-19.1 (NS3-9) 1800-1853** | 1800-1853 | RGYISTRVEMGEAAAIFMTA TPPGTRDAFPDSNSPIMDTE VEVPERAWSSGFDW | 72% | 76% | 76% | 80% | 48% | 69% | 100% |
| **Z-19.2 (NS3-10) 1813-1885** | 1813-1885 | AAIFMTATPPGTRDAFPDSN SPIMDTEVEVPERAWSSGFD WVTDHSGKTVWFVPSVRNGN EIAACLTKAGKRV | 67% | 70% | 68% | 70% | 51% | 67% | 100% |
| **Z-46 (NS3-11) 1861-1934** | 1861-1934 | TVWFVPSVRNGNEIAACLTK AGKRVIQLSRKTFETEFQKT KHQEWDFVVTTDISEMGANF KADRVIDSRRCLKP | 78% | 76% | 81% | 77% | 53% | 73% | 97% |
| **Z-47 (NS3-12) 1891-1996** | 1891-1996 | KTFETEFQKTKHQEWDFVVT TDISEMGANFKADRVIDSRR CLKPVILDGERVILAGPMPV THASAAQRRGRIGRNPNKPG DEYLYGGGCAETDEDHAHWL EARMLL | 77% | 72% | 76% | 72% | 48% | 63% | 96% |
| Z-20 (NS3-5) 1910-2027 | 1910-2027 | TTDISEMGANFKADRVIDSR RCLKPVILDGERVILAGPMP VTHASAAQRRGRIGRNPNKP GDEYLYGGGCAETDEDHAHW LEARMLLDNIYLQDGLIASL YRPEADKVAAIEGEFKLR | 73% | 71% | 71% | 70% | 49% | 63% | 98% |
| Z-21 (NS3-6) 2021-2119 | 2021-2136 | EGEFKLRTEQRKTFVELMKR GDLPVWLAYQVASAGITYTD RRWCFDGTTNNTIMEDSVPA EVWTRHGEKRVLKPRWMDAR VCSDHAALKSFKEFAAGKRG AAFGVMEALGTLPGHM | 57% | 60% | 58% | 59% | 47% | 59% | 97% |
| Z-21.1 (NS3-7) 2028-2111 | 2028-2111 | TEQRKTFVELMKRGDLPVWL AYQVASAGITYTDRRWCFDG TTNNTIMEDSVPAEVWTRHG EKRVLKPRWMDARVCSDHAA LKSF | 43% | 54% | 43% | 38% | 32% | 35% | 98% |

TABLE 8-continued

Sequence conservation of antigenic sites among different flavivirus strains

| Antigenic Site | AA of SEQ ID NO: 9 | Sequence | Dengue 1 | Dengue 2 | Dengue 3 | Dengue 4 | Yellow Fever | West Nile | MR766 |
|---|---|---|---|---|---|---|---|---|---|
| Z-22 (NS4A) 2135-2171 | 2135-2171 | HMTERFQEAIDNLAVLMRAE TGSRPYKAAAAQLPETL | 52% | 55% | 52% | 50% | 31% | 42% | 100% |
| **Z-48 (NS4B-4) 2294-2349** | 2294-2349 | TIGFSMDIDLRPASAWAIYA ALTTFITPAVQHAVTTSYNN YSLMAMATQAGVLFGM | 44% | 51% | 49% | 46% | 35% | 42% | 96% |
| Z-23 (NS4B-1) 2316-2468 | 2316-2468 | TTFITPAVQHAVTTSYNNYS LMAMATQAGVLFGMGKGMPF YAWDFGVPLLMIGCYSQLTP LTLIVAIILLVAHYMYLIPG LQAAAARAAQKRTAAGIMKN PVVDGIVVTDIDTMTIDPQV EKKMGQVLLIAVAVSSAILS RTAWGWGEAGALI | 47% | 49% | 47% | 44% | 34% | 42% | 96% |
| Z-23.1 (NS4B-2) 2320-2365 | 2320-2365 | TPAVQHAVTTSYNNYSLMAM ATQAGVLFGMGKGMPFYAWD FGVPLL | 46% | 52% | 50% | 50% | 37% | 37% | 98% |
| Z-23.2 (NS4B-3) 2375-2462 | 2375-2462 | PLTLIVAIILLVAHYMYLIP GLQAAAARAAQKRTAAGIMK NPVVDGIVVTDIDTMTIDPQ VEKKMGQVLLIAVAVSSAIL SRTAWGWG | 55% | 55% | 52% | 50% | 30% | 44% | 97% |
| Z-24 (NS5-1) 2413-2484 | 2413-2484 | MKNPVVDGIVVTDIDTMTID PQVEKKMGQVLLIAVAVSSA ILSRTAWGWGEAGALITAAT STLWEGSPNKYW | 47% | 49% | 47% | 44% | 34% | 42% | 96% |
| Z-25 (NS5-2) 2525-2608 | 2525-2608 | GETLGEKWKARLNQMSALEF YSYKKSGITEVCREEARRAL KDGVATGGHAVSRGSAKLRW LVERGYLQPYGKVIDLGCGR GGWS | 69% | 67% | 70% | 67% | 57% | 64% | 99% |
| Z-26 (NS5-3) 2609-2665 | 2609-2665 | YYAATIRKVQEVKGYTKGGP GHEEPVLVQSYGWNIVRLKS GVDVFHMAAEPCDTLLC | 67% | 65% | 69% | 67% | 51% | 77% | 96% |
| Z-27 (NS5-4) 2671-2753 | 2671-2753 | SSSPEVEEARTERVLSMVGD WLEKRPGAFCIKVLCPYTST MMETLERLQRRYGGGLVRVP LSRNSTHEMYWVSGAKSNTI KSV | 58% | 60% | 63% | 66% | 57% | 69% | 95% |
| Z-28 (NS-5) 2736-2829 | 2736-2829 | THEMYWVSGAKSNTIKSVST TSQLLLGRMDGPRRPVKYEE DVNLGSGTRAVVSCAEAPNM KIIGNRIERIRSEHAETWFF DENHPYRTWAYHGS | 53% | 52% | 52% | 57% | 49% | 57% | 95% |
| Z-28.1 (NS5-6) 2798-2831 | 2798-2831 | IGNRIERIRSEHAETWFFDE NHPYRTWAYHGSYE | 68% | 65% | 65% | 65% | 56% | 68% | 91% |
| Z-29 (NS5-7) 2826-2898 | 2826-2898 | YHGSYEAPTQGSASSLINGV VRLLSKPWDVVTGVTGIAMT DTTPYGQQRVFKEKVDTRVP DPQEGTRQVMSMV | 70% | 70% | 71% | 73% | 62% | 70% | 96% |
| Z-30 (NS5-8) 2917-2979 | 2917-2979 | KEEFINKVRSNAALGAIFEE EKEWKTAVEAVNDPRFWALV DKEREHHLRGECQSCVYNMM GKR | 63% | 71% | 63% | 71% | 68% | 71% | 97% |
| Z-31 (NS5-9) 2997-3050 | 2997-3050 | YMWLGARFLEFEALGFLNED HWMGRENSGGGVEGLGLQRL GYVLEEMSRIPGGR | 74% | 72% | 74% | 76% | 74% | 80% | 92% |

TABLE 8-continued

Sequence conservation of antigenic sites among different flavivirus strains

| Antigenic Site | AA of SEQ ID NO: 9 | Sequence | Dengue 1 | Dengue 2 | Dengue 3 | Dengue 4 | Yellow Fever | West Nile | MR766 |
|---|---|---|---|---|---|---|---|---|---|
| Z-32 (NS5-10) 3029-3174 | 3029-3174 | EGLGLQRLGYVLEEMSRIPG GRMYADDTAGWDTRISRFDL ENEALITNQMEKGHRALALA IIKYTYQNKVVKVLRPAEKG KTVMDIISRQDQRGSGQVVT YALNTFTNLVVQLIRNMEAL EVLEMQDLWLLRRSEKVTNW LQSNGW | 60% | 60% | 62% | 62% | 57% | 62% | 92% |
| Z-32.1 (NS5-11) 3039-3068 | 3039-3068 | VLEEMSRIPGGRMYADDTAG WDTRISRFDL | 70% | 63% | 70% | 63% | 57% | 63% | 83% |
| Z-32.2 (NS5-12) 3104-3168 | 3104-3168 | PAEKGKTVMDIISRQDQRGS GQVVTYALNTFTNLVVQLIR NMEALEVLEMQDLWLLRRSE KVTNW | 52% | 58% | 54% | 55% | 58% | 64% | 94% |
| Z-33 (NS5-13) 3162-3241 | 3162-3241 | SEKVTNWLQSNGWDRLKRMA VSGDDCVVKPIDDRFAHALR FLNDMGKVRKDTQEWKPSTG WDNWEEVPFCSHHFNKLHLK | 68% | 65% | 68% | 65% | 66% | 67% | 95% |
| Z-33.1 (NS5-14) 3181-3239 | 3181-3239 | AVSGDDCVVKPIDDRFAHAL RFLNDMGKVRKDTQEWKPST GWDNWEEVPFCSHHFNKLH | 73% | 71% | 73% | 71% | 71% | 75% | 97% |
| Z-34 (NS5-15) 3241-3275 | 3241-3275 | KDGRSIVVPCRHQDELIGRA RVSPGAGWSIRETAC | 86% | 83% | 83% | 86% | 83% | 80% | 100% |
| Z-35 (NS5-16) 3308-3368 | 3308-3368 | DWVPTGRTTWSIHGKGEWMT TEDMLVVWNRVWIEENDHME DKTPVTKWTDIPYLGKREDL W | 77% | 79% | 77% | 75% | 75% | 81% | 98% |
| Z-36 (NS5-17) 3357-3417 | 3357-3417 | DIPYLGKREDLWCGSLIGHR PRTTWAENIKNTVNMVRRII GDEEKYMDYLSTQVRYLGEE G | 54% | 57% | 52% | 57% | 46% | 57% | 98% |

Sites in bold represent the new sites identified in this study compared with those identified in Example 1

TABLE 9

Frequency of differentially recognized antigenic sites by serum vs AF following ZIKV infection in first trimester ($1^{st}$) or $3^{rd}$ trimester ($3^{rd}$)

| Antigenic Site | Serum | AF |
|---|---|---|
| Z-5 (E-3) 417-526 | IgA $1^{st}$- 2% | IgA $1^{st}$- 22% |
| Z-8 (E-6) 595-729 | IgG $1^{st}$- 79% | IgG $1^{st}$- 59% |
| | IgG $3^{rd}$- 12% | IgG $3^{rd}$- 10% |
| Z-42 (NS1-9) 925-965 | None | IgA $3^{rd}$- 36% |
| Z-12 (NS1-3) 958-1023 | IgA $3^{rd}$- 38% | None |
| Z-43 (NS1-10) 966-1081 | None | IgA $3^{rd}$- 9% |
| Z-14 (NS1-5) 1046-1127 | None | IgG $3^{rd}$- 47% |
| Z-25 (NS5-2) 2525-2608 | IgA $3^{rd}$- 16% | None |

TABLE 9-continued

Frequency of differentially recognized antigenic sites by serum vs AF following ZIKV infection in first trimester ($1^{st}$) or $3^{rd}$ trimester ($3^{rd}$)

| Antigenic Site | Serum | AF |
|---|---|---|
| Z-28 (NS-5) 2736-2829 | IgA $1^{st}$- 7% | IgA $1^{st}$- 21% |
| Z-29 (NS5-7) 2826-2898 | IgA $1^{st}$-47% | IgA $1^{st}$- 16% |
| | | IgA $3^{rd}$- 17% |

In view of the many possible embodiments to which the principles of the disclosed subject matter may be applied, it should be recognized that the illustrated embodiments are only preferred examples of the disclosure and should not be taken as limiting the scope of the disclosure. Rather, the scope of the disclosure is defined by the following claims. We therefore claim all that comes within the scope and spirit of these claims.

The invention claimed is:

1. An isolated peptide, wherein the amino acid sequence of the peptide consists or consists essentially of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 10, and wherein:

the peptide is linked to a solid support;

the peptide is fused to a heterologous protein; or the peptide is conjugated to a heterologous carrier.

2. The isolated peptide of claim 1, wherein the amino acid sequence of the peptide consists or consists essentially of SEQ ID NO: 2, SEQ ID NO: 5, SEQ ID NO: 7 or SEQ ID NO: 8.

3. The isolated peptide of claim 1, wherein the peptide is linked to the solid support by a linker.

4. The isolated peptide of claim 3, wherein the linker comprises biotin, streptavidin, maleimide, polyethylene glycol (PEG), a peptide, or combinations of thereof.

5. The isolated peptide of claim 1, wherein the solid support comprises a bead, a membrane, a reaction tray, a multi-well plate, or a test tube.

6. The isolated peptide of claim 1, wherein the heterologous protein comprises a tag or linker.

7. The isolated peptide of claim 1, wherein the heterologous carrier comprises a protein from bacteria, a protein from a virus, keyhole limpet hemocyanin (KLH), ovalbumin (OVA), or bovine serum albumin (BSA).

8. A solid support linked to one or more peptides, wherein the one or more peptides consist or consist essentially of the amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 10.

9. The solid support of claim 8, wherein the one or more peptides consist or consist essentially of the amino acid sequences set forth as SEQ ID NO: 2, SEQ ID NO: 5, SEQ ID NO: 7 and SEQ ID NO: 8.

10. The solid support of claim 8, wherein the solid support comprises a bead, a membrane, a reaction tray, a multi-well plate, or a test tube.

11. A method for detecting anti-flavivirus antibodies in a biological sample containing antibodies, comprising:

contacting the biological sample with one or more peptides, wherein the one or more peptides consist or consist essentially of the amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 10, under conditions sufficient to form an immune complex between the one or more peptides and the antibodies present in the biological sample; and detecting the presence or absence of the immune complex, wherein the presence of the immune complex indicates anti-flavivirus antibodies are present in the sample and the absence of the immune complex indicates anti-flavivirus antibodies are not present in the sample.

12. The method of claim 11, wherein the flavivirus is Zika virus (ZIKV).

13. The method of claim 11, wherein the biological sample is from a human subject.

14. The method of claim 13, wherein the subject is one who is at risk of or is suspected of having a flavivirus infection.

15. The method of claim 11, wherein the biological sample comprises blood, serum, plasma, urine, saliva, tears, feces, semen, mucous, tissue, tissue homogenate, cellular extract, spinal fluid, or any combination of two or more thereof.

16. The method of claim 11, wherein the one or more peptides consist or consist essentially of the amino acid sequences selected from SEQ ID NO: 2, SEQ ID NO: 5, SEQ ID NO: 7 and SEQ ID NO: 8.

17. The method of claim 11, wherein the one or more peptides consist or consist essentially of the amino acid sequence of SEQ ID NO: 2.

18. The isolated peptide of claim 1, wherein the amino acid sequence of the peptide consists or consists essentially of SEQ ID NO: 2.

19. The isolated peptide of claim 18, wherein the peptide is linked to a solid support.

20. The solid support of claim 8, wherein the one or more peptides consist or consist essentially of the amino acid sequence of SEQ ID NO: 2.

21. The solid support of claim 20, wherein the solid support comprises a multi-well plate.

* * * * *

SEQUENCE LISTING

```
<160> NUMBER OF SEQ ID NOS: 10

<210> SEQ ID NO 1
<211> LENGTH: 35
<212> TYPE: PRT
<213> ORGANISM: Zika virus Paraiba strain

<400> SEQUENCE: 1

Ser Asp Leu Ile Ile Pro Lys Ser Leu Ala Gly Pro Leu Ser His His
1               5                   10                  15

Asn Thr Arg Glu Gly Tyr Arg Thr Gln Met Lys Gly Pro Trp His Ser
            20                  25                  30

Glu Glu Leu
        35


<210> SEQ ID NO 2
<211> LENGTH: 49
<212> TYPE: PRT
<213> ORGANISM: Zika virus Paraiba strain

<400> SEQUENCE: 2

Val Asp Met Tyr Ile Glu Arg Ala Gly Asp Ile Thr Trp Glu Lys Asp
1               5                   10                  15

Ala Glu Val Thr Gly Asn Ser Pro Arg Leu Asp Val Ala Leu Asp Glu
            20                  25                  30

Ser Gly Asp Phe Ser Leu Val Glu Asp Asp Gly Pro Pro Met Arg Glu
        35                  40                  45

Ile


<210> SEQ ID NO 3
<211> LENGTH: 69
<212> TYPE: PRT
<213> ORGANISM: Zika virus Paraiba strain

<400> SEQUENCE: 3

Thr Arg Val Glu Met Gly Glu Ala Ala Ala Ile Phe Met Thr Ala Thr
1               5                   10                  15

Pro Pro Gly Thr Arg Asp Ala Phe Pro Asp Ser Asn Ser Pro Ile Met
            20                  25                  30

Asp Thr Glu Val Glu Val Pro Glu Arg Ala Trp Ser Ser Gly Phe Asp
        35                  40                  45

Trp Val Thr Asp His Ser Gly Lys Thr Val Trp Phe Val Pro Ser Val
    50                  55                  60

Arg Asn Gly Asn Glu
65


<210> SEQ ID NO 4
<211> LENGTH: 44
<212> TYPE: PRT
<213> ORGANISM: Zika virus Paraiba strain

<400> SEQUENCE: 4

Val Val Thr Asp Ile Asp Thr Met Thr Ile Asp Pro Gln Val Glu Lys
1               5                   10                  15

Lys Met Gly Gln Val Leu Leu Ile Ala Val Ala Val Ser Ser Ala Ile
            20                  25                  30

Leu Ser Arg Thr Ala Trp Gly Trp Gly Glu Ala Gly
```

```
        35                  40


<210> SEQ ID NO 5
<211> LENGTH: 52
<212> TYPE: PRT
<213> ORGANISM: Zika virus Paraiba strain

<400> SEQUENCE: 5

Tyr Ala Ala Leu Thr Thr Phe Ile Thr Pro Ala Val Gln His Ala Val
1               5                   10                  15

Thr Thr Ser Tyr Asn Asn Tyr Ser Leu Met Ala Met Ala Thr Gln Ala
            20                  25                  30

Gly Val Leu Phe Gly Met Gly Lys Gly Met Pro Phe Tyr Ala Trp Asp
        35                  40                  45

Phe Gly Val Pro
    50


<210> SEQ ID NO 6
<211> LENGTH: 32
<212> TYPE: PRT
<213> ORGANISM: Zika virus Paraiba strain

<400> SEQUENCE: 6

Thr Gly Ile Ala Met Thr Asp Thr Thr Pro Tyr Gly Gln Gln Arg Val
1               5                   10                  15

Phe Lys Glu Lys Val Asp Thr Arg Val Pro Asp Pro Gln Glu Gly Thr
            20                  25                  30


<210> SEQ ID NO 7
<211> LENGTH: 35
<212> TYPE: PRT
<213> ORGANISM: Zika virus Paraiba strain

<400> SEQUENCE: 7

Ala Val Glu Ala Val Asn Asp Pro Arg Phe Trp Ala Leu Val Asp Lys
1               5                   10                  15

Glu Arg Glu His His Leu Arg Gly Glu Cys Gln Ser Cys Val Tyr Asn
            20                  25                  30

Met Met Gly
        35


<210> SEQ ID NO 8
<211> LENGTH: 44
<212> TYPE: PRT
<213> ORGANISM: Zika virus Paraiba strain

<400> SEQUENCE: 8

Asn Leu Val Val Gln Leu Ile Arg Asn Met Glu Ala Glu Glu Val Leu
1               5                   10                  15

Glu Met Gln Asp Leu Trp Leu Leu Arg Arg Ser Glu Lys Val Thr Asn
            20                  25                  30

Trp Leu Gln Ser Asn Gly Trp Asp Arg Leu Lys Arg
        35                  40


<210> SEQ ID NO 9
<211> LENGTH: 3423
<212> TYPE: PRT
<213> ORGANISM: Zika virus Paraiba strain

<400> SEQUENCE: 9

Met Lys Asn Pro Lys Lys Lys Ser Gly Gly Phe Arg Ile Val Asn Met
```

-continued

```
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430
```

-continued

```
Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845
```

-continued

```
Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
        995                 1000                1005

Ala His  Leu Ile Glu Met Lys  Thr Cys Glu Trp Pro  Lys Ser His
    1010                1015                1020

Thr Leu  Trp Thr Asp Gly Ile  Glu Glu Ser Asp Leu  Ile Ile Pro
    1025                1030                1035

Lys Ser  Leu Ala Gly Pro Leu  Ser His His Asn Thr  Arg Glu Gly
    1040                1045                1050

Tyr Arg  Thr Gln Met Lys Gly  Pro Trp His Ser Glu  Glu Leu Glu
    1055                1060                1065

Ile Arg  Phe Glu Glu Cys Pro  Gly Thr Lys Val His  Val Glu Glu
    1070                1075                1080

Thr Cys  Gly Thr Arg Gly Pro  Ser Leu Arg Ser Thr  Thr Ala Ser
    1085                1090                1095

Gly Arg  Val Ile Glu Glu Trp  Cys Cys Arg Glu Cys  Thr Met Pro
    1100                1105                1110

Pro Leu  Ser Phe Arg Ala Lys  Asp Gly Cys Trp Tyr  Gly Met Glu
    1115                1120                1125

Ile Arg  Pro Arg Lys Glu Pro  Glu Ser Asn Leu Val  Arg Ser Val
    1130                1135                1140

Val Thr  Ala Gly Ser Thr Asp  His Met Asp His Phe  Ser Leu Gly
    1145                1150                1155

Val Leu  Val Ile Leu Leu Met  Val Gln Glu Gly Leu  Lys Lys Arg
    1160                1165                1170

Met Thr  Thr Lys Ile Ile Ile  Ser Thr Ser Met Ala  Val Leu Val
    1175                1180                1185

Ala Met  Ile Leu Gly Gly Phe  Ser Met Ser Asp Leu  Ala Lys Leu
    1190                1195                1200

Ala Ile  Leu Met Gly Ala Thr  Phe Ala Glu Met Asn  Thr Gly Gly
    1205                1210                1215

Asp Val  Ala His Leu Ala Leu  Ile Ala Ala Phe Lys  Val Arg Pro
    1220                1225                1230

Ala Leu  Leu Val Ser Phe Ile  Phe Arg Ala Asn Trp  Thr Pro Arg
    1235                1240                1245

Glu Ser  Met Leu Leu Ala Leu  Ala Ser Cys Leu Leu  Gln Thr Ala
```

```
    1250                1255                1260

Ile Ser  Ala Leu Glu Gly Asp  Leu Met Val Leu Ile  Asn Gly Phe
    1265                1270                1275

Ala Leu  Ala Trp Leu Ala Ile  Arg Ala Met Val Val  Pro Arg Thr
    1280                1285                1290

Asp Asn  Ile Thr Leu Ala Ile  Leu Ala Ala Leu Thr  Pro Leu Ala
    1295                1300                1305

Arg Gly  Thr Leu Leu Val Ala  Trp Arg Ala Gly Leu  Ala Thr Cys
    1310                1315                1320

Gly Gly  Phe Met Leu Leu Ser  Leu Lys Gly Lys Gly  Ser Val Lys
    1325                1330                1335

Lys Asn  Leu Pro Phe Val Met  Ala Leu Gly Leu Thr  Ala Val Arg
    1340                1345                1350

Leu Val  Asp Pro Ile Asn Val  Val Gly Leu Leu Leu  Leu Thr Arg
    1355                1360                1365

Ser Gly  Lys Arg Ser Trp Pro  Pro Ser Glu Val Leu  Thr Ala Val
    1370                1375                1380

Gly Leu  Ile Cys Ala Leu Ala  Gly Gly Phe Ala Lys  Ala Asp Ile
    1385                1390                1395

Glu Met  Ala Gly Pro Met Ala  Ala Val Gly Leu Leu  Ile Val Ser
    1400                1405                1410

Tyr Val  Val Ser Gly Lys Ser  Val Asp Met Tyr Ile  Glu Arg Ala
    1415                1420                1425

Gly Asp  Ile Thr Trp Glu Lys  Asp Ala Glu Val Thr  Gly Asn Ser
    1430                1435                1440

Pro Arg  Leu Asp Val Ala Leu  Asp Glu Ser Gly Asp  Phe Ser Leu
    1445                1450                1455

Val Glu  Asp Asp Gly Pro Pro  Met Arg Glu Ile Ile  Leu Lys Val
    1460                1465                1470

Val Leu  Met Thr Ile Cys Gly  Met Asn Pro Ile Ala  Ile Pro Phe
    1475                1480                1485

Ala Ala  Gly Ala Trp Tyr Val  Tyr Val Lys Thr Gly  Lys Arg Ser
    1490                1495                1500

Gly Ala  Leu Trp Asp Val Pro  Ala Pro Lys Glu Val  Lys Lys Gly
    1505                1510                1515

Glu Thr  Thr Asp Gly Val Tyr  Arg Val Met Thr Arg  Arg Leu Leu
    1520                1525                1530

Gly Ser  Thr Gln Val Gly Val  Gly Val Met Gln Glu  Gly Val Phe
    1535                1540                1545

His Thr  Met Trp His Val Thr  Lys Gly Ser Ala Leu  Arg Ser Gly
    1550                1555                1560

Glu Gly  Arg Leu Asp Pro Tyr  Trp Gly Asp Val Lys  Gln Asp Leu
    1565                1570                1575

Val Ser  Tyr Cys Gly Pro Trp  Lys Leu Asp Ala Ala  Trp Asp Gly
    1580                1585                1590

His Ser  Glu Val Gln Leu Leu  Ala Val Pro Pro Gly  Glu Arg Ala
    1595                1600                1605

Arg Asn  Ile Gln Thr Leu Pro  Gly Ile Phe Lys Thr  Lys Asp Gly
    1610                1615                1620

Asp Ile  Gly Ala Val Ala Leu  Asp Tyr Pro Ala Gly  Thr Ser Gly
    1625                1630                1635

Ser Pro  Ile Leu Asp Lys Cys  Gly Arg Val Ile Gly  Leu Tyr Gly
    1640                1645                1650
```

Asn Gly Val Val Ile Lys Asn Gly Ser Tyr Val Ser Ala Ile Thr
1655 1660 1665

Gln Gly Arg Arg Glu Glu Glu Thr Pro Val Glu Cys Phe Glu Pro
1670 1675 1680

Ser Met Leu Lys Lys Lys Gln Leu Thr Val Leu Asp Leu His Pro
1685 1690 1695

Gly Ala Gly Lys Thr Arg Arg Val Leu Pro Glu Ile Val Arg Glu
1700 1705 1710

Ala Ile Lys Thr Arg Leu Arg Thr Val Ile Leu Ala Pro Thr Arg
1715 1720 1725

Val Val Ala Ala Glu Met Glu Glu Ala Leu Arg Gly Leu Pro Val
1730 1735 1740

Arg Tyr Met Thr Thr Ala Val Asn Val Thr His Ser Gly Thr Glu
1745 1750 1755

Ile Val Asp Leu Met Cys His Ala Thr Phe Thr Ser Arg Leu Leu
1760 1765 1770

Gln Pro Ile Arg Val Pro Asn Tyr Asn Leu Tyr Ile Met Asp Glu
1775 1780 1785

Ala His Phe Thr Asp Pro Ser Ser Ile Ala Ala Arg Gly Tyr Ile
1790 1795 1800

Ser Thr Arg Val Glu Met Gly Glu Ala Ala Ala Ile Phe Met Thr
1805 1810 1815

Ala Thr Pro Pro Gly Thr Arg Asp Ala Phe Pro Asp Ser Asn Ser
1820 1825 1830

Pro Ile Met Asp Thr Glu Val Glu Val Pro Glu Arg Ala Trp Ser
1835 1840 1845

Ser Gly Phe Asp Trp Val Thr Asp His Ser Gly Lys Thr Val Trp
1850 1855 1860

Phe Val Pro Ser Val Arg Asn Gly Asn Glu Ile Ala Ala Cys Leu
1865 1870 1875

Thr Lys Ala Gly Lys Arg Val Ile Gln Leu Ser Arg Lys Thr Phe
1880 1885 1890

Glu Thr Glu Phe Gln Lys Thr Lys His Gln Glu Trp Asp Phe Val
1895 1900 1905

Val Thr Thr Asp Ile Ser Glu Met Gly Ala Asn Phe Lys Ala Asp
1910 1915 1920

Arg Val Ile Asp Ser Arg Arg Cys Leu Lys Pro Val Ile Leu Asp
1925 1930 1935

Gly Glu Arg Val Ile Leu Ala Gly Pro Met Pro Val Thr His Ala
1940 1945 1950

Ser Ala Ala Gln Arg Arg Gly Arg Ile Gly Arg Asn Pro Asn Lys
1955 1960 1965

Pro Gly Asp Glu Tyr Leu Tyr Gly Gly Gly Cys Ala Glu Thr Asp
1970 1975 1980

Glu Asp His Ala His Trp Leu Glu Ala Arg Met Leu Leu Asp Asn
1985 1990 1995

Ile Tyr Leu Gln Asp Gly Leu Ile Ala Ser Leu Tyr Arg Pro Glu
2000 2005 2010

Ala Asp Lys Val Ala Ala Ile Glu Gly Glu Phe Lys Leu Arg Thr
2015 2020 2025

Glu Gln Arg Lys Thr Phe Val Glu Leu Met Lys Arg Gly Asp Leu
2030 2035 2040

-continued

```
Pro Val  Trp Leu Ala Tyr Gln  Val Ala Ser Ala Gly  Ile Thr Tyr
    2045                 2050                 2055

Thr Asp  Arg Arg Trp Cys Phe  Asp Gly Thr Thr Asn  Asn Thr Ile
    2060                 2065                 2070

Met Glu  Asp Ser Val Pro Ala  Glu Val Trp Thr Arg  His Gly Glu
    2075                 2080                 2085

Lys Arg  Val Leu Lys Pro Arg  Trp Met Asp Ala Arg  Val Cys Ser
    2090                 2095                 2100

Asp His  Ala Ala Leu Lys Ser  Phe Lys Glu Phe Ala  Ala Gly Lys
    2105                 2110                 2115

Arg Gly  Ala Ala Phe Gly Val  Met Glu Ala Leu Gly  Thr Leu Pro
    2120                 2125                 2130

Gly His  Met Thr Glu Arg Phe  Gln Glu Ala Ile Asp  Asn Leu Ala
    2135                 2140                 2145

Val Leu  Met Arg Ala Glu Thr  Gly Ser Arg Pro Tyr  Lys Ala Ala
    2150                 2155                 2160

Ala Ala  Gln Leu Pro Glu Thr  Leu Glu Thr Ile Met  Leu Leu Gly
    2165                 2170                 2175

Leu Leu  Gly Thr Val Ser Leu  Gly Ile Phe Phe Val  Leu Met Arg
    2180                 2185                 2190

Asn Lys  Gly Ile Gly Lys Met  Gly Phe Gly Met Val  Thr Leu Gly
    2195                 2200                 2205

Ala Ser  Ala Trp Leu Met Trp  Leu Ser Glu Ile Glu  Pro Ala Arg
    2210                 2215                 2220

Ile Ala  Cys Val Leu Ile Val  Val Phe Leu Leu Leu  Val Val Leu
    2225                 2230                 2235

Ile Pro  Glu Pro Glu Lys Gln  Arg Ser Pro Gln Asp  Asn Gln Met
    2240                 2245                 2250

Ala Ile  Ile Ile Met Val Ala  Val Gly Leu Leu Gly  Leu Ile Thr
    2255                 2260                 2265

Ala Asn  Glu Leu Gly Trp Leu  Glu Arg Thr Lys Ser  Asp Leu Ser
    2270                 2275                 2280

His Leu  Met Gly Arg Arg Glu  Glu Gly Ala Thr Ile  Gly Phe Ser
    2285                 2290                 2295

Met Asp  Ile Asp Leu Arg Pro  Ala Ser Ala Trp Ala  Ile Tyr Ala
    2300                 2305                 2310

Ala Leu  Thr Thr Phe Ile Thr  Pro Ala Val Gln His  Ala Val Thr
    2315                 2320                 2325

Thr Ser  Tyr Asn Asn Tyr Ser  Leu Met Ala Met Ala  Thr Gln Ala
    2330                 2335                 2340

Gly Val  Leu Phe Gly Met Gly  Lys Gly Met Pro Phe  Tyr Ala Trp
    2345                 2350                 2355

Asp Phe  Gly Val Pro Leu Leu  Met Ile Gly Cys Tyr  Ser Gln Leu
    2360                 2365                 2370

Thr Pro  Leu Thr Leu Ile Val  Ala Ile Ile Leu Leu  Val Ala His
    2375                 2380                 2385

Tyr Met  Tyr Leu Ile Pro Gly  Leu Gln Ala Ala Ala  Ala Arg Ala
    2390                 2395                 2400

Ala Gln  Lys Arg Thr Ala Ala  Gly Ile Met Lys Asn  Pro Val Val
    2405                 2410                 2415

Asp Gly  Ile Val Val Thr Asp  Ile Asp Thr Met Thr  Ile Asp Pro
    2420                 2425                 2430

Gln Val  Glu Lys Lys Met Gly  Gln Val Leu Leu Ile  Ala Val Ala
```

2435 2440 2445

Val Ser Ser Ala Ile Leu Ser Arg Thr Ala Trp Gly Trp Gly Glu
2450 2455 2460

Ala Gly Ala Leu Ile Thr Ala Ala Thr Ser Thr Leu Trp Glu Gly
2465 2470 2475

Ser Pro Asn Lys Tyr Trp Asn Ser Ser Thr Ala Thr Ser Leu Cys
2480 2485 2490

Asn Ile Phe Arg Gly Ser Tyr Leu Ala Gly Ala Ser Leu Ile Tyr
2495 2500 2505

Thr Val Thr Arg Asn Ala Gly Leu Val Lys Arg Arg Gly Gly Gly
2510 2515 2520

Thr Gly Glu Thr Leu Gly Glu Lys Trp Lys Ala Arg Leu Asn Gln
2525 2530 2535

Met Ser Ala Leu Glu Phe Tyr Ser Tyr Lys Lys Ser Gly Ile Thr
2540 2545 2550

Glu Val Cys Arg Glu Glu Ala Arg Arg Ala Leu Lys Asp Gly Val
2555 2560 2565

Ala Thr Gly Gly His Ala Val Ser Arg Gly Ser Ala Lys Leu Arg
2570 2575 2580

Trp Leu Val Glu Arg Gly Tyr Leu Gln Pro Tyr Gly Lys Val Ile
2585 2590 2595

Asp Leu Gly Cys Gly Arg Gly Gly Trp Ser Tyr Tyr Ala Ala Thr
2600 2605 2610

Ile Arg Lys Val Gln Glu Val Lys Gly Tyr Thr Lys Gly Gly Pro
2615 2620 2625

Gly His Glu Glu Pro Val Leu Val Gln Ser Tyr Gly Trp Asn Ile
2630 2635 2640

Val Arg Leu Lys Ser Gly Val Asp Val Phe His Met Ala Ala Glu
2645 2650 2655

Pro Cys Asp Thr Leu Leu Cys Asp Ile Gly Glu Ser Ser Ser Ser
2660 2665 2670

Pro Glu Val Glu Glu Ala Arg Thr Leu Arg Val Leu Ser Met Val
2675 2680 2685

Gly Asp Trp Leu Glu Lys Arg Pro Gly Ala Phe Cys Ile Lys Val
2690 2695 2700

Leu Cys Pro Tyr Thr Ser Thr Met Met Glu Thr Leu Glu Arg Leu
2705 2710 2715

Gln Arg Arg Tyr Gly Gly Gly Leu Val Arg Val Pro Leu Ser Arg
2720 2725 2730

Asn Ser Thr His Glu Met Tyr Trp Val Ser Gly Ala Lys Ser Asn
2735 2740 2745

Thr Ile Lys Ser Val Ser Thr Thr Ser Gln Leu Leu Leu Gly Arg
2750 2755 2760

Met Asp Gly Pro Arg Arg Pro Val Lys Tyr Glu Glu Asp Val Asn
2765 2770 2775

Leu Gly Ser Gly Thr Arg Ala Val Val Ser Cys Ala Glu Ala Pro
2780 2785 2790

Asn Met Lys Ile Ile Gly Asn Arg Ile Glu Arg Ile Arg Ser Glu
2795 2800 2805

His Ala Glu Thr Trp Phe Phe Asp Glu Asn His Pro Tyr Arg Thr
2810 2815 2820

Trp Ala Tyr His Gly Ser Tyr Glu Ala Pro Thr Gln Gly Ser Ala
2825 2830 2835

-continued

Ser Ser Leu Ile Asn Gly Val Val Arg Leu Leu Ser Lys Pro Trp
2840 2845 2850

Asp Val Val Thr Gly Val Thr Gly Ile Ala Met Thr Asp Thr Thr
2855 2860 2865

Pro Tyr Gly Gln Gln Arg Val Phe Lys Glu Lys Val Asp Thr Arg
2870 2875 2880

Val Pro Asp Pro Gln Glu Gly Thr Arg Gln Val Met Ser Met Val
2885 2890 2895

Ser Ser Trp Leu Trp Lys Glu Leu Gly Lys His Lys Arg Pro Arg
2900 2905 2910

Val Cys Thr Lys Glu Glu Phe Ile Asn Lys Val Arg Ser Asn Ala
2915 2920 2925

Ala Leu Gly Ala Ile Phe Glu Glu Glu Lys Glu Trp Lys Thr Ala
2930 2935 2940

Val Glu Ala Val Asn Asp Pro Arg Phe Trp Ala Leu Val Asp Lys
2945 2950 2955

Glu Arg Glu His His Leu Arg Gly Glu Cys Gln Ser Cys Val Tyr
2960 2965 2970

Asn Met Met Gly Lys Arg Glu Lys Lys Gln Gly Glu Phe Gly Lys
2975 2980 2985

Ala Lys Gly Ser Arg Ala Ile Trp Tyr Met Trp Leu Gly Ala Arg
2990 2995 3000

Phe Leu Glu Phe Glu Ala Leu Gly Phe Leu Asn Glu Asp His Trp
3005 3010 3015

Met Gly Arg Glu Asn Ser Gly Gly Gly Val Glu Gly Leu Gly Leu
3020 3025 3030

Gln Arg Leu Gly Tyr Val Leu Glu Glu Met Ser Arg Ile Pro Gly
3035 3040 3045

Gly Arg Met Tyr Ala Asp Asp Thr Ala Gly Trp Asp Thr Arg Ile
3050 3055 3060

Ser Arg Phe Asp Leu Glu Asn Glu Ala Leu Ile Thr Asn Gln Met
3065 3070 3075

Glu Lys Gly His Arg Ala Leu Ala Leu Ala Ile Ile Lys Tyr Thr
3080 3085 3090

Tyr Gln Asn Lys Val Val Lys Val Leu Arg Pro Ala Glu Lys Gly
3095 3100 3105

Lys Thr Val Met Asp Ile Ile Ser Arg Gln Asp Gln Arg Gly Ser
3110 3115 3120

Gly Gln Val Val Thr Tyr Ala Leu Asn Thr Phe Thr Asn Leu Val
3125 3130 3135

Val Gln Leu Ile Arg Asn Met Glu Ala Glu Glu Val Leu Glu Met
3140 3145 3150

Gln Asp Leu Trp Leu Leu Arg Arg Ser Glu Lys Val Thr Asn Trp
3155 3160 3165

Leu Gln Ser Asn Gly Trp Asp Arg Leu Lys Arg Met Ala Val Ser
3170 3175 3180

Gly Asp Asp Cys Val Val Lys Pro Ile Asp Asp Arg Phe Ala His
3185 3190 3195

Ala Leu Arg Phe Leu Asn Asp Met Gly Lys Val Arg Lys Asp Thr
3200 3205 3210

Gln Glu Trp Lys Pro Ser Thr Gly Trp Asp Asn Trp Glu Glu Val
3215 3220 3225

-continued

```
Pro Phe Cys Ser His His Phe Asn Lys Leu His Leu Lys Asp Gly
    3230                3235                3240

Arg Ser Ile Val Val Pro Cys Arg His Gln Asp Glu Leu Ile Gly
    3245                3250                3255

Arg Ala Arg Val Ser Pro Gly Ala Gly Trp Ser Ile Arg Glu Thr
    3260                3265                3270

Ala Cys Leu Ala Lys Ser Tyr Ala Gln Met Trp Gln Leu Leu Tyr
    3275                3280                3285

Phe His Arg Arg Asp Leu Arg Leu Met Ala Asn Ala Ile Cys Ser
    3290                3295                3300

Ser Val Pro Val Asp Trp Val Pro Thr Gly Arg Thr Thr Trp Ser
    3305                3310                3315

Ile His Gly Lys Gly Glu Trp Met Thr Thr Glu Asp Met Leu Val
    3320                3325                3330

Val Trp Asn Arg Val Trp Ile Glu Glu Asn Asp His Met Glu Asp
    3335                3340                3345

Lys Thr Pro Val Thr Lys Trp Thr Asp Ile Pro Tyr Leu Gly Lys
    3350                3355                3360

Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420


<210> SEQ ID NO 10
<211> LENGTH: 34
<212> TYPE: PRT
<213> ORGANISM: Zika virus Paraiba strain

<400> SEQUENCE: 10

Tyr Ile Glu Arg Ala Gly Asp Ile Thr Trp Glu Lys Asp Ala Glu Val
1               5                   10                  15

Thr Gly Asn Ser Pro Arg Leu Asp Val Ala Leu Asp Glu Ser Gly Asp
            20                  25                  30

Phe Ser
```